(12) United States Patent
Dhugga et al.

(10) Patent No.: US 7,582,808 B2
(45) Date of Patent: Sep. 1, 2009

(54) CELLULOSE SYNTHASE ENCODING NUCLEIC ACIDS AND USES THEREOF

(75) Inventors: Kanwarpal S Dhugga, Johnston, IA (US); Timothy G Helentjaris, Tucson, AZ (US); Benjamin A Bowen, Berkeley, CA (US); Xun Wang, Chapel Hill, NC (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 11/867,246

(22) Filed: Oct. 4, 2007

(65) Prior Publication Data

US 2008/0083043 A1 Apr. 3, 2008

Related U.S. Application Data

(60) Division of application No. 11/493,187, filed on Jul. 26, 2006, now Pat. No. 7,312,377, which is a division of application No. 10/961,254, filed on Oct. 8, 2004, now Pat. No. 7,214,852, which is a division of application No. 10/160,719, filed on Jun. 3, 2002, now Pat. No. 6,803,498, which is a continuation of application No. 09/371,383, filed on Aug. 6, 1999, now abandoned.

(60) Provisional application No. 60/096,822, filed on Aug. 17, 1998.

(51) Int. Cl.
C12N 15/29 (2006.01)
C12N 15/82 (2006.01)
A01H 1/00 (2006.01)
A01H 5/10 (2006.01)

(52) U.S. Cl. ........................ 800/284; 800/290; 800/278; 800/295; 800/298; 800/286; 800/317; 800/320; 435/69.1; 435/468; 435/430.1

(58) Field of Classification Search ........................ None
See application file for complete search history.

(56) References Cited

U.S. PATENT DOCUMENTS 5,723,764 A 3/1998 Nichols

FOREIGN PATENT DOCUMENTS

WO 9800549 A1 1/1998
WO 9818949 A2 5/1998
WO 0004168 A2 1/2000

OTHER PUBLICATIONS

Amor, Y., et al.; "A membrane-associated form of sucrose synthase and its potential role in synthesis of cellulose and callose in plants"; PNAS (Sep. 1995) 92:9353-9357; National Academy of Sciences; Washington, DC US.
Haigler, C., et al.; "New hope for old dreams: Evidence that plant cellulose synthase genes have finally been identified"; PNAS (Oct. 1996) 93:12082-12085; National Academy of Sciences; Washington, DC US.
Pear, J.R., et al.; "Higher plants contain homologs of the bacterial celA genes encoding the catalytic subunit of cellulose synthase"; PNAS (Oct. 1996) 93:12637-12642; National Academy of Sciences; Washington, DC US.
Arioli, T., et al.; "Molecular analysis of cellulose biosynthesis in Arabidopsis"; Science (Jan. 1998) 279:717-720; American Association for the Advancement of Science; Washington, DC US.
AF027174; "*A. thaliana* cellulose synthase catalytic subunit EMBL/GenBank/DDBJ database entry" (Feb. 1999).
AC048947; "*A. thaliana* cellulose synthase catalytic subunit EMBL database entry" (Jun. 1998).
Amor, Y., et al.; "Evidence for a cyclic diguanylic acid-dependent cellulose synthase in plants"; Plant Cell (1991) 3(9):989-995; American Society of Plant Physiologists; Rockville, MD US.
Delmer, D.; "Cellulose Biosynthesis: Exciting Times for a Difficult Field of Study"; Ann. Rev. Plant Physiol. Plant Mol. Bio. (1999) 50:245-276; Springer; The Netherlands.
Arioli, et al.; "Accession No. AC048948, Molecular Analysis of Cellulose Biosynthesis in Arabidopsis"; Science (1998) 279:717-720 (XP-002140697); American Association for the Advancement of Science; Washington, DC US.
Arioli, et al.; "Accession No. AF030052, Molecular Analysis of Cellulose Biosynthesis in Arabidopsis"; Science (1998) 279:717-720 (XP-002140698); American Association for the Advancement of Science; Washington, DC US.
Arioli, et al.; "Accession No. AC048946, Molecular Analysis of Cellulose Biosynthesis in Arabidopsis"; Science (1998) 279:717-720 (XP-002140699); American Association for the Advancement of Science; Washington, DC US.
Arioli, et al.; "Accession No. AF027173, Molecular Analysis of Cellulose Biosynthesis in Arabidopsis" Science (1998) 279:717-720 (XP-00214700); American Association for the Advancement of Science; Washington, DC US.
Wu, et al.; "Accession No. AC065338"; (1998) (XP-002140701).

*Primary Examiner*—Medina A Ibrahim

(57) ABSTRACT

The invention provides isolated cellulose synthase nucleic acids and their encoded proteins. The present invention provides methods and compositions relating to altering cellulose synthase concentration and/or composition of plants. The invention further provides recombinant expression cassettes, host cells, and transgenic plants.

13 Claims, No Drawings

SEQUENCE LISTING

```
<160> NUMBER OF SEQ ID NOS: 61

<210> SEQ ID NO 1
<211> LENGTH: 3568
<212> TYPE: DNA
<213> ORGANISM: Zea mays
<220> FEATURE:
<221> NAME/KEY: CDS
<222> LOCATION: (63)...(3239)
<220> FEATURE:
<221> NAME/KEY: unsure
<222> LOCATION: (3487)...(3487)
<220> FEATURE:
<221> NAME/KEY: misc_feature
<222> LOCATION: (1)...(3568)
<223> OTHER INFORMATION: n = A,T,C or G
<220> FEATURE:
<221> NAME/KEY: misc_feature
<222> LOCATION: 3487
<223> OTHER INFORMATION: n = A,T,C or G
```

<400> SEQUENCE: 1

```
gtcgacccac gcgtccggag ctcgtcgtca tccgccgcga tggcgagcca gggccgaagc      60 cc atg gac cag cgg aac ggc cag gtg tgc cag att tgc ggc gac gac         107
   Met Asp Gln Arg Asn Gly Gln Val Cys Gln Ile Cys Gly Asp Asp
   1               5                   10                  15 gtg ggg cgc aac ccc gac ggg gag cct ttc gtg gcc tgc aac gag tgc        155
Val Gly Arg Asn Pro Asp Gly Glu Pro Phe Val Ala Cys Asn Glu Cys
                20                  25                  30 gcc ttc ccc atc tgc cgg gac tgc tac gag tac gag cgc cgc gag ggc        203
Ala Phe Pro Ile Cys Arg Asp Cys Tyr Glu Tyr Glu Arg Arg Glu Gly
            35                  40                  45 acg cag aac tgc ccc cag tgc aag acc cgc ttc aag cgc ttc aag ggg        251
Thr Gln Asn Cys Pro Gln Cys Lys Thr Arg Phe Lys Arg Phe Lys Gly
        50                  55                  60 tgc gcg cgc gtg ccc ggg gac gag gag gag gac ggc gtc gac gac ctg        299
Cys Ala Arg Val Pro Gly Asp Glu Glu Glu Asp Gly Val Asp Asp Leu
    65                  70                  75 gag aac gag ttc aac tgg agc gac aag cac gac tcc cag tac ctc gcc        347
Glu Asn Glu Phe Asn Trp Ser Asp Lys His Asp Ser Gln Tyr Leu Ala
80                  85                  90                  95 gag tcc atg ctc cac gcc cac atg agc tac ggc cgc ggc gcc gac ctc        395
Glu Ser Met Leu His Ala His Met Ser Tyr Gly Arg Gly Ala Asp Leu
                100                 105                 110 gac ggc gtg ccg cag cca ttc cac ccc atc ccc aat gtt ccc ctc ctc        443
Asp Gly Val Pro Gln Pro Phe His Pro Ile Pro Asn Val Pro Leu Leu
            115                 120                 125 acc aac gga cag atg gtc gat gac atc ccg ccg gac cag cac gcc ctt        491
Thr Asn Gly Gln Met Val Asp Asp Ile Pro Pro Asp Gln His Ala Leu
        130                 135                 140 gtg ccc tcg ttc gtg ggt ggc ggg ggg aag agg att cac cct ctc ccg        539
Val Pro Ser Phe Val Gly Gly Gly Gly Lys Arg Ile His Pro Leu Pro
    145                 150                 155 tac gcg gat ccc aac ctt cct gtg caa ccg agg tct atg gac cct tcc        587
Tyr Ala Asp Pro Asn Leu Pro Val Gln Pro Arg Ser Met Asp Pro Ser
160                 165                 170                 175 aag gat ctc gcc gca tat ggc tac ggg agc gta gca tgg aag gag agg        635
Lys Asp Leu Ala Ala Tyr Gly Tyr Gly Ser Val Ala Trp Lys Glu Arg
                180                 185                 190 atg gag agc tgg aag cag aag cag gag agg atg cac cag acg agg aac        683
Met Glu Ser Trp Lys Gln Lys Gln Glu Arg Met His Gln Thr Arg Asn
            195                 200                 205 gat ggc ggc ggc gat gat ggt gat gat gca gat cta cca cta atg gat        731
Asp Gly Gly Gly Asp Asp Gly Asp Asp Ala Asp Leu Pro Leu Met Asp
        210                 215                 220 gaa gct aga cag cca ttg tcc aga aag atc ccg ctt cct tca agc caa        779
Glu Ala Arg Gln Pro Leu Ser Arg Lys Ile Pro Leu Pro Ser Ser Gln
    225                 230                 235 atc aac ccc tat agg atg att ata ata att cgg cta gtg gtt ttg tgt        827
Ile Asn Pro Tyr Arg Met Ile Ile Ile Ile Arg Leu Val Val Leu Cys
240                 245                 250                 255 ttc ttc ttc cac tac cga gtg atg cat ccg gtg cct gat gca ttt gct        875
Phe Phe Phe His Tyr Arg Val Met His Pro Val Pro Asp Ala Phe Ala
                260                 265                 270 tta tgg ctc ata tct gtg atc tgt gaa att tgg ttt gcc atg tct tgg        923
Leu Trp Leu Ile Ser Val Ile Cys Glu Ile Trp Phe Ala Met Ser Trp
            275                 280                 285 att ctt gac cag ttt cca aag tgg ttt cct atc gag agg gaa acc tat        971
Ile Leu Asp Gln Phe Pro Lys Trp Phe Pro Ile Glu Arg Glu Thr Tyr
```

-continued

```
                       290                      295                      300
ctt gac cgg ctg agt tta agg ttt gac aag gaa ggg cat cct tct caa     1019
Leu Asp Arg Leu Ser Leu Arg Phe Asp Lys Glu Gly His Pro Ser Gln
    305                      310                      315 ctc gcc cct gtt gat ttc ttt gtc agt acg gtt gat ccc ttg aag gaa     1067
Leu Ala Pro Val Asp Phe Phe Val Ser Thr Val Asp Pro Leu Lys Glu
320                      325                      330                 335 cct cca ttg gtc act gct aat act gtt cta tct atc ctt tcg gtg gat     1115
Pro Pro Leu Val Thr Ala Asn Thr Val Leu Ser Ile Leu Ser Val Asp
                     340                      345                 350 tat cca gtt gat aag gtt tca tgc tac gtt tct gat gat ggt gct gcc     1163
Tyr Pro Val Asp Lys Val Ser Cys Tyr Val Ser Asp Asp Gly Ala Ala
                355                      360                  365 atg ctg aca ttt gaa gca ttg tct gaa aca tct gaa ttt gca aag aaa     1211
Met Leu Thr Phe Glu Ala Leu Ser Glu Thr Ser Glu Phe Ala Lys Lys
        370                      375                      380 tgg gtt cct ttc tgc aaa aga tat agc ctt gag cct cgt gct cca gag     1259
Trp Val Pro Phe Cys Lys Arg Tyr Ser Leu Glu Pro Arg Ala Pro Glu
    385                      390                      395 tgg tac ttc caa cag aag ata gac tac ctg aaa gac aag gtg gcg cca     1307
Trp Tyr Phe Gln Gln Lys Ile Asp Tyr Leu Lys Asp Lys Val Ala Pro
400                      405                      410                  415 aac ttt gtt aga gaa cgg aga gca atg aag aga gag tat gag gaa ttc     1355
Asn Phe Val Arg Glu Arg Arg Ala Met Lys Arg Glu Tyr Glu Glu Phe
                     420                      425                 430 aag gtc aga atc aat gcc ttg gtt gct aaa gcc caa aag gtt cct gag     1403
Lys Val Arg Ile Asn Ala Leu Val Ala Lys Ala Gln Lys Val Pro Glu
                435                      440                  445 gaa gga tgg aca atg cag gat gga act cca tgg ccc gga aat aat gtc     1451
Glu Gly Trp Thr Met Gln Asp Gly Thr Pro Trp Pro Gly Asn Asn Val
        450                      455                      460 cgt gat cat cct gga atg att cag gtt ttc ctt ggt caa agt ggt ggc     1499
Arg Asp His Pro Gly Met Ile Gln Val Phe Leu Gly Gln Ser Gly Gly
    465                      470                      475 cat gat gtg gaa gga aat gag ctg cct cga ttg gtt tat gtt tca aga     1547
His Asp Val Glu Gly Asn Glu Leu Pro Arg Leu Val Tyr Val Ser Arg
480                      485                      490                  495 gaa aaa cgg cca ggc tac aac cat cac aag aag gct ggt gct atg aat     1595
Glu Lys Arg Pro Gly Tyr Asn His His Lys Lys Ala Gly Ala Met Asn
                     500                      505                 510 gca ttg gtc cga gtc tct gct gta cta act aat gct cct tat ttg ctg     1643
Ala Leu Val Arg Val Ser Ala Val Leu Thr Asn Ala Pro Tyr Leu Leu
                515                      520                  525 aac ttg gat tgt gat cac tat atc aat aat agt aag gct ata aag gaa     1691
Asn Leu Asp Cys Asp His Tyr Ile Asn Asn Ser Lys Ala Ile Lys Glu
        530                      535                      540 gca atg tgt ttt atg atg gat cct ttg ctt gga aag aaa gtt tgc tat     1739
Ala Met Cys Phe Met Met Asp Pro Leu Leu Gly Lys Lys Val Cys Tyr
545                      550                      555 gtg cag ttt cct caa aga ttt gat ggg att gat cgc cat gat cga tat     1787
Val Gln Phe Pro Gln Arg Phe Asp Gly Ile Asp Arg His Asp Arg Tyr
    560                      565                      570                 575 gct aac aga aat gtt gtc ttt ttc gat atc aac atg aaa ggt ttg gat     1835
Ala Asn Arg Asn Val Val Phe Phe Asp Ile Asn Met Lys Gly Leu Asp
                     580                      585                 590 ggt atc cag ggc cca att tat gtg ggt act gga tgt gtc ttc aga agg     1883
Gly Ile Gln Gly Pro Ile Tyr Val Gly Thr Gly Cys Val Phe Arg Arg
                595                      600                  605 cag gca tta tat ggc tac gat gct ccc aaa aca aag aag cca cca tca     1931
```

-continued

| | | | | | | | | | | | | |
|---|---|---|---|---|---|---|---|---|---|---|---|---|
| Gln | Ala | Leu | Tyr | Gly | Tyr | Asp | Ala | Pro | Lys | Thr | Lys | Lys | Pro | Pro | Ser |
| | | 610 | | | | 615 | | | | 620 | | | |

```
aga act tgc aac tgc tgg cca aag tgg tgc att tgc tgt tgc tgt ttt      1979
Arg Thr Cys Asn Cys Trp Pro Lys Trp Cys Ile Cys Cys Cys Cys Phe
625                 630                 635 ggt aac agg aag acc aag aag aag acc aag acc tct aaa cct aaa ttt      2027
Gly Asn Arg Lys Thr Lys Lys Lys Thr Lys Thr Ser Lys Pro Lys Phe
640                 645                 650                 655 gag aag ata aag aaa ctt ttt aag aaa aag gaa aat caa gcc cct gca      2075
Glu Lys Ile Lys Lys Leu Phe Lys Lys Lys Glu Asn Gln Ala Pro Ala
            660                 665                 670 tat gct ctt ggt gaa att gat gaa gcc gct cca gga gct gaa aat gaa      2123
Tyr Ala Leu Gly Glu Ile Asp Glu Ala Ala Pro Gly Ala Glu Asn Glu
675                 680                 685 aag gct agt att gta aat caa cag aag ttg gaa aag aaa ttt ggc cag      2171
Lys Ala Ser Ile Val Asn Gln Gln Lys Leu Glu Lys Lys Phe Gly Gln
    690                 695                 700 tct tca gtt ttt gtt gca tcc aca ctt ctt gag aat ggt gga acc ctg      2219
Ser Ser Val Phe Val Ala Ser Thr Leu Leu Glu Asn Gly Gly Thr Leu
705                 710                 715 aag agt gcc agt cca gct tct ctt ctg aag gaa gct ata cat gtc atc      2267
Lys Ser Ala Ser Pro Ala Ser Leu Leu Lys Glu Ala Ile His Val Ile
720                 725                 730                 735 agt tgt gga tat gaa gac aaa aca ggc tgg gga aaa gat att ggt tgg      2315
Ser Cys Gly Tyr Glu Asp Lys Thr Gly Trp Gly Lys Asp Ile Gly Trp
            740                 745                 750 att tat gga tca gtc aca gaa gat att ctt act ggg ttt aag atg cac      2363
Ile Tyr Gly Ser Val Thr Glu Asp Ile Leu Thr Gly Phe Lys Met His
            755                 760                 765 tgc cat ggt tgg cgg tca att tac tgc ata cct aaa cgg gcc gcc ttc      2411
Cys His Gly Trp Arg Ser Ile Tyr Cys Ile Pro Lys Arg Ala Ala Phe
770                 775                 780 aaa ggt tcc gca cct ctc aat ctt tcc gat cgt ttt cac cag gtt ctt      2459
Lys Gly Ser Ala Pro Leu Asn Leu Ser Asp Arg Phe His Gln Val Leu
785                 790                 795 cgg tgg gct ctt ggt tca att gaa att ttg ttc agc aac cac tgc cct      2507
Arg Trp Ala Leu Gly Ser Ile Glu Ile Leu Phe Ser Asn His Cys Pro
800                 805                 810                 815 ctc tgg tat ggg tat ggt ggt gga cta aag ttc ctg gaa agg ttt tcg      2555
Leu Trp Tyr Gly Tyr Gly Gly Gly Leu Lys Phe Leu Glu Arg Phe Ser
            820                 825                 830 tac att aac tcc atc gta tac cct tgg aca tct atc ccg ctc ttg gcc      2603
Tyr Ile Asn Ser Ile Val Tyr Pro Trp Thr Ser Ile Pro Leu Leu Ala
            835                 840                 845 tat tgc aca ttg cct gcc atc tgc ttg ctg aca ggg aaa ttt atc acg      2651
Tyr Cys Thr Leu Pro Ala Ile Cys Leu Leu Thr Gly Lys Phe Ile Thr
850                 855                 860 cca gag ctt aac aat gtt gcc agc ctc tgg ttc atg tca ctt ttc atc      2699
Pro Glu Leu Asn Asn Val Ala Ser Leu Trp Phe Met Ser Leu Phe Ile
865                 870                 875 tgc att ttt gct acg agc atc ctg gaa atg aga tgg agt ggt gta ggc      2747
Cys Ile Phe Ala Thr Ser Ile Leu Glu Met Arg Trp Ser Gly Val Gly
880                 885                 890                 895 atc gat gac tgg tgg aga aac gag cag ttt tgg gtc att gga ggc gtg      2795
Ile Asp Asp Trp Trp Arg Asn Glu Gln Phe Trp Val Ile Gly Gly Val
            900                 905                 910 tct tca cat ctc ttt gct gtg ttc cag gga ctc ctc aag gtc ata gct      2843
Ser Ser His Leu Phe Ala Val Phe Gln Gly Leu Leu Lys Val Ile Ala
            915                 920                 925
```

```
ggt gta gac acg agc ttc act gtg aca tcc aag ggc gga gac gac gag    2891
Gly Val Asp Thr Ser Phe Thr Val Thr Ser Lys Gly Gly Asp Asp Glu
            930                 935                 940 gag ttc tca gag ctg tac aca ttc aaa tgg acg acc ctt ctg ata cct    2939
Glu Phe Ser Glu Leu Tyr Thr Phe Lys Trp Thr Thr Leu Leu Ile Pro
945                 950                 955 ccg aca acc ctg ctc cta ctg aac ttc att gga gtg gta gct ggc atc    2987
Pro Thr Thr Leu Leu Leu Leu Asn Phe Ile Gly Val Val Ala Gly Ile
960                 965                 970                 975 tcc aat gcg atc aac aac gga tat gaa tca tgg ggc ccc ctg ttc ggg    3035
Ser Asn Ala Ile Asn Asn Gly Tyr Glu Ser Trp Gly Pro Leu Phe Gly
            980                 985                 990 aag ctc ttc ttt gca ttt tgg gtg atc gtc cat ctt tac ccg ttc ctc    3083
Lys Leu Phe Phe Ala Phe Trp Val Ile Val His Leu Tyr Pro Phe Leu
            995                 1000                1005 aag ggt ctg gtt ggg agg cag aac agg acg cca acg att gtc att gtc    3131
Lys Gly Leu Val Gly Arg Gln Asn Arg Thr Pro Thr Ile Val Ile Val
            1010                1015                1020 tgg tcc atc ctc ctg gct tcg atc ttc tcg ctg ctt tgg gtc cgg atc    3179
Trp Ser Ile Leu Leu Ala Ser Ile Phe Ser Leu Leu Trp Val Arg Ile
            1025                1030                1035 gac ccg ttc ctt gcg aag gat gat ggt ccc ctg ttg gag gag tgt ggt    3227
Asp Pro Phe Leu Ala Lys Asp Asp Gly Pro Leu Leu Glu Glu Cys Gly
1040                1045                1050                1055 ctg gat tgc aac taggaggtca gcacgtggac ttccccgtca gtgtgtggtc        3279
Leu Asp Cys Asn gaagaagtat ttttgcagat gttttgtgcc catatttctt tactcaattt ttgtccctct  3339
gtagattgaa acaagggtg aaggggaaaa aaagtacttg tatttctttt gttccatggt   3399
ggtggtggtg gtgggcggct cagcctcgtg agtgcaatat tgggcaaacc ggaggttgcg  3459
gcaaccttgt gcagttcgtc cacgaatnta ctagggatga tcgcgaccaa tcaatcaatc  3519
gatgaccgag ttcaattgtt caaaaaaaaa aaaaaaaaag gcggccgc               3568

<210> SEQ ID NO 2
<211> LENGTH: 1059
<212> TYPE: PRT
<213> ORGANISM: Zea mays

<400> SEQUENCE: 2

Met Asp Gln Arg Asn Gly Gln Val Cys Gln Ile Cys Gly Asp Asp Val
1               5                   10                  15

Gly Arg Asn Pro Asp Gly Glu Pro Phe Val Ala Cys Asn Glu Cys Ala
            20                  25                  30

Phe Pro Ile Cys Arg Asp Cys Tyr Glu Tyr Glu Arg Arg Glu Gly Thr
        35                  40                  45

Gln Asn Cys Pro Gln Cys Lys Thr Arg Phe Lys Arg Phe Lys Gly Cys
    50                  55                  60

Ala Arg Val Pro Gly Asp Glu Glu Glu Asp Gly Val Asp Asp Leu Glu
65                  70                  75                  80

Asn Glu Phe Asn Trp Ser Asp Lys His Asp Ser Gln Tyr Leu Ala Glu
                85                  90                  95

Ser Met Leu His Ala His Met Ser Tyr Gly Arg Gly Ala Asp Leu Asp
            100                 105                 110

Gly Val Pro Gln Pro Phe His Pro Ile Pro Asn Val Pro Leu Leu Thr
        115                 120                 125

Asn Gly Gln Met Val Asp Asp Ile Pro Pro Asp Gln His Ala Leu Val
    130                 135                 140
```

```
Pro Ser Phe Val Gly Gly Gly Lys Arg Ile His Pro Leu Pro Tyr
145                 150                 155                 160

Ala Asp Pro Asn Leu Pro Val Gln Pro Arg Ser Met Asp Pro Ser Lys
                165                 170                 175

Asp Leu Ala Ala Tyr Gly Tyr Gly Ser Val Ala Trp Lys Glu Arg Met
            180                 185                 190

Glu Ser Trp Lys Gln Lys Gln Glu Arg Met His Gln Thr Arg Asn Asp
                195                 200                 205

Gly Gly Gly Asp Asp Gly Asp Asp Ala Asp Leu Pro Leu Met Asp Glu
            210                 215                 220

Ala Arg Gln Pro Leu Ser Arg Lys Ile Pro Leu Pro Ser Ser Gln Ile
225                 230                 235                 240

Asn Pro Tyr Arg Met Ile Ile Ile Arg Leu Val Val Leu Cys Phe
                245                 250                 255

Phe Phe His Tyr Arg Val Met His Pro Val Pro Asp Ala Phe Ala Leu
            260                 265                 270

Trp Leu Ile Ser Val Ile Cys Glu Ile Trp Phe Ala Met Ser Trp Ile
            275                 280                 285

Leu Asp Gln Phe Pro Lys Trp Phe Pro Ile Glu Arg Glu Thr Tyr Leu
            290                 295                 300

Asp Arg Leu Ser Leu Arg Phe Asp Lys Glu Gly His Pro Ser Gln Leu
305                 310                 315                 320

Ala Pro Val Asp Phe Phe Val Ser Thr Val Asp Pro Leu Lys Glu Pro
                325                 330                 335

Pro Leu Val Thr Ala Asn Thr Val Leu Ser Ile Leu Ser Val Asp Tyr
            340                 345                 350

Pro Val Asp Lys Val Ser Cys Tyr Val Ser Asp Gly Ala Ala Met
                355                 360                 365

Leu Thr Phe Glu Ala Leu Ser Glu Thr Ser Glu Phe Ala Lys Lys Trp
            370                 375                 380

Val Pro Phe Cys Lys Arg Tyr Ser Leu Glu Pro Arg Ala Pro Glu Trp
385                 390                 395                 400

Tyr Phe Gln Gln Lys Ile Asp Tyr Leu Lys Asp Lys Val Ala Pro Asn
                405                 410                 415

Phe Val Arg Glu Arg Arg Ala Met Lys Arg Glu Tyr Glu Glu Phe Lys
            420                 425                 430

Val Arg Ile Asn Ala Leu Val Ala Lys Ala Gln Lys Val Pro Glu Glu
            435                 440                 445

Gly Trp Thr Met Gln Asp Gly Thr Pro Trp Pro Gly Asn Asn Val Arg
            450                 455                 460

Asp His Pro Gly Met Ile Gln Val Phe Leu Gly Gln Ser Gly Gly His
465                 470                 475                 480

Asp Val Glu Gly Asn Glu Leu Pro Arg Leu Val Tyr Val Ser Arg Glu
                485                 490                 495

Lys Arg Pro Gly Tyr Asn His His Lys Lys Ala Gly Ala Met Asn Ala
                500                 505                 510

Leu Val Arg Val Ser Ala Val Leu Thr Asn Ala Pro Tyr Leu Leu Asn
            515                 520                 525

Leu Asp Cys Asp His Tyr Ile Asn Asn Ser Lys Ala Ile Lys Glu Ala
            530                 535                 540

Met Cys Phe Met Met Asp Pro Leu Leu Gly Lys Lys Val Cys Tyr Val
545                 550                 555                 560
```

-continued

```
Gln Phe Pro Gln Arg Phe Asp Gly Ile Asp Arg His Asp Arg Tyr Ala
            565                 570                 575
Asn Arg Asn Val Val Phe Phe Asp Ile Asn Met Lys Gly Leu Asp Gly
        580                 585                 590
Ile Gln Gly Pro Ile Tyr Val Gly Thr Gly Cys Val Phe Arg Arg Gln
    595                 600                 605
Ala Leu Tyr Gly Tyr Asp Ala Pro Lys Thr Lys Lys Pro Pro Ser Arg
610                 615                 620
Thr Cys Asn Cys Trp Pro Lys Trp Cys Ile Cys Cys Cys Phe Gly
625                 630                 635                 640
Asn Arg Lys Thr Lys Lys Thr Lys Thr Ser Lys Pro Lys Phe Glu
            645                 650                 655
Lys Ile Lys Lys Leu Phe Lys Lys Lys Glu Asn Gln Ala Pro Ala Tyr
        660                 665                 670
Ala Leu Gly Glu Ile Asp Glu Ala Ala Pro Gly Ala Glu Asn Glu Lys
    675                 680                 685
Ala Ser Ile Val Asn Gln Gln Lys Leu Glu Lys Lys Phe Gly Gln Ser
690                 695                 700
Ser Val Phe Val Ala Ser Thr Leu Leu Glu Asn Gly Gly Thr Leu Lys
705                 710                 715                 720
Ser Ala Ser Pro Ala Ser Leu Leu Lys Glu Ala Ile His Val Ile Ser
            725                 730                 735
Cys Gly Tyr Glu Asp Lys Thr Gly Trp Gly Lys Asp Ile Gly Trp Ile
        740                 745                 750
Tyr Gly Ser Val Thr Glu Asp Ile Leu Thr Gly Phe Lys Met His Cys
    755                 760                 765
His Gly Trp Arg Ser Ile Tyr Cys Ile Pro Lys Arg Ala Ala Phe Lys
770                 775                 780
Gly Ser Ala Pro Leu Asn Leu Ser Asp Arg Phe His Gln Val Leu Arg
785                 790                 795                 800
Trp Ala Leu Gly Ser Ile Glu Ile Leu Phe Ser Asn His Cys Pro Leu
            805                 810                 815
Trp Tyr Gly Tyr Gly Gly Gly Leu Lys Phe Leu Glu Arg Phe Ser Tyr
        820                 825                 830
Ile Asn Ser Ile Val Tyr Pro Trp Thr Ser Ile Pro Leu Leu Ala Tyr
    835                 840                 845
Cys Thr Leu Pro Ala Ile Cys Leu Leu Thr Gly Lys Phe Ile Thr Pro
850                 855                 860
Glu Leu Asn Asn Val Ala Ser Leu Trp Phe Met Ser Leu Phe Ile Cys
865                 870                 875                 880
Ile Phe Ala Thr Ser Ile Leu Glu Met Arg Trp Ser Gly Val Gly Ile
            885                 890                 895
Asp Asp Trp Trp Arg Asn Glu Gln Phe Trp Val Ile Gly Gly Val Ser
        900                 905                 910
Ser His Leu Phe Ala Val Phe Gln Gly Leu Leu Lys Val Ile Ala Gly
    915                 920                 925
Val Asp Thr Ser Phe Thr Val Thr Ser Lys Gly Gly Asp Asp Glu Glu
930                 935                 940
Phe Ser Glu Leu Tyr Thr Phe Lys Trp Thr Thr Leu Leu Ile Pro Pro
945                 950                 955                 960
Thr Thr Leu Leu Leu Leu Asn Phe Ile Gly Val Val Ala Gly Ile Ser
            965                 970                 975
Asn Ala Ile Asn Asn Gly Tyr Glu Ser Trp Gly Pro Leu Phe Gly Lys
```

```
                980            985             990
Leu Phe Phe Ala Phe Trp Val Ile Val His Leu Tyr Pro Phe Leu Lys
        995                   1000                  1005

Gly Leu Val Gly Arg Gln Asn Arg Thr Pro Thr Ile Val Ile Val Trp
        1010                  1015                  1020

Ser Ile Leu Leu Ala Ser Ile Phe Ser Leu Leu Trp Val Arg Ile Asp
1025                1030                  1035                  1040

Pro Phe Leu Ala Lys Asp Asp Gly Pro Leu Leu Glu Glu Cys Gly Leu
                1045                  1050                  1055

Asp Cys Asn

<210> SEQ ID NO 3
<211> LENGTH: 25
<212> TYPE: DNA
<213> ORGANISM: Zea mays

<400> SEQUENCE: 3
atggaccagc ggaacggcca ggtgt                                            25

<210> SEQ ID NO 4
<211> LENGTH: 25
<212> TYPE: DNA
<213> ORGANISM: Zea mays

<400> SEQUENCE: 4
ctagttgcaa tccagaccac actcc                                            25

<210> SEQ ID NO 5
<211> LENGTH: 3773
<212> TYPE: DNA
<213> ORGANISM: Zea mays
<220> FEATURE:
<221> NAME/KEY: CDS
<222> LOCATION: (338)...(3568)

<400> SEQUENCE: 5
gtcgacccac gcgtccgcta ggatcaaaac cgtctcgccg ctgcaataat cttttgtcaa      60
ttcttaatcc ctcgcgtcga cagcgacagc ggaaccaact cacgttgccg cggcttcctc     120
catcggtgcg gtgccctgtc cttttctctc gtccctcctc cccccgtata gttaagcccc     180
gccccgctac tactactact agcagcagca gcgctctcgc agcgggagat gcggtgttga     240
tccgtgcccc gctcggatct cgggactggt gccggctctg cccaggcccc aggctccagg     300
ccagctccct cgacgtttct cggcgagctc gcttgcc atg gag ggc gac gcg gac     355
                                         Met Glu Gly Asp Ala Asp
                                           1               5 ggc gtg aag tcg ggg agg cgc ggt ggc gga cag gtg tgc cag atc tgc       403
Gly Val Lys Ser Gly Arg Arg Gly Gly Gly Gln Val Cys Gln Ile Cys
         10                  15                  20 ggc gac ggc gtg ggc acc acg gcg gag ggg gac gtc ttc gcc gcc tgc       451
Gly Asp Gly Val Gly Thr Thr Ala Glu Gly Asp Val Phe Ala Ala Cys
     25                  30                  35 gac gtc tgc ggg ttt ccg gtg tgc cgc ccc tgc tac gag tac gag cgc       499
Asp Val Cys Gly Phe Pro Val Cys Arg Pro Cys Tyr Glu Tyr Glu Arg
 40                  45                  50 aag gac ggc acg cag gcg tgc ccc cag tgc aag acc aag tac aag cgc       547
Lys Asp Gly Thr Gln Ala Cys Pro Gln Cys Lys Thr Lys Tyr Lys Arg
 55                  60                  65                  70 cac aag ggg agc ccg gcg atc cgt ggg gag gaa gga gac gac act gat       595
His Lys Gly Ser Pro Ala Ile Arg Gly Glu Glu Gly Asp Asp Thr Asp
```

-continued

|  |  |  | 75 |  |  |  | 80 |  |  |  | 85 |  |  |  |
|---|---|---|---|---|---|---|---|---|---|---|---|---|---|---|
| gcc | gat | agc | gac | ttc | aat | tac | ctt | gca | tct | ggc | aat | gag | gac | cag | aag | 643 |
| Ala | Asp | Ser | Asp | Phe | Asn | Tyr | Leu | Ala | Ser | Gly | Asn | Glu | Asp | Gln | Lys |
|  |  |  | 90 |  |  |  | 95 |  |  |  | 100 |  | cag aag att gcc gac aga atg cgc agc tgg cgc atg aac gtt ggg ggc    691
Gln Lys Ile Ala Asp Arg Met Arg Ser Trp Arg Met Asn Val Gly Gly
        105                 110                 115 agc ggg gat gtt ggt cgc ccc aag tat gac agt ggc gag atc ggg ctt    739
Ser Gly Asp Val Gly Arg Pro Lys Tyr Asp Ser Gly Glu Ile Gly Leu
    120                 125                 130 acc aag tat gac agt ggc gag att cct cgg gga tac atc cca tca gtc    787
Thr Lys Tyr Asp Ser Gly Glu Ile Pro Arg Gly Tyr Ile Pro Ser Val
135                 140                 145                 150 act aac agc cag atc tca gga gaa atc cct ggt gct tcc cct gac cat    835
Thr Asn Ser Gln Ile Ser Gly Glu Ile Pro Gly Ala Ser Pro Asp His
                155                 160                 165 cat atg atg tcc cca act ggg aac att ggc aag cgt gct cca ttt ccc    883
His Met Met Ser Pro Thr Gly Asn Ile Gly Lys Arg Ala Pro Phe Pro
            170                 175                 180 tat gtg aac cat tcg cca aat ccg tca agg gag ttc tct ggt agc att    931
Tyr Val Asn His Ser Pro Asn Pro Ser Arg Glu Phe Ser Gly Ser Ile
        185                 190                 195 ggg aat gtt gcc tgg aaa gag agg gtt gat ggc tgg aaa atg aag cag    979
Gly Asn Val Ala Trp Lys Glu Arg Val Asp Gly Trp Lys Met Lys Gln
    200                 205                 210 gac aag ggg acg att ccc atg acg aat ggc aca agc att gct ccc tct   1027
Asp Lys Gly Thr Ile Pro Met Thr Asn Gly Thr Ser Ile Ala Pro Ser
215                 220                 225                 230 gag ggt cgg ggt gtt ggt gat att gat gca tca act gat tac aac atg   1075
Glu Gly Arg Gly Val Gly Asp Ile Asp Ala Ser Thr Asp Tyr Asn Met
                235                 240                 245 gaa gat gcc tta ttg aac gac gaa act cga cag cct cta tct agg aaa   1123
Glu Asp Ala Leu Leu Asn Asp Glu Thr Arg Gln Pro Leu Ser Arg Lys
            250                 255                 260 gtt cca ctt cct tcc tcc agg ata aat cca tac agg atg gtc att gtg   1171
Val Pro Leu Pro Ser Ser Arg Ile Asn Pro Tyr Arg Met Val Ile Val
        265                 270                 275 ctg cga ttg att gtt cta agc atc ttc ttg cac tac cgt atc aca aat   1219
Leu Arg Leu Ile Val Leu Ser Ile Phe Leu His Tyr Arg Ile Thr Asn
    280                 285                 290 cct gtg cgc aat gca tac cca tta tgg ctt cta tct gtt ata tgt gag   1267
Pro Val Arg Asn Ala Tyr Pro Leu Trp Leu Leu Ser Val Ile Cys Glu
295                 300                 305                 310 atc tgg ttt gct ctt tcg tgg ata ttg gat cag ttc cct aag tgg ttt   1315
Ile Trp Phe Ala Leu Ser Trp Ile Leu Asp Gln Phe Pro Lys Trp Phe
                315                 320                 325 cca atc aac cgg gag acg tac ctt gat agg ctg gca tta agg tat gac   1363
Pro Ile Asn Arg Glu Thr Tyr Leu Asp Arg Leu Ala Leu Arg Tyr Asp
            330                 335                 340 cgg gaa ggt gag cca tct cag ttg gct gct gtt gac att ttc gtc agt   1411
Arg Glu Gly Glu Pro Ser Gln Leu Ala Ala Val Asp Ile Phe Val Ser
        345                 350                 355 aca gtc gac cca atg aag gag cct cct ctt gtc act gcc aat acc gtg   1459
Thr Val Asp Pro Met Lys Glu Pro Pro Leu Val Thr Ala Asn Thr Val
    360                 365                 370 cta tcc att ctt gct gtg gat tac cct gtg gat aag gtc tct tgc tat   1507
Leu Ser Ile Leu Ala Val Asp Tyr Pro Val Asp Lys Val Ser Cys Tyr
375                 380                 385                 390 gta tct gat gat gga gct gcg atg ctg aca ttt gat gca cta gct gag   1555

```
                                   -continued

Val Ser Asp Asp Gly Ala Ala Met Leu Thr Phe Asp Ala Leu Ala Glu
            395                 400                 405 act tca gag ttt gct aga aaa tgg gta cca ttt gtt aag aag tac aac    1603
Thr Ser Glu Phe Ala Arg Lys Trp Val Pro Phe Val Lys Lys Tyr Asn
            410                 415                 420 att gaa cct aga gct cct gaa tgg tac ttc tcc cag aaa att gat tac    1651
Ile Glu Pro Arg Ala Pro Glu Trp Tyr Phe Ser Gln Lys Ile Asp Tyr
            425                 430                 435 ttg aag gac aaa gtg cac cct tca ttt gtt aaa gac cgc cgg gcc atg    1699
Leu Lys Asp Lys Val His Pro Ser Phe Val Lys Asp Arg Arg Ala Met
    440                 445                 450 aag aga gaa tat gaa gaa ttc aaa gtt agg gta aat ggc ctt gtt gct    1747
Lys Arg Glu Tyr Glu Glu Phe Lys Val Arg Val Asn Gly Leu Val Ala
455                 460                 465                 470 aag gca cag aaa gtt cct gag gaa gga tgg atc atg caa gat ggc aca    1795
Lys Ala Gln Lys Val Pro Glu Glu Gly Trp Ile Met Gln Asp Gly Thr
                475                 480                 485 cca tgg cca gga aac aat acc agg gac cat cct gga atg att cag gtt    1843
Pro Trp Pro Gly Asn Asn Thr Arg Asp His Pro Gly Met Ile Gln Val
            490                 495                 500 ttc ctt ggt cac agt ggt ggc ctt gat act gag ggc aat gag cta ccc    1891
Phe Leu Gly His Ser Gly Gly Leu Asp Thr Glu Gly Asn Glu Leu Pro
            505                 510                 515 cgt ttg gtc tat gtt tct cgt gaa aag cgt cct gga ttc cag cat cac    1939
Arg Leu Val Tyr Val Ser Arg Glu Lys Arg Pro Gly Phe Gln His His
    520                 525                 530 aag aaa gct ggt gcc atg aat gct ctt gtt cgt gtc tca gct gtg ctt    1987
Lys Lys Ala Gly Ala Met Asn Ala Leu Val Arg Val Ser Ala Val Leu
535                 540                 545                 550 acc aat gga caa tac atg ttg aat ctt gat tgt gat cac tac att aac    2035
Thr Asn Gly Gln Tyr Met Leu Asn Leu Asp Cys Asp His Tyr Ile Asn
                555                 560                 565 aac agt aag gct ctc agg gaa gct atg tgc ttc ctt atg gac cct aac    2083
Asn Ser Lys Ala Leu Arg Glu Ala Met Cys Phe Leu Met Asp Pro Asn
            570                 575                 580 cta gga agg agt gtc tgc tac gtc cag ttt ccc cag aga ttc gat ggc    2131
Leu Gly Arg Ser Val Cys Tyr Val Gln Phe Pro Gln Arg Phe Asp Gly
            585                 590                 595 att gac agg aat gat cga tat gcc aac agg aac acc gtg ttt ttc gat    2179
Ile Asp Arg Asn Asp Arg Tyr Ala Asn Arg Asn Thr Val Phe Phe Asp
    600                 605                 610 att aac ttg aga ggt ctt gat ggc atc caa gga cca gtt tat gtc gga    2227
Ile Asn Leu Arg Gly Leu Asp Gly Ile Gln Gly Pro Val Tyr Val Gly
615                 620                 625                 630 act ggc tgt gtt ttc aac cga aca gct cta tat ggt tat gag ccc cca    2275
Thr Gly Cys Val Phe Asn Arg Thr Ala Leu Tyr Gly Tyr Glu Pro Pro
                635                 640                 645 att aag cag aag aag ggt ggt ttc ttg tca tca cta tgt ggc ggt agg    2323
Ile Lys Gln Lys Lys Gly Gly Phe Leu Ser Ser Leu Cys Gly Gly Arg
            650                 655                 660 aag aag gca agc aaa tca aag aag ggc tcg gac aag aag aag tcg cag    2371
Lys Lys Ala Ser Lys Ser Lys Lys Gly Ser Asp Lys Lys Lys Ser Gln
            665                 670                 675 aag cat gtg gac agt tct gtg cca gta ttc aac ctt gaa gat ata gag    2419
Lys His Val Asp Ser Ser Val Pro Val Phe Asn Leu Glu Asp Ile Glu
    680                 685                 690 gag gga gtt gaa ggc gct gga ttt gac gac gag aaa tca ctt ctt atg    2467
Glu Gly Val Glu Gly Ala Gly Phe Asp Asp Glu Lys Ser Leu Leu Met
695                 700                 705                 710
```

```
tct caa atg agc ctg gag aag aga ttt ggc cag tcc gcg gcg ttt gtt      2515
Ser Gln Met Ser Leu Glu Lys Arg Phe Gly Gln Ser Ala Ala Phe Val
            715                 720                 725 gcc tcc act ctg atg gag tat ggt ggt gtt cct cag tcc gca act ccg      2563
Ala Ser Thr Leu Met Glu Tyr Gly Gly Val Pro Gln Ser Ala Thr Pro
        730                 735                 740 gag tct ctt ctg aaa gaa gct atc cat gtt ata agc tgt ggc tat gag      2611
Glu Ser Leu Leu Lys Glu Ala Ile His Val Ile Ser Cys Gly Tyr Glu
    745                 750                 755 gac aag act gaa tgg gga act gag atc ggg tgg atc tac ggt tct gtg      2659
Asp Lys Thr Glu Trp Gly Thr Glu Ile Gly Trp Ile Tyr Gly Ser Val
760                 765                 770 aca gaa gac att ctc acc gga ttc aag atg cac gcg cga ggc tgg cgg      2707
Thr Glu Asp Ile Leu Thr Gly Phe Lys Met His Ala Arg Gly Trp Arg
775                 780                 785                 790 tcg atc tac tgc atg ccc aag cgg cca gct ttc aag ggg tct gcc ccc      2755
Ser Ile Tyr Cys Met Pro Lys Arg Pro Ala Phe Lys Gly Ser Ala Pro
            795                 800                 805 atc aat ctt tcg gac cgt ctg aac cag gtg ctc cgg tgg gct ctt ggg      2803
Ile Asn Leu Ser Asp Arg Leu Asn Gln Val Leu Arg Trp Ala Leu Gly
        810                 815                 820 tcc gtg gag atc ctc ttc agc cgg cac tgc ccc ctg tgg tac ggc tac      2851
Ser Val Glu Ile Leu Phe Ser Arg His Cys Pro Leu Trp Tyr Gly Tyr
    825                 830                 835 gga ggg cgg ctc aag ttc ctg gag aga ttc gcg tac atc aac acc acc      2899
Gly Gly Arg Leu Lys Phe Leu Glu Arg Phe Ala Tyr Ile Asn Thr Thr
840                 845                 850 atc tac ccg ctc acg tcc atc ccg ctt ctc atc tac tgc atc ctg ccc      2947
Ile Tyr Pro Leu Thr Ser Ile Pro Leu Leu Ile Tyr Cys Ile Leu Pro
855                 860                 865                 870 gcc atc tgt ctg ctc acc gga aag ttc atc att cca gag atc agc aac      2995
Ala Ile Cys Leu Leu Thr Gly Lys Phe Ile Ile Pro Glu Ile Ser Asn
            875                 880                 885 ttc gcc agc atc tgg ttc atc tcc ctc ttc atc tcg atc ttc gcc acg      3043
Phe Ala Ser Ile Trp Phe Ile Ser Leu Phe Ile Ser Ile Phe Ala Thr
        890                 895                 900 ggc atc ctg gag atg agg tgg agc ggg gtg ggc atc gac gag tgg tgg      3091
Gly Ile Leu Glu Met Arg Trp Ser Gly Val Gly Ile Asp Glu Trp Trp
    905                 910                 915 agg aac gag cag ttc tgg gtg atc ggg ggc atc tcc gcg cac ctc ttc      3139
Arg Asn Glu Gln Phe Trp Val Ile Gly Gly Ile Ser Ala His Leu Phe
920                 925                 930 gcc gtg ttc cag ggc ctg ctc aag gtg ctg gcc ggc atc gac acc aac      3187
Ala Val Phe Gln Gly Leu Leu Lys Val Leu Ala Gly Ile Asp Thr Asn
935                 940                 945                 950 ttc acc gtc acc tcc aag gcc tcg gac gag gac ggc gac ttc gcg gag      3235
Phe Thr Val Thr Ser Lys Ala Ser Asp Glu Asp Gly Asp Phe Ala Glu
            955                 960                 965 ctg tac atg ttc aag tgg acg acg ctg ctg atc ccg ccc acc acc atc      3283
Leu Tyr Met Phe Lys Trp Thr Thr Leu Leu Ile Pro Pro Thr Thr Ile
        970                 975                 980 ctg atc atc aac ctg gtc ggc gtc gtc gcc ggc atc tcc tac gcc atc      3331
Leu Ile Ile Asn Leu Val Gly Val Val Ala Gly Ile Ser Tyr Ala Ile
    985                 990                 995 aac agc gga tac cag tcg tgg ggc ccg ctc ttc ggc aag ctc ttc ttc      3379
Asn Ser Gly Tyr Gln Ser Trp Gly Pro Leu Phe Gly Lys Leu Phe Phe
1000                1005                1010 gcc ttc tgg gtc atc gtc cac ctg tac ccg ttc ctc aag ggc ctc atg      3427
Ala Phe Trp Val Ile Val His Leu Tyr Pro Phe Leu Lys Gly Leu Met
1015                1020                1025                1030
```

-continued

```
ggc agg cag aac cgc acc ccg acc atc gtc gtc gtc tgg gcc atc ctg          3475
Gly Arg Gln Asn Arg Thr Pro Thr Ile Val Val Val Trp Ala Ile Leu
             1035                1040                1045 ctg gcg tcc atc ttc tcc ttg ctg tgg gtt cgc atc gac ccc ttc acc          3523
Leu Ala Ser Ile Phe Ser Leu Leu Trp Val Arg Ile Asp Pro Phe Thr
         1050                1055                1060 acc cgc gtc act ggc ccg gat acc cag acg tgt ggc atc aac tgc              3568
Thr Arg Val Thr Gly Pro Asp Thr Gln Thr Cys Gly Ile Asn Cys
     1065                1070                1075 tagggaagtg aaggtttgt actttgtaga acggaggaa taccacgtgc catctgttgt          3628
ctgttaagtt atatatatat aagcagcaag tggcgttatt tacagctacg tacagaccag        3688
tggatattgt ttaccacaaa gtttacttg tgttaatatg cattcttttg ttgatataaa         3748
aaaaaaaaaa aaaaagggcg gccgc                                              3773

<210> SEQ ID NO 6
<211> LENGTH: 1077
<212> TYPE: PRT
<213> ORGANISM: Zea mays

<400> SEQUENCE: 6

Met Glu Gly Asp Ala Asp Gly Val Lys Ser Gly Arg Arg Gly Gly Gly
 1               5                  10                  15

Gln Val Cys Gln Ile Cys Gly Asp Val Gly Thr Thr Ala Glu Gly
             20                  25                  30

Asp Val Phe Ala Ala Cys Asp Val Cys Gly Phe Pro Val Cys Arg Pro
         35                  40                  45

Cys Tyr Glu Tyr Glu Arg Lys Asp Gly Thr Gln Ala Cys Pro Gln Cys
     50                  55                  60

Lys Thr Lys Tyr Lys Arg His Lys Gly Ser Pro Ala Ile Arg Gly Glu
65                  70                  75                  80

Glu Gly Asp Asp Thr Asp Ala Asp Ser Asp Phe Asn Tyr Leu Ala Ser
                 85                  90                  95

Gly Asn Glu Asp Gln Lys Gln Lys Ile Ala Asp Arg Met Arg Ser Trp
            100                 105                 110

Arg Met Asn Val Gly Gly Ser Gly Asp Val Gly Arg Pro Lys Tyr Asp
        115                 120                 125

Ser Gly Glu Ile Gly Leu Thr Lys Tyr Asp Ser Gly Glu Ile Pro Arg
    130                 135                 140

Gly Tyr Ile Pro Ser Val Thr Asn Ser Gln Ile Ser Gly Glu Ile Pro
145                 150                 155                 160

Gly Ala Ser Pro Asp His His Met Met Ser Pro Thr Gly Asn Ile Gly
                165                 170                 175

Lys Arg Ala Pro Phe Pro Tyr Val Asn His Ser Pro Asn Pro Ser Arg
            180                 185                 190

Glu Phe Ser Gly Ser Ile Gly Asn Val Ala Trp Lys Glu Arg Val Asp
        195                 200                 205

Gly Trp Lys Met Lys Gln Asp Lys Gly Thr Ile Pro Met Thr Asn Gly
    210                 215                 220

Thr Ser Ile Ala Pro Ser Glu Gly Arg Gly Val Gly Asp Ile Asp Ala
225                 230                 235                 240

Ser Thr Asp Tyr Asn Met Glu Asp Ala Leu Leu Asn Asp Glu Thr Arg
                245                 250                 255

Gln Pro Leu Ser Arg Lys Val Pro Leu Pro Ser Ser Arg Ile Asn Pro
            260                 265                 270
```

```
Tyr Arg Met Val Ile Val Leu Arg Leu Ile Val Leu Ser Ile Phe Leu
        275                 280                 285

His Tyr Arg Ile Thr Asn Pro Val Arg Asn Ala Tyr Pro Leu Trp Leu
        290                 295                 300

Leu Ser Val Ile Cys Glu Ile Trp Phe Ala Leu Ser Trp Ile Leu Asp
305                 310                 315                 320

Gln Phe Pro Lys Trp Phe Pro Ile Asn Arg Glu Thr Tyr Leu Asp Arg
                325                 330                 335

Leu Ala Leu Arg Tyr Asp Arg Glu Gly Glu Pro Ser Gln Leu Ala Ala
            340                 345                 350

Val Asp Ile Phe Val Ser Thr Val Asp Pro Met Lys Glu Pro Pro Leu
        355                 360                 365

Val Thr Ala Asn Thr Val Leu Ser Ile Leu Ala Val Asp Tyr Pro Val
        370                 375                 380

Asp Lys Val Ser Cys Tyr Val Ser Asp Gly Ala Ala Met Leu Thr
385                 390                 395                 400

Phe Asp Ala Leu Ala Glu Thr Ser Glu Phe Ala Arg Lys Trp Val Pro
                405                 410                 415

Phe Val Lys Lys Tyr Asn Ile Glu Pro Arg Ala Pro Glu Trp Tyr Phe
                420                 425                 430

Ser Gln Lys Ile Asp Tyr Leu Lys Asp Lys Val His Pro Ser Phe Val
            435                 440                 445

Lys Asp Arg Arg Ala Met Lys Arg Glu Tyr Glu Glu Phe Lys Val Arg
450                 455                 460

Val Asn Gly Leu Val Ala Lys Ala Gln Lys Val Pro Glu Glu Gly Trp
465                 470                 475                 480

Ile Met Gln Asp Gly Thr Pro Trp Pro Gly Asn Asn Thr Arg Asp His
                485                 490                 495

Pro Gly Met Ile Gln Val Phe Leu Gly His Ser Gly Gly Leu Asp Thr
            500                 505                 510

Glu Gly Asn Glu Leu Pro Arg Leu Val Tyr Val Ser Arg Glu Lys Arg
            515                 520                 525

Pro Gly Phe Gln His His Lys Lys Ala Gly Ala Met Asn Ala Leu Val
        530                 535                 540

Arg Val Ser Ala Val Leu Thr Asn Gly Gln Tyr Met Leu Asn Leu Asp
545                 550                 555                 560

Cys Asp His Tyr Ile Asn Asn Ser Lys Ala Leu Arg Glu Ala Met Cys
                565                 570                 575

Phe Leu Met Asp Pro Asn Leu Gly Arg Ser Val Cys Tyr Val Gln Phe
            580                 585                 590

Pro Gln Arg Phe Asp Gly Ile Asp Arg Asn Asp Arg Tyr Ala Asn Arg
        595                 600                 605

Asn Thr Val Phe Phe Asp Ile Asn Leu Arg Gly Leu Asp Gly Ile Gln
        610                 615                 620

Gly Pro Val Tyr Val Gly Thr Gly Cys Val Phe Asn Arg Thr Ala Leu
625                 630                 635                 640

Tyr Gly Tyr Glu Pro Pro Ile Lys Gln Lys Gly Gly Phe Leu Ser
                645                 650                 655

Ser Leu Cys Gly Gly Arg Lys Lys Ala Ser Lys Ser Lys Lys Gly Ser
            660                 665                 670

Asp Lys Lys Lys Ser Gln Lys His Val Asp Ser Ser Val Pro Val Phe
        675                 680                 685
```

```
Asn Leu Glu Asp Ile Glu Glu Gly Val Glu Gly Ala Gly Phe Asp Asp
    690                 695                 700
Glu Lys Ser Leu Leu Met Ser Gln Met Ser Leu Glu Lys Arg Phe Gly
705                 710                 715                 720
Gln Ser Ala Ala Phe Val Ala Ser Thr Leu Met Glu Tyr Gly Gly Val
                725                 730                 735
Pro Gln Ser Ala Thr Pro Glu Ser Leu Leu Lys Glu Ala Ile His Val
                740                 745                 750
Ile Ser Cys Gly Tyr Glu Asp Lys Thr Glu Trp Gly Thr Glu Ile Gly
            755                 760                 765
Trp Ile Tyr Gly Ser Val Thr Glu Asp Ile Leu Thr Gly Phe Lys Met
    770                 775                 780
His Ala Arg Gly Trp Arg Ser Ile Tyr Cys Met Pro Lys Arg Pro Ala
785                 790                 795                 800
Phe Lys Gly Ser Ala Pro Ile Asn Leu Ser Asp Arg Leu Asn Gln Val
                805                 810                 815
Leu Arg Trp Ala Leu Gly Ser Val Glu Ile Leu Phe Ser Arg His Cys
                820                 825                 830
Pro Leu Trp Tyr Gly Tyr Gly Gly Arg Leu Lys Phe Leu Glu Arg Phe
            835                 840                 845
Ala Tyr Ile Asn Thr Thr Ile Tyr Pro Leu Thr Ser Ile Pro Leu Leu
    850                 855                 860
Ile Tyr Cys Ile Leu Pro Ala Ile Cys Leu Leu Thr Gly Lys Phe Ile
865                 870                 875                 880
Ile Pro Glu Ile Ser Asn Phe Ala Ser Ile Trp Phe Ile Ser Leu Phe
                885                 890                 895
Ile Ser Ile Phe Ala Thr Gly Ile Leu Glu Met Arg Trp Ser Gly Val
                900                 905                 910
Gly Ile Asp Glu Trp Trp Arg Asn Glu Gln Phe Trp Val Ile Gly Gly
            915                 920                 925
Ile Ser Ala His Leu Phe Ala Val Phe Gln Gly Leu Leu Lys Val Leu
    930                 935                 940
Ala Gly Ile Asp Thr Asn Phe Thr Val Thr Ser Lys Ala Ser Asp Glu
945                 950                 955                 960
Asp Gly Asp Phe Ala Glu Leu Tyr Met Phe Lys Trp Thr Thr Leu Leu
                965                 970                 975
Ile Pro Pro Thr Thr Ile Leu Ile Ile Asn Leu Val Gly Val Val Ala
                980                 985                 990
Gly Ile Ser Tyr Ala Ile Asn Ser Gly Tyr Gln Ser Trp Gly Pro Leu
            995                 1000                1005
Phe Gly Lys Leu Phe Phe Ala Phe Trp Val Ile Val His Leu Tyr Pro
    1010                1015                1020
Phe Leu Lys Gly Leu Met Gly Arg Gln Asn Arg Thr Pro Thr Ile Val
1025                1030                1035                1040
Val Val Trp Ala Ile Leu Leu Ala Ser Ile Phe Ser Leu Leu Trp Val
                1045                1050                1055
Arg Ile Asp Pro Phe Thr Thr Arg Val Thr Gly Pro Asp Thr Gln Thr
                1060                1065                1070
Cys Gly Ile Asn Cys
            1075

<210> SEQ ID NO 7
<211> LENGTH: 25
<212> TYPE: DNA
```

-continued

```
<213> ORGANISM: Zea mays

<400> SEQUENCE: 7 atggaggcg acgcggacgg cgtga                                          25

<210> SEQ ID NO 8
<211> LENGTH: 25
<212> TYPE: DNA
<213> ORGANISM: Zea mays

<400> SEQUENCE: 8
ctagcagttg atgccacacg tctgg                                         25

<210> SEQ ID NO 9
<211> LENGTH: 3780
<212> TYPE: DNA
<213> ORGANISM: Zea mays
<220> FEATURE:
<221> NAME/KEY: CDS
<222> LOCATION: (201)...(3425)

<400> SEQUENCE: 9
gtcgacccac gcgtccgcag cagcagaagc actgcgcggc attgcagcga tcgagcggga     60
ggaatttggg gcatggtggt cgccaacgcc gctcggatct agaggcccgc acgggccgat    120
tggtctccgc ccgcctcgtc ggtgttggtg tcgttggcgt gtggagccgt ctcggtggga    180
gcagcgggga gggagcggag atg gcg gcc aac aag ggg atg gtg gcg ggc tcg   233
                      Met Ala Ala Asn Lys Gly Met Val Ala Gly Ser
                       1               5                  10 cac aac cgc aac gag ttc gtc atg atc cgc cac gac ggc gat gtg ccg    281
His Asn Arg Asn Glu Phe Val Met Ile Arg His Asp Gly Asp Val Pro
             15                  20                  25 ggc tcg gct aag ccc aca aag agt gcg aat gga cag gtc tgc cag att    329
Gly Ser Ala Lys Pro Thr Lys Ser Ala Asn Gly Gln Val Cys Gln Ile
         30                  35                  40 tgc ggt gac tct gtg ggt gtt tca gcc act ggt gat gtc ttt gtt gcc    377
Cys Gly Asp Ser Val Gly Val Ser Ala Thr Gly Asp Val Phe Val Ala
     45                  50                  55 tgc aat gag tgt gcc ttc cct gtc tgc cgc cca tgc tat gag tat gag    425
Cys Asn Glu Cys Ala Phe Pro Val Cys Arg Pro Cys Tyr Glu Tyr Glu
 60                  65                  70                  75 cgc aag gag ggg aac caa tgc tgc ccc cag tgc aag act aga tac aag    473
Arg Lys Glu Gly Asn Gln Cys Cys Pro Gln Cys Lys Thr Arg Tyr Lys
                 80                  85                  90 aga cag aaa ggt agc cct cga gtt cat ggt gat gag gat gag gaa gat    521
Arg Gln Lys Gly Ser Pro Arg Val His Gly Asp Glu Asp Glu Glu Asp
             95                 100                 105 gtt gat gac cta gac aat gaa ttc aac tac aag caa ggc agt ggg aaa    569
Val Asp Asp Leu Asp Asn Glu Phe Asn Tyr Lys Gln Gly Ser Gly Lys
         110                 115                 120 ggc cca gag tgg caa ctg caa gga gat gat gct gat ctg tct tca tct    617
Gly Pro Glu Trp Gln Leu Gln Gly Asp Asp Ala Asp Leu Ser Ser Ser
     125                 130                 135 gct cgc cat gag cca cat cat cgg att cca cgc ctg aca agc ggt caa    665
Ala Arg His Glu Pro His His Arg Ile Pro Arg Leu Thr Ser Gly Gln
140                 145                 150                 155 cag ata tct gga gag att cct gat gct tcc cct gac cgt cat tct atc    713
Gln Ile Ser Gly Glu Ile Pro Asp Ala Ser Pro Asp Arg His Ser Ile
                 160                 165                 170 cgc agt cca aca tcg agc tat gtt gat cca agc gtc cca gtt cct gtg    761
Arg Ser Pro Thr Ser Ser Tyr Val Asp Pro Ser Val Pro Val Pro Val
```

-continued

```
                    175                 180                 185
agg att gtg gac ccc tcg aag gac ttg aat tcc tat ggg ctt aat agt      809
Arg Ile Val Asp Pro Ser Lys Asp Leu Asn Ser Tyr Gly Leu Asn Ser
            190                 195                 200 gtt gac tgg aag gaa aga gtt gag agc tgg agg gtt aaa cag gac aaa      857
Val Asp Trp Lys Glu Arg Val Glu Ser Trp Arg Val Lys Gln Asp Lys
205                 210                 215 aat atg atg caa gtg act aat aaa tat cca gag gct aga gga gga gac      905
Asn Met Met Gln Val Thr Asn Lys Tyr Pro Glu Ala Arg Gly Gly Asp
220                 225                 230                 235 atg gag ggg act ggc tca aat gga gaa gat atg caa atg gtt gat gat      953
Met Glu Gly Thr Gly Ser Asn Gly Glu Asp Met Gln Met Val Asp Asp
                240                 245                 250 gca cgg cta cct ttg agc cgt atc gtg cca att tcc tca aac cag ctc     1001
Ala Arg Leu Pro Leu Ser Arg Ile Val Pro Ile Ser Ser Asn Gln Leu
            255                 260                 265 aac ctt tac cgg gta gtg atc att ctc cgt ctt atc atc ctg tgc ttc     1049
Asn Leu Tyr Arg Val Val Ile Ile Leu Arg Leu Ile Ile Leu Cys Phe
        270                 275                 280 ttc ttc cag tat cgt gtc agt cat cca gtg cgt gat gct tat gga tta     1097
Phe Phe Gln Tyr Arg Val Ser His Pro Val Arg Asp Ala Tyr Gly Leu
285                 290                 295 tgg cta gta tct gtt atc tgc gag gtc tgg ttt gcc ttg tct tgg ctt     1145
Trp Leu Val Ser Val Ile Cys Glu Val Trp Phe Ala Leu Ser Trp Leu
300                 305                 310                 315 cta gat cag ttc cca aaa tgg tat cca atc aac cgt gag aca tat ctt     1193
Leu Asp Gln Phe Pro Lys Trp Tyr Pro Ile Asn Arg Glu Thr Tyr Leu
                320                 325                 330 gac agg ctt gca ttg agg tat gat aga gag gga gag cca tca cag ctg     1241
Asp Arg Leu Ala Leu Arg Tyr Asp Arg Glu Gly Glu Pro Ser Gln Leu
            335                 340                 345 gct ccc att gat gtc ttc gtc agt aca gtg gat cca ttg aag gaa cct     1289
Ala Pro Ile Asp Val Phe Val Ser Thr Val Asp Pro Leu Lys Glu Pro
        350                 355                 360 cca ctg atc aca gcc aac act gtt ttg tcc att ctt tct gtg gat tac     1337
Pro Leu Ile Thr Ala Asn Thr Val Leu Ser Ile Leu Ser Val Asp Tyr
365                 370                 375 cct gtt gac aaa gtg tca tgc tat gtt tct gat gat ggt tca gct atg     1385
Pro Val Asp Lys Val Ser Cys Tyr Val Ser Asp Asp Gly Ser Ala Met
380                 385                 390                 395 ctg act ttt gag tct ctc tca gaa acc gca gaa ttt gct aga aag tgg     1433
Leu Thr Phe Glu Ser Leu Ser Glu Thr Ala Glu Phe Ala Arg Lys Trp
                400                 405                 410 gtt ccc ttt tgt aag aag cac aat att gaa cca aga gct cca gaa ttt     1481
Val Pro Phe Cys Lys Lys His Asn Ile Glu Pro Arg Ala Pro Glu Phe
            415                 420                 425 tac ttt gct caa aaa ata gat tac ctg aag gac aaa att caa cct tca     1529
Tyr Phe Ala Gln Lys Ile Asp Tyr Leu Lys Asp Lys Ile Gln Pro Ser
        430                 435                 440 ttt gtt aag gaa aga cgc gca atg aag agg gag tat gaa gaa ttc aaa     1577
Phe Val Lys Glu Arg Arg Ala Met Lys Arg Glu Tyr Glu Glu Phe Lys
445                 450                 455 gta aga atc aat gcc ctt gtt gcc aaa gca cag aaa gtg cct gaa gag     1625
Val Arg Ile Asn Ala Leu Val Ala Lys Ala Gln Lys Val Pro Glu Glu
460                 465                 470                 475 ggg tgg acc atg gct gat gga act gca tgg cct ggg aat aat cct agg     1673
Gly Trp Thr Met Ala Asp Gly Thr Ala Trp Pro Gly Asn Asn Pro Arg
                480                 485                 490 gac cat cct ggc atg att cag gtt ttc ttg ggg cac agt ggt ggg ctc     1721
```

```
            Asp His Pro Gly Met Ile Gln Val Phe Leu Gly His Ser Gly Gly Leu
                        495                 500                 505 gac act gat gga aat gag tta cca cgt ctt gtc tat gtc tct cgt gaa         1769
Asp Thr Asp Gly Asn Glu Leu Pro Arg Leu Val Tyr Val Ser Arg Glu
            510                 515                 520 aag aga cca ggc ttt cag cat cac aag aag gct ggt gca atg aat gcg         1817
Lys Arg Pro Gly Phe Gln His His Lys Lys Ala Gly Ala Met Asn Ala
525                 530                 535 ctg att cgt gta tct gct gtg ctg aca aat ggt gcc tat ctt ctc aat         1865
Leu Ile Arg Val Ser Ala Val Leu Thr Asn Gly Ala Tyr Leu Leu Asn
540                 545                 550                 555 gtg gat tgc gac cat tac ttc aat agc agc aaa gct ctt aga gaa gca         1913
Val Asp Cys Asp His Tyr Phe Asn Ser Ser Lys Ala Leu Arg Glu Ala
                560                 565                 570 atg tgc ttc atg atg gat ccg gct cta gga agg aaa act tgt tat gta         1961
Met Cys Phe Met Met Asp Pro Ala Leu Gly Arg Lys Thr Cys Tyr Val
            575                 580                 585 caa ttt cca cag aga ttt gat ggc att gac ttg cac gat cga tat gct         2009
Gln Phe Pro Gln Arg Phe Asp Gly Ile Asp Leu His Asp Arg Tyr Ala
            590                 595                 600 aat cgg aac ata gtt ttc ttt gat atc aac atg aaa ggt ctg gat ggc         2057
Asn Arg Asn Ile Val Phe Phe Asp Ile Asn Met Lys Gly Leu Asp Gly
            605                 610                 615 att cag ggt cca gtt tac gtg gga aca gga tgc tgt ttc aat aga cag         2105
Ile Gln Gly Pro Val Tyr Val Gly Thr Gly Cys Cys Phe Asn Arg Gln
620                 625                 630                 635 gct ttg tat gga tac gat cct gtt ttg act gaa gct gat ctg gag cca         2153
Ala Leu Tyr Gly Tyr Asp Pro Val Leu Thr Glu Ala Asp Leu Glu Pro
                640                 645                 650 aac att gtt att aag agc tgc tgt ggt aga agg aag aaa aag aac aag         2201
Asn Ile Val Ile Lys Ser Cys Cys Gly Arg Arg Lys Lys Lys Asn Lys
            655                 660                 665 agt tat atg gat agt caa agc cgt att atg aag aga aca gaa tct tca         2249
Ser Tyr Met Asp Ser Gln Ser Arg Ile Met Lys Arg Thr Glu Ser Ser
            670                 675                 680 gct ccc atc ttc aat atg gaa gac atc gaa gag ggt att gaa ggt tac         2297
Ala Pro Ile Phe Asn Met Glu Asp Ile Glu Glu Gly Ile Glu Gly Tyr
685                 690                 695 gag gat gaa agg tca gtg ctt atg tcc cag agg aaa ttg gag aaa cgc         2345
Glu Asp Glu Arg Ser Val Leu Met Ser Gln Arg Lys Leu Glu Lys Arg
700                 705                 710                 715 ttt ggt cag tct cct att ttc att gca tcc acc ttt atg aca caa ggt         2393
Phe Gly Gln Ser Pro Ile Phe Ile Ala Ser Thr Phe Met Thr Gln Gly
                720                 725                 730 ggc ata cca cct tca aca aac cca gct tct cta cta aag gaa gct atc         2441
Gly Ile Pro Pro Ser Thr Asn Pro Ala Ser Leu Leu Lys Glu Ala Ile
            735                 740                 745 cat gtc atc agt tgt gga tat gag gac aaa act gaa tgg gga aaa gag         2489
His Val Ile Ser Cys Gly Tyr Glu Asp Lys Thr Glu Trp Gly Lys Glu
            750                 755                 760 att ggc tgg atc tat ggt tca gta acg gag gat att ctg act ggg ttt         2537
Ile Gly Trp Ile Tyr Gly Ser Val Thr Glu Asp Ile Leu Thr Gly Phe
765                 770                 775 aaa atg cat gca agg ggc tgg caa tca atc tac tgc atg cca cca cga         2585
Lys Met His Ala Arg Gly Trp Gln Ser Ile Tyr Cys Met Pro Pro Arg
780                 785                 790                 795 cct tgt ttc aag ggt tct gca cca atc aat ctt tcc gat cgt ctt aat         2633
Pro Cys Phe Lys Gly Ser Ala Pro Ile Asn Leu Ser Asp Arg Leu Asn
                800                 805                 810
```

-continued

```
cag gtg ctc cgt tgg gct ctt ggg tca gtg gaa att ctg ctt agt aga      2681
Gln Val Leu Arg Trp Ala Leu Gly Ser Val Glu Ile Leu Leu Ser Arg
            815                 820                 825 cat tgt cct atc tgg tat ggt tac aat gga cga ttg aag ctt ttg gag      2729
His Cys Pro Ile Trp Tyr Gly Tyr Asn Gly Arg Leu Lys Leu Leu Glu
    830                 835                 840 agg ctg gct tac atc aac act att gta tat cca atc aca tcc att ccg      2777
Arg Leu Ala Tyr Ile Asn Thr Ile Val Tyr Pro Ile Thr Ser Ile Pro
845                 850                 855 ctt att gcc tat tgt gtg ctt ccc gct atc tgc ctc ctt acc aat aaa      2825
Leu Ile Ala Tyr Cys Val Leu Pro Ala Ile Cys Leu Leu Thr Asn Lys
860                 865                 870                 875 ttt atc att cct gag att agc aat tat gct ggg atg ttc ttc att ctt      2873
Phe Ile Ile Pro Glu Ile Ser Asn Tyr Ala Gly Met Phe Phe Ile Leu
                880                 885                 890 ctt ttc gcc tcc att ttt gcc act ggt ata ttg gag ctt aga tgg agt      2921
Leu Phe Ala Ser Ile Phe Ala Thr Gly Ile Leu Glu Leu Arg Trp Ser
            895                 900                 905 ggt gtt ggc att gaa gat tgg tgg aga aat gag cag ttt tgg gtt att      2969
Gly Val Gly Ile Glu Asp Trp Trp Arg Asn Glu Gln Phe Trp Val Ile
        910                 915                 920 ggt ggc acc tct gcc cat ctc ttc gca gtg ttc cag ggt ctg ctg aaa      3017
Gly Gly Thr Ser Ala His Leu Phe Ala Val Phe Gln Gly Leu Leu Lys
    925                 930                 935 gtg ttg gct ggg att gat acc aac ttc aca gtt acc tca aag gca tct      3065
Val Leu Ala Gly Ile Asp Thr Asn Phe Thr Val Thr Ser Lys Ala Ser
940                 945                 950                 955 gat gag gat ggc gac ttt gct gag cta tat gtg ttc aag tgg acc agt      3113
Asp Glu Asp Gly Asp Phe Ala Glu Leu Tyr Val Phe Lys Trp Thr Ser
                960                 965                 970 ttg ctc att cct ccg acc act gtt ctt gtc att aac ctg gtc gga atg      3161
Leu Leu Ile Pro Pro Thr Thr Val Leu Val Ile Asn Leu Val Gly Met
            975                 980                 985 gtg gca gga att tct tat gcc att aac agt ggc tac caa tcc tgg ggt      3209
Val Ala Gly Ile Ser Tyr Ala Ile Asn Ser Gly Tyr Gln Ser Trp Gly
        990                 995                 1000 ccg ctc ttt gga aag ctg ttc ttc tcg atc tgg gtg atc ctc cat ctc      3257
Pro Leu Phe Gly Lys Leu Phe Phe Ser Ile Trp Val Ile Leu His Leu
    1005                1010                1015 tac ccc ttc ctc aag ggt ctc atg gga agg cag aac cgc aca cca aca      3305
Tyr Pro Phe Leu Lys Gly Leu Met Gly Arg Gln Asn Arg Thr Pro Thr
1020                1025                1030                1035 atc gtc att gtc tgg tcc atc ctt ctt gca tct atc ttc tcc ttg ctg      3353
Ile Val Ile Val Trp Ser Ile Leu Leu Ala Ser Ile Phe Ser Leu Leu
                1040                1045                1050 tgg gtg aag atc gat cct ttc atc tcc ccg aca cag aaa gct gct gcc      3401
Trp Val Lys Ile Asp Pro Phe Ile Ser Pro Thr Gln Lys Ala Ala Ala
            1055                1060                1065 ttg ggg caa tgt ggc gtc aac tgc tgatcgagac agtgactctt atttgaagag    3455
Leu Gly Gln Cys Gly Val Asn Cys
        1070                1075 gctcaatcaa gatctgcccc ctcgtgtaaa tacctgagga ggctagatgg gaattccttt    3515
tgttgtaggt gaggatggat ttgcatctaa gttatgcctc tgttcattag cttcttccgt    3575
gccggtgctg ctgcggacta agaatcacgg agcctttcta ccttccatgt agcgccagcc    3635
agcagcgtaa gatgtgaatt ttgaagtttt gttatgcgtg cagtttattg ttttagagta    3695
aattatcatt tgtttgtggg aactgttcac acgagcttat aatggcaatg ctgttattta    3755
aaaaaaaaaa aaaagggcg gccgc                                          3780
```

<210> SEQ ID NO 10
<211> LENGTH: 1075
<212> TYPE: PRT
<213> ORGANISM: Zea mays

<400> SEQUENCE: 10

```
Met Ala Ala Asn Lys Gly Met Val Ala Gly Ser His Asn Arg Asn Glu
 1               5                  10                  15

Phe Val Met Ile Arg His Asp Gly Asp Val Pro Gly Ser Ala Lys Pro
            20                  25                  30

Thr Lys Ser Ala Asn Gly Gln Val Cys Gln Ile Cys Gly Asp Ser Val
        35                  40                  45

Gly Val Ser Ala Thr Gly Asp Val Phe Val Ala Cys Asn Glu Cys Ala
    50                  55                  60

Phe Pro Val Cys Arg Pro Cys Tyr Glu Tyr Glu Arg Lys Glu Gly Asn
65                  70                  75                  80

Gln Cys Cys Pro Gln Cys Lys Thr Arg Tyr Lys Arg Gln Lys Gly Ser
                85                  90                  95

Pro Arg Val His Gly Asp Glu Asp Glu Asp Val Asp Asp Leu Asp
            100                 105                 110

Asn Glu Phe Asn Tyr Lys Gln Gly Ser Gly Lys Gly Pro Glu Trp Gln
        115                 120                 125

Leu Gln Gly Asp Asp Ala Asp Leu Ser Ser Ser Ala Arg His Glu Pro
130                 135                 140

His His Arg Ile Pro Arg Leu Thr Ser Gly Gln Gln Ile Ser Gly Glu
145                 150                 155                 160

Ile Pro Asp Ala Ser Pro Asp Arg His Ser Ile Arg Ser Pro Thr Ser
                165                 170                 175

Ser Tyr Val Asp Pro Ser Val Pro Val Pro Val Arg Ile Val Asp Pro
            180                 185                 190

Ser Lys Asp Leu Asn Ser Tyr Gly Leu Asn Ser Val Asp Trp Lys Glu
        195                 200                 205

Arg Val Glu Ser Trp Arg Val Lys Gln Asp Lys Asn Met Met Gln Val
    210                 215                 220

Thr Asn Lys Tyr Pro Glu Ala Arg Gly Gly Asp Met Glu Gly Thr Gly
225                 230                 235                 240

Ser Asn Gly Glu Asp Met Gln Met Val Asp Asp Ala Arg Leu Pro Leu
                245                 250                 255

Ser Arg Ile Val Pro Ile Ser Ser Asn Gln Leu Asn Leu Tyr Arg Val
            260                 265                 270

Val Ile Ile Leu Arg Leu Ile Ile Leu Cys Phe Phe Phe Gln Tyr Arg
        275                 280                 285

Val Ser His Pro Val Arg Asp Ala Tyr Gly Leu Trp Leu Val Ser Val
    290                 295                 300

Ile Cys Glu Val Trp Phe Ala Leu Ser Trp Leu Leu Asp Gln Phe Pro
305                 310                 315                 320

Lys Trp Tyr Pro Ile Asn Arg Glu Thr Tyr Leu Asp Arg Leu Ala Leu
                325                 330                 335

Arg Tyr Asp Arg Glu Gly Glu Pro Ser Gln Leu Ala Pro Ile Asp Val
            340                 345                 350

Phe Val Ser Thr Val Asp Pro Leu Lys Glu Pro Pro Leu Ile Thr Ala
        355                 360                 365

Asn Thr Val Leu Ser Ile Leu Ser Val Asp Tyr Pro Val Asp Lys Val
```

-continued

```
            370                 375                 380
Ser Cys Tyr Val Ser Asp Asp Gly Ser Ala Met Leu Thr Phe Glu Ser
385                 390                 395                 400

Leu Ser Glu Thr Ala Glu Phe Ala Arg Lys Trp Val Pro Phe Cys Lys
                405                 410                 415

Lys His Asn Ile Glu Pro Arg Ala Pro Glu Phe Tyr Phe Ala Gln Lys
                420                 425                 430

Ile Asp Tyr Leu Lys Asp Lys Ile Gln Pro Ser Phe Val Lys Glu Arg
                435                 440                 445

Arg Ala Met Lys Arg Glu Tyr Glu Glu Phe Lys Val Arg Ile Asn Ala
450                 455                 460

Leu Val Ala Lys Ala Gln Lys Val Pro Glu Glu Gly Trp Thr Met Ala
465                 470                 475                 480

Asp Gly Thr Ala Trp Pro Gly Asn Asn Pro Arg Asp His Pro Gly Met
                485                 490                 495

Ile Gln Val Phe Leu Gly His Ser Gly Gly Leu Asp Thr Asp Gly Asn
                500                 505                 510

Glu Leu Pro Arg Leu Val Tyr Val Ser Arg Glu Lys Arg Pro Gly Phe
                515                 520                 525

Gln His His Lys Lys Ala Gly Ala Met Asn Ala Leu Ile Arg Val Ser
                530                 535                 540

Ala Val Leu Thr Asn Gly Ala Tyr Leu Leu Asn Val Asp Cys Asp His
545                 550                 555                 560

Tyr Phe Asn Ser Ser Lys Ala Leu Arg Glu Ala Met Cys Phe Met Met
                565                 570                 575

Asp Pro Ala Leu Gly Arg Lys Thr Cys Tyr Val Gln Phe Pro Gln Arg
                580                 585                 590

Phe Asp Gly Ile Asp Leu His Asp Arg Tyr Ala Asn Arg Asn Ile Val
                595                 600                 605

Phe Phe Asp Ile Asn Met Lys Gly Leu Asp Gly Ile Gln Gly Pro Val
                610                 615                 620

Tyr Val Gly Thr Gly Cys Cys Phe Asn Arg Gln Ala Leu Tyr Gly Tyr
625                 630                 635                 640

Asp Pro Val Leu Thr Glu Ala Asp Leu Glu Pro Asn Ile Val Ile Lys
                645                 650                 655

Ser Cys Cys Gly Arg Arg Lys Lys Asn Lys Ser Tyr Met Asp Ser
                660                 665                 670

Gln Ser Arg Ile Met Lys Arg Thr Glu Ser Ser Ala Pro Ile Phe Asn
                675                 680                 685

Met Glu Asp Ile Glu Glu Gly Ile Glu Gly Tyr Glu Asp Glu Arg Ser
690                 695                 700

Val Leu Met Ser Gln Arg Lys Leu Glu Lys Arg Phe Gly Gln Ser Pro
705                 710                 715                 720

Ile Phe Ile Ala Ser Thr Phe Met Thr Gln Gly Gly Ile Pro Pro Ser
                725                 730                 735

Thr Asn Pro Ala Ser Leu Leu Lys Glu Ala Ile His Val Ile Ser Cys
                740                 745                 750

Gly Tyr Glu Asp Lys Thr Glu Trp Gly Lys Glu Ile Gly Trp Ile Tyr
                755                 760                 765

Gly Ser Val Thr Glu Asp Ile Leu Thr Gly Phe Lys Met His Ala Arg
                770                 775                 780

Gly Trp Gln Ser Ile Tyr Cys Met Pro Pro Arg Pro Cys Phe Lys Gly
785                 790                 795                 800
```

```
Ser Ala Pro Ile Asn Leu Ser Asp Arg Leu Asn Gln Val Leu Arg Trp
            805                 810                 815
Ala Leu Gly Ser Val Glu Ile Leu Leu Ser Arg His Cys Pro Ile Trp
        820                 825                 830
Tyr Gly Tyr Asn Gly Arg Leu Lys Leu Leu Glu Arg Leu Ala Tyr Ile
    835                 840                 845
Asn Thr Ile Val Tyr Pro Ile Thr Ser Ile Pro Leu Ile Ala Tyr Cys
850                 855                 860
Val Leu Pro Ala Ile Cys Leu Leu Thr Asn Lys Phe Ile Ile Pro Glu
865                 870                 875                 880
Ile Ser Asn Tyr Ala Gly Met Phe Phe Ile Leu Leu Phe Ala Ser Ile
            885                 890                 895
Phe Ala Thr Gly Ile Leu Glu Leu Arg Trp Ser Gly Val Gly Ile Glu
        900                 905                 910
Asp Trp Trp Arg Asn Glu Gln Phe Trp Val Ile Gly Gly Thr Ser Ala
    915                 920                 925
His Leu Phe Ala Val Phe Gln Gly Leu Leu Lys Val Leu Ala Gly Ile
    930                 935                 940
Asp Thr Asn Phe Thr Val Thr Ser Lys Ala Ser Asp Glu Asp Gly Asp
945                 950                 955                 960
Phe Ala Glu Leu Tyr Val Phe Lys Trp Thr Ser Leu Leu Ile Pro Pro
            965                 970                 975
Thr Thr Val Leu Val Ile Asn Leu Val Gly Met Val Ala Gly Ile Ser
        980                 985                 990
Tyr Ala Ile Asn Ser Gly Tyr Gln Ser Trp Gly Pro Leu Phe Gly Lys
    995                 1000                1005
Leu Phe Phe Ser Ile Trp Val Ile Leu His Leu Tyr Pro Phe Leu Lys
    1010                1015                1020
Gly Leu Met Gly Arg Gln Asn Arg Thr Pro Thr Ile Val Ile Val Trp
1025                1030                1035                1040
Ser Ile Leu Leu Ala Ser Ile Phe Ser Leu Leu Trp Val Lys Ile Asp
            1045                1050                1055
Pro Phe Ile Ser Pro Thr Gln Lys Ala Ala Ala Leu Gly Gln Cys Gly
        1060                1065                1070
Val Asn Cys
    1075

<210> SEQ ID NO 11
<211> LENGTH: 25
<212> TYPE: DNA
<213> ORGANISM: Zea mays

<400> SEQUENCE: 11
atggcggcca acaaggggat ggtgg                                       25

<210> SEQ ID NO 12
<211> LENGTH: 25
<212> TYPE: DNA
<213> ORGANISM: Zea mays

<400> SEQUENCE: 12
tcagcagttg acgccacatt gcccc                                       25

<210> SEQ ID NO 13
<211> LENGTH: 3725
<212> TYPE: DNA
```

<213> ORGANISM: Zea mays
<220> FEATURE:
<221> NAME/KEY: CDS
<222> LOCATION: (179)...(3400)

<400> SEQUENCE: 13

```
gcagcagcag caccaccact gcgcggcatt gcagcgagca agcgggaggg atctggggca      60
tggtggcggt cgctgccgct gccgctcgga tctagagggc cgcacgggct gattgccctc     120
cgccggcctc gtcggtgtcg gtggagtgtg aatcggtgtg tgtaggagga gcgcggag      178 atg gcg gcc aac aag ggg atg gtg gca ggc tct cac aac cgc aac gag      226
Met Ala Ala Asn Lys Gly Met Val Ala Gly Ser His Asn Arg Asn Glu
  1               5                  10                  15 ttc gtc atg atc cgc cac gac ggc gac gcg cct gtc ccg gct aag ccc      274
Phe Val Met Ile Arg His Asp Gly Asp Ala Pro Val Pro Ala Lys Pro
             20                  25                  30 acg aag agt gcg aat ggg cag gtc tgc cag att tgt ggc gac act gtt      322
Thr Lys Ser Ala Asn Gly Gln Val Cys Gln Ile Cys Gly Asp Thr Val
         35                  40                  45 ggc gtt tca gcc act ggt gat gtc ttt gtt gcc tgc aat gag tgt gcc      370
Gly Val Ser Ala Thr Gly Asp Val Phe Val Ala Cys Asn Glu Cys Ala
     50                  55                  60 ttc cct gtc tgc cgc cct tgc tat gag tac gag cgc aag gaa ggg aac      418
Phe Pro Val Cys Arg Pro Cys Tyr Glu Tyr Glu Arg Lys Glu Gly Asn
 65                  70                  75                  80 caa tgc tgc cct cag tgc aag act aga tac aag aga cag aaa ggt agc      466
Gln Cys Cys Pro Gln Cys Lys Thr Arg Tyr Lys Arg Gln Lys Gly Ser
                 85                  90                  95 cct cga gtt cat ggt gat gat gag gag gaa gat gtt gat gac ctg gac      514
Pro Arg Val His Gly Asp Asp Glu Glu Glu Asp Val Asp Asp Leu Asp
            100                 105                 110 aat gaa ttc aac tat aag caa ggc aat ggg aag ggc cca gag tgg cag      562
Asn Glu Phe Asn Tyr Lys Gln Gly Asn Gly Lys Gly Pro Glu Trp Gln
        115                 120                 125 ctt caa gga gat gac gct gat ctg tct tca tct gct cgc cat gac cca      610
Leu Gln Gly Asp Asp Ala Asp Leu Ser Ser Ser Ala Arg His Asp Pro
    130                 135                 140 cac cat cgg att cca cgc ctt aca agt gga caa cag ata tct gga gag      658
His His Arg Ile Pro Arg Leu Thr Ser Gly Gln Gln Ile Ser Gly Glu
145                 150                 155                 160 atc cct gat gca tcc cct gac cgt cat tct atc cgc agt cca aca tcg      706
Ile Pro Asp Ala Ser Pro Asp Arg His Ser Ile Arg Ser Pro Thr Ser
                165                 170                 175 agc tat gtt gat cca agc gtt cca gtt cct gtg agg att gtg gac ccc      754
Ser Tyr Val Asp Pro Ser Val Pro Val Pro Val Arg Ile Val Asp Pro
            180                 185                 190 tcg aag gac ttg aat tcc tat ggg ctt aat agt gtt gac tgg aag gaa      802
Ser Lys Asp Leu Asn Ser Tyr Gly Leu Asn Ser Val Asp Trp Lys Glu
        195                 200                 205 aga gtt gag agc tgg agg gtt aaa cag gac aaa aat atg ttg caa gtg      850
Arg Val Glu Ser Trp Arg Val Lys Gln Asp Lys Asn Met Leu Gln Val
    210                 215                 220 act aat aaa tat cca gag gct aga gga gac atg gag ggg act ggc tca      898
Thr Asn Lys Tyr Pro Glu Ala Arg Gly Asp Met Glu Gly Thr Gly Ser
225                 230                 235                 240 aat gga gaa gat atg caa atg gtt gat gat gca cgc cta cct ttg agc      946
Asn Gly Glu Asp Met Gln Met Val Asp Asp Ala Arg Leu Pro Leu Ser
                245                 250                 255 cgc att gtg cca att tcc tca aac cag ctc aac ctt tac cgg ata gta      994
Arg Ile Val Pro Ile Ser Ser Asn Gln Leu Asn Leu Tyr Arg Ile Val
```

-continued

```
                    260                 265                 270
atc att ctc cgt ctt atc atc ctg tgc ttc ttc ttc caa tat cgt atc          1042
Ile Ile Leu Arg Leu Ile Ile Leu Cys Phe Phe Phe Gln Tyr Arg Ile
            275                 280                 285 agt cat cca gtg cgt aat gct tat gga ttg tgg cta gta tct gtt atc          1090
Ser His Pro Val Arg Asn Ala Tyr Gly Leu Trp Leu Val Ser Val Ile
        290                 295                 300 tgt gag gtc tgg ttt gcc ttg tcc tgg ctt cta gat cag ttc cca aaa          1138
Cys Glu Val Trp Phe Ala Leu Ser Trp Leu Leu Asp Gln Phe Pro Lys
305                 310                 315                 320 tgg tat cca atc aac cgt gag aca tat ctc gac agg ctt gca ttg agg          1186
Trp Tyr Pro Ile Asn Arg Glu Thr Tyr Leu Asp Arg Leu Ala Leu Arg
                325                 330                 335 tat gat aga gag gga gag cca tca cag ctg gct ccc att gat gtc ttt          1234
Tyr Asp Arg Glu Gly Glu Pro Ser Gln Leu Ala Pro Ile Asp Val Phe
            340                 345                 350 gtc agt aca gtg gat cca ttg aag gaa cct cca ctg atc aca gcc aac          1282
Val Ser Thr Val Asp Pro Leu Lys Glu Pro Pro Leu Ile Thr Ala Asn
        355                 360                 365 act gtt ttg tcc att ctt gct gtg gat tac cct gtt gac aaa gtg tca          1330
Thr Val Leu Ser Ile Leu Ala Val Asp Tyr Pro Val Asp Lys Val Ser
370                 375                 380 tgc tat gtt tct gat gat ggc tca gct atg ctg act ttt gag tct ctc          1378
Cys Tyr Val Ser Asp Asp Gly Ser Ala Met Leu Thr Phe Glu Ser Leu
385                 390                 395                 400 tct gaa act gcc gaa ttt gct aga aag tgg gtt ccc ttt tgt aag aag          1426
Ser Glu Thr Ala Glu Phe Ala Arg Lys Trp Val Pro Phe Cys Lys Lys
                405                 410                 415 cac aat att gaa cca aga gct cca gaa ttt tac ttt gct caa aaa ata          1474
His Asn Ile Glu Pro Arg Ala Pro Glu Phe Tyr Phe Ala Gln Lys Ile
            420                 425                 430 gat tac ctg aag gac aaa att caa cct tca ttt gtt aag gaa aga cga          1522
Asp Tyr Leu Lys Asp Lys Ile Gln Pro Ser Phe Val Lys Glu Arg Arg
        435                 440                 445 gca atg aag aga gag tat gaa gaa ttc aaa ata aga atc aat gcc ctt          1570
Ala Met Lys Arg Glu Tyr Glu Glu Phe Lys Ile Arg Ile Asn Ala Leu
450                 455                 460 gtt gcc aaa gca cag aaa gtg cct gaa gag ggg tgg acc atg gct gat          1618
Val Ala Lys Ala Gln Lys Val Pro Glu Glu Gly Trp Thr Met Ala Asp
465                 470                 475                 480 gga act gct tgg cct ggg aat aac cct agg gac cat cct ggc atg att          1666
Gly Thr Ala Trp Pro Gly Asn Asn Pro Arg Asp His Pro Gly Met Ile
                485                 490                 495 cag gtg ttc ttg ggg cac agt ggt ggg ctt gac act gat gga aat gaa          1714
Gln Val Phe Leu Gly His Ser Gly Gly Leu Asp Thr Asp Gly Asn Glu
            500                 505                 510 tta cca cgt ctt gtc tat gtc tct cgt gaa aag aga cca ggc ttt cag          1762
Leu Pro Arg Leu Val Tyr Val Ser Arg Glu Lys Arg Pro Gly Phe Gln
        515                 520                 525 cat cac aag aag gct ggt gca atg aat gca ctg att cgt gta tct gct          1810
His His Lys Lys Ala Gly Ala Met Asn Ala Leu Ile Arg Val Ser Ala
530                 535                 540 gtg ctg aca aat ggt gcc tat ctt ctc aat gtg gat tgt gac cat tac          1858
Val Leu Thr Asn Gly Ala Tyr Leu Leu Asn Val Asp Cys Asp His Tyr
545                 550                 555                 560 ttc aat agc agc aaa gct ctt aga gaa gca atg tgc ttc atg atg gat          1906
Phe Asn Ser Ser Lys Ala Leu Arg Glu Ala Met Cys Phe Met Met Asp
                565                 570                 575 cca gct cta gga agg aaa act tgt tat gta caa ttt cca caa aga ttt          1954
```

```
Pro Ala Leu Gly Arg Lys Thr Cys Tyr Val Gln Phe Pro Gln Arg Phe
            580                 585                 590 gat ggc att gac ttg cac gat cga tat gct aat agg aac ata gtc ttc      2002
Asp Gly Ile Asp Leu His Asp Arg Tyr Ala Asn Arg Asn Ile Val Phe
            595                 600                 605 ttt gat atc aac atg aaa ggt cta gat ggc att cag ggt cca gtc tat      2050
Phe Asp Ile Asn Met Lys Gly Leu Asp Gly Ile Gln Gly Pro Val Tyr
        610                 615                 620 gtg gga aca gga tgc tgt ttc aat agg cag gct ttg tat gga tat gat      2098
Val Gly Thr Gly Cys Cys Phe Asn Arg Gln Ala Leu Tyr Gly Tyr Asp
625                 630                 635                 640 cct gtt ttg act gaa gct gat ctg gaa cct aac att gtt gtt aag agc      2146
Pro Val Leu Thr Glu Ala Asp Leu Glu Pro Asn Ile Val Val Lys Ser
                645                 650                 655 tgc tgt ggt aga agg aag aga aag aac aag agt tat atg gat agt caa      2194
Cys Cys Gly Arg Arg Lys Arg Lys Asn Lys Ser Tyr Met Asp Ser Gln
            660                 665                 670 agc cgt att atg aag aga aca gaa tct tca gct ccc atc ttt aac atg      2242
Ser Arg Ile Met Lys Arg Thr Glu Ser Ser Ala Pro Ile Phe Asn Met
        675                 680                 685 gaa gac atc gag gag ggt att gaa ggt tat gag gat gaa agg tca gtg      2290
Glu Asp Ile Glu Glu Gly Ile Glu Gly Tyr Glu Asp Glu Arg Ser Val
    690                 695                 700 ctt atg tcc cag agg aaa ttg gag aaa cgc ttt ggt cag tct cca atc      2338
Leu Met Ser Gln Arg Lys Leu Glu Lys Arg Phe Gly Gln Ser Pro Ile
705                 710                 715                 720 ttc att gca tcc acc ttt atg act caa ggt ggc ata cca cct tca aca      2386
Phe Ile Ala Ser Thr Phe Met Thr Gln Gly Gly Ile Pro Pro Ser Thr
                725                 730                 735 aac cca gct tct cta ctg aag gaa gct atc cat gtt atc agc tgt ggg      2434
Asn Pro Ala Ser Leu Leu Lys Glu Ala Ile His Val Ile Ser Cys Gly
            740                 745                 750 tac gag gac aaa act gaa tgg gga aaa gag att ggc tgg atc tat ggt      2482
Tyr Glu Asp Lys Thr Glu Trp Gly Lys Glu Ile Gly Trp Ile Tyr Gly
        755                 760                 765 tca gtt aca gag gat att ctg act ggg ttt aaa atg cat gca aga ggc      2530
Ser Val Thr Glu Asp Ile Leu Thr Gly Phe Lys Met His Ala Arg Gly
    770                 775                 780 tgg caa tca atc tac tgc atg cca cca cga cct tgt ttc aag ggt tct      2578
Trp Gln Ser Ile Tyr Cys Met Pro Pro Arg Pro Cys Phe Lys Gly Ser
785                 790                 795                 800 gca cca atc aat ctt tct gat cgt ctt aat cag gtg ctc cgt tgg gct      2626
Ala Pro Ile Asn Leu Ser Asp Arg Leu Asn Gln Val Leu Arg Trp Ala
                805                 810                 815 ctt ggg tca gtg gaa att ctg ctt agc aga cat tgt cct ata tgg tat      2674
Leu Gly Ser Val Glu Ile Leu Leu Ser Arg His Cys Pro Ile Trp Tyr
            820                 825                 830 ggc tac aat ggg cga ttg aag ctt ttg gag agg ctg gct tac att aac      2722
Gly Tyr Asn Gly Arg Leu Lys Leu Leu Glu Arg Leu Ala Tyr Ile Asn
        835                 840                 845 acc att gtt tat cca atc aca tct gtt ccg ctt atc gcc tat tgt gtg      2770
Thr Ile Val Tyr Pro Ile Thr Ser Val Pro Leu Ile Ala Tyr Cys Val
    850                 855                 860 ctt cct gct atc tgt ctt ctt acc aat aaa ttt atc att cct gag att      2818
Leu Pro Ala Ile Cys Leu Leu Thr Asn Lys Phe Ile Ile Pro Glu Ile
865                 870                 875                 880 agt aat tat gct gga atg ttc ttc att ctt ctt ttt gcc tcc att ttc      2866
Ser Asn Tyr Ala Gly Met Phe Phe Ile Leu Leu Phe Ala Ser Ile Phe
                885                 890                 895
```

```
gca act ggt ata ttg gag ctc aga tgg agt ggt gtt ggc att gaa gat      2914
Ala Thr Gly Ile Leu Glu Leu Arg Trp Ser Gly Val Gly Ile Glu Asp
            900                 905                 910 tgg tgg aga aat gag cag ttt tgg gtt att ggt ggc acc tct gcc cat      2962
Trp Trp Arg Asn Glu Gln Phe Trp Val Ile Gly Gly Thr Ser Ala His
        915                 920                 925 ctc ttc gcg gtg ttc cag ggt ctg ctg aaa gtg ttg gct ggg att gat      3010
Leu Phe Ala Val Phe Gln Gly Leu Leu Lys Val Leu Ala Gly Ile Asp
    930                 935                 940 acc aac ttc aca gtt acc tca aag gca tct gat gag gat ggc gac ttt      3058
Thr Asn Phe Thr Val Thr Ser Lys Ala Ser Asp Glu Asp Gly Asp Phe
945                 950                 955                 960 gct gag cta tat gtg ttc aag tgg acc agt ttg ctc atc cct ccg acc      3106
Ala Glu Leu Tyr Val Phe Lys Trp Thr Ser Leu Leu Ile Pro Pro Thr
                965                 970                 975 act gtt ctt gtc att aac ctg gtc gga atg gtg gca gga att tcg tat      3154
Thr Val Leu Val Ile Asn Leu Val Gly Met Val Ala Gly Ile Ser Tyr
            980                 985                 990 gcc att aac agc ggc tac caa tcc tgg ggt ccg ctc ttt gga aag ctg      3202
Ala Ile Asn Ser Gly Tyr Gln Ser Trp Gly Pro Leu Phe Gly Lys Leu
        995                 1000                1005 ttc ttc tcg atc tgg gtg atc ctc cat ctc tac ccc ttc ctc aag ggt      3250
Phe Phe Ser Ile Trp Val Ile Leu His Leu Tyr Pro Phe Leu Lys Gly
    1010                1015                1020 ctc atg ggc agg cag aac cgc acg cca aca atc gtc atc gtt tgg tcc      3298
Leu Met Gly Arg Gln Asn Arg Thr Pro Thr Ile Val Ile Val Trp Ser
1025                1030                1035                1040 atc ctc ctt gcg tct atc ttc tcc ttg ctg tgg gtg aag atc gat cct      3346
Ile Leu Leu Ala Ser Ile Phe Ser Leu Leu Trp Val Lys Ile Asp Pro
                1045                1050                1055 ttc atc tcc ccg aca cag aaa gct gcc gcc ttg ggg caa tgt ggt gtg      3394
Phe Ile Ser Pro Thr Gln Lys Ala Ala Ala Leu Gly Gln Cys Gly Val
            1060                1065                1070 aac tgc tgatccagat tgtgactctt atctgaagag gctcagccaa agatctgccc      3450
Asn Cys cctcgtgtaa atacctgagg gggctagatg ggaattttt gttgtagatg aggatggatc     3510
tgcatccaag ttatgcctct gtttattagc ttcttcggtg ccggtgctgc tgcagacaat     3570
catggagcct ttctaccttg cttgtagtgc tggccagcag cgtaaattgt gaattctgca     3630 ttttttata cgtggtgttt attgttttag agtaaattat catttgtttg aggtaactat      3690
tcacacgaac tatatggcaa tgctgttatt taaaa                               3725
```

<210> SEQ ID NO 14
<211> LENGTH: 1074
<212> TYPE: PRT
<213> ORGANISM: Zea mays

<400> SEQUENCE: 14

```
Met Ala Ala Asn Lys Gly Met Val Ala Gly Ser His Asn Arg Asn Glu
1               5                   10                  15

Phe Val Met Ile Arg His Asp Gly Asp Ala Pro Val Pro Ala Lys Pro
            20                  25                  30

Thr Lys Ser Ala Asn Gly Gln Val Cys Gln Ile Cys Gly Asp Thr Val
        35                  40                  45

Gly Val Ser Ala Thr Gly Asp Val Phe Val Ala Cys Asn Glu Cys Ala
    50                  55                  60

Phe Pro Val Cys Arg Pro Cys Tyr Glu Tyr Glu Arg Lys Glu Gly Asn
65                  70                  75                  80
```

-continued

```
Gln Cys Cys Pro Gln Cys Lys Thr Arg Tyr Lys Arg Gln Lys Gly Ser
                85                  90                  95
Pro Arg Val His Gly Asp Asp Glu Glu Glu Asp Val Asp Asp Leu Asp
            100                 105                 110
Asn Glu Phe Asn Tyr Lys Gln Gly Asn Gly Lys Gly Pro Glu Trp Gln
        115                 120                 125
Leu Gln Gly Asp Asp Ala Asp Leu Ser Ser Ser Ala Arg His Asp Pro
    130                 135                 140
His His Arg Ile Pro Arg Leu Thr Ser Gly Gln Gln Ile Ser Gly Glu
145                 150                 155                 160
Ile Pro Asp Ala Ser Pro Asp Arg His Ser Ile Arg Ser Pro Thr Ser
                165                 170                 175
Ser Tyr Val Asp Pro Ser Val Pro Val Arg Ile Val Asp Pro
            180                 185                 190
Ser Lys Asp Leu Asn Ser Tyr Gly Leu Asn Ser Val Asp Trp Lys Glu
        195                 200                 205
Arg Val Glu Ser Trp Arg Val Lys Gln Asp Lys Asn Met Leu Gln Val
    210                 215                 220
Thr Asn Lys Tyr Pro Glu Ala Arg Gly Asp Met Glu Gly Thr Gly Ser
225                 230                 235                 240
Asn Gly Glu Asp Met Gln Met Val Asp Asp Ala Arg Leu Pro Leu Ser
                245                 250                 255
Arg Ile Val Pro Ile Ser Ser Asn Gln Leu Asn Leu Tyr Arg Ile Val
            260                 265                 270
Ile Ile Leu Arg Leu Ile Ile Leu Cys Phe Phe Gln Tyr Arg Ile
        275                 280                 285
Ser His Pro Val Arg Asn Ala Tyr Gly Leu Trp Leu Val Ser Val Ile
    290                 295                 300
Cys Glu Val Trp Phe Ala Leu Ser Trp Leu Leu Asp Gln Phe Pro Lys
305                 310                 315                 320
Trp Tyr Pro Ile Asn Arg Glu Thr Tyr Leu Asp Arg Leu Ala Leu Arg
                325                 330                 335
Tyr Asp Arg Glu Gly Glu Pro Ser Gln Leu Ala Pro Ile Asp Val Phe
            340                 345                 350
Val Ser Thr Val Asp Pro Leu Lys Glu Pro Pro Leu Ile Thr Ala Asn
        355                 360                 365
Thr Val Leu Ser Ile Leu Ala Val Asp Tyr Pro Val Asp Lys Val Ser
    370                 375                 380
Cys Tyr Val Ser Asp Asp Gly Ser Ala Met Leu Thr Phe Glu Ser Leu
385                 390                 395                 400
Ser Glu Thr Ala Glu Phe Ala Arg Lys Trp Val Pro Phe Cys Lys Lys
                405                 410                 415
His Asn Ile Glu Pro Arg Ala Pro Glu Phe Tyr Phe Ala Gln Lys Ile
            420                 425                 430
Asp Tyr Leu Lys Asp Lys Ile Gln Pro Ser Phe Val Lys Glu Arg Arg
        435                 440                 445
Ala Met Lys Arg Glu Tyr Glu Glu Phe Lys Ile Arg Ile Asn Ala Leu
    450                 455                 460
Val Ala Lys Ala Gln Lys Val Pro Glu Glu Gly Trp Thr Met Ala Asp
465                 470                 475                 480
Gly Thr Ala Trp Pro Gly Asn Asn Pro Arg Asp His Pro Gly Met Ile
                485                 490                 495
```

-continued

```
Gln Val Phe Leu Gly His Ser Gly Gly Leu Asp Thr Asp Gly Asn Glu
            500                 505             510

Leu Pro Arg Leu Val Tyr Val Ser Arg Glu Lys Arg Pro Gly Phe Gln
            515                 520             525

His His Lys Lys Ala Gly Ala Met Asn Ala Leu Ile Arg Val Ser Ala
            530                 535             540

Val Leu Thr Asn Gly Ala Tyr Leu Leu Asn Val Asp Cys Asp His Tyr
545                 550                 555                 560

Phe Asn Ser Ser Lys Ala Leu Arg Glu Ala Met Cys Phe Met Met Asp
                565                 570             575

Pro Ala Leu Gly Arg Lys Thr Cys Tyr Val Gln Phe Pro Gln Arg Phe
            580                 585             590

Asp Gly Ile Asp Leu His Asp Arg Tyr Ala Asn Arg Asn Ile Val Phe
            595                 600             605

Phe Asp Ile Asn Met Lys Gly Leu Asp Gly Ile Gln Gly Pro Val Tyr
            610                 615             620

Val Gly Thr Gly Cys Cys Phe Asn Arg Gln Ala Leu Tyr Gly Tyr Asp
625                 630                 635                 640

Pro Val Leu Thr Glu Ala Asp Leu Glu Pro Asn Ile Val Val Lys Ser
                645                 650             655

Cys Cys Gly Arg Arg Lys Arg Lys Asn Lys Ser Tyr Met Asp Ser Gln
            660                 665             670

Ser Arg Ile Met Lys Arg Thr Glu Ser Ser Ala Pro Ile Phe Asn Met
            675                 680             685

Glu Asp Ile Glu Glu Gly Ile Glu Gly Tyr Glu Asp Glu Arg Ser Val
            690                 695             700

Leu Met Ser Gln Arg Lys Leu Glu Lys Arg Phe Gly Gln Ser Pro Ile
705                 710                 715                 720

Phe Ile Ala Ser Thr Phe Met Thr Gln Gly Gly Ile Pro Pro Ser Thr
                725                 730             735

Asn Pro Ala Ser Leu Leu Lys Glu Ala Ile His Val Ile Ser Cys Gly
            740                 745             750

Tyr Glu Asp Lys Thr Glu Trp Gly Lys Glu Ile Gly Trp Ile Tyr Gly
            755                 760             765

Ser Val Thr Glu Asp Ile Leu Thr Gly Phe Lys Met His Ala Arg Gly
770                 775                 780

Trp Gln Ser Ile Tyr Cys Met Pro Pro Arg Pro Cys Phe Lys Gly Ser
785                 790                 795             800

Ala Pro Ile Asn Leu Ser Asp Arg Leu Asn Gln Val Leu Arg Trp Ala
            805                 810             815

Leu Gly Ser Val Glu Ile Leu Leu Ser Arg His Cys Pro Ile Trp Tyr
            820                 825             830

Gly Tyr Asn Gly Arg Leu Lys Leu Leu Glu Arg Leu Ala Tyr Ile Asn
            835                 840             845

Thr Ile Val Tyr Pro Ile Thr Ser Val Pro Leu Ile Ala Tyr Cys Val
850                 855                 860

Leu Pro Ala Ile Cys Leu Leu Thr Asn Lys Phe Ile Ile Pro Glu Ile
865                 870                 875                 880

Ser Asn Tyr Ala Gly Met Phe Phe Ile Leu Leu Phe Ala Ser Ile Phe
                885                 890             895

Ala Thr Gly Ile Leu Glu Leu Arg Trp Ser Gly Val Gly Ile Glu Asp
            900                 905             910

Trp Trp Arg Asn Glu Gln Phe Trp Val Ile Gly Gly Thr Ser Ala His
```

-continued

```
                    915                 920                 925
Leu Phe Ala Val Phe Gln Gly Leu Leu Lys Val Leu Ala Gly Ile Asp
        930                 935                 940
Thr Asn Phe Thr Val Thr Ser Lys Ala Ser Asp Glu Asp Gly Asp Phe
945                 950                 955                 960
Ala Glu Leu Tyr Val Phe Lys Trp Thr Ser Leu Leu Ile Pro Pro Thr
                965                 970                 975
Thr Val Leu Val Ile Asn Leu Val Gly Met Val Ala Gly Ile Ser Tyr
            980                 985                 990
Ala Ile Asn Ser Gly Tyr Gln Ser Trp Gly Pro Leu Phe Gly Lys Leu
        995                 1000                1005
Phe Phe Ser Ile Trp Val Ile Leu His Leu Tyr Pro Phe Leu Lys Gly
    1010                1015                1020
Leu Met Gly Arg Gln Asn Arg Thr Pro Thr Ile Val Ile Val Trp Ser
1025                1030                1035                1040
Ile Leu Leu Ala Ser Ile Phe Ser Leu Leu Trp Val Lys Ile Asp Pro
                1045                1050                1055
Phe Ile Ser Pro Thr Gln Lys Ala Ala Ala Leu Gly Gln Cys Gly Val
                1060                1065                1070
Asn Cys

<210> SEQ ID NO 15
<211> LENGTH: 25
<212> TYPE: DNA
<213> ORGANISM: Zea mays

<400> SEQUENCE: 15
atggcggcca acaaggggat ggtgg                                           25

<210> SEQ ID NO 16
<211> LENGTH: 25
<212> TYPE: DNA
<213> ORGANISM: Zea mays

<400> SEQUENCE: 16
tcagcagttc acaccacatt gcccc                                           25

<210> SEQ ID NO 17
<211> LENGTH: 3969
<212> TYPE: DNA
<213> ORGANISM: Zea mays
<220> FEATURE:
<221> NAME/KEY: CDS
<222> LOCATION: (144)...(3401)

<400> SEQUENCE: 17
cttctccctc gtcggtgcgg cgtggcgcgg ctcggcgttc ggtgagaaac cactcggggg     60
atgaggatct gctgctagag tgagaggagc tacggtcagt atcctctgcc ttcgtcggcg    120
gcggaagtgg aggggaggaa gcg atg gag gcg agc gcc ggg ctg gtg gcc ggc    173
                         Met Glu Ala Ser Ala Gly Leu Val Ala Gly
                           1               5                  10 tcc cac aac cgc aac gag ctc gtc gtc atc cgc cgc gac ggc gat ccc      221
Ser His Asn Arg Asn Glu Leu Val Val Ile Arg Arg Asp Gly Asp Pro
             15                  20                  25 ggg ccg aag ccg ccg cgg gag cag aac ggg cag gtg tgc cag att tgc      269
Gly Pro Lys Pro Pro Arg Glu Gln Asn Gly Gln Val Cys Gln Ile Cys
         30                  35                  40 ggc gac gac gtc ggc ctt gcc ccc ggc ggg gac ccc ttc gtg gcg tgc      317
```

-continued

```
                Gly Asp Asp Val Gly Leu Ala Pro Gly Gly Asp Pro Phe Val Ala Cys
                         45                  50                  55 aac gag tgc gcc ttc ccc gtc tgc cgg gac tgc tac gaa tac gag cgc        365
Asn Glu Cys Ala Phe Pro Val Cys Arg Asp Cys Tyr Glu Tyr Glu Arg
         60                  65                  70 cgg gag ggc acg cag aac tgc ccc cag tgc aag act cga tac aag cgc        413
Arg Glu Gly Thr Gln Asn Cys Pro Gln Cys Lys Thr Arg Tyr Lys Arg
 75                  80                  85                  90 ctc aag ggc tgc caa cgt gtg acc ggt gac gag gag gag gac ggc gtc        461
Leu Lys Gly Cys Gln Arg Val Thr Gly Asp Glu Glu Glu Asp Gly Val
                 95                 100                 105 gat gac ctg gac aac gag ttc aac tgg gac ggc cat gac tcg cag tct        509
Asp Asp Leu Asp Asn Glu Phe Asn Trp Asp Gly His Asp Ser Gln Ser
            110                 115                 120 gtg gcc gag tcc atg ctc tac ggc cac atg agc tac ggc cgt gga ggt        557
Val Ala Glu Ser Met Leu Tyr Gly His Met Ser Tyr Gly Arg Gly Gly
        125                 130                 135 gac cct aat ggc gcg cca caa gct ttc cag ctc aac ccc aat gtt cca        605
Asp Pro Asn Gly Ala Pro Gln Ala Phe Gln Leu Asn Pro Asn Val Pro
    140                 145                 150 ctc ctc acc aac ggg caa atg gtg gat gac atc cca ccg gag cag cac        653
Leu Leu Thr Asn Gly Gln Met Val Asp Asp Ile Pro Pro Glu Gln His
155                 160                 165                 170 gcg ctg gtg cct tct ttc atg ggt ggt ggg gga aag agg ata cat ccc        701
Ala Leu Val Pro Ser Phe Met Gly Gly Gly Gly Lys Arg Ile His Pro
                175                 180                 185 ctt cct tat gcg gat ccc agc tta cct gtg caa ccc agg tct atg gac        749
Leu Pro Tyr Ala Asp Pro Ser Leu Pro Val Gln Pro Arg Ser Met Asp
            190                 195                 200 cca tcc aag gat ctt gct gca tat ggg tat ggt agt gtt gct tgg aag        797
Pro Ser Lys Asp Leu Ala Ala Tyr Gly Tyr Gly Ser Val Ala Trp Lys
        205                 210                 215 gaa cgg atg gag aat tgg aag cag aga caa gag agg atg cac cag acg        845
Glu Arg Met Glu Asn Trp Lys Gln Arg Gln Glu Arg Met His Gln Thr
    220                 225                 230 ggg aat gat ggt ggt ggt gat gat ggt gac gat gct gat cta cca cta        893
Gly Asn Asp Gly Gly Gly Asp Asp Gly Asp Asp Ala Asp Leu Pro Leu
235                 240                 245                 250 atg gat gaa gca aga caa caa ctg tcc agg aaa att cca ctt cca tca        941
Met Asp Glu Ala Arg Gln Gln Leu Ser Arg Lys Ile Pro Leu Pro Ser
                255                 260                 265 agc cag att aat cca tat agg atg att atc att att cgg ctt gtg gtt        989
Ser Gln Ile Asn Pro Tyr Arg Met Ile Ile Ile Ile Arg Leu Val Val
            270                 275                 280 ttg ggg ttc ttc ttc cac tac cga gtg atg cat ccg gtg aat gat gca       1037
Leu Gly Phe Phe Phe His Tyr Arg Val Met His Pro Val Asn Asp Ala
        285                 290                 295 ttt gct ttg tgg ctc ata tct gtt atc tgt gaa atc tgg ttt gcc atg       1085
Phe Ala Leu Trp Leu Ile Ser Val Ile Cys Glu Ile Trp Phe Ala Met
    300                 305                 310 tct tgg att ctt gat caa ttc cca aag tgg ttc cct att gag aga gag       1133
Ser Trp Ile Leu Asp Gln Phe Pro Lys Trp Phe Pro Ile Glu Arg Glu
315                 320                 325                 330 act tac cta gac cgg ctg tca ctg agg ttc gac aag gaa ggc cag cca       1181
Thr Tyr Leu Asp Arg Leu Ser Leu Arg Phe Asp Lys Glu Gly Gln Pro
                335                 340                 345 tct caa ctt gct cca att gat ttc ttt gtc agt acg gtt gat ccc tta       1229
Ser Gln Leu Ala Pro Ile Asp Phe Phe Val Ser Thr Val Asp Pro Leu
            350                 355                 360
```

-continued

```
aag gaa cct cct ttg gtc aca aca aat act gtt cta tct atc ctt tcg      1277
Lys Glu Pro Pro Leu Val Thr Thr Asn Thr Val Leu Ser Ile Leu Ser
        365                 370                 375 gtg gat tat cct gtt gat aag gtt tct tgc tat gtt tct gat gat ggt      1325
Val Asp Tyr Pro Val Asp Lys Val Ser Cys Tyr Val Ser Asp Asp Gly
    380                 385                 390 gct gca atg cta acg ttt gaa gca tta tct gaa aca tct gaa ttt gca      1373
Ala Ala Met Leu Thr Phe Glu Ala Leu Ser Glu Thr Ser Glu Phe Ala
395                 400                 405                 410 aag aaa tgg gtt cct ttc tgc aaa cgg tac aat att gaa cct cgc gct      1421
Lys Lys Trp Val Pro Phe Cys Lys Arg Tyr Asn Ile Glu Pro Arg Ala
                415                 420                 425 cca gag tgg tac ttc caa cag aag ata gac tac ttg aaa gac aag gtg      1469
Pro Glu Trp Tyr Phe Gln Gln Lys Ile Asp Tyr Leu Lys Asp Lys Val
            430                 435                 440 gca gca aac ttt gtt agg gag agg aga gca atg aag aga gag tat gag      1517
Ala Ala Asn Phe Val Arg Glu Arg Arg Ala Met Lys Arg Glu Tyr Glu
        445                 450                 455 gaa ttc aag gtg aga atc aat gcc tta gtt gcc aaa gcc cag aaa gtt      1565
Glu Phe Lys Val Arg Ile Asn Ala Leu Val Ala Lys Ala Gln Lys Val
    460                 465                 470 cct gaa gaa gga tgg aca atg caa gat gga acc ccc tgg cct gga aac      1613
Pro Glu Glu Gly Trp Thr Met Gln Asp Gly Thr Pro Trp Pro Gly Asn
475                 480                 485                 490 aat gtt cgt gat cat cct gga atg att cag gtc ttc ctt ggc caa agc      1661
Asn Val Arg Asp His Pro Gly Met Ile Gln Val Phe Leu Gly Gln Ser
                495                 500                 505 gga ggc ctt gac tgt gag gga aat gaa ctg cca cga ttg gtt tat gtt      1709
Gly Gly Leu Asp Cys Glu Gly Asn Glu Leu Pro Arg Leu Val Tyr Val
            510                 515                 520 tct aga gag aaa cga cca ggc tat aac cat cat aag aaa gct ggt gct      1757
Ser Arg Glu Lys Arg Pro Gly Tyr Asn His His Lys Lys Ala Gly Ala
        525                 530                 535 atg aat gca ttg gtc cga gtc tct gct gta cta aca aat gct cca tat      1805
Met Asn Ala Leu Val Arg Val Ser Ala Val Leu Thr Asn Ala Pro Tyr
    540                 545                 550 ttg tta aac ttg gat tgt gat cac tac atc aac aac agc aag gct ata      1853
Leu Leu Asn Leu Asp Cys Asp His Tyr Ile Asn Asn Ser Lys Ala Ile
555                 560                 565                 570 aag gaa gca atg tgt ttt atg atg gac cct tta cta gga aag aag gtt      1901
Lys Glu Ala Met Cys Phe Met Met Asp Pro Leu Leu Gly Lys Lys Val
                575                 580                 585 tgc tat gta cag ttc cct caa aga ttt gat ggg att gat cgc cat gac      1949
Cys Tyr Val Gln Phe Pro Gln Arg Phe Asp Gly Ile Asp Arg His Asp
            590                 595                 600 cga tat gct aac cgg aat gtt gtc ttt ttt gat atc aac atg aaa ggt      1997
Arg Tyr Ala Asn Arg Asn Val Val Phe Phe Asp Ile Asn Met Lys Gly
        605                 610                 615 ttg gat ggt att cag ggt cca att tat gtt ggt act gga tgt gta ttt      2045
Leu Asp Gly Ile Gln Gly Pro Ile Tyr Val Gly Thr Gly Cys Val Phe
    620                 625                 630 aga agg cag gca tta tat ggt tat gat gcc ccc aaa aca aag aag cca      2093
Arg Arg Gln Ala Leu Tyr Gly Tyr Asp Ala Pro Lys Thr Lys Lys Pro
635                 640                 645                 650 cca tca agg act tgc aac tgc tgg ccc aag tgg tgc ttt tgc tgt tgc      2141
Pro Ser Arg Thr Cys Asn Cys Trp Pro Lys Trp Cys Phe Cys Cys Cys
                655                 660                 665 tgc ttt ggc aat agg aag caa aag aag act acc aaa ccc aaa aca gag      2189
Cys Phe Gly Asn Arg Lys Gln Lys Lys Thr Thr Lys Pro Lys Thr Glu
            670                 675                 680
```

```
aag aaa aag tta tta ttt ttc aag aaa gaa gag aac caa tcc cct gca      2237
Lys Lys Lys Leu Leu Phe Phe Lys Lys Glu Glu Asn Gln Ser Pro Ala
        685                 690                 695 tat gct ctt ggt gaa att gac gaa gct gct cca gga gct gag aat gaa      2285
Tyr Ala Leu Gly Glu Ile Asp Glu Ala Ala Pro Gly Ala Glu Asn Glu
    700                 705                 710 aag gcc ggt att gta aat caa caa aaa tta gaa aag aaa ttt ggc caa      2333
Lys Ala Gly Ile Val Asn Gln Gln Lys Leu Glu Lys Lys Phe Gly Gln
715                 720                 725                 730 tct tct gtt ttt gtt aca tcc aca ctt ctc gag aat ggt gga acc ttg      2381
Ser Ser Val Phe Val Thr Ser Thr Leu Leu Glu Asn Gly Gly Thr Leu
                735                 740                 745 aag agt gca agt cct gct tct ctt ttg aaa gaa gct ata cat gtc att      2429
Lys Ser Ala Ser Pro Ala Ser Leu Leu Lys Glu Ala Ile His Val Ile
        750                 755                 760 agt tgt ggt tat gaa gac aag aca gac tgg gga aaa gag att ggc tgg      2477
Ser Cys Gly Tyr Glu Asp Lys Thr Asp Trp Gly Lys Glu Ile Gly Trp
    765                 770                 775 atc tat gga tca gtt aca gaa gat att cta act ggt ttc aag atg cat      2525
Ile Tyr Gly Ser Val Thr Glu Asp Ile Leu Thr Gly Phe Lys Met His
780                 785                 790 tgt cat ggt tgg cgg tca att tac tgc ata cct aaa cgg gtt gca ttc      2573
Cys His Gly Trp Arg Ser Ile Tyr Cys Ile Pro Lys Arg Val Ala Phe
795                 800                 805                 810 aaa ggt tct gca cct ctg aat ctt tca gat cgt ctt cac cag gtg ctt      2621
Lys Gly Ser Ala Pro Leu Asn Leu Ser Asp Arg Leu His Gln Val Leu
                815                 820                 825 cgg tgg gct ctt ggg tct att gag atc ttc ttc agc aat cat tgc cct      2669
Arg Trp Ala Leu Gly Ser Ile Glu Ile Phe Phe Ser Asn His Cys Pro
        830                 835                 840 ctt tgg tat ggg tat ggt ggc gtg ctg aaa ttt ttg gaa aga ttt tcc      2717
Leu Trp Tyr Gly Tyr Gly Gly Val Leu Lys Phe Leu Glu Arg Phe Ser
    845                 850                 855 tac atc aac tcc atc gtg tat cct tgg aca tct att ccc ctc ttg gct      2765
Tyr Ile Asn Ser Ile Val Tyr Pro Trp Thr Ser Ile Pro Leu Leu Ala
860                 865                 870 tac tgt aca ttg cct gcc atc tgt tta ttg aca ggg aaa ttt atc act      2813
Tyr Cys Thr Leu Pro Ala Ile Cys Leu Leu Thr Gly Lys Phe Ile Thr
875                 880                 885                 890 cca gag ctg aat aat gtt gcc agc ctg tgg ttc atg tca ctt ttt atc      2861
Pro Glu Leu Asn Asn Val Ala Ser Leu Trp Phe Met Ser Leu Phe Ile
                895                 900                 905 tgc att ttt gct acg agc atc cta gaa atg aga tgg agt ggt gtt gga      2909
Cys Ile Phe Ala Thr Ser Ile Leu Glu Met Arg Trp Ser Gly Val Gly
        910                 915                 920 att gat gac tgg tgg agg aat gag cag ttc tgg gtc att gga ggt gtg      2957
Ile Asp Asp Trp Trp Arg Asn Glu Gln Phe Trp Val Ile Gly Gly Val
    925                 930                 935 tcc tca cac ctc ttt gct gtg ttc cag gga ctt ctc aag gtc ata gct      3005
Ser Ser His Leu Phe Ala Val Phe Gln Gly Leu Leu Lys Val Ile Ala
940                 945                 950 ggt gtt gat aca agc ttc acc gtg aca tca aag gga gat gat gag      3053
Gly Val Asp Thr Ser Phe Thr Val Thr Ser Lys Gly Gly Asp Asp Glu
955                 960                 965                 970 gag ttc tca gag cta tat aca ttc aaa tgg act acc tta ttg ata cct      3101
Glu Phe Ser Glu Leu Tyr Thr Phe Lys Trp Thr Thr Leu Leu Ile Pro
                975                 980                 985 cct acc acc ttg ctt cta ttg aac ttc att ggt gtg gtc gct ggc gtt      3149
Pro Thr Thr Leu Leu Leu Leu Asn Phe Ile Gly Val Val Ala Gly Val
```

```
                990             995             1000
tca aat gcg atc aat aac gga tat gag tca tgg ggc ccc ctc ttt ggg    3197
Ser Asn Ala Ile Asn Asn Gly Tyr Glu Ser Trp Gly Pro Leu Phe Gly
            1005                1010                1015 aag cta ttc ttt gca ttt tgg gtg att gtc cat ctt tat ccc ttt ctc    3245
Lys Leu Phe Phe Ala Phe Trp Val Ile Val His Leu Tyr Pro Phe Leu
    1020                1025                1030 aaa ggt ttg gtt gga agg caa aac agg aca cca acg att gtc atc gtc    3293
Lys Gly Leu Val Gly Arg Gln Asn Arg Thr Pro Thr Ile Val Ile Val
1035                1040                1045                1050 tgg tcc att ctg ctg gct tca atc ttc tcg ctc ctt tgg gtt cgg att    3341
Trp Ser Ile Leu Leu Ala Ser Ile Phe Ser Leu Leu Trp Val Arg Ile
                1055                1060                1065 gat cct ttc ctt gcg aag gat gat ggt ccg ctt ctt gag gag tgt ggt    3389
Asp Pro Phe Leu Ala Lys Asp Asp Gly Pro Leu Leu Glu Glu Cys Gly
            1070                1075                1080 ttg gat tgc aac taggatgtca gtgcatcagc tcccccaatc tgcatatgct        3441
Leu Asp Cys Asn
            1085 tgaagtatat tttctggtgt ttgtccccat attcagtgtc tgtagataag agacatgaaa  3501 tgtcccaagt ttcttttgat ccatggtgaa cctacttaat atctgagaga tatactgggg  3561 gaaaatggag gctgcggcaa tccttgtgca gttgggccgt ggaatacagc atatgcaagt  3621 gtttgattgt gcagcattct ttattacttg gtcgcaatat agatgggctg agccgaacag  3681 caaggtattt tgattctgca ctgctcccgt gtacaaactt ggttctcaat aaggcaggca  3741 ggaatgcatc tgccagtgga acagagcaac ctgcacatta tttatgtatg cctgttcatt  3801 ggagggcttg ttcattacat gttcgtctat actagaaaaa acagaatatt agcattaatc  3861 tatagttaat taaagtatgt aaatgcgcct gttttttgtt gtgtactgta atcatctgag  3921 ttggttttgt gaaaaaaaaa aaaaaaaaaa aaaaaaaaa aaaaaaaa                3969

<210> SEQ ID NO 18
<211> LENGTH: 1086
<212> TYPE: PRT
<213> ORGANISM: Zea mays

<400> SEQUENCE: 18

Met Glu Ala Ser Ala Gly Leu Val Ala Gly Ser His Asn Arg Asn Glu
1               5                   10                  15

Leu Val Val Ile Arg Arg Asp Gly Asp Pro Gly Pro Lys Pro Pro Arg
            20                  25                  30

Glu Gln Asn Gly Gln Val Cys Gln Ile Cys Gly Asp Asp Val Gly Leu
        35                  40                  45

Ala Pro Gly Gly Asp Pro Phe Val Ala Cys Asn Glu Cys Ala Phe Pro
    50                  55                  60

Val Cys Arg Asp Cys Tyr Glu Tyr Glu Arg Arg Glu Gly Thr Gln Asn
65                  70                  75                  80

Cys Pro Gln Cys Lys Thr Arg Tyr Lys Arg Leu Lys Gly Cys Gln Arg
                85                  90                  95

Val Thr Gly Asp Glu Glu Glu Asp Gly Val Asp Asp Leu Asp Asn Glu
            100                 105                 110

Phe Asn Trp Asp Gly His Asp Ser Gln Ser Val Ala Glu Ser Met Leu
        115                 120                 125

Tyr Gly His Met Ser Tyr Gly Arg Gly Gly Asp Pro Asn Gly Ala Pro
    130                 135                 140
```

```
Gln Ala Phe Gln Leu Asn Pro Asn Val Pro Leu Leu Thr Asn Gly Gln
145                 150                 155                 160

Met Val Asp Asp Ile Pro Pro Glu Gln His Ala Leu Val Pro Ser Phe
                165                 170                 175

Met Gly Gly Gly Lys Arg Ile His Pro Leu Pro Tyr Ala Asp Pro
            180                 185                 190

Ser Leu Pro Val Gln Pro Arg Ser Met Asp Pro Ser Lys Asp Leu Ala
        195                 200                 205

Ala Tyr Gly Tyr Gly Ser Val Ala Trp Lys Glu Arg Met Glu Asn Trp
    210                 215                 220

Lys Gln Arg Gln Glu Arg Met His Gln Thr Gly Asn Asp Gly Gly Gly
225                 230                 235                 240

Asp Asp Gly Asp Asp Ala Asp Leu Pro Leu Met Asp Glu Ala Arg Gln
            245                 250                 255

Gln Leu Ser Arg Lys Ile Pro Leu Pro Ser Ser Gln Ile Asn Pro Tyr
        260                 265                 270

Arg Met Ile Ile Ile Ile Arg Leu Val Val Leu Gly Phe Phe Phe His
    275                 280                 285

Tyr Arg Val Met His Pro Val Asn Asp Ala Phe Ala Leu Trp Leu Ile
290                 295                 300

Ser Val Ile Cys Glu Ile Trp Phe Ala Met Ser Trp Ile Leu Asp Gln
305                 310                 315                 320

Phe Pro Lys Trp Phe Pro Ile Glu Arg Glu Thr Tyr Leu Asp Arg Leu
                325                 330                 335

Ser Leu Arg Phe Asp Lys Glu Gly Gln Pro Ser Gln Leu Ala Pro Ile
            340                 345                 350

Asp Phe Phe Val Ser Thr Val Asp Pro Leu Lys Glu Pro Pro Leu Val
        355                 360                 365

Thr Thr Asn Thr Val Leu Ser Ile Leu Ser Val Asp Tyr Pro Val Asp
    370                 375                 380

Lys Val Ser Cys Tyr Val Ser Asp Asp Gly Ala Ala Met Leu Thr Phe
385                 390                 395                 400

Glu Ala Leu Ser Glu Thr Ser Glu Phe Ala Lys Lys Trp Val Pro Phe
                405                 410                 415

Cys Lys Arg Tyr Asn Ile Glu Pro Arg Ala Pro Glu Trp Tyr Phe Gln
            420                 425                 430

Gln Lys Ile Asp Tyr Leu Lys Asp Lys Val Ala Ala Asn Phe Val Arg
        435                 440                 445

Glu Arg Arg Ala Met Lys Arg Glu Tyr Glu Glu Phe Lys Val Arg Ile
    450                 455                 460

Asn Ala Leu Val Ala Lys Ala Gln Lys Val Pro Glu Glu Gly Trp Thr
465                 470                 475                 480

Met Gln Asp Gly Thr Pro Trp Pro Gly Asn Asn Val Arg Asp His Pro
                485                 490                 495

Gly Met Ile Gln Val Phe Leu Gly Gln Ser Gly Gly Leu Asp Cys Glu
            500                 505                 510

Gly Asn Glu Leu Pro Arg Leu Val Tyr Val Ser Arg Glu Lys Arg Pro
        515                 520                 525

Gly Tyr Asn His His Lys Lys Ala Gly Ala Met Asn Ala Leu Val Arg
    530                 535                 540

Val Ser Ala Val Leu Thr Asn Ala Pro Tyr Leu Leu Asn Leu Asp Cys
545                 550                 555                 560

Asp His Tyr Ile Asn Asn Ser Lys Ala Ile Lys Glu Ala Met Cys Phe
```

```
                565                 570                 575
Met Met Asp Pro Leu Gly Lys Lys Val Cys Tyr Val Gln Phe Pro
            580                 585                 590

Gln Arg Phe Asp Gly Ile Asp Arg His Asp Arg Tyr Ala Asn Arg Asn
        595                 600                 605

Val Val Phe Phe Asp Ile Asn Met Lys Gly Leu Asp Gly Ile Gln Gly
    610                 615                 620

Pro Ile Tyr Val Gly Thr Gly Cys Val Phe Arg Arg Gln Ala Leu Tyr
625                 630                 635                 640

Gly Tyr Asp Ala Pro Lys Thr Lys Lys Pro Pro Ser Arg Thr Cys Asn
                645                 650                 655

Cys Trp Pro Lys Trp Cys Phe Cys Cys Cys Phe Gly Asn Arg Lys
            660                 665                 670

Gln Lys Lys Thr Thr Lys Pro Lys Thr Glu Lys Lys Lys Leu Leu Phe
        675                 680                 685

Phe Lys Lys Glu Glu Asn Gln Ser Pro Ala Tyr Ala Leu Gly Glu Ile
    690                 695                 700

Asp Glu Ala Ala Pro Gly Ala Glu Asn Glu Lys Ala Gly Ile Val Asn
705                 710                 715                 720

Gln Gln Lys Leu Glu Lys Lys Phe Gly Gln Ser Ser Val Phe Val Thr
                725                 730                 735

Ser Thr Leu Leu Glu Asn Gly Gly Thr Leu Lys Ser Ala Ser Pro Ala
            740                 745                 750

Ser Leu Leu Lys Glu Ala Ile His Val Ile Ser Cys Gly Tyr Glu Asp
        755                 760                 765

Lys Thr Asp Trp Gly Lys Glu Ile Gly Trp Ile Tyr Gly Ser Val Thr
    770                 775                 780

Glu Asp Ile Leu Thr Gly Phe Lys Met His Cys His Gly Trp Arg Ser
785                 790                 795                 800

Ile Tyr Cys Ile Pro Lys Arg Val Ala Phe Lys Gly Ser Ala Pro Leu
                805                 810                 815

Asn Leu Ser Asp Arg Leu His Gln Val Leu Arg Trp Ala Leu Gly Ser
            820                 825                 830

Ile Glu Ile Phe Phe Ser Asn His Cys Pro Leu Trp Tyr Gly Tyr Gly
        835                 840                 845

Gly Gly Leu Lys Phe Leu Glu Arg Phe Ser Tyr Ile Asn Ser Ile Val
    850                 855                 860

Tyr Pro Trp Thr Ser Ile Pro Leu Leu Ala Tyr Cys Thr Leu Pro Ala
865                 870                 875                 880

Ile Cys Leu Leu Thr Gly Lys Phe Ile Thr Pro Glu Leu Asn Asn Val
                885                 890                 895

Ala Ser Leu Trp Phe Met Ser Leu Phe Ile Cys Ile Phe Ala Thr Ser
            900                 905                 910

Ile Leu Glu Met Arg Trp Ser Gly Val Gly Ile Asp Trp Trp Arg
        915                 920                 925

Asn Glu Gln Phe Trp Val Ile Gly Gly Val Ser Ser His Leu Phe Ala
    930                 935                 940

Val Phe Gln Gly Leu Leu Lys Val Ile Ala Gly Val Asp Thr Ser Phe
945                 950                 955                 960

Thr Val Thr Ser Lys Gly Gly Asp Asp Glu Glu Phe Ser Glu Leu Tyr
                965                 970                 975

Thr Phe Lys Trp Thr Thr Leu Leu Ile Pro Pro Thr Thr Leu Leu Leu
            980                 985                 990
```

```
Leu Asn Phe Ile Gly Val Val Ala Gly Val Ser Asn Ala Ile Asn Asn
        995                 1000                1005

Gly Tyr Glu Ser Trp Gly Pro Leu Phe Gly Lys Leu Phe Ala Phe
    1010                1015                1020

Trp Val Ile Val His Leu Tyr Pro Phe Leu Lys Gly Leu Val Gly Arg
1025                1030                1035                1040

Gln Asn Arg Thr Pro Thr Ile Val Ile Val Trp Ser Ile Leu Ala
        1045                1050                1055

Ser Ile Phe Ser Leu Leu Trp Val Arg Ile Asp Pro Phe Leu Ala Lys
    1060                1065                1070

Asp Asp Gly Pro Leu Leu Glu Glu Cys Gly Leu Asp Cys Asn
        1075                1080                1085

<210> SEQ ID NO 19
<211> LENGTH: 25
<212> TYPE: DNA
<213> ORGANISM: Zea mays

<400> SEQUENCE: 19
atggaggcga gcgccgggct ggtgg                                            25

<210> SEQ ID NO 20
<211> LENGTH: 25
<212> TYPE: DNA
<213> ORGANISM: Zea mays

<400> SEQUENCE: 20
ctagttgcaa tccaaaccac actcc                                            25

<210> SEQ ID NO 21
<211> LENGTH: 3725
<212> TYPE: DNA
<213> ORGANISM: Zea mays
<220> FEATURE:
<221> NAME/KEY: CDS
<222> LOCATION: (179)...(3400)

<400> SEQUENCE: 21
gcagcagcag caccaccact gcgcggcatt gcagcgagca agcgggaggg atctggggca      60
tggtggcggt cgctgccgct gccgctcgga tctagagggc gcacgggct gattgccctc      120 cgccggcctc gtcggtgtcg gtggagtgtg aatcggtgtg tgtaggagga gcgcggag       178 atg gcg gcc aac aag ggg atg gtg gca ggc tct cac aac cgc aac gag       226
Met Ala Ala Asn Lys Gly Met Val Ala Gly Ser His Asn Arg Asn Glu
1               5                   10                  15 ttc gtc atg atc cgc cac gac ggc gac gcg cct gtc ccg gct aag ccc       274
Phe Val Met Ile Arg His Asp Gly Asp Ala Pro Val Pro Ala Lys Pro
            20                  25                  30 acg aag agt gcg aat ggg cag gtc tgc cag att tgt ggc gac act gtt       322
Thr Lys Ser Ala Asn Gly Gln Val Cys Gln Ile Cys Gly Asp Thr Val
        35                  40                  45 ggc gtt tca gcc act ggt gat gtc ttt gtt gcc tgc aat gag tgt gcc       370
Gly Val Ser Ala Thr Gly Asp Val Phe Val Ala Cys Asn Glu Cys Ala
    50                  55                  60 ttc cct gtc tgc cgc cct tgc tat gag tac gag cgc aag gaa ggg aac       418
Phe Pro Val Cys Arg Pro Cys Tyr Glu Tyr Glu Arg Lys Glu Gly Asn
65                  70                  75                  80 caa tgc tgc cct cag tgc aag act aga tac aag aga cag aaa ggt agc       466
Gln Cys Cys Pro Gln Cys Lys Thr Arg Tyr Lys Arg Gln Lys Gly Ser
                85                  90                  95
```

```
cct cga gtt cat ggt gat gat gag gag gaa gat gtt gat gac ctg gac      514
Pro Arg Val His Gly Asp Asp Glu Glu Glu Asp Val Asp Asp Leu Asp
        100                 105                 110 aat gaa ttc aac tat aag caa ggc aat ggg aag ggc cca gag tgg cag      562
Asn Glu Phe Asn Tyr Lys Gln Gly Asn Gly Lys Gly Pro Glu Trp Gln
            115                 120                 125 ctt caa gga gat gac gct gat ctg tct tca tct gct cgc cat gac cca      610
Leu Gln Gly Asp Asp Ala Asp Leu Ser Ser Ser Ala Arg His Asp Pro
130                 135                 140 cac cat cgg att cca cgc ctt aca agt gga caa cag ata tct gga gag      658
His His Arg Ile Pro Arg Leu Thr Ser Gly Gln Gln Ile Ser Gly Glu
145                 150                 155                 160 atc cct gat gca tcc cct gac cgt cat tct atc cgc agt cca aca tcg      706
Ile Pro Asp Ala Ser Pro Asp Arg His Ser Ile Arg Ser Pro Thr Ser
                165                 170                 175 agc tat gtt gat cca agc gtt cca gtt cct gtg agg att gtg gac ccc      754
Ser Tyr Val Asp Pro Ser Val Pro Val Pro Val Arg Ile Val Asp Pro
            180                 185                 190 tcg aag gac ttg aat tcc tat ggg ctt aat agt gtt gac tgg aag gaa      802
Ser Lys Asp Leu Asn Ser Tyr Gly Leu Asn Ser Val Asp Trp Lys Glu
        195                 200                 205 aga gtt gag agc tgg agg gtt aaa cag gac aaa aat atg ttg caa gtg      850
Arg Val Glu Ser Trp Arg Val Lys Gln Asp Lys Asn Met Leu Gln Val
    210                 215                 220 act aat aaa tat cca gag gct aga gga gac atg gag ggg act ggc tca      898
Thr Asn Lys Tyr Pro Glu Ala Arg Gly Asp Met Glu Gly Thr Gly Ser
225                 230                 235                 240 aat gga gaa gat atg caa atg gtt gat gat gca cgc cta cct ttg agc      946
Asn Gly Glu Asp Met Gln Met Val Asp Asp Ala Arg Leu Pro Leu Ser
                245                 250                 255 cgc att gtg cca att tcc tca aac cag ctc aac ctt tac cgg ata gta      994
Arg Ile Val Pro Ile Ser Ser Asn Gln Leu Asn Leu Tyr Arg Ile Val
            260                 265                 270 atc att ctc cgt ctt atc atc ctg tgc ttc ttc ttc caa tat cgt atc     1042
Ile Ile Leu Arg Leu Ile Ile Leu Cys Phe Phe Phe Gln Tyr Arg Ile
        275                 280                 285 agt cat cca gtg cgt aat gct tat gga ttg tgg cta gta tct gtt atc     1090
Ser His Pro Val Arg Asn Ala Tyr Gly Leu Trp Leu Val Ser Val Ile
    290                 295                 300 tgt gag gtc tgg ttt gcc ttg tcc tgg ctt cta gat cag ttc cca aaa     1138
Cys Glu Val Trp Phe Ala Leu Ser Trp Leu Leu Asp Gln Phe Pro Lys
305                 310                 315                 320 tgg tat cca atc aac cgt gag aca tat ctc gac agg ctt gca ttg agg     1186
Trp Tyr Pro Ile Asn Arg Glu Thr Tyr Leu Asp Arg Leu Ala Leu Arg
                325                 330                 335 tat gat aga gag gga gag cca tca cag ctg gct ccc att gat gtc ttt     1234
Tyr Asp Arg Glu Gly Glu Pro Ser Gln Leu Ala Pro Ile Asp Val Phe
            340                 345                 350 gtc agt aca gtg gat cca ttg aag gaa cct cca ctg atc aca gcc aac     1282
Val Ser Thr Val Asp Pro Leu Lys Glu Pro Pro Leu Ile Thr Ala Asn
        355                 360                 365 act gtt ttg tcc att ctt gct gtg gat tac cct gtt gac aaa gtg tca     1330
Thr Val Leu Ser Ile Leu Ala Val Asp Tyr Pro Val Asp Lys Val Ser
    370                 375                 380 tgc tat gtt tct gat gat ggc tca gct atg ctg act ttt gag tct ctc     1378
Cys Tyr Val Ser Asp Asp Gly Ser Ala Met Leu Thr Phe Glu Ser Leu
385                 390                 395                 400 tct gaa act gcc gaa ttt gct aga aag tgg gtt ccc ttt tgt aag aag     1426
Ser Glu Thr Ala Glu Phe Ala Arg Lys Trp Val Pro Phe Cys Lys Lys
```

-continued

```
                    405                 410                 415
cac aat att gaa cca aga gct cca gaa ttt tac ttt gct caa aaa ata     1474
His Asn Ile Glu Pro Arg Ala Pro Glu Phe Tyr Phe Ala Gln Lys Ile
            420                 425                 430 gat tac ctg aag gac aaa att caa cct tca ttt gtt aag gaa aga cga     1522
Asp Tyr Leu Lys Asp Lys Ile Gln Pro Ser Phe Val Lys Glu Arg Arg
                435                 440                 445 gca atg aag aga gag tat gaa gaa ttc aaa ata aga atc aat gcc ctt     1570
Ala Met Lys Arg Glu Tyr Glu Glu Phe Lys Ile Arg Ile Asn Ala Leu
    450                 455                 460 gtt gcc aaa gca cag aaa gtg cct gaa gag ggg tgg acc atg gct gat     1618
Val Ala Lys Ala Gln Lys Val Pro Glu Glu Gly Trp Thr Met Ala Asp
465                 470                 475                 480 gga act gct tgg cct ggg aat aac cct agg gac cat cct ggc atg att     1666
Gly Thr Ala Trp Pro Gly Asn Asn Pro Arg Asp His Pro Gly Met Ile
                485                 490                 495 cag gtg ttc ttg ggg cac agt ggt ggg ctt gac act gat gga aat gaa     1714
Gln Val Phe Leu Gly His Ser Gly Gly Leu Asp Thr Asp Gly Asn Glu
            500                 505                 510 tta cca cgt ctt gtc tat gtc tct cgt gaa aag aga cca ggc ttt cag     1762
Leu Pro Arg Leu Val Tyr Val Ser Arg Glu Lys Arg Pro Gly Phe Gln
                515                 520                 525 cat cac aag aag gct ggt gca atg aat gca ctg att cgt gta tct gct     1810
His His Lys Lys Ala Gly Ala Met Asn Ala Leu Ile Arg Val Ser Ala
    530                 535                 540 gtg ctg aca aat ggt gcc tat ctt ctc aat gtg gat tgt gac cat tac     1858
Val Leu Thr Asn Gly Ala Tyr Leu Leu Asn Val Asp Cys Asp His Tyr
545                 550                 555                 560 ttc aat agc agc aaa gct ctt aga gaa gca atg tgc ttc atg atg gat     1906
Phe Asn Ser Ser Lys Ala Leu Arg Glu Ala Met Cys Phe Met Met Asp
                565                 570                 575 cca gct cta gga agg aaa act tgt tat gta caa ttt cca caa aga ttt     1954
Pro Ala Leu Gly Arg Lys Thr Cys Tyr Val Gln Phe Pro Gln Arg Phe
            580                 585                 590 gat ggc att gac ttg cac gat cga tat gct aat agg aac ata gtc ttc     2002
Asp Gly Ile Asp Leu His Asp Arg Tyr Ala Asn Arg Asn Ile Val Phe
                595                 600                 605 ttt gat atc aac atg aaa ggt cta gat ggc att cag ggt cca gtc tat     2050
Phe Asp Ile Asn Met Lys Gly Leu Asp Gly Ile Gln Gly Pro Val Tyr
    610                 615                 620 gtg gga aca gga tgc tgt ttc aat agg cag gct ttg tat gga tat gat     2098
Val Gly Thr Gly Cys Cys Phe Asn Arg Gln Ala Leu Tyr Gly Tyr Asp
625                 630                 635                 640 cct gtt ttg act gaa gct gat ctg gaa cct aac att gtt gtt aag agc     2146
Pro Val Leu Thr Glu Ala Asp Leu Glu Pro Asn Ile Val Val Lys Ser
                645                 650                 655 tgc tgt ggt aga agg aag aga aag aac aag agt tat atg gat agt caa     2194
Cys Cys Gly Arg Arg Lys Arg Lys Asn Lys Ser Tyr Met Asp Ser Gln
            660                 665                 670 agc cgt att atg aag aga aca gaa tct tca gct ccc atc ttt aac atg     2242
Ser Arg Ile Met Lys Arg Thr Glu Ser Ser Ala Pro Ile Phe Asn Met
                675                 680                 685 gaa gac atc gag gag ggt att gaa ggt tat gag gat gaa agg tca gtg     2290
Glu Asp Ile Glu Glu Gly Ile Glu Gly Tyr Glu Asp Glu Arg Ser Val
    690                 695                 700 ctt atg tcc cag agg aaa ttg gag aaa cgc ttt ggt cag tct cca atc     2338
Leu Met Ser Gln Arg Lys Leu Glu Lys Arg Phe Gly Gln Ser Pro Ile
705                 710                 715                 720 ttc att gca tcc acc ttt atg act caa ggt ggc ata cca cct tca aca     2386
Phe Ile Ala Ser Thr Phe Met Thr Gln Gly Gly Ile Pro Pro Ser Thr
```

-continued

| | | | | | | | | | | | | |
|---|---|---|---|---|---|---|---|---|---|---|---|---|
| Phe | Ile | Ala | Ser | Thr | Phe | Met | Thr | Gln | Gly | Gly | Ile | Pro | Pro | Ser | Thr |
| | | | | 725 | | | | 730 | | | | 735 | |

```
aac cca gct tct cta ctg aag gaa gct atc cat gtt atc agc tgt ggg    2434
Asn Pro Ala Ser Leu Leu Lys Glu Ala Ile His Val Ile Ser Cys Gly
        740                 745                 750 tac gag gac aaa act gaa tgg gga aaa gag att ggc tgg atc tat ggt    2482
Tyr Glu Asp Lys Thr Glu Trp Gly Lys Glu Ile Gly Trp Ile Tyr Gly
        755                 760                 765 tca gtt aca gag gat att ctg act ggg ttt aaa atg cat gca aga ggc    2530
Ser Val Thr Glu Asp Ile Leu Thr Gly Phe Lys Met His Ala Arg Gly
        770                 775                 780 tgg caa tca atc tac tgc atg cca cca cga cct tgt ttc aag ggt tct    2578
Trp Gln Ser Ile Tyr Cys Met Pro Pro Arg Pro Cys Phe Lys Gly Ser
785                 790                 795                 800 gca cca atc aat ctt tct gat cgt ctt aat cag gtg ctc cgt tgg gct    2626
Ala Pro Ile Asn Leu Ser Asp Arg Leu Asn Gln Val Leu Arg Trp Ala
                805                 810                 815 ctt ggg tca gtg gaa att ctg ctt agc aga cat tgt cct ata tgg tat    2674
Leu Gly Ser Val Glu Ile Leu Leu Ser Arg His Cys Pro Ile Trp Tyr
            820                 825                 830 ggc tac aat ggg cga ttg aag ctt ttg gag agg ctg gct tac att aac    2722
Gly Tyr Asn Gly Arg Leu Lys Leu Leu Glu Arg Leu Ala Tyr Ile Asn
            835                 840                 845 acc att gtt tat cca atc aca tct gtt ccg ctt atc gcc tat tgt gtg    2770
Thr Ile Val Tyr Pro Ile Thr Ser Val Pro Leu Ile Ala Tyr Cys Val
        850                 855                 860 ctt cct gct atc tgt ctt ctt acc aat aaa ttt atc att cct gag att    2818
Leu Pro Ala Ile Cys Leu Leu Thr Asn Lys Phe Ile Ile Pro Glu Ile
865                 870                 875                 880 agt aat tat gct gga atg ttc ttc att ctt ctt ttt gcc tcc att ttc    2866
Ser Asn Tyr Ala Gly Met Phe Phe Ile Leu Leu Phe Ala Ser Ile Phe
                885                 890                 895 gca act ggt ata ttg gag ctc aga tgg agt ggt gtt ggc att gaa gat    2914
Ala Thr Gly Ile Leu Glu Leu Arg Trp Ser Gly Val Gly Ile Glu Asp
            900                 905                 910 tgg tgg aga aat gag cag ttt tgg gtt att ggt ggc acc tct gcc cat    2962
Trp Trp Arg Asn Glu Gln Phe Trp Val Ile Gly Gly Thr Ser Ala His
            915                 920                 925 ctc ttc gcg gtg ttc cag ggt ctg ctg aaa gtg ttg gct ggg att gat    3010
Leu Phe Ala Val Phe Gln Gly Leu Leu Lys Val Leu Ala Gly Ile Asp
        930                 935                 940 acc aac ttc aca gtt acc tca aag gca tct gat gag gat ggc gac ttt    3058
Thr Asn Phe Thr Val Thr Ser Lys Ala Ser Asp Glu Asp Gly Asp Phe
945                 950                 955                 960 gct gag cta tat gtg ttc aag tgg acc agt ttg ctc atc cct ccg acc    3106
Ala Glu Leu Tyr Val Phe Lys Trp Thr Ser Leu Leu Ile Pro Pro Thr
                965                 970                 975 act gtt ctt gtc att aac ctg gtc gga atg gtg gca gga att tcg tat    3154
Thr Val Leu Val Ile Asn Leu Val Gly Met Val Ala Gly Ile Ser Tyr
            980                 985                 990 gcc att aac agc ggc tac caa tcc tgg ggt ccg ctc ttt gga aag ctg    3202
Ala Ile Asn Ser Gly Tyr Gln Ser Trp Gly Pro Leu Phe Gly Lys Leu
            995                 1000                1005 ttc ttc tcg atc tgg gtg atc ctc cat ctc tac ccc ttc ctc aag ggt    3250
Phe Phe Ser Ile Trp Val Ile Leu His Leu Tyr Pro Phe Leu Lys Gly
        1010                1015                1020 ctc atg ggc agg cag aac cgc acg cca aca atc gtc atc gtt tgg tcc    3298
Leu Met Gly Arg Gln Asn Arg Thr Pro Thr Ile Val Ile Val Trp Ser
1025                1030                1035                1040
```

```
atc ctc ctt gcg tct atc ttc tcc ttg ctg tgg gtg aag atc gat cct    3346
Ile Leu Leu Ala Ser Ile Phe Ser Leu Leu Trp Val Lys Ile Asp Pro
                1045                1050                1055 ttc atc tcc ccg aca cag aaa gct gcc gcc ttg ggg caa tgt ggt gtg    3394
Phe Ile Ser Pro Thr Gln Lys Ala Ala Ala Leu Gly Gln Cys Gly Val
                1060                1065                1070 aac tgc tgatccagat tgtgactctt atctgaagag gctcagccaa agatctgccc    3450
Asn Cys cctcgtgtaa ataccctgagg gggctagatg ggaattttt gttgtagatg aggatggatc    3510
tgcatccaag ttatgcctct gtttattagc ttcttcggtg ccggtgctgc tgcagacaat    3570
catggagcct ttctaccttg cttgtagtgc tggccagcag cgtaaattgt gaattctgca    3630 ttttttata cgtggtgttt attgttttag agtaaattat catttgtttg aggtaactat    3690
tcacacgaac tatatggcaa tgctgttatt taaaa                              3725
```

<210> SEQ ID NO 22
<211> LENGTH: 1074
<212> TYPE: PRT
<213> ORGANISM: Zea mays

<400> SEQUENCE: 22

```
Met Ala Ala Asn Lys Gly Met Val Ala Gly Ser His Asn Arg Asn Glu
1               5                   10                  15

Phe Val Met Ile Arg His Asp Gly Asp Ala Pro Val Pro Ala Lys Pro
                20                  25                  30

Thr Lys Ser Ala Asn Gly Gln Val Cys Gln Ile Cys Gly Asp Thr Val
            35                  40                  45

Gly Val Ser Ala Thr Gly Asp Val Phe Val Ala Cys Asn Glu Cys Ala
        50                  55                  60

Phe Pro Val Cys Arg Pro Cys Tyr Glu Tyr Glu Arg Lys Glu Gly Asn
65                  70                  75                  80

Gln Cys Cys Pro Gln Cys Lys Thr Arg Tyr Lys Arg Gln Lys Gly Ser
                85                  90                  95

Pro Arg Val His Gly Asp Asp Glu Glu Glu Asp Val Asp Asp Leu Asp
            100                 105                 110

Asn Glu Phe Asn Tyr Lys Gln Gly Asn Gly Lys Gly Pro Glu Trp Gln
        115                 120                 125

Leu Gln Gly Asp Asp Ala Asp Leu Ser Ser Ser Ala Arg His Asp Pro
    130                 135                 140

His His Arg Ile Pro Arg Leu Thr Ser Gly Gln Gln Ile Ser Gly Glu
145                 150                 155                 160

Ile Pro Asp Ala Ser Pro Asp Arg His Ser Ile Arg Ser Pro Thr Ser
                165                 170                 175

Ser Tyr Val Asp Pro Ser Val Pro Val Pro Val Arg Ile Val Asp Pro
            180                 185                 190

Ser Lys Asp Leu Asn Ser Tyr Gly Leu Asn Ser Val Asp Trp Lys Glu
        195                 200                 205

Arg Val Glu Ser Trp Arg Val Lys Gln Asp Lys Asn Met Leu Gln Val
    210                 215                 220

Thr Asn Lys Tyr Pro Glu Ala Arg Gly Asp Met Glu Gly Thr Gly Ser
225                 230                 235                 240

Asn Gly Glu Asp Met Gln Met Val Asp Asp Ala Arg Leu Pro Leu Ser
                245                 250                 255

Arg Ile Val Pro Ile Ser Ser Asn Gln Leu Asn Leu Tyr Arg Ile Val
            260                 265                 270
```

-continued

```
Ile Ile Leu Arg Leu Ile Ile Leu Cys Phe Phe Phe Gln Tyr Arg Ile
            275                 280                 285

Ser His Pro Val Arg Asn Ala Tyr Gly Leu Trp Leu Val Ser Val Ile
        290                 295                 300

Cys Glu Val Trp Phe Ala Leu Ser Trp Leu Leu Asp Gln Phe Pro Lys
305                 310                 315                 320

Trp Tyr Pro Ile Asn Arg Glu Thr Tyr Leu Asp Arg Leu Ala Leu Arg
                325                 330                 335

Tyr Asp Arg Glu Gly Glu Pro Ser Gln Leu Ala Pro Ile Asp Val Phe
            340                 345                 350

Val Ser Thr Val Asp Pro Leu Lys Glu Pro Leu Ile Thr Ala Asn
        355                 360                 365

Thr Val Leu Ser Ile Leu Ala Val Asp Tyr Pro Val Asp Lys Val Ser
    370                 375                 380

Cys Tyr Val Ser Asp Asp Gly Ser Ala Met Leu Thr Phe Glu Ser Leu
385                 390                 395                 400

Ser Glu Thr Ala Glu Phe Ala Arg Lys Trp Val Pro Phe Cys Lys Lys
                405                 410                 415

His Asn Ile Glu Pro Arg Ala Pro Glu Phe Tyr Phe Ala Gln Lys Ile
            420                 425                 430

Asp Tyr Leu Lys Asp Lys Ile Gln Pro Ser Phe Val Lys Glu Arg Arg
        435                 440                 445

Ala Met Lys Arg Glu Tyr Glu Glu Phe Lys Ile Arg Ile Asn Ala Leu
    450                 455                 460

Val Ala Lys Ala Gln Lys Val Pro Glu Glu Gly Trp Thr Met Ala Asp
465                 470                 475                 480

Gly Thr Ala Trp Pro Gly Asn Asn Pro Arg Asp His Pro Gly Met Ile
                485                 490                 495

Gln Val Phe Leu Gly His Ser Gly Gly Leu Asp Thr Asp Gly Asn Glu
            500                 505                 510

Leu Pro Arg Leu Val Tyr Val Ser Arg Glu Lys Arg Pro Gly Phe Gln
        515                 520                 525

His His Lys Lys Ala Gly Ala Met Asn Ala Leu Ile Arg Val Ser Ala
    530                 535                 540

Val Leu Thr Asn Gly Ala Tyr Leu Leu Asn Val Asp Cys Asp His Tyr
545                 550                 555                 560

Phe Asn Ser Ser Lys Ala Leu Arg Glu Ala Met Cys Phe Met Met Asp
                565                 570                 575

Pro Ala Leu Gly Arg Lys Thr Cys Tyr Val Gln Phe Pro Gln Arg Phe
            580                 585                 590

Asp Gly Ile Asp Leu His Asp Arg Tyr Ala Asn Arg Asn Ile Val Phe
        595                 600                 605

Phe Asp Ile Asn Met Lys Gly Leu Asp Gly Ile Gln Gly Pro Val Tyr
    610                 615                 620

Val Gly Thr Gly Cys Cys Phe Asn Arg Gln Ala Leu Tyr Gly Tyr Asp
625                 630                 635                 640

Pro Val Leu Thr Glu Ala Asp Leu Glu Pro Asn Ile Val Val Lys Ser
                645                 650                 655

Cys Cys Gly Arg Arg Lys Arg Lys Asn Lys Ser Tyr Met Asp Ser Gln
            660                 665                 670

Ser Arg Ile Met Lys Arg Thr Glu Ser Ser Ala Pro Ile Phe Asn Met
        675                 680                 685
```

Glu Asp Ile Glu Glu Gly Ile Glu Gly Tyr Glu Asp Glu Arg Ser Val
    690                 695                 700

Leu Met Ser Gln Arg Lys Leu Glu Lys Arg Phe Gly Gln Ser Pro Ile
705                 710                 715                 720

Phe Ile Ala Ser Thr Phe Met Thr Gln Gly Gly Ile Pro Pro Ser Thr
            725                 730                 735

Asn Pro Ala Ser Leu Leu Lys Glu Ala Ile His Val Ile Ser Cys Gly
            740                 745                 750

Tyr Glu Asp Lys Thr Glu Trp Gly Lys Glu Ile Gly Trp Ile Tyr Gly
        755                 760                 765

Ser Val Thr Glu Asp Ile Leu Thr Gly Phe Lys Met His Ala Arg Gly
770                 775                 780

Trp Gln Ser Ile Tyr Cys Met Pro Pro Arg Pro Cys Phe Lys Gly Ser
785                 790                 795                 800

Ala Pro Ile Asn Leu Ser Asp Arg Leu Asn Gln Val Leu Arg Trp Ala
            805                 810                 815

Leu Gly Ser Val Glu Ile Leu Leu Ser Arg His Cys Pro Ile Trp Tyr
            820                 825                 830

Gly Tyr Asn Gly Arg Leu Lys Leu Leu Glu Arg Leu Ala Tyr Ile Asn
        835                 840                 845

Thr Ile Val Tyr Pro Ile Thr Ser Val Pro Leu Ile Ala Tyr Cys Val
    850                 855                 860

Leu Pro Ala Ile Cys Leu Leu Thr Asn Lys Phe Ile Ile Pro Glu Ile
865                 870                 875                 880

Ser Asn Tyr Ala Gly Met Phe Phe Ile Leu Leu Phe Ala Ser Ile Phe
            885                 890                 895

Ala Thr Gly Ile Leu Glu Leu Arg Trp Ser Gly Val Gly Ile Glu Asp
            900                 905                 910

Trp Trp Arg Asn Glu Gln Phe Trp Val Ile Gly Gly Thr Ser Ala His
        915                 920                 925

Leu Phe Ala Val Phe Gln Gly Leu Leu Lys Val Leu Ala Gly Ile Asp
    930                 935                 940

Thr Asn Phe Thr Val Thr Ser Lys Ala Ser Asp Glu Asp Gly Asp Phe
945                 950                 955                 960

Ala Glu Leu Tyr Val Phe Lys Trp Thr Ser Leu Leu Ile Pro Pro Thr
            965                 970                 975

Thr Val Leu Val Ile Asn Leu Val Gly Met Val Ala Gly Ile Ser Tyr
            980                 985                 990

Ala Ile Asn Ser Gly Tyr Gln Ser Trp Gly Pro Leu Phe Gly Lys Leu
        995                 1000                1005

Phe Phe Ser Ile Trp Val Ile Leu His Leu Tyr Pro Phe Leu Lys Gly
    1010                1015                1020

Leu Met Gly Arg Gln Asn Arg Thr Pro Thr Ile Val Ile Val Trp Ser
1025                1030                1035                1040

Ile Leu Leu Ala Ser Ile Phe Ser Leu Leu Trp Val Lys Ile Asp Pro
            1045                1050                1055

Phe Ile Ser Pro Thr Gln Lys Ala Ala Ala Leu Gly Gln Cys Gly Val
            1060                1065                1070

Asn Cys

<210> SEQ ID NO 23
<211> LENGTH: 25
<212> TYPE: DNA
<213> ORGANISM: Zea mays

-continued

<400> SEQUENCE: 23
atggcggcca acaagggat ggtgg                                    25

<210> SEQ ID NO 24
<211> LENGTH: 25
<212> TYPE: DNA
<213> ORGANISM: Zea mays

<400> SEQUENCE: 24
tcagcagttc acaccacatt gcccc                                   25

<210> SEQ ID NO 25
<211> LENGTH: 3813
<212> TYPE: DNA
<213> ORGANISM: Zea mays
<220> FEATURE:
<221> NAME/KEY: CDS
<222> LOCATION: (215)...(3496)

<400> SEQUENCE: 25

```
ccacagctca tataccaaga gccggagcag cttagcgcag cccagagcgg cgccgcgcca      60
agcacaaccc ccacccgcca cagccgcgtg cgcatgtgag cggtcgccgc ggccgggaga     120
ccagaggagg ggaggactac gtgcatttcg ctgtgccgcc gccgcggggt tcgtgcgcga     180
gcgagatccg gcggggcggg gcgggggcc tgag atg gag gct agc gcg ggg ctg     235
                                     Met Glu Ala Ser Ala Gly Leu
                                       1               5 gtg gcc ggc tcg cat aac cgg aac gag ctg gtg gtg atc cgc cgc gac      283
Val Ala Gly Ser His Asn Arg Asn Glu Leu Val Val Ile Arg Arg Asp
         10                  15                  20 cgc gag tcg gga gcc gcg ggc ggc ggc gcg gcg cgc cgg gcg gag gcg      331
Arg Glu Ser Gly Ala Ala Gly Gly Gly Ala Ala Arg Arg Ala Glu Ala
     25                  30                  35 ccg tgc cag ata tgc ggc gac gag gtc ggg gtg ggc ttc gac ggg gag      379
Pro Cys Gln Ile Cys Gly Asp Glu Val Gly Val Gly Phe Asp Gly Glu
 40                  45                  50                  55 ccc ttc gtg gcg tgc aac gag tgc gcc ttc ccc gtc tgc cgc gcc tgc      427
Pro Phe Val Ala Cys Asn Glu Cys Ala Phe Pro Val Cys Arg Ala Cys
                 60                  65                  70 tac gag tac gag cgc cgc gag ggc tcg caa gcg tgc ccg cag tgc agg      475
Tyr Glu Tyr Glu Arg Arg Glu Gly Ser Gln Ala Cys Pro Gln Cys Arg
             75                  80                  85 acc cgc tac aag cgc ctc aag ggc tgc ccg cgg gtg gcc ggc gac gag      523
Thr Arg Tyr Lys Arg Leu Lys Gly Cys Pro Arg Val Ala Gly Asp Glu
         90                  95                 100 gag gag gac ggc gtc gac gac ctg gag ggc gag ttc ggc ctg cag gac      571
Glu Glu Asp Gly Val Asp Asp Leu Glu Gly Glu Phe Gly Leu Gln Asp
105                 110                 115 ggc gcc gcc cac gag gac gac ccg cag tac gtc gcc gag tcc atg ctc      619
Gly Ala Ala His Glu Asp Asp Pro Gln Tyr Val Ala Glu Ser Met Leu
120                 125                 130                 135 agg gcg cag atg agc tac ggc cgc ggc ggc gac gcg cac ccc ggc ttc      667
Arg Ala Gln Met Ser Tyr Gly Arg Gly Gly Asp Ala His Pro Gly Phe
                140                 145                 150 agc ccc gtc ccc aac gtg ccg ctc ctc acc aac ggc cag atg gtt gat      715
Ser Pro Val Pro Asn Val Pro Leu Leu Thr Asn Gly Gln Met Val Asp
            155                 160                 165 gac atc ccg ccg gag cag cac gcg ctc gtg ccg tcc tac atg agc ggc      763
Asp Ile Pro Pro Glu Gln His Ala Leu Val Pro Ser Tyr Met Ser Gly
        170                 175                 180
```

```
ggc ggc ggc ggg ggc aag agg atc cac ccg ctc cct ttc gca gat ccc        811
Gly Gly Gly Gly Gly Lys Arg Ile His Pro Leu Pro Phe Ala Asp Pro
            185                 190                 195 aac ctt cca gtg caa ccg aga tcc atg gac ccg tcc aag gat ctg gcc        859
Asn Leu Pro Val Gln Pro Arg Ser Met Asp Pro Ser Lys Asp Leu Ala
200                 205                 210                 215 gcc tac gga tat ggc agc gtg gcc tgg aag gag aga atg gag ggc tgg        907
Ala Tyr Gly Tyr Gly Ser Val Ala Trp Lys Glu Arg Met Glu Gly Trp
                220                 225                 230 aag cag aag cag gag cgc ctg cag cat gtc agg agc gag ggt ggc ggt        955
Lys Gln Lys Gln Glu Arg Leu Gln His Val Arg Ser Glu Gly Gly Gly
    235                 240                 245 gat tgg gat ggc gac gat gca gat ctg cca cta atg gat gaa gct agg       1003
Asp Trp Asp Gly Asp Asp Ala Asp Leu Pro Leu Met Asp Glu Ala Arg
                250                 255                 260 cag cca ttg tcc aga aaa gtc cct ata tca tca agc cga att aat ccc       1051
Gln Pro Leu Ser Arg Lys Val Pro Ile Ser Ser Ser Arg Ile Asn Pro
265                 270                 275 tac agg atg att atc gtt atc cgg ttg gtg gtt ttg ggt ttc ttc ttc       1099
Tyr Arg Met Ile Ile Val Ile Arg Leu Val Val Leu Gly Phe Phe Phe
280                 285                 290                 295 cac tac cga gtg atg cat ccg gcg aaa gat gca ttt gca ttg tgg ctc       1147
His Tyr Arg Val Met His Pro Ala Lys Asp Ala Phe Ala Leu Trp Leu
                300                 305                 310 ata tct gta atc tgt gaa atc tgg ttt gcg atg tcc tgg att ctt gat       1195
Ile Ser Val Ile Cys Glu Ile Trp Phe Ala Met Ser Trp Ile Leu Asp
            315                 320                 325 cag ttc cca aag tgg ctt cca atc gag aga gag act tac ctg gac cgt       1243
Gln Phe Pro Lys Trp Leu Pro Ile Glu Arg Glu Thr Tyr Leu Asp Arg
        330                 335                 340 ttg tca cta agg ttt gac aag gaa ggt caa ccc tct cag ctt gct cca       1291
Leu Ser Leu Arg Phe Asp Lys Glu Gly Gln Pro Ser Gln Leu Ala Pro
345                 350                 355 atc gac ttc ttt gtc agt acg gtt gat ccc aca aag gaa cct ccc ttg       1339
Ile Asp Phe Phe Val Ser Thr Val Asp Pro Thr Lys Glu Pro Pro Leu
360                 365                 370                 375 gtc aca gcg aac act gtc ctt tcc atc ctt tct gtg gat tat ccg gtt       1387
Val Thr Ala Asn Thr Val Leu Ser Ile Leu Ser Val Asp Tyr Pro Val
                380                 385                 390 gag aag gtc tcc tgc tat gtt tct gat gat ggt gct gca atg ctt acg       1435
Glu Lys Val Ser Cys Tyr Val Ser Asp Asp Gly Ala Ala Met Leu Thr
            395                 400                 405 ttt gaa gca ttg tct gaa aca tct gaa ttt gca aag aaa tgg gtt cct       1483
Phe Glu Ala Leu Ser Glu Thr Ser Glu Phe Ala Lys Lys Trp Val Pro
        410                 415                 420 ttc agc aaa aag ttt aat atc gag cct cgt gct cct gag tgg tac ttc       1531
Phe Ser Lys Lys Phe Asn Ile Glu Pro Arg Ala Pro Glu Trp Tyr Phe
425                 430                 435 caa cag aag ata gac tac ctg aaa gac aag gtt gct gct tca ttt gtt       1579
Gln Gln Lys Ile Asp Tyr Leu Lys Asp Lys Val Ala Ala Ser Phe Val
440                 445                 450                 455 agg gag agg agg gcg atg aag aga gaa tac gag gaa ttc aag gta agg       1627
Arg Glu Arg Arg Ala Met Lys Arg Glu Tyr Glu Glu Phe Lys Val Arg
                460                 465                 470 atc aat gcc ttg gtt gca aaa gcc caa aag gtt cct gag gaa gga tgg       1675
Ile Asn Ala Leu Val Ala Lys Ala Gln Lys Val Pro Glu Glu Gly Trp
            475                 480                 485 aca atg caa gat gga agc ccc tgg cct gga aac aac gta cgc gat cat       1723
Thr Met Gln Asp Gly Ser Pro Trp Pro Gly Asn Asn Val Arg Asp His
```

```
                490                 495                 500
cct gga atg att cag gta ttc ctt ggc caa agt ggc ggt cgt gat gtg   1771
Pro Gly Met Ile Gln Val Phe Leu Gly Gln Ser Gly Gly Arg Asp Val
    505                 510                 515 gaa gga aat gag ttg cct cgc ctg gtt tat gtc tcg aga gaa aag agg   1819
Glu Gly Asn Glu Leu Pro Arg Leu Val Tyr Val Ser Arg Glu Lys Arg
520                 525                 530                 535 cca ggt tat aac cat cac aag aag gct ggt gcc atg aat gca ctg gtc   1867
Pro Gly Tyr Asn His His Lys Lys Ala Gly Ala Met Asn Ala Leu Val
                540                 545                 550 cgt gtc tct gct gtc tta tca aat gct gca tac cta ttg aac ttg gac   1915
Arg Val Ser Ala Val Leu Ser Asn Ala Ala Tyr Leu Leu Asn Leu Asp
        555                 560                 565 tgt gat cac tac atc aac aat agc aag gcc ata aaa gag gct atg tgt   1963
Cys Asp His Tyr Ile Asn Asn Ser Lys Ala Ile Lys Glu Ala Met Cys
            570                 575                 580 ttc atg atg gat cct ttg gtg ggg aag aaa gtg tgc tat gta cag ttc   2011
Phe Met Met Asp Pro Leu Val Gly Lys Lys Val Cys Tyr Val Gln Phe
    585                 590                 595 cct cag agg ttt gat ggt att gac aaa aat gat cga tac gct aac agg   2059
Pro Gln Arg Phe Asp Gly Ile Asp Lys Asn Asp Arg Tyr Ala Asn Arg
600                 605                 610                 615 aac gtt gtc ttt ttt gac atc aac atg aaa ggt ttg gac ggt att caa   2107
Asn Val Val Phe Phe Asp Ile Asn Met Lys Gly Leu Asp Gly Ile Gln
                620                 625                 630 gga ccc att tat gtg ggt act gga tgt gtt ttc aga cgg cag gca ctg   2155
Gly Pro Ile Tyr Val Gly Thr Gly Cys Val Phe Arg Arg Gln Ala Leu
        635                 640                 645 tat ggt tat gat gct cct aaa acg aag aag cca cca tca aga act tgc   2203
Tyr Gly Tyr Asp Ala Pro Lys Thr Lys Lys Pro Pro Ser Arg Thr Cys
            650                 655                 660 aac tgc tgg ccc aag tgg tgc ctc tct tgc tgc tgc agc agg aac aag   2251
Asn Cys Trp Pro Lys Trp Cys Leu Ser Cys Cys Cys Ser Arg Asn Lys
    665                 670                 675 aat aaa aag aag act aca aaa cca aag acg gag aag aag aaa aga tta   2299
Asn Lys Lys Lys Thr Thr Lys Pro Lys Thr Glu Lys Lys Lys Arg Leu
680                 685                 690                 695 ttt ttc aag aaa gca gaa aac cca tct cct gca tat gct ttg ggt gaa   2347
Phe Phe Lys Lys Ala Glu Asn Pro Ser Pro Ala Tyr Ala Leu Gly Glu
                700                 705                 710 att gat gaa ggt gct cca ggt gct gat atc gag aag gcc gga atc gta   2395
Ile Asp Glu Gly Ala Pro Gly Ala Asp Ile Glu Lys Ala Gly Ile Val
        715                 720                 725 aat caa cag aaa cta gag aag aaa ttt ggg cag tct tct gtt ttt gtc   2443
Asn Gln Gln Lys Leu Glu Lys Lys Phe Gly Gln Ser Ser Val Phe Val
            730                 735                 740 gca tca aca ctt ctt gag aac gga ggg acc ctg aag agc gca agt cca   2491
Ala Ser Thr Leu Leu Glu Asn Gly Gly Thr Leu Lys Ser Ala Ser Pro
    745                 750                 755 gct tct ctt ctg aag gaa gct ata cat gtt atc agc tgc ggc tac gaa   2539
Ala Ser Leu Leu Lys Glu Ala Ile His Val Ile Ser Cys Gly Tyr Glu
760                 765                 770                 775 gac aag acc gac tgg gga aaa gag att ggc tgg att tac gga tcg atc   2587
Asp Lys Thr Asp Trp Gly Lys Glu Ile Gly Trp Ile Tyr Gly Ser Ile
                780                 785                 790 aca gag gat atc ttg act gga ttt aag atg cac tgc cat ggc tgg cgg   2635
Thr Glu Asp Ile Leu Thr Gly Phe Lys Met His Cys His Gly Trp Arg
        795                 800                 805 tct att tac tgc atc ccg aag cgg cct gca ttc aaa ggt tct gcg cct   2683
```

```
Ser Ile Tyr Cys Ile Pro Lys Arg Pro Ala Phe Lys Gly Ser Ala Pro
        810                 815                 820 ctg aac ctt tcc gac cgt ctt cac cag gtc ctt cgc tgg gcc ctt ggg      2731
Leu Asn Leu Ser Asp Arg Leu His Gln Val Leu Arg Trp Ala Leu Gly
    825                 830                 835 tcc gtc gaa att ttc ttc agc aag cac tgc cca ctt tgg tac gga tac      2779
Ser Val Glu Ile Phe Phe Ser Lys His Cys Pro Leu Trp Tyr Gly Tyr
840                 845                 850                 855 ggc ggc ggg cta aaa ttc ctg gaa agg ttt tct tat atc aac tcc atc      2827
Gly Gly Gly Leu Lys Phe Leu Glu Arg Phe Ser Tyr Ile Asn Ser Ile
                860                 865                 870 gtt tat ccc tgg acg tcc att cct ctc ctg gct tac tgt acc ttg cct      2875
Val Tyr Pro Trp Thr Ser Ile Pro Leu Leu Ala Tyr Cys Thr Leu Pro
            875                 880                 885 gcc atc tgc ctg ctc acg ggg aag ttt atc aca cca gag ctt acc aat      2923
Ala Ile Cys Leu Leu Thr Gly Lys Phe Ile Thr Pro Glu Leu Thr Asn
        890                 895                 900 gtc gcc agt atc tgg ttc atg gca ctt ttc atc tgc atc tcc gtg acc      2971
Val Ala Ser Ile Trp Phe Met Ala Leu Phe Ile Cys Ile Ser Val Thr
    905                 910                 915 ggc atc ctg gaa atg agg tgg agt ggc gtg gcc atc gac gac tgg tgg      3019
Gly Ile Leu Glu Met Arg Trp Ser Gly Val Ala Ile Asp Asp Trp Trp
920                 925                 930                 935 agg aac gag cag ttc tgg gtc atc gga ggc gtt tcg gcg cat ctg ttc      3067
Arg Asn Glu Gln Phe Trp Val Ile Gly Gly Val Ser Ala His Leu Phe
                940                 945                 950 gcg gtg ttc cag ggc ctg ctg aag gtg ttc gcc ggc atc gac acg agc      3115
Ala Val Phe Gln Gly Leu Leu Lys Val Phe Ala Gly Ile Asp Thr Ser
            955                 960                 965 ttc acc gtg acg tcg aag gcc ggg gac gac gag gag ttc tcg gag ctg      3163
Phe Thr Val Thr Ser Lys Ala Gly Asp Asp Glu Glu Phe Ser Glu Leu
        970                 975                 980 tac acg ttc aag tgg acc acc ctg ctg ata ccc ccg acc acg ctc ctc      3211
Tyr Thr Phe Lys Trp Thr Thr Leu Leu Ile Pro Pro Thr Thr Leu Leu
    985                 990                 995 ctg ctg aac ttc atc ggg gtg gtg gcc ggg atc tcg aac gcg atc aac      3259
Leu Leu Asn Phe Ile Gly Val Val Ala Gly Ile Ser Asn Ala Ile Asn
1000                1005                1010                1015 aac ggg tac gag tcg tgg ggc ccc ctg ttc ggg aag ctc ttc ttc gcc      3307
Asn Gly Tyr Glu Ser Trp Gly Pro Leu Phe Gly Lys Leu Phe Phe Ala
                1020                1025                1030 ttc tgg gtg atc gtc cac ctg tac ccg ttc ctc aag ggt ctg gtg ggg      3355
Phe Trp Val Ile Val His Leu Tyr Pro Phe Leu Lys Gly Leu Val Gly
            1035                1040                1045 agg cag aac agg acg ccg acg atc gtc atc gtc tgg tcc atc ctg ctg      3403
Arg Gln Asn Arg Thr Pro Thr Ile Val Ile Val Trp Ser Ile Leu Leu
        1050                1055                1060 gcc tcg atc ttc tcg ctc ctg tgg gtc cgc gtc gac ccg ttc ctc gcc      3451
Ala Ser Ile Phe Ser Leu Leu Trp Val Arg Val Asp Pro Phe Leu Ala
    1065                1070                1075 aag agc aac ggc ccg ctc ctg gag gag tgt ggc ctg gac tgc aac           3496
Lys Ser Asn Gly Pro Leu Leu Glu Glu Cys Gly Leu Asp Cys Asn
1080                1085                1090 tgaagtgggg gccccctgtc actcgaagtt ctgtcacggg cgaattacgc ctgattttt      3556 gttgttgttg ttgttggaat tctttgctgt agatagaaac cacatgtcca cggcatctct     3616
gctgtgtcca ttggagcagg agagaggtgc ctgctgctgt tgttgagta aattaaaagt      3676 tttaaagtta tacagtgatg cacattccag tgcccagtgt attccctttt tacagtctgt     3736
```

```
atattagcga caaaggacat attggttagg agtttgattc ttttgtaaaa aaaaaaaaa      3796 aaaaaaaaaa aaaaaa                                                     3813
```

<210> SEQ ID NO 26
<211> LENGTH: 1094
<212> TYPE: PRT
<213> ORGANISM: Zea mays

<400> SEQUENCE: 26

| Met | Glu | Ala | Ser | Ala | Gly | Leu | Val | Ala | Gly | Ser | His | Asn | Arg | Asn | Glu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Leu Val Val Ile Arg Arg Asp Arg Glu Ser Gly Ala Ala Gly Gly Gly
            20                  25                  30

Ala Ala Arg Arg Ala Glu Ala Pro Cys Gln Ile Cys Gly Asp Glu Val
        35                  40                  45

Gly Val Gly Phe Asp Gly Glu Pro Phe Val Ala Cys Asn Glu Cys Ala
    50                  55                  60

Phe Pro Val Cys Arg Ala Cys Tyr Glu Tyr Glu Arg Arg Glu Gly Ser
65                  70                  75                  80

Gln Ala Cys Pro Gln Cys Arg Thr Arg Tyr Lys Arg Leu Lys Gly Cys
                85                  90                  95

Pro Arg Val Ala Gly Asp Glu Glu Asp Gly Val Asp Asp Leu Glu
            100                 105                 110

Gly Glu Phe Gly Leu Gln Asp Gly Ala Ala His Glu Asp Asp Pro Gln
        115                 120                 125

Tyr Val Ala Glu Ser Met Leu Arg Ala Gln Met Ser Tyr Gly Arg Gly
    130                 135                 140

Gly Asp Ala His Pro Gly Phe Ser Pro Val Pro Asn Val Pro Leu Leu
145                 150                 155                 160

Thr Asn Gly Gln Met Val Asp Asp Ile Pro Pro Glu Gln His Ala Leu
                165                 170                 175

Val Pro Ser Tyr Met Ser Gly Gly Gly Gly Gly Lys Arg Ile His
            180                 185                 190

Pro Leu Pro Phe Ala Asp Pro Asn Leu Pro Val Gln Pro Arg Ser Met
        195                 200                 205

Asp Pro Ser Lys Asp Leu Ala Ala Tyr Gly Tyr Gly Ser Val Ala Trp
    210                 215                 220

Lys Glu Arg Met Glu Gly Trp Lys Gln Lys Gln Glu Arg Leu Gln His
225                 230                 235                 240

Val Arg Ser Glu Gly Gly Gly Asp Trp Asp Gly Asp Asp Ala Asp Leu
                245                 250                 255

Pro Leu Met Asp Glu Ala Arg Gln Pro Leu Ser Arg Lys Val Pro Ile
            260                 265                 270

Ser Ser Ser Arg Ile Asn Pro Tyr Arg Met Ile Ile Val Ile Arg Leu
        275                 280                 285

Val Val Leu Gly Phe Phe Phe His Tyr Arg Val Met His Pro Ala Lys
    290                 295                 300

Asp Ala Phe Ala Leu Trp Leu Ile Ser Val Ile Cys Glu Ile Trp Phe
305                 310                 315                 320

Ala Met Ser Trp Ile Leu Asp Gln Phe Pro Lys Trp Leu Pro Ile Glu
                325                 330                 335

Arg Glu Thr Tyr Leu Asp Arg Leu Ser Leu Arg Phe Asp Lys Glu Gly
            340                 345                 350

Gln Pro Ser Gln Leu Ala Pro Ile Asp Phe Phe Val Ser Thr Val Asp

-continued

```
                355                 360                 365
Pro Thr Lys Glu Pro Pro Leu Val Thr Ala Asn Thr Val Leu Ser Ile
    370                 375                 380
Leu Ser Val Asp Tyr Pro Val Glu Lys Val Ser Cys Tyr Val Ser Asp
385                 390                 395                 400
Asp Gly Ala Ala Met Leu Thr Phe Glu Ala Leu Ser Glu Thr Ser Glu
                    405                 410                 415
Phe Ala Lys Lys Trp Val Pro Phe Ser Lys Lys Phe Asn Ile Glu Pro
                420                 425                 430
Arg Ala Pro Glu Trp Tyr Phe Gln Gln Lys Ile Asp Tyr Leu Lys Asp
                435                 440                 445
Lys Val Ala Ala Ser Phe Val Arg Glu Arg Ala Met Lys Arg Glu
    450                 455                 460
Tyr Glu Glu Phe Lys Val Arg Ile Asn Ala Leu Val Ala Lys Ala Gln
465                 470                 475                 480
Lys Val Pro Glu Glu Gly Trp Thr Met Gln Asp Gly Ser Pro Trp Pro
                    485                 490                 495
Gly Asn Asn Val Arg Asp His Pro Gly Met Ile Gln Val Phe Leu Gly
                500                 505                 510
Gln Ser Gly Gly Arg Asp Val Glu Gly Asn Glu Leu Pro Arg Leu Val
                515                 520                 525
Tyr Val Ser Arg Glu Lys Arg Pro Gly Tyr Asn His His Lys Lys Ala
            530                 535                 540
Gly Ala Met Asn Ala Leu Val Arg Val Ser Ala Val Leu Ser Asn Ala
545                 550                 555                 560
Ala Tyr Leu Leu Asn Leu Asp Cys Asp His Tyr Ile Asn Asn Ser Lys
                    565                 570                 575
Ala Ile Lys Glu Ala Met Cys Phe Met Met Asp Pro Leu Val Gly Lys
                580                 585                 590
Lys Val Cys Tyr Val Gln Phe Pro Gln Arg Phe Asp Gly Ile Asp Lys
                595                 600                 605
Asn Asp Arg Tyr Ala Asn Arg Asn Val Val Phe Phe Asp Ile Asn Met
610                 615                 620
Lys Gly Leu Asp Gly Ile Gln Gly Pro Ile Tyr Val Gly Thr Gly Cys
625                 630                 635                 640
Val Phe Arg Arg Gln Ala Leu Tyr Gly Tyr Asp Ala Pro Lys Thr Lys
                    645                 650                 655
Lys Pro Pro Ser Arg Thr Cys Asn Cys Trp Pro Lys Trp Cys Leu Ser
                660                 665                 670
Cys Cys Cys Ser Arg Asn Lys Asn Lys Lys Thr Thr Lys Pro Lys
                675                 680                 685
Thr Glu Lys Lys Lys Arg Leu Phe Phe Lys Lys Ala Glu Asn Pro Ser
        690                 695                 700
Pro Ala Tyr Ala Leu Gly Glu Ile Asp Glu Gly Ala Pro Gly Ala Asp
705                 710                 715                 720
Ile Glu Lys Ala Gly Ile Val Asn Gln Gln Lys Leu Glu Lys Lys Phe
                725                 730                 735
Gly Gln Ser Ser Val Phe Val Ala Ser Thr Leu Leu Glu Asn Gly Gly
                740                 745                 750
Thr Leu Lys Ser Ala Ser Pro Ala Ser Leu Leu Lys Glu Ala Ile His
        755                 760                 765
Val Ile Ser Cys Gly Tyr Glu Asp Lys Thr Asp Trp Gly Lys Glu Ile
770                 775                 780
```

-continued

```
Gly Trp Ile Tyr Gly Ser Ile Thr Glu Asp Ile Leu Thr Gly Phe Lys
785                 790                 795                 800

Met His Cys His Gly Trp Arg Ser Ile Tyr Cys Ile Pro Lys Arg Pro
                805                 810                 815

Ala Phe Lys Gly Ser Ala Pro Leu Asn Leu Ser Asp Arg Leu His Gln
            820                 825                 830

Val Leu Arg Trp Ala Leu Gly Ser Val Glu Ile Phe Phe Ser Lys His
        835                 840                 845

Cys Pro Leu Trp Tyr Gly Tyr Gly Gly Leu Lys Phe Leu Glu Arg
    850                 855                 860

Phe Ser Tyr Ile Asn Ser Ile Val Tyr Pro Trp Thr Ser Ile Pro Leu
865                 870                 875                 880

Leu Ala Tyr Cys Thr Leu Pro Ala Ile Cys Leu Leu Thr Gly Lys Phe
                885                 890                 895

Ile Thr Pro Glu Leu Thr Asn Val Ala Ser Ile Trp Phe Met Ala Leu
            900                 905                 910

Phe Ile Cys Ile Ser Val Thr Gly Ile Leu Glu Met Arg Trp Ser Gly
        915                 920                 925

Val Ala Ile Asp Asp Trp Trp Arg Asn Glu Gln Phe Trp Val Ile Gly
    930                 935                 940

Gly Val Ser Ala His Leu Phe Ala Val Phe Gln Gly Leu Leu Lys Val
945                 950                 955                 960

Phe Ala Gly Ile Asp Thr Ser Phe Thr Val Thr Ser Lys Ala Gly Asp
                965                 970                 975

Asp Glu Glu Phe Ser Glu Leu Tyr Thr Phe Lys Trp Thr Thr Leu Leu
            980                 985                 990

Ile Pro Pro Thr Thr Leu Leu Leu Leu Asn Phe Ile Gly Val Val Ala
        995                 1000                1005

Gly Ile Ser Asn Ala Ile Asn Asn Gly Tyr Glu Ser Trp Gly Pro Leu
    1010                1015                1020

Phe Gly Lys Leu Phe Phe Ala Phe Trp Val Ile Val His Leu Tyr Pro
1025                1030                1035                1040

Phe Leu Lys Gly Leu Val Gly Arg Gln Asn Arg Thr Pro Thr Ile Val
                1045                1050                1055

Ile Val Trp Ser Ile Leu Leu Ala Ser Ile Phe Ser Leu Leu Trp Val
            1060                1065                1070

Arg Val Asp Pro Phe Leu Ala Lys Ser Asn Gly Pro Leu Leu Glu Glu
        1075                1080                1085

Cys Gly Leu Asp Cys Asn
    1090

<210> SEQ ID NO 27
<211> LENGTH: 25
<212> TYPE: DNA
<213> ORGANISM: Zea mays

<400> SEQUENCE: 27
atggaggcta gcgcggggct ggtgg                                              25

<210> SEQ ID NO 28
<211> LENGTH: 25
<212> TYPE: DNA
<213> ORGANISM: Zea mays

<400> SEQUENCE: 28
```

```
tcagttgcag tccaggccac actcc                                           25
```

<210> SEQ ID NO 29
<211> LENGTH: 3746
<212> TYPE: DNA
<213> ORGANISM: Zea mays
<220> FEATURE:
<221> NAME/KEY: CDS
<222> LOCATION: (321)...(3551)

<400> SEQUENCE: 29

```
ctaggatcaa aaccgtctcg ccgctgcaat aatcttttgt caattcttaa tccctcgcgt     60
cgacagcgac agcggaacca actcacgttg ccgcggcttc ctccatcggt gcggtgccct    120
gtccttttct ctcgtccctc ctcccccgt atagttaagc cccgcccgc tactactact     180 actagcagca gcagcgctct cgcagcggga gatgcggtgt tgatccgtgc cccgctcgga    240
tctcgggact ggtgccggct ctgcccaggc cccaggctcc aggccagctc cctcgacgtt    300
tctcggcgag ctcgcttgcc atg gag ggc gac gcg gac ggc gtg aag tcg ggg   353
                         Met Glu Gly Asp Ala Asp Gly Val Lys Ser Gly
                           1               5                      10 agg cgc ggt ggc gga cag gtg tgc cag atc tgc ggc gac ggc gtg ggc     401
Arg Arg Gly Gly Gly Gln Val Cys Gln Ile Cys Gly Asp Gly Val Gly
          15                  20                  25 acc acg gcg gag ggg gac gtc ttc gcc gcc tgc gac gtc tgc ggg ttt     449
Thr Thr Ala Glu Gly Asp Val Phe Ala Ala Cys Asp Val Cys Gly Phe
 30                  35                  40 ccg gtg tgc cgc ccc tgc tac gag tac gag cgc aag gac ggc acg cag     497
Pro Val Cys Arg Pro Cys Tyr Glu Tyr Glu Arg Lys Asp Gly Thr Gln
 45                  50                  55 gcg tgc ccc cag tgc aag acc aag tac aag cgc cac aag ggg agc ccg     545
Ala Cys Pro Gln Cys Lys Thr Lys Tyr Lys Arg His Lys Gly Ser Pro
 60                  65                  70                  75 gcg atc cgt ggg gag gaa gga gac gac act gat gcc gat agc gac ttc     593
Ala Ile Arg Gly Glu Glu Gly Asp Asp Thr Asp Ala Asp Ser Asp Phe
             80                  85                  90 aat tac ctt gca tct ggc aat gag gac cag aag cag aag att gcc gac     641
Asn Tyr Leu Ala Ser Gly Asn Glu Asp Gln Lys Gln Lys Ile Ala Asp
         95                 100                 105 aga atg cgc agc tgg cgc atg aac gtt ggg ggc agc ggg gat gtt ggt     689
Arg Met Arg Ser Trp Arg Met Asn Val Gly Gly Ser Gly Asp Val Gly
     110                 115                 120 cgc ccc aag tat gac agt ggc gag atc ggg ctt acc aag tat gac agt     737
Arg Pro Lys Tyr Asp Ser Gly Glu Ile Gly Leu Thr Lys Tyr Asp Ser
 125                 130                 135 ggc gag att cct cgg gga tac atc cca tca gtc act aac agc cag atc     785
Gly Glu Ile Pro Arg Gly Tyr Ile Pro Ser Val Thr Asn Ser Gln Ile
140                 145                 150                 155 tca gga gaa atc cct ggt gct tcc cct gac cat cat atg atg tcc cca     833
Ser Gly Glu Ile Pro Gly Ala Ser Pro Asp His His Met Met Ser Pro
             160                 165                 170 act ggg aac att ggc aag cgt gct cca ttt ccc tat gtg aac cat tcg     881
Thr Gly Asn Ile Gly Lys Arg Ala Pro Phe Pro Tyr Val Asn His Ser
         175                 180                 185 cca aat ccg tca agg gag ttc tct ggt agc att ggg aat gtt gcc tgg     929
Pro Asn Pro Ser Arg Glu Phe Ser Gly Ser Ile Gly Asn Val Ala Trp
     190                 195                 200 aaa gag agg gtt gat ggc tgg aaa atg aag cag gac aag ggg acg att     977
Lys Glu Arg Val Asp Gly Trp Lys Met Lys Gln Asp Lys Gly Thr Ile
 205                 210                 215
```

```
                                                      -continued ccc atg acg aat ggc aca agc att gct ccc tct gag ggt cgg ggt gtt        1025
Pro Met Thr Asn Gly Thr Ser Ile Ala Pro Ser Glu Gly Arg Gly Val
220             225                 230                 235 ggt gat att gat gca tca act gat tac aac atg gaa gat gcc tta ttg        1073
Gly Asp Ile Asp Ala Ser Thr Asp Tyr Asn Met Glu Asp Ala Leu Leu
                240                 245                 250 aac gac gaa act cga cag cct cta tct agg aaa gtt cca ctt cct tcc        1121
Asn Asp Glu Thr Arg Gln Pro Leu Ser Arg Lys Val Pro Leu Pro Ser
            255                 260                 265 tcc agg ata aat cca tac agg atg gtc att gtg ctg cga ttg att gtt        1169
Ser Arg Ile Asn Pro Tyr Arg Met Val Ile Val Leu Arg Leu Ile Val
        270                 275                 280 cta agc atc ttc ttg cac tac cgt atc aca aat cct gtg cgc aat gca        1217
Leu Ser Ile Phe Leu His Tyr Arg Ile Thr Asn Pro Val Arg Asn Ala
285                 290                 295 tac cca tta tgg ctt cta tct gtt ata tgt gag atc tgg ttt gct ctt        1265
Tyr Pro Leu Trp Leu Leu Ser Val Ile Cys Glu Ile Trp Phe Ala Leu
300                 305                 310                 315 tcg tgg ata ttg gat cag ttc cct aag tgg ttt cca atc aac cgg gag        1313
Ser Trp Ile Leu Asp Gln Phe Pro Lys Trp Phe Pro Ile Asn Arg Glu
                320                 325                 330 acg tac ctt gat agg ctg gca tta agg tat gac cgg gaa ggt gag cca        1361
Thr Tyr Leu Asp Arg Leu Ala Leu Arg Tyr Asp Arg Glu Gly Glu Pro
            335                 340                 345 tct cag ttg gct gct gtt gac att ttc gtc agt aca gtc gac cca atg        1409
Ser Gln Leu Ala Ala Val Asp Ile Phe Val Ser Thr Val Asp Pro Met
        350                 355                 360 aag gag cct cct ctt gtc act gcc aat acc gtg cta tcc att ctt gct        1457
Lys Glu Pro Pro Leu Val Thr Ala Asn Thr Val Leu Ser Ile Leu Ala
365                 370                 375 gtg gat tac cct gtg gat aag gtc tct tgc tat gta tct gat gat gga        1505
Val Asp Tyr Pro Val Asp Lys Val Ser Cys Tyr Val Ser Asp Asp Gly
380                 385                 390                 395 gct gcg atg ctg aca ttt gat gca cta gct gag act tca gag ttt gct        1553
Ala Ala Met Leu Thr Phe Asp Ala Leu Ala Glu Thr Ser Glu Phe Ala
                400                 405                 410 aga aaa tgg gta cca ttt gtt aag aag tac aac att gaa cct aga gct        1601
Arg Lys Trp Val Pro Phe Val Lys Lys Tyr Asn Ile Glu Pro Arg Ala
            415                 420                 425 cct gaa tgg tac ttc tcc cag aaa att gat tac ttg aag gac aaa gtg        1649
Pro Glu Trp Tyr Phe Ser Gln Lys Ile Asp Tyr Leu Lys Asp Lys Val
        430                 435                 440 cac cct tca ttt gtt aaa gac cgc cgg gcc atg aag aga gaa tat gaa        1697
His Pro Ser Phe Val Lys Asp Arg Arg Ala Met Lys Arg Glu Tyr Glu
445                 450                 455 gaa ttc aaa gtt agg gta aat ggc ctt gtt gct aag gca cag aaa gtt        1745
Glu Phe Lys Val Arg Val Asn Gly Leu Val Ala Lys Ala Gln Lys Val
460                 465                 470                 475 cct gag gaa gga tgg atc atg caa gat ggc aca cca tgg cca gga aac        1793
Pro Glu Glu Gly Trp Ile Met Gln Asp Gly Thr Pro Trp Pro Gly Asn
                480                 485                 490 aat acc agg gac cat cct gga atg att cag gtt ttc ctt ggt cac agt        1841
Asn Thr Arg Asp His Pro Gly Met Ile Gln Val Phe Leu Gly His Ser
            495                 500                 505 ggt ggc ctt gat act gag ggc aat gag cta ccc cgt ttg gtc tat gtt        1889
Gly Gly Leu Asp Thr Glu Gly Asn Glu Leu Pro Arg Leu Val Tyr Val
        510                 515                 520 tct cgt gaa aag cgt cct gga ttc cag cat cac aag aaa gct ggt gcc        1937
Ser Arg Glu Lys Arg Pro Gly Phe Gln His His Lys Lys Ala Gly Ala
525                 530                 535
```

-continued

| | |
|---|---|
| atg aat gct ctt gtt cgt gtc tca gct gtg ctt acc aat gga caa tac<br>Met Asn Ala Leu Val Arg Val Ser Ala Val Leu Thr Asn Gly Gln Tyr<br>540                        545                      550                      555 | 1985 |
| atg ttg aat ctt gat tgt gat cac tac att aac aac agt aag gct ctc<br>Met Leu Asn Leu Asp Cys Asp His Tyr Ile Asn Asn Ser Lys Ala Leu<br>                    560                      565                      570 | 2033 |
| agg gaa gct atg tgc ttc ctt atg gac cct aac cta gga agg agt gtc<br>Arg Glu Ala Met Cys Phe Leu Met Asp Pro Asn Leu Gly Arg Ser Val<br>              575                      580                      585 | 2081 |
| tgc tac gtc cag ttt ccc cag aga ttc gat ggc att gac agg aat gat<br>Cys Tyr Val Gln Phe Pro Gln Arg Phe Asp Gly Ile Asp Arg Asn Asp<br>          590                      595                      600 | 2129 |
| cga tat gcc aac agg aac acc gtg ttt ttc gat att aac ttg aga ggt<br>Arg Tyr Ala Asn Arg Asn Thr Val Phe Phe Asp Ile Asn Leu Arg Gly<br>605                        610                      615 | 2177 |
| ctt gat ggc atc caa gga cca gtt tat gtc gga act ggc tgt gtt ttc<br>Leu Asp Gly Ile Gln Gly Pro Val Tyr Val Gly Thr Gly Cys Val Phe<br>620                        625                      630                      635 | 2225 |
| aac cga aca gct cta tat ggt tat gag ccc cca att aag cag aag aag<br>Asn Arg Thr Ala Leu Tyr Gly Tyr Glu Pro Pro Ile Lys Gln Lys Lys<br>                    640                      645                      650 | 2273 |
| ggt ggt ttc ttg tca tca cta tgt ggc ggt agg aag aag gca agc aaa<br>Gly Gly Phe Leu Ser Ser Leu Cys Gly Gly Arg Lys Lys Ala Ser Lys<br>              655                      660                      665 | 2321 |
| tca aag aag ggc tcg gac aag aag aag tcg cag aag cat gtg gac agt<br>Ser Lys Lys Gly Ser Asp Lys Lys Lys Ser Gln Lys His Val Asp Ser<br>          670                      675                      680 | 2369 |
| tct gtg cca gta ttc aac ctt gaa gat ata gag gag gga gtt gaa ggc<br>Ser Val Pro Val Phe Asn Leu Glu Asp Ile Glu Glu Gly Val Glu Gly<br>685                        690                      695 | 2417 |
| gct gga ttt gac gac gag aaa tca ctt ctt atg tct caa atg agc ctg<br>Ala Gly Phe Asp Asp Glu Lys Ser Leu Leu Met Ser Gln Met Ser Leu<br>700                        705                      710                      715 | 2465 |
| gag aag aga ttt ggc cag tcc gca gcg ttt gtt gcc tcc act ctg atg<br>Glu Lys Arg Phe Gly Gln Ser Ala Ala Phe Val Ala Ser Thr Leu Met<br>                    720                      725                      730 | 2513 |
| gag tat ggt ggt gtt cct cag tcc gca act ccg gag tct ctt ctg aaa<br>Glu Tyr Gly Gly Val Pro Gln Ser Ala Thr Pro Glu Ser Leu Leu Lys<br>              735                      740                      745 | 2561 |
| gaa gct atc cat gtt ata agc tgt ggc tat gag gac aag act gaa tgg<br>Glu Ala Ile His Val Ile Ser Cys Gly Tyr Glu Asp Lys Thr Glu Trp<br>          750                      755                      760 | 2609 |
| gga act gag atc ggg tgg atc tac ggt tct gtg aca gaa gac att ctc<br>Gly Thr Glu Ile Gly Trp Ile Tyr Gly Ser Val Thr Glu Asp Ile Leu<br>765                        770                      775 | 2657 |
| acc gga ttc aag atg cac gcg cga ggc tgg cgg tcg atc tac tgc atg<br>Thr Gly Phe Lys Met His Ala Arg Gly Trp Arg Ser Ile Tyr Cys Met<br>780                        785                      790                      795 | 2705 |
| ccc aag cgg cca gct ttc aag ggg tct gcc ccc atc aat ctt tcg gac<br>Pro Lys Arg Pro Ala Phe Lys Gly Ser Ala Pro Ile Asn Leu Ser Asp<br>                    800                      805                      810 | 2753 |
| cgt ctg aac cag gtg ctc cgg tgg gct ctt ggg tcc gtg gag atc ctc<br>Arg Leu Asn Gln Val Leu Arg Trp Ala Leu Gly Ser Val Glu Ile Leu<br>              815                      820                      825 | 2801 |
| ttc agc cgg cac tgc ccc ctg tgg tac ggc tac gga ggg cgg ctc aag<br>Phe Ser Arg His Cys Pro Leu Trp Tyr Gly Tyr Gly Gly Arg Leu Lys<br>          830                      835                      840 | 2849 |
| ttc ctg gag aga ttc gcg tac atc aac acc acc atc tac ccg ctc acg<br>Phe Leu Glu Arg Phe Ala Tyr Ile Asn Thr Thr Ile Tyr Pro Leu Thr | 2897 |

```
                    845                 850                 855
tcc atc ccg ctt ctc atc tac tgc atc ctg ccc gcc atc tgt ctg ctc      2945
Ser Ile Pro Leu Leu Ile Tyr Cys Ile Leu Pro Ala Ile Cys Leu Leu
860                 865                 870                 875 acc gga aag ttc atc att cca gag atc agc aac ttc gcc agc atc tgg      2993
Thr Gly Lys Phe Ile Ile Pro Glu Ile Ser Asn Phe Ala Ser Ile Trp
                880                 885                 890 ttc atc tcc ctc ttc atc tcg atc ttc gcc acg ggc atc ctg gag atg      3041
Phe Ile Ser Leu Phe Ile Ser Ile Phe Ala Thr Gly Ile Leu Glu Met
            895                 900                 905 agg tgg agc ggg gtg ggc atc gac gag tgg tgg agg aac gag cag ttc      3089
Arg Trp Ser Gly Val Gly Ile Asp Glu Trp Trp Arg Asn Glu Gln Phe
        910                 915                 920 tgg gtg atc ggg ggc atc tcc gcg cac ctc ttc gcc gtg ttc cag ggc      3137
Trp Val Ile Gly Gly Ile Ser Ala His Leu Phe Ala Val Phe Gln Gly
    925                 930                 935 ctg ctc aag gtg ctg gcc ggc atc gac acc aac ttc acc gtc acc tcc      3185
Leu Leu Lys Val Leu Ala Gly Ile Asp Thr Asn Phe Thr Val Thr Ser
940                 945                 950                 955 aag gcc tcg gac gag gac ggc gac ttc gcg gag ctg tac atg ttc aag      3233
Lys Ala Ser Asp Glu Asp Gly Asp Phe Ala Glu Leu Tyr Met Phe Lys
                960                 965                 970 tgg acg acg ctc ctg atc ccg ccc acc acc atc ctg atc atc aac ctg      3281
Trp Thr Thr Leu Leu Ile Pro Pro Thr Thr Ile Leu Ile Ile Asn Leu
            975                 980                 985 gtc ggc gtc gtc gcc ggc atc tcc tac gcc atc aac agc gga tac cag      3329
Val Gly Val Val Ala Gly Ile Ser Tyr Ala Ile Asn Ser Gly Tyr Gln
        990                 995                 1000 tcg tgg ggc ccg ctc ttc ggc aag ctc ttc ttc gcc ttc tgg gtc atc      3377
Ser Trp Gly Pro Leu Phe Gly Lys Leu Phe Phe Ala Phe Trp Val Ile
    1005                1010                1015 gtc cac ctg tac ccg ttc ctc aag ggc ctc atg ggc agg cag aac cgc      3425
Val His Leu Tyr Pro Phe Leu Lys Gly Leu Met Gly Arg Gln Asn Arg
1020                1025                1030                1035 acc ccg acc atc gtc gtc gtc tgg gcc atc ctg ctg gcg tcc atc ttc      3473
Thr Pro Thr Ile Val Val Val Trp Ala Ile Leu Leu Ala Ser Ile Phe
                1040                1045                1050 tcc ttg ctg tgg gtt cgc atc gac ccc ttc acc acc cgc gtc act ggc      3521
Ser Leu Leu Trp Val Arg Ile Asp Pro Phe Thr Thr Arg Val Thr Gly
            1055                1060                1065 ccg gat acc cag acg tgt ggc atc aac tgc tagggaagtg aaggtttgt         3571
Pro Asp Thr Gln Thr Cys Gly Ile Asn Cys
        1070                1075 actttgtaga aacggaggaa taccacgtgc catctgttgt ctgttaagtt atatatatat    3631
aagcagcaag tggcgttatt tacagctacg tacagaccag tggatattgt ttaccacaaa   3691
gttttacttg tgttaatatg cattcttttg ttgatataaa aaaaaaaaaa aaaaa         3746

<210> SEQ ID NO 30
<211> LENGTH: 1077
<212> TYPE: PRT
<213> ORGANISM: Zea mays

<400> SEQUENCE: 30

Met Glu Gly Asp Ala Asp Gly Val Lys Ser Gly Arg Arg Gly Gly
  1               5                  10                  15

Gln Val Cys Gln Ile Cys Gly Asp Gly Val Gly Thr Thr Ala Glu Gly
                20                  25                  30

Asp Val Phe Ala Ala Cys Asp Val Cys Gly Phe Pro Val Cys Arg Pro
```

-continued

```
                35                  40                  45
Cys Tyr Glu Tyr Glu Arg Lys Asp Gly Thr Gln Ala Cys Pro Gln Cys
 50                  55                  60
Lys Thr Lys Tyr Lys Arg His Lys Gly Ser Pro Ala Ile Arg Gly Glu
 65                  70                  75                  80
Glu Gly Asp Asp Thr Asp Ala Asp Ser Asp Phe Asn Tyr Leu Ala Ser
                     85                  90                  95
Gly Asn Glu Asp Gln Lys Gln Lys Ile Ala Asp Arg Met Arg Ser Trp
                100                 105                 110
Arg Met Asn Val Gly Gly Ser Gly Asp Val Gly Arg Pro Lys Tyr Asp
                115                 120                 125
Ser Gly Glu Ile Gly Leu Thr Lys Tyr Asp Ser Gly Glu Ile Pro Arg
130                 135                 140
Gly Tyr Ile Pro Ser Val Thr Asn Ser Gln Ile Ser Gly Glu Ile Pro
145                 150                 155                 160
Gly Ala Ser Pro Asp His His Met Met Ser Pro Thr Gly Asn Ile Gly
                165                 170                 175
Lys Arg Ala Pro Phe Pro Tyr Val Asn His Ser Pro Asn Pro Ser Arg
                180                 185                 190
Glu Phe Ser Gly Ser Ile Gly Asn Val Ala Trp Lys Glu Arg Val Asp
                195                 200                 205
Gly Trp Lys Met Lys Gln Asp Lys Gly Thr Ile Pro Met Thr Asn Gly
210                 215                 220
Thr Ser Ile Ala Pro Ser Glu Gly Arg Gly Val Gly Asp Ile Asp Ala
225                 230                 235                 240
Ser Thr Asp Tyr Asn Met Glu Asp Ala Leu Leu Asn Asp Glu Thr Arg
                245                 250                 255
Gln Pro Leu Ser Arg Lys Val Pro Leu Pro Ser Ser Arg Ile Asn Pro
                260                 265                 270
Tyr Arg Met Val Ile Val Leu Arg Leu Ile Val Leu Ser Ile Phe Leu
                275                 280                 285
His Tyr Arg Ile Thr Asn Pro Val Arg Asn Ala Tyr Pro Leu Trp Leu
                290                 295                 300
Leu Ser Val Ile Cys Glu Ile Trp Phe Ala Leu Ser Trp Ile Leu Asp
305                 310                 315                 320
Gln Phe Pro Lys Trp Phe Pro Ile Asn Arg Glu Thr Tyr Leu Asp Arg
                325                 330                 335
Leu Ala Leu Arg Tyr Asp Arg Glu Gly Glu Pro Ser Gln Leu Ala Ala
                340                 345                 350
Val Asp Ile Phe Val Ser Thr Val Asp Pro Met Lys Glu Pro Pro Leu
                355                 360                 365
Val Thr Ala Asn Thr Val Leu Ser Ile Leu Ala Val Asp Tyr Pro Val
                370                 375                 380
Asp Lys Val Ser Cys Tyr Val Ser Asp Asp Gly Ala Ala Met Leu Thr
385                 390                 395                 400
Phe Asp Ala Leu Ala Glu Thr Ser Glu Phe Ala Arg Lys Trp Val Pro
                405                 410                 415
Phe Val Lys Lys Tyr Asn Ile Glu Pro Arg Ala Pro Glu Trp Tyr Phe
                420                 425                 430
Ser Gln Lys Ile Asp Tyr Leu Lys Asp Lys Val His Pro Ser Phe Val
                435                 440                 445
Lys Asp Arg Arg Ala Met Lys Arg Glu Tyr Glu Glu Phe Lys Val Arg
                450                 455                 460
```

-continued

```
Val Asn Gly Leu Val Ala Lys Ala Gln Lys Val Pro Glu Glu Gly Trp
465                 470                 475                 480

Ile Met Gln Asp Gly Thr Pro Trp Pro Gly Asn Asn Thr Arg Asp His
            485                 490                 495

Pro Gly Met Ile Gln Val Phe Leu Gly His Ser Gly Gly Leu Asp Thr
        500                 505                 510

Glu Gly Asn Glu Leu Pro Arg Leu Val Tyr Val Ser Arg Glu Lys Arg
    515                 520                 525

Pro Gly Phe Gln His His Lys Lys Ala Gly Ala Met Asn Ala Leu Val
530                 535                 540

Arg Val Ser Ala Val Leu Thr Asn Gly Gln Tyr Met Leu Asn Leu Asp
545                 550                 555                 560

Cys Asp His Tyr Ile Asn Asn Ser Lys Ala Leu Arg Glu Ala Met Cys
                565                 570                 575

Phe Leu Met Asp Pro Asn Leu Gly Arg Ser Val Cys Tyr Val Gln Phe
            580                 585                 590

Pro Gln Arg Phe Asp Gly Ile Asp Arg Asn Asp Arg Tyr Ala Asn Arg
        595                 600                 605

Asn Thr Val Phe Phe Asp Ile Asn Leu Arg Gly Leu Asp Gly Ile Gln
    610                 615                 620

Gly Pro Val Tyr Val Gly Thr Gly Cys Val Phe Asn Arg Thr Ala Leu
625                 630                 635                 640

Tyr Gly Tyr Glu Pro Pro Ile Lys Gln Lys Gly Gly Phe Leu Ser
                645                 650                 655

Ser Leu Cys Gly Gly Arg Lys Lys Ala Ser Lys Ser Lys Lys Gly Ser
            660                 665                 670

Asp Lys Lys Lys Ser Gln Lys His Val Asp Ser Ser Val Pro Val Phe
        675                 680                 685

Asn Leu Glu Asp Ile Glu Glu Gly Val Glu Gly Ala Gly Phe Asp Asp
    690                 695                 700

Glu Lys Ser Leu Leu Met Ser Gln Met Ser Leu Glu Lys Arg Phe Gly
705                 710                 715                 720

Gln Ser Ala Ala Phe Val Ala Ser Thr Leu Met Glu Tyr Gly Gly Val
                725                 730                 735

Pro Gln Ser Ala Thr Pro Glu Ser Leu Lys Glu Ala Ile His Val
            740                 745                 750

Ile Ser Cys Gly Tyr Glu Asp Lys Thr Glu Trp Gly Thr Glu Ile Gly
        755                 760                 765

Trp Ile Tyr Gly Ser Val Thr Glu Asp Ile Leu Thr Gly Phe Lys Met
    770                 775                 780

His Ala Arg Gly Trp Arg Ser Ile Tyr Cys Met Pro Lys Arg Pro Ala
785                 790                 795                 800

Phe Lys Gly Ser Ala Pro Ile Asn Leu Ser Asp Arg Leu Asn Gln Val
                805                 810                 815

Leu Arg Trp Ala Leu Gly Ser Val Glu Ile Leu Phe Ser Arg His Cys
            820                 825                 830

Pro Leu Trp Tyr Gly Tyr Gly Gly Arg Leu Lys Phe Leu Glu Arg Phe
        835                 840                 845

Ala Tyr Ile Asn Thr Thr Ile Tyr Pro Leu Thr Ser Ile Pro Leu Leu
    850                 855                 860

Ile Tyr Cys Ile Leu Pro Ala Ile Cys Leu Leu Thr Gly Lys Phe Ile
865                 870                 875                 880
```

```
Ile Pro Glu Ile Ser Asn Phe Ala Ser Ile Trp Phe Ile Ser Leu Phe
            885                 890                 895

Ile Ser Ile Phe Ala Thr Gly Ile Leu Glu Met Arg Trp Ser Gly Val
            900                 905                 910

Gly Ile Asp Glu Trp Trp Arg Asn Glu Gln Phe Trp Val Ile Gly Gly
            915                 920                 925

Ile Ser Ala His Leu Phe Ala Val Phe Gln Gly Leu Leu Lys Val Leu
            930                 935                 940

Ala Gly Ile Asp Thr Asn Phe Thr Val Thr Ser Lys Ala Ser Asp Glu
945                 950                 955                 960

Asp Gly Asp Phe Ala Glu Leu Tyr Met Phe Lys Trp Thr Thr Leu Leu
                965                 970                 975

Ile Pro Pro Thr Thr Ile Leu Ile Ile Asn Leu Val Gly Val Val Ala
                980                 985                 990

Gly Ile Ser Tyr Ala Ile Asn Ser Gly Tyr Gln Ser Trp Gly Pro Leu
                995                 1000                1005

Phe Gly Lys Leu Phe Phe Ala Phe Trp Val Ile Val His Leu Tyr Pro
            1010                1015                1020

Phe Leu Lys Gly Leu Met Gly Arg Gln Asn Arg Thr Pro Thr Ile Val
1025                1030                1035                1040

Val Val Trp Ala Ile Leu Leu Ala Ser Ile Phe Ser Leu Leu Trp Val
                1045                1050                1055

Arg Ile Asp Pro Phe Thr Thr Arg Val Thr Gly Pro Asp Thr Gln Thr
                1060                1065                1070

Cys Gly Ile Asn Cys
        1075

<210> SEQ ID NO 31
<211> LENGTH: 25
<212> TYPE: DNA
<213> ORGANISM: Zea mays

<400> SEQUENCE: 31
atggagggcg acgcggacgg cgtga                                         25

<210> SEQ ID NO 32
<211> LENGTH: 25
<212> TYPE: DNA
<213> ORGANISM: Zea mays

<400> SEQUENCE: 32
ctagcagttg atgccacacg tctgg                                         25

<210> SEQ ID NO 33
<211> LENGTH: 3753
<212> TYPE: DNA
<213> ORGANISM: Zea mays
<220> FEATURE:
<221> NAME/KEY: CDS
<222> LOCATION: (184)...(3408)

<400> SEQUENCE: 33
cagcagcaga agcactgcgc ggcattgcag cgatcgagcg ggaggaattt ggggcatggt   60
ggtcgccaac gccgctcgga tctagaggcc gcacgggcc gattggtctc cgcccgcctc   120
gtcggtgttg gtgtcgttgg cgtgtggagc cgtctcggtg ggagcagcgg ggagggagcg   180 gag atg gcg gcc aac aag ggg atg gtg gcg ggc tcg cac aac cgc aac   228
    Met Ala Ala Asn Lys Gly Met Val Ala Gly Ser His Asn Arg Asn
    1               5                   10                  15
```

-continued

```
gag ttc gtc atg atc cgc cac gac ggc gat gtg ccg ggc tcg gct aag      276
Glu Phe Val Met Ile Arg His Asp Gly Asp Val Pro Gly Ser Ala Lys
             20                  25                  30 ccc aca aag agt gcg aat gga cag gtc tgc cag att tgc ggt gac tct      324
Pro Thr Lys Ser Ala Asn Gly Gln Val Cys Gln Ile Cys Gly Asp Ser
         35                  40                  45 gtg ggt gtt tca gcc act ggt gat gtc ttt gtt gcc tgc aat gag tgt      372
Val Gly Val Ser Ala Thr Gly Asp Val Phe Val Ala Cys Asn Glu Cys
     50                  55                  60 gcc ttc cct gtc tgc cgc cca tgc tat gag tat gag cgc aag gag ggg      420
Ala Phe Pro Val Cys Arg Pro Cys Tyr Glu Tyr Glu Arg Lys Glu Gly
 65                  70                  75 aac caa tgc tgc ccc cag tgc aag act aga tac aag aga cag aaa ggt      468
Asn Gln Cys Cys Pro Gln Cys Lys Thr Arg Tyr Lys Arg Gln Lys Gly
 80                  85                  90                  95 agc cct cga gtt cat ggt gat gag gat gag gaa gat gtt gat gac cta      516
Ser Pro Arg Val His Gly Asp Glu Asp Glu Glu Asp Val Asp Asp Leu
                100                 105                 110 gac aat gaa ttc aac tac aag caa ggc agt ggg aaa ggc cca gag tgg      564
Asp Asn Glu Phe Asn Tyr Lys Gln Gly Ser Gly Lys Gly Pro Glu Trp
            115                 120                 125 caa ctg caa gga gat gat gct gat ctg tct tca tct gct cgc cat gag      612
Gln Leu Gln Gly Asp Asp Ala Asp Leu Ser Ser Ser Ala Arg His Glu
        130                 135                 140 cca cat cat cgg att cca cgc ctg aca agc ggt caa cag ata tct gga      660
Pro His His Arg Ile Pro Arg Leu Thr Ser Gly Gln Gln Ile Ser Gly
    145                 150                 155 gag att cct gat gct tcc cct gac cgt cat tct atc cgc agt cca aca      708
Glu Ile Pro Asp Ala Ser Pro Asp Arg His Ser Ile Arg Ser Pro Thr
160                 165                 170                 175 tcg agc tat gtt gat cca agc gtc cca gtt cct gtg agg att gtg gac      756
Ser Ser Tyr Val Asp Pro Ser Val Pro Val Pro Val Arg Ile Val Asp
                180                 185                 190 ccc tcg aag gac ttg aat tcc tat ggg ctt aat agt gtt gac tgg aag      804
Pro Ser Lys Asp Leu Asn Ser Tyr Gly Leu Asn Ser Val Asp Trp Lys
            195                 200                 205 gaa aga gtt gag agc tgg agg gtt aaa cag gac aaa aat atg atg caa      852
Glu Arg Val Glu Ser Trp Arg Val Lys Gln Asp Lys Asn Met Met Gln
        210                 215                 220 gtg act aat aaa tat cca gag gct aga gga gga gac atg gag ggg act      900
Val Thr Asn Lys Tyr Pro Glu Ala Arg Gly Gly Asp Met Glu Gly Thr
    225                 230                 235 ggc tca aat gga gaa gat atg caa atg gtt gat gat gca cgg cta cct      948
Gly Ser Asn Gly Glu Asp Met Gln Met Val Asp Asp Ala Arg Leu Pro
240                 245                 250                 255 ttg agc cgt atc gtg cca att tcc tca aac cag ctc aac ctt tac cgg      996
Leu Ser Arg Ile Val Pro Ile Ser Ser Asn Gln Leu Asn Leu Tyr Arg
                260                 265                 270 gta gtg atc att ctc cgt ctt atc atc ctg tgc ttc ttc ttc cag tat     1044
Val Val Ile Ile Leu Arg Leu Ile Ile Leu Cys Phe Phe Phe Gln Tyr
            275                 280                 285 cgt gtc agt cat cca gtg cgt gat gct tat gga tta tgg cta gta tct     1092
Arg Val Ser His Pro Val Arg Asp Ala Tyr Gly Leu Trp Leu Val Ser
        290                 295                 300 gtt atc tgc gag gtc tgg ttt gcc ttg tct tgg ctt cta gat cag ttc     1140
Val Ile Cys Glu Val Trp Phe Ala Leu Ser Trp Leu Leu Asp Gln Phe
    305                 310                 315 cca aaa tgg tat cca atc aac cgt gag aca tat ctt gac agg ctt gca     1188
Pro Lys Trp Tyr Pro Ile Asn Arg Glu Thr Tyr Leu Asp Arg Leu Ala
```

-continued

```
            320                 325                 330                 335
ttg agg tat gat aga gag gga gag cca tca cag ctg gct ccc att gat        1236
Leu Arg Tyr Asp Arg Glu Gly Glu Pro Ser Gln Leu Ala Pro Ile Asp
                        340                 345                 350 gtc ttc gtc agt aca gtg gat cca ttg aag gaa cct cca ctg atc aca        1284
Val Phe Val Ser Thr Val Asp Pro Leu Lys Glu Pro Pro Leu Ile Thr
                355                 360                 365 gcc aac act gtt ttg tcc att ctt tct gtg gat tac cct gtt gac aaa        1332
Ala Asn Thr Val Leu Ser Ile Leu Ser Val Asp Tyr Pro Val Asp Lys
            370                 375                 380 gtg tca tgc tat gtt tct gat gat ggt tca gct atg ctg act ttt gag        1380
Val Ser Cys Tyr Val Ser Asp Asp Gly Ser Ala Met Leu Thr Phe Glu
        385                 390                 395 tct ctc tca gaa acc gca gaa ttt gct aga aag tgg gtt ccc ttt tgt        1428
Ser Leu Ser Glu Thr Ala Glu Phe Ala Arg Lys Trp Val Pro Phe Cys
    400                 405                 410                 415 aag aag cac aat att gaa cca aga gct cca gaa ttt tac ttt gct caa        1476
Lys Lys His Asn Ile Glu Pro Arg Ala Pro Glu Phe Tyr Phe Ala Gln
                        420                 425                 430 aaa ata gat tac ctg aag gac aaa att caa cct tca ttt gtt aag gaa        1524
Lys Ile Asp Tyr Leu Lys Asp Lys Ile Gln Pro Ser Phe Val Lys Glu
                435                 440                 445 aga cgc gca atg aag agg gag tat gaa gaa ttc aaa gta aga atc aat        1572
Arg Arg Ala Met Lys Arg Glu Tyr Glu Glu Phe Lys Val Arg Ile Asn
            450                 455                 460 gcc ctt gtt gcc aaa gca cag aaa gtg cct gaa gag ggg tgg acc atg        1620
Ala Leu Val Ala Lys Ala Gln Lys Val Pro Glu Glu Gly Trp Thr Met
        465                 470                 475 gct gat gga act gca tgg cct ggg aat aat cct agg gac cat cct ggc        1668
Ala Asp Gly Thr Ala Trp Pro Gly Asn Asn Pro Arg Asp His Pro Gly
    480                 485                 490                 495 atg att cag gtt ttc ttg ggg cac agt ggt ggg ctc gac act gat gga        1716
Met Ile Gln Val Phe Leu Gly His Ser Gly Gly Leu Asp Thr Asp Gly
                        500                 505                 510 aat gag tta cca cgt ctt gtc tat gtc tct cgt gaa aag aga cca ggc        1764
Asn Glu Leu Pro Arg Leu Val Tyr Val Ser Arg Glu Lys Arg Pro Gly
                515                 520                 525 ttt cag cat cac aag aag gct ggt gca atg aat gcg ctg att cgt gta        1812
Phe Gln His His Lys Lys Ala Gly Ala Met Asn Ala Leu Ile Arg Val
            530                 535                 540 tct gct gtg ctg aca aat ggt gcc tat ctt ctc aat gtg gat tgc gac        1860
Ser Ala Val Leu Thr Asn Gly Ala Tyr Leu Leu Asn Val Asp Cys Asp
        545                 550                 555 cat tac ttc aat agc agc aaa gct ctt aga gaa gca atg tgc ttc atg        1908
His Tyr Phe Asn Ser Ser Lys Ala Leu Arg Glu Ala Met Cys Phe Met
560                 565                 570                 575 atg gat ccg gct cta gga agg aaa act tgt tat gta caa ttt cca cag        1956
Met Asp Pro Ala Leu Gly Arg Lys Thr Cys Tyr Val Gln Phe Pro Gln
                580                 585                 590 aga ttt gat ggc att gac ttg cac gat cga tat gct aat cgg aac ata        2004
Arg Phe Asp Gly Ile Asp Leu His Asp Arg Tyr Ala Asn Arg Asn Ile
                595                 600                 605 gtt ttc ttt gat atc aac atg aaa ggt ctg gat ggc att cag ggt cca        2052
Val Phe Phe Asp Ile Asn Met Lys Gly Leu Asp Gly Ile Gln Gly Pro
            610                 615                 620 gtt tac gtg gga aca gga tgc tgt ttc aat aga cag gct ttg tat gga        2100
Val Tyr Val Gly Thr Gly Cys Cys Phe Asn Arg Gln Ala Leu Tyr Gly
        625                 630                 635 tac gat cct gtt ttg act gaa gct gat ctg gag cca aac att gtt att        2148
```

```
Tyr Asp Pro Val Leu Thr Glu Ala Asp Leu Glu Pro Asn Ile Val Ile
640             645                 650                 655 aag agc tgc tgt ggt aga agg aaa aag aac aag agt tat atg gat          2196
Lys Ser Cys Cys Gly Arg Arg Lys Lys Asn Lys Ser Tyr Met Asp
                660                 665                 670 agt caa agc cgt att atg aag aga aca gaa tct tca gct ccc atc ttc      2244
Ser Gln Ser Arg Ile Met Lys Arg Thr Glu Ser Ser Ala Pro Ile Phe
            675                 680                 685 aat atg gaa gac atc gaa gag ggt att gaa ggt tac gag gat gaa agg      2292
Asn Met Glu Asp Ile Glu Glu Gly Ile Glu Gly Tyr Glu Asp Glu Arg
        690                 695                 700 tca gtg ctt atg tcc cag agg aaa ttg gag aaa cgc ttt ggt cag tct      2340
Ser Val Leu Met Ser Gln Arg Lys Leu Glu Lys Arg Phe Gly Gln Ser
    705                 710                 715 cct att ttc att gca tcc acc ttt atg aca caa ggt ggc ata cca cct      2388
Pro Ile Phe Ile Ala Ser Thr Phe Met Thr Gln Gly Gly Ile Pro Pro
720                 725                 730                 735 tca aca aac cca gct tct cta cta aag gaa gct atc cat gtc atc agt      2436
Ser Thr Asn Pro Ala Ser Leu Leu Lys Glu Ala Ile His Val Ile Ser
                740                 745                 750 tgt gga tat gag gac aaa act gaa tgg gga aaa gag att ggc tgg atc      2484
Cys Gly Tyr Glu Asp Lys Thr Glu Trp Gly Lys Glu Ile Gly Trp Ile
            755                 760                 765 tat ggt tca gta acg gag gat att ctg act ggg ttt aaa atg cat gca      2532
Tyr Gly Ser Val Thr Glu Asp Ile Leu Thr Gly Phe Lys Met His Ala
        770                 775                 780 agg ggc tgg caa tca atc tac tgc atg cca cca cga cct tgt ttc aag      2580
Arg Gly Trp Gln Ser Ile Tyr Cys Met Pro Pro Arg Pro Cys Phe Lys
    785                 790                 795 ggt tct gca cca atc aat ctt tcc gat cgt ctt aat cag gtg ctc cgt      2628
Gly Ser Ala Pro Ile Asn Leu Ser Asp Arg Leu Asn Gln Val Leu Arg
800                 805                 810                 815 tgg gct ctt ggg tca gtg gaa att ctg ctt agt aga cat tgt cct atc      2676
Trp Ala Leu Gly Ser Val Glu Ile Leu Leu Ser Arg His Cys Pro Ile
                820                 825                 830 tgg tat ggt tac aat gga cga ttg aag ctt ttg gag agg ctg gct tac      2724
Trp Tyr Gly Tyr Asn Gly Arg Leu Lys Leu Leu Glu Arg Leu Ala Tyr
            835                 840                 845 atc aac act att gta tat cca atc aca tcc att ccg ctt att gcc tat      2772
Ile Asn Thr Ile Val Tyr Pro Ile Thr Ser Ile Pro Leu Ile Ala Tyr
        850                 855                 860 tgt gtg ctt ccc gct atc tgc ctc ctt acc aat aaa ttt atc att cct      2820
Cys Val Leu Pro Ala Ile Cys Leu Leu Thr Asn Lys Phe Ile Ile Pro
    865                 870                 875 gag att agc aat tat gct ggg atg ttc ttc att ctt ctt ttc gcc tcc      2868
Glu Ile Ser Asn Tyr Ala Gly Met Phe Phe Ile Leu Leu Phe Ala Ser
880                 885                 890                 895 att ttt gcc act ggt ata ttg gag ctt aga tgg agt ggt gtt ggc att      2916
Ile Phe Ala Thr Gly Ile Leu Glu Leu Arg Trp Ser Gly Val Gly Ile
                900                 905                 910 gaa gat tgg tgg aga aat gag cag ttt tgg gtt att ggt ggc acc tct      2964
Glu Asp Trp Trp Arg Asn Glu Gln Phe Trp Val Ile Gly Gly Thr Ser
            915                 920                 925 gcc cat ctc ttc gca gtg ttc cag ggt ctg ctg aaa gtg ttg gct ggg      3012
Ala His Leu Phe Ala Val Phe Gln Gly Leu Leu Lys Val Leu Ala Gly
        930                 935                 940 att gat acc aac ttc aca gtt acc tca aag gca tct gat gag gat ggc      3060
Ile Asp Thr Asn Phe Thr Val Thr Ser Lys Ala Ser Asp Glu Asp Gly
    945                 950                 955
```

```
gac ttt gct gag cta tat gtg ttc aag tgg acc agt ttg ctc att cct       3108
Asp Phe Ala Glu Leu Tyr Val Phe Lys Trp Thr Ser Leu Leu Ile Pro
960                 965                 970                 975 ccg acc act gtt ctt gtc att aac ctg gtc gga atg gtg gca gga att       3156
Pro Thr Thr Val Leu Val Ile Asn Leu Val Gly Met Val Ala Gly Ile
                980                 985                 990 tct tat gcc att aac agt ggc tac caa tcc tgg ggt ccg ctc ttt gga       3204
Ser Tyr Ala Ile Asn Ser Gly Tyr Gln Ser Trp Gly Pro Leu Phe Gly
                995                 1000                1005 aag ctg ttc ttc tcg atc tgg gtg atc ctc cat ctc tac ccc ttc ctc       3252
Lys Leu Phe Phe Ser Ile Trp Val Ile Leu His Leu Tyr Pro Phe Leu
                1010                1015                1020 aag ggt ctc atg gga agg cag aac cgc aca cca aca atc gtc att gtc       3300
Lys Gly Leu Met Gly Arg Gln Asn Arg Thr Pro Thr Ile Val Ile Val
        1025                1030                1035 tgg tcc atc ctt ctt gca tct atc ttc tcc ttg ctg tgg gtg aag atc       3348
Trp Ser Ile Leu Leu Ala Ser Ile Phe Ser Leu Leu Trp Val Lys Ile
1040                1045                1050                1055 gat cct ttc atc tcc ccg aca cag aaa gct gct gcc ttg ggg caa tgt       3396
Asp Pro Phe Ile Ser Pro Thr Gln Lys Ala Ala Ala Leu Gly Gln Cys
                1060                1065                1070 ggc gtc aac tgc tgatcgagac agtgactctt atttgaagag gctcaatcaa           3448
Gly Val Asn Cys
            1075 gatctgcccc ctcgtgtaaa tacctgagga ggctagatgg gaattccttt tgttgtaggt    3508 gaggatggat ttgcatctaa gttatgcctc tgttcattag cttcttccgt gccggtgctg    3568 ctgcggacta agaatcacgg agcctttcta ccttccatgt agcgccagcc agcagcgtaa    3628 gatgtgaatt ttgaagtttt gttatgcgtg cagtttattg ttttagagta aattatcatt    3688 tgtttgtggg aactgttcac acgagcttat aatggcaatg ctgttattta aaaaaaaaaa    3748 aaaaa                                                                 3753

<210> SEQ ID NO 34
<211> LENGTH: 1075
<212> TYPE: PRT
<213> ORGANISM: Zea mays

<400> SEQUENCE: 34

Met Ala Ala Asn Lys Gly Met Val Ala Gly Ser His Asn Arg Asn Glu
1               5                   10                  15

Phe Val Met Ile Arg His Asp Gly Asp Val Pro Gly Ser Ala Lys Pro
            20                  25                  30

Thr Lys Ser Ala Asn Gly Gln Val Cys Gln Ile Cys Gly Asp Ser Val
        35                  40                  45

Gly Val Ser Ala Thr Gly Asp Val Phe Val Ala Cys Asn Glu Cys Ala
    50                  55                  60

Phe Pro Val Cys Arg Pro Cys Tyr Glu Tyr Glu Arg Lys Glu Gly Asn
65                  70                  75                  80

Gln Cys Cys Pro Gln Cys Lys Thr Arg Tyr Lys Arg Gln Lys Gly Ser
                85                  90                  95

Pro Arg Val His Gly Asp Glu Asp Glu Glu Asp Val Asp Asp Leu Asp
            100                 105                 110

Asn Glu Phe Asn Tyr Lys Gln Gly Ser Gly Lys Gly Pro Glu Trp Gln
        115                 120                 125

Leu Gln Gly Asp Asp Ala Asp Leu Ser Ser Ser Ala Arg His Glu Pro
    130                 135                 140
```

```
His His Arg Ile Pro Arg Leu Thr Ser Gly Gln Gln Ile Ser Gly Glu
145                 150                 155                 160

Ile Pro Asp Ala Ser Pro Asp Arg His Ser Ile Arg Ser Pro Thr Ser
            165                 170                 175

Ser Tyr Val Asp Pro Ser Val Pro Val Arg Ile Val Asp Pro
            180                 185                 190

Ser Lys Asp Leu Asn Ser Tyr Gly Leu Asn Ser Val Asp Trp Lys Glu
            195                 200                 205

Arg Val Glu Ser Trp Arg Val Lys Gln Asp Lys Asn Met Met Gln Val
            210                 215                 220

Thr Asn Lys Tyr Pro Glu Ala Arg Gly Gly Asp Met Glu Gly Thr Gly
225                 230                 235                 240

Ser Asn Gly Glu Asp Met Gln Met Val Asp Asp Ala Arg Leu Pro Leu
                245                 250                 255

Ser Arg Ile Val Pro Ile Ser Ser Asn Gln Leu Asn Leu Tyr Arg Val
            260                 265                 270

Val Ile Ile Leu Arg Leu Ile Ile Leu Cys Phe Phe Phe Gln Tyr Arg
            275                 280                 285

Val Ser His Pro Val Arg Asp Ala Tyr Gly Leu Trp Leu Val Ser Val
            290                 295                 300

Ile Cys Glu Val Trp Phe Ala Leu Ser Trp Leu Leu Asp Gln Phe Pro
305                 310                 315                 320

Lys Trp Tyr Pro Ile Asn Arg Glu Thr Tyr Leu Asp Arg Leu Ala Leu
                325                 330                 335

Arg Tyr Asp Arg Glu Gly Glu Pro Ser Gln Leu Ala Pro Ile Asp Val
            340                 345                 350

Phe Val Ser Thr Val Asp Pro Leu Lys Glu Pro Pro Leu Ile Thr Ala
            355                 360                 365

Asn Thr Val Leu Ser Ile Leu Ser Val Asp Tyr Pro Val Asp Lys Val
            370                 375                 380

Ser Cys Tyr Val Ser Asp Asp Gly Ser Ala Met Leu Thr Phe Glu Ser
385                 390                 395                 400

Leu Ser Glu Thr Ala Glu Phe Ala Arg Lys Trp Val Pro Phe Cys Lys
                405                 410                 415

Lys His Asn Ile Glu Pro Arg Ala Pro Glu Phe Tyr Phe Ala Gln Lys
            420                 425                 430

Ile Asp Tyr Leu Lys Asp Lys Ile Gln Pro Ser Phe Val Lys Glu Arg
            435                 440                 445

Arg Ala Met Lys Arg Glu Tyr Glu Glu Phe Lys Val Arg Ile Asn Ala
            450                 455                 460

Leu Val Ala Lys Ala Gln Lys Val Pro Glu Glu Gly Trp Thr Met Ala
465                 470                 475                 480

Asp Gly Thr Ala Trp Pro Gly Asn Asn Pro Arg Asp His Pro Gly Met
                485                 490                 495

Ile Gln Val Phe Leu Gly His Ser Gly Gly Leu Asp Thr Asp Gly Asn
            500                 505                 510

Glu Leu Pro Arg Leu Val Tyr Val Ser Arg Glu Lys Arg Pro Gly Phe
            515                 520                 525

Gln His His Lys Lys Ala Gly Ala Met Asn Ala Leu Ile Arg Val Ser
            530                 535                 540

Ala Val Leu Thr Asn Gly Ala Tyr Leu Leu Asn Val Asp Cys Asp His
545                 550                 555                 560

Tyr Phe Asn Ser Ser Lys Ala Leu Arg Glu Ala Met Cys Phe Met Met
```

-continued

```
                565                 570                 575
Asp Pro Ala Leu Gly Arg Lys Thr Cys Tyr Val Gln Phe Pro Gln Arg
                580                 585                 590
Phe Asp Gly Ile Asp Leu His Asp Arg Tyr Ala Asn Arg Asn Ile Val
                595                 600                 605
Phe Phe Asp Ile Asn Met Lys Gly Leu Asp Gly Ile Gln Gly Pro Val
                610                 615                 620
Tyr Val Gly Thr Gly Cys Cys Phe Asn Arg Gln Ala Leu Tyr Gly Tyr
625                 630                 635                 640
Asp Pro Val Leu Thr Glu Ala Asp Leu Glu Pro Asn Ile Val Ile Lys
                645                 650                 655
Ser Cys Cys Gly Arg Arg Lys Lys Lys Asn Lys Ser Tyr Met Asp Ser
                660                 665                 670
Gln Ser Arg Ile Met Lys Arg Thr Glu Ser Ser Ala Pro Ile Phe Asn
                675                 680                 685
Met Glu Asp Ile Glu Glu Gly Ile Glu Gly Tyr Glu Asp Glu Arg Ser
                690                 695                 700
Val Leu Met Ser Gln Arg Lys Leu Glu Lys Arg Phe Gly Gln Ser Pro
705                 710                 715                 720
Ile Phe Ile Ala Ser Thr Phe Met Thr Gln Gly Gly Ile Pro Pro Ser
                725                 730                 735
Thr Asn Pro Ala Ser Leu Leu Lys Glu Ala Ile His Val Ile Ser Cys
                740                 745                 750
Gly Tyr Glu Asp Lys Thr Glu Trp Gly Lys Glu Ile Gly Trp Ile Tyr
                755                 760                 765
Gly Ser Val Thr Glu Asp Ile Leu Thr Gly Phe Lys Met His Ala Arg
                770                 775                 780
Gly Trp Gln Ser Ile Tyr Cys Met Pro Pro Arg Pro Cys Phe Lys Gly
785                 790                 795                 800
Ser Ala Pro Ile Asn Leu Ser Asp Arg Leu Asn Gln Val Leu Arg Trp
                805                 810                 815
Ala Leu Gly Ser Val Glu Ile Leu Leu Ser Arg His Cys Pro Ile Trp
                820                 825                 830
Tyr Gly Tyr Asn Gly Arg Leu Lys Leu Leu Glu Arg Leu Ala Tyr Ile
                835                 840                 845
Asn Thr Ile Val Tyr Pro Ile Thr Ser Ile Pro Leu Ile Ala Tyr Cys
                850                 855                 860
Val Leu Pro Ala Ile Cys Leu Leu Thr Asn Lys Phe Ile Ile Pro Glu
865                 870                 875                 880
Ile Ser Asn Tyr Ala Gly Met Phe Phe Ile Leu Phe Ala Ser Ile
                885                 890                 895
Phe Ala Thr Gly Ile Leu Glu Leu Arg Trp Ser Gly Val Gly Ile Glu
                900                 905                 910
Asp Trp Trp Arg Asn Glu Gln Phe Trp Val Ile Gly Thr Ser Ala
                915                 920                 925
His Leu Phe Ala Val Phe Gln Gly Leu Leu Lys Val Leu Ala Gly Ile
                930                 935                 940
Asp Thr Asn Phe Thr Val Thr Ser Lys Ala Ser Asp Glu Asp Gly Asp
945                 950                 955                 960
Phe Ala Glu Leu Tyr Val Phe Lys Trp Thr Ser Leu Leu Ile Pro Pro
                965                 970                 975
Thr Thr Val Leu Val Ile Asn Leu Val Gly Met Val Ala Gly Ile Ser
                980                 985                 990
```

```
Tyr Ala Ile Asn Ser Gly Tyr Gln Ser Trp Gly Pro Leu Phe Gly Lys
        995                 1000                1005

Leu Phe Phe Ser Ile Trp Val Ile Leu His Leu Tyr Pro Phe Leu Lys
    1010                1015                1020

Gly Leu Met Gly Arg Gln Asn Arg Thr Pro Thr Ile Val Ile Val Trp
1025                1030                1035                1040

Ser Ile Leu Leu Ala Ser Ile Phe Ser Leu Leu Trp Val Lys Ile Asp
                1045                1050                1055

Pro Phe Ile Ser Pro Thr Gln Lys Ala Ala Ala Leu Gly Gln Cys Gly
            1060                1065                1070

Val Asn Cys
        1075

<210> SEQ ID NO 35
<211> LENGTH: 25
<212> TYPE: DNA
<213> ORGANISM: Zea mays

<400> SEQUENCE: 35
atggcggcca acaaggggat ggtgg                                           25

<210> SEQ ID NO 36
<211> LENGTH: 25
<212> TYPE: DNA
<213> ORGANISM: Zea mays

<400> SEQUENCE: 36
tcagcagttg acgccacatt gcccc                                           25

<210> SEQ ID NO 37
<211> LENGTH: 3969
<212> TYPE: DNA
<213> ORGANISM: Zea mays
<220> FEATURE:
<221> NAME/KEY: CDS
<222> LOCATION: (144)...(3401)

<400> SEQUENCE: 37
cttctccctc gtcggtgcgg cgtggcgcgg ctcggcgttc ggtgagaaac cactcggggg     60
atgaggatct gctgctagag tgagaggagc tacggtcagt atcctctgcc ttcgtcggcg    120
gcggaagtgg aggggaggaa gcg atg gag gcg agc gcc ggg ctg gtg gcc ggc   173
                         Met Glu Ala Ser Ala Gly Leu Val Ala Gly
                          1               5                  10 tcc cac aac cgc aac gag ctc gtc gtc atc cgc cgc gac ggc gat ccc      221
Ser His Asn Arg Asn Glu Leu Val Val Ile Arg Arg Asp Gly Asp Pro
             15                  20                  25 ggg ccg aag ccg ccg cgg gag cag aac ggg cag gtg tgc cag att tgc      269
Gly Pro Lys Pro Pro Arg Glu Gln Asn Gly Gln Val Cys Gln Ile Cys
         30                  35                  40 ggc gac gac gtc ggc ctt gcc ccc ggc ggg gac ccc ttc gtg gcg tgc      317
Gly Asp Asp Val Gly Leu Ala Pro Gly Gly Asp Pro Phe Val Ala Cys
     45                  50                  55 aac gag tgc gcc ttc ccc gtc tgc cgg gac tgc tac gaa tac gag cgc      365
Asn Glu Cys Ala Phe Pro Val Cys Arg Asp Cys Tyr Glu Tyr Glu Arg
 60                  65                  70 cgg gag ggc acg cag aac tgc ccc cag tgc aag act cga tac aag cgc      413
Arg Glu Gly Thr Gln Asn Cys Pro Gln Cys Lys Thr Arg Tyr Lys Arg
 75                  80                  85                  90 ctc aag ggc tgc caa cgt gtg acc ggt gac gag gag gag gac ggc gtc      461
```

-continued

| | | | | | | | | | | | | | | | |
|---|---|---|---|---|---|---|---|---|---|---|---|---|---|---|---|
| Leu | Lys | Gly | Cys | Gln | Arg | Val | Thr | Gly | Asp | Glu | Glu | Asp | Gly | Val | |
| | | | 95 | | | | | 100 | | | | 105 | | | |

| gat | gac | ctg | gac | aac | gag | ttc | aac | tgg | gac | ggc | cat | gac | tcg | cag | tct | 509 |
|---|---|---|---|---|---|---|---|---|---|---|---|---|---|---|---|---|
| Asp | Asp | Leu | Asp | Asn | Glu | Phe | Asn | Trp | Asp | Gly | His | Asp | Ser | Gln | Ser | |
| | | 110 | | | | | 115 | | | | | 120 | | | | |

| gtg | gcc | gag | tcc | atg | ctc | tac | ggc | cac | atg | agc | tac | ggc | cgt | gga | ggt | 557 |
|---|---|---|---|---|---|---|---|---|---|---|---|---|---|---|---|---|
| Val | Ala | Glu | Ser | Met | Leu | Tyr | Gly | His | Met | Ser | Tyr | Gly | Arg | Gly | Gly | |
| | | 125 | | | | | 130 | | | | | 135 | | | | |

| gac | cct | aat | ggc | gcg | cca | caa | gct | ttc | cag | ctc | aac | ccc | aat | gtt | cca | 605 |
|---|---|---|---|---|---|---|---|---|---|---|---|---|---|---|---|---|
| Asp | Pro | Asn | Gly | Ala | Pro | Gln | Ala | Phe | Gln | Leu | Asn | Pro | Asn | Val | Pro | |
| | 140 | | | | | 145 | | | | | 150 | | | | | |

| ctc | ctc | acc | aac | ggg | caa | atg | gtg | gat | gac | atc | cca | ccg | gag | cag | cac | 653 |
|---|---|---|---|---|---|---|---|---|---|---|---|---|---|---|---|---|
| Leu | Leu | Thr | Asn | Gly | Gln | Met | Val | Asp | Asp | Ile | Pro | Pro | Glu | Gln | His | |
| 155 | | | | | 160 | | | | | 165 | | | | | 170 | |

| gcg | ctg | gtg | cct | tct | ttc | atg | ggt | ggt | ggg | gga | aag | agg | ata | cat | ccc | 701 |
|---|---|---|---|---|---|---|---|---|---|---|---|---|---|---|---|---|
| Ala | Leu | Val | Pro | Ser | Phe | Met | Gly | Gly | Gly | Gly | Lys | Arg | Ile | His | Pro | |
| | | | | 175 | | | | | 180 | | | | | 185 | | |

| ctt | cct | tat | gcg | gat | ccc | agc | tta | cct | gtg | caa | ccc | agg | tct | atg | gac | 749 |
|---|---|---|---|---|---|---|---|---|---|---|---|---|---|---|---|---|
| Leu | Pro | Tyr | Ala | Asp | Pro | Ser | Leu | Pro | Val | Gln | Pro | Arg | Ser | Met | Asp | |
| | | | 190 | | | | | 195 | | | | | 200 | | | |

| cca | tcc | aag | gat | ctt | gct | gca | tat | ggg | tat | ggt | agt | gtt | gct | tgg | aag | 797 |
|---|---|---|---|---|---|---|---|---|---|---|---|---|---|---|---|---|
| Pro | Ser | Lys | Asp | Leu | Ala | Ala | Tyr | Gly | Tyr | Gly | Ser | Val | Ala | Trp | Lys | |
| | | 205 | | | | | 210 | | | | | 215 | | | | |

| gaa | cgg | atg | gag | aat | tgg | aag | cag | aga | caa | gag | agg | atg | cac | cag | acg | 845 |
|---|---|---|---|---|---|---|---|---|---|---|---|---|---|---|---|---|
| Glu | Arg | Met | Glu | Asn | Trp | Lys | Gln | Arg | Gln | Glu | Arg | Met | His | Gln | Thr | |
| | 220 | | | | | 225 | | | | | 230 | | | | | |

| ggg | aat | gat | ggt | ggt | ggt | gat | gat | ggt | gac | gat | gct | gat | cta | cca | cta | 893 |
|---|---|---|---|---|---|---|---|---|---|---|---|---|---|---|---|---|
| Gly | Asn | Asp | Gly | Gly | Gly | Asp | Asp | Gly | Asp | Asp | Ala | Asp | Leu | Pro | Leu | |
| 235 | | | | | 240 | | | | | 245 | | | | | 250 | |

| atg | gat | gaa | gca | aga | caa | caa | ctg | tcc | agg | aaa | att | cca | ctt | cca | tca | 941 |
|---|---|---|---|---|---|---|---|---|---|---|---|---|---|---|---|---|
| Met | Asp | Glu | Ala | Arg | Gln | Gln | Leu | Ser | Arg | Lys | Ile | Pro | Leu | Pro | Ser | |
| | | | | 255 | | | | | 260 | | | | | 265 | | |

| agc | cag | att | aat | cca | tat | agg | atg | att | atc | att | att | cgg | ctt | gtg | gtt | 989 |
|---|---|---|---|---|---|---|---|---|---|---|---|---|---|---|---|---|
| Ser | Gln | Ile | Asn | Pro | Tyr | Arg | Met | Ile | Ile | Ile | Ile | Arg | Leu | Val | Val | |
| | | | 270 | | | | | 275 | | | | | 280 | | | |

| ttg | ggg | ttc | ttc | ttc | cac | tac | cga | gtg | atg | cat | ccg | gtg | aat | gat | gca | 1037 |
|---|---|---|---|---|---|---|---|---|---|---|---|---|---|---|---|---|
| Leu | Gly | Phe | Phe | Phe | His | Tyr | Arg | Val | Met | His | Pro | Val | Asn | Asp | Ala | |
| | | 285 | | | | | 290 | | | | | 295 | | | | |

| ttt | gct | ttg | tgg | ctc | ata | tct | gtt | atc | tgt | gaa | atc | tgg | ttt | gcc | atg | 1085 |
|---|---|---|---|---|---|---|---|---|---|---|---|---|---|---|---|---|
| Phe | Ala | Leu | Trp | Leu | Ile | Ser | Val | Ile | Cys | Glu | Ile | Trp | Phe | Ala | Met | |
| | | 300 | | | | | 305 | | | | | 310 | | | | |

| tct | tgg | att | ctt | gat | caa | ttc | cca | aag | tgg | ttc | cct | att | gag | aga | gag | 1133 |
|---|---|---|---|---|---|---|---|---|---|---|---|---|---|---|---|---|
| Ser | Trp | Ile | Leu | Asp | Gln | Phe | Pro | Lys | Trp | Phe | Pro | Ile | Glu | Arg | Glu | |
| 315 | | | | | 320 | | | | | 325 | | | | | 330 | |

| act | tac | cta | gac | cgg | ctg | tca | ctg | agg | ttc | gac | aag | gaa | ggc | cag | cca | 1181 |
|---|---|---|---|---|---|---|---|---|---|---|---|---|---|---|---|---|
| Thr | Tyr | Leu | Asp | Arg | Leu | Ser | Leu | Arg | Phe | Asp | Lys | Glu | Gly | Gln | Pro | |
| | | | | 335 | | | | | 340 | | | | | 345 | | |

| tct | caa | ctt | gct | cca | att | gat | ttc | ttt | gtc | agt | acg | gtt | gat | ccc | tta | 1229 |
|---|---|---|---|---|---|---|---|---|---|---|---|---|---|---|---|---|
| Ser | Gln | Leu | Ala | Pro | Ile | Asp | Phe | Phe | Val | Ser | Thr | Val | Asp | Pro | Leu | |
| | | | 350 | | | | | 355 | | | | | 360 | | | |

| aag | gaa | cct | cct | ttg | gtc | aca | aca | aat | act | gtt | cta | tct | atc | ctt | tcg | 1277 |
|---|---|---|---|---|---|---|---|---|---|---|---|---|---|---|---|---|
| Lys | Glu | Pro | Pro | Leu | Val | Thr | Thr | Asn | Thr | Val | Leu | Ser | Ile | Leu | Ser | |
| | | 365 | | | | | 370 | | | | | 375 | | | | |

| gtg | gat | tat | cct | gtt | gat | aag | gtt | tct | tgc | tat | gtt | tct | gat | gat | ggt | 1325 |
|---|---|---|---|---|---|---|---|---|---|---|---|---|---|---|---|---|
| Val | Asp | Tyr | Pro | Val | Asp | Lys | Val | Ser | Cys | Tyr | Val | Ser | Asp | Asp | Gly | |
| | 380 | | | | | 385 | | | | | 390 | | | | | |

| gct | gca | atg | cta | acg | ttt | gaa | gca | tta | tct | gaa | aca | tct | gaa | ttt | gca | 1373 |
|---|---|---|---|---|---|---|---|---|---|---|---|---|---|---|---|---|
| Ala | Ala | Met | Leu | Thr | Phe | Glu | Ala | Leu | Ser | Glu | Thr | Ser | Glu | Phe | Ala | |
| 395 | | | | | 400 | | | | | 405 | | | | | 410 | |

-continued

```
aag aaa tgg gtt cct ttc tgc aaa cgg tac aat att gaa cct cgc gct    1421
Lys Lys Trp Val Pro Phe Cys Lys Arg Tyr Asn Ile Glu Pro Arg Ala
            415                 420                 425 cca gag tgg tac ttc caa cag aag ata gac tac ttg aaa gac aag gtg    1469
Pro Glu Trp Tyr Phe Gln Gln Lys Ile Asp Tyr Leu Lys Asp Lys Val
        430                 435                 440 gca gca aac ttt gtt agg gag agg aga gca atg aag aga gag tat gag    1517
Ala Ala Asn Phe Val Arg Glu Arg Arg Ala Met Lys Arg Glu Tyr Glu
    445                 450                 455 gaa ttc aag gtg aga atc aat gcc tta gtt gcc aaa gcc cag aaa gtt    1565
Glu Phe Lys Val Arg Ile Asn Ala Leu Val Ala Lys Ala Gln Lys Val
460                 465                 470 cct gaa gaa gga tgg aca atg caa gat gga acc ccc tgg cct gga aac    1613
Pro Glu Glu Gly Trp Thr Met Gln Asp Gly Thr Pro Trp Pro Gly Asn
475                 480                 485                 490 aat gtt cgt gat cat cct gga atg att cag gtc ttc ctt ggc caa agc    1661
Asn Val Arg Asp His Pro Gly Met Ile Gln Val Phe Leu Gly Gln Ser
                495                 500                 505 gga ggc ctt gac tgt gag gga aat gaa ctg cca cga ttg gtt tat gtt    1709
Gly Gly Leu Asp Cys Glu Gly Asn Glu Leu Pro Arg Leu Val Tyr Val
            510                 515                 520 tct aga gag aaa cga cca ggc tat aac cat cat aag aaa gct ggt gct    1757
Ser Arg Glu Lys Arg Pro Gly Tyr Asn His His Lys Lys Ala Gly Ala
        525                 530                 535 atg aat gca ttg gtc cga gtc tct gct gta cta aca aat gct cca tat    1805
Met Asn Ala Leu Val Arg Val Ser Ala Val Leu Thr Asn Ala Pro Tyr
    540                 545                 550 ttg tta aac ttg gat tgt gat cac tac atc aac aac agc aag gct ata    1853
Leu Leu Asn Leu Asp Cys Asp His Tyr Ile Asn Asn Ser Lys Ala Ile
555                 560                 565                 570 aag gaa gca atg tgt ttt atg atg gac cct tta cta gga aag aag gtt    1901
Lys Glu Ala Met Cys Phe Met Met Asp Pro Leu Leu Gly Lys Lys Val
                575                 580                 585 tgc tat gta cag ttc cct caa aga ttt gat ggg att gat cgc cat gac    1949
Cys Tyr Val Gln Phe Pro Gln Arg Phe Asp Gly Ile Asp Arg His Asp
            590                 595                 600 cga tat gct aac cgg aat gtt gtc ttt ttt gat atc aac atg aaa ggt    1997
Arg Tyr Ala Asn Arg Asn Val Val Phe Phe Asp Ile Asn Met Lys Gly
        605                 610                 615 ttg gat ggt att cag ggt cca att tat gtt ggt act gga tgt gta ttt    2045
Leu Asp Gly Ile Gln Gly Pro Ile Tyr Val Gly Thr Gly Cys Val Phe
    620                 625                 630 aga agg cag gca tta tat ggt tat gat gcc ccc aaa aca aag aag cca    2093
Arg Arg Gln Ala Leu Tyr Gly Tyr Asp Ala Pro Lys Thr Lys Lys Pro
635                 640                 645                 650 cca tca agg act tgc aac tgc tgg ccc aag tgg tgc ttt tgc tgt tgc    2141
Pro Ser Arg Thr Cys Asn Cys Trp Pro Lys Trp Cys Phe Cys Cys Cys
                655                 660                 665 tgc ttt ggc aat agg aag caa aag aag act acc aaa ccc aaa aca gag    2189
Cys Phe Gly Asn Arg Lys Gln Lys Lys Thr Thr Lys Pro Lys Thr Glu
            670                 675                 680 aag aaa aag tta tta ttt ttc aag aaa gaa gag aac caa tcc cct gca    2237
Lys Lys Lys Leu Leu Phe Phe Lys Lys Glu Glu Asn Gln Ser Pro Ala
        685                 690                 695 tat gct ctt ggt gaa att gac gaa gct gct cca gga gct gag aat gaa    2285
Tyr Ala Leu Gly Glu Ile Asp Glu Ala Ala Pro Gly Ala Glu Asn Glu
    700                 705                 710 aag gcc ggt att gta aat caa caa aaa tta gaa aag aaa ttt ggc caa    2333
Lys Ala Gly Ile Val Asn Gln Gln Lys Leu Glu Lys Lys Phe Gly Gln
715                 720                 725                 730
```

| | | |
|---|---|---|
| tct tct gtt ttt gtt aca tcc aca ctt ctc gag aat ggt gga acc ttg<br>Ser Ser Val Phe Val Thr Ser Thr Leu Leu Glu Asn Gly Gly Thr Leu<br>             735                    740                    745 | 2381 |

```
tct tct gtt ttt gtt aca tcc aca ctt ctc gag aat ggt gga acc ttg    2381
Ser Ser Val Phe Val Thr Ser Thr Leu Leu Glu Asn Gly Gly Thr Leu
            735                 740                 745 aag agt gca agt cct gct tct ctt ttg aaa gaa gct ata cat gtc att    2429
Lys Ser Ala Ser Pro Ala Ser Leu Leu Lys Glu Ala Ile His Val Ile
            750                 755                 760 agt tgt ggt tat gaa gac aag aca gac tgg gga aaa gag att ggc tgg    2477
Ser Cys Gly Tyr Glu Asp Lys Thr Asp Trp Gly Lys Glu Ile Gly Trp
            765                 770                 775 atc tat gga tca gtt aca gaa gat att cta act ggt ttc aag atg cat    2525
Ile Tyr Gly Ser Val Thr Glu Asp Ile Leu Thr Gly Phe Lys Met His
            780                 785                 790 tgt cat ggt tgg cgg tca att tac tgc ata cct aaa cgg gtt gca ttc    2573
Cys His Gly Trp Arg Ser Ile Tyr Cys Ile Pro Lys Arg Val Ala Phe
795                 800                 805                 810 aaa ggt tct gca cct ctg aat ctt tca gat cgt ctt cac cag gtg ctt    2621
Lys Gly Ser Ala Pro Leu Asn Leu Ser Asp Arg Leu His Gln Val Leu
            815                 820                 825 cgg tgg gct ctt ggg tct att gag atc ttc ttc agc aat cat tgc cct    2669
Arg Trp Ala Leu Gly Ser Ile Glu Ile Phe Phe Ser Asn His Cys Pro
            830                 835                 840 ctt tgg tat ggg tat ggt ggc ggt ctg aaa ttt ttg gaa aga ttt tcc    2717
Leu Trp Tyr Gly Tyr Gly Gly Gly Leu Lys Phe Leu Glu Arg Phe Ser
            845                 850                 855 tac atc aac tcc atc gtg tat cct tgg aca tct att ccc ctc ttg gct    2765
Tyr Ile Asn Ser Ile Val Tyr Pro Trp Thr Ser Ile Pro Leu Leu Ala
            860                 865                 870 tac tgt aca ttg cct gcc atc tgt tta ttg aca ggg aaa ttt atc act    2813
Tyr Cys Thr Leu Pro Ala Ile Cys Leu Leu Thr Gly Lys Phe Ile Thr
875                 880                 885                 890 cca gag ctg aat aat gtt gcc agc ctg tgg ttc atg tca ctt ttt atc    2861
Pro Glu Leu Asn Asn Val Ala Ser Leu Trp Phe Met Ser Leu Phe Ile
            895                 900                 905 tgc att ttt gct acg agc atc cta gaa atg aga tgg agt ggt gtt gga    2909
Cys Ile Phe Ala Thr Ser Ile Leu Glu Met Arg Trp Ser Gly Val Gly
            910                 915                 920 att gat gac tgg tgg agg aat gag cag ttc tgg gtc att gga ggt gtg    2957
Ile Asp Asp Trp Trp Arg Asn Glu Gln Phe Trp Val Ile Gly Gly Val
            925                 930                 935 tcc tca cac ctc ttt gct gtg ttc cag gga ctt ctc aag gtc ata gct    3005
Ser Ser His Leu Phe Ala Val Phe Gln Gly Leu Leu Lys Val Ile Ala
            940                 945                 950 ggt gtt gat aca agc ttc acc gtg aca tca aag ggt gga gat gat gag    3053
Gly Val Asp Thr Ser Phe Thr Val Thr Ser Lys Gly Gly Asp Asp Glu
955                 960                 965                 970 gag ttc tca gag cta tat aca ttc aaa tgg act acc tta ttg ata cct    3101
Glu Phe Ser Glu Leu Tyr Thr Phe Lys Trp Thr Thr Leu Leu Ile Pro
            975                 980                 985 cct acc acc ttg ctt cta ttg aac ttc att ggt gtg gtc gct ggc gtt    3149
Pro Thr Thr Leu Leu Leu Leu Asn Phe Ile Gly Val Val Ala Gly Val
            990                 995                 1000 tca aat gcg atc aat aac gga tat gag tca tgg ggc ccc ctc ttt ggg    3197
Ser Asn Ala Ile Asn Asn Gly Tyr Glu Ser Trp Gly Pro Leu Phe Gly
            1005                1010                1015 aag cta ttc ttt gca ttt tgg gtg att gtc cat ctt tat ccc ttt ctc    3245
Lys Leu Phe Phe Ala Phe Trp Val Ile Val His Leu Tyr Pro Phe Leu
            1020                1025                1030 aaa ggt ttg gtt gga agg caa aac agg aca cca acg att gtc atc gtc    3293
Lys Gly Leu Val Gly Arg Gln Asn Arg Thr Pro Thr Ile Val Ile Val
```

-continued

```
                1035                1040                1045                1050
tgg tcc att ctg ctg gct tca atc ttc tcg ctc ctt tgg gtt cgg att      3341
Trp Ser Ile Leu Leu Ala Ser Ile Phe Ser Leu Leu Trp Val Arg Ile
                    1055                1060                1065 gat cct ttc ctt gcg aag gat gat ggt ccg ctt ctt gag gag tgt ggt      3389
Asp Pro Phe Leu Ala Lys Asp Asp Gly Pro Leu Leu Glu Glu Cys Gly
                    1070                1075                1080 ttg gat tgc aac taggatgtca gtgcatcagc tcccccaatc tgcatatgct          3441
Leu Asp Cys Asn
            1085 tgaagtatat tttctggtgt ttgtccccat attcagtgtc tgtagataag agacatgaaa    3501 tgtcccaagt ttcttttgat ccatggtgaa cctacttaat atctgagaga tatactgggg    3561 gaaaatggag gctgcggcaa tccttgtgca gttgggccgt ggaatacagc atatgcaagt    3621 gtttgattgt gcagcattct ttattacttg gtcgcaatat agatgggctg agccgaacag    3681 caaggtattt tgattctgca ctgctcccgt gtacaaactt ggttctcaat aaggcaggca    3741 ggaatgcatc tgccagtgga acagagcaac ctgcacatta tttatgtatg cctgttcatt    3801 ggagggcttg ttcattacat gttcgtctat actagaaaaa acagaatatt agcattaatc    3861 tatagttaat taaagtatgt aaatgcgcct gttttttgtt gtgtactgta atcatctgag    3921 ttggttttgt gaaaaaaaaa aaaaaaaaaa aaaaaaaaa aaaaaaaa                  3969
```

<210> SEQ ID NO 38
<211> LENGTH: 1086
<212> TYPE: PRT
<213> ORGANISM: Zea mays

<400> SEQUENCE: 38

```
Met Glu Ala Ser Ala Gly Leu Val Ala Gly Ser His Asn Arg Asn Glu
1               5                   10                  15

Leu Val Val Ile Arg Arg Asp Gly Asp Pro Gly Pro Lys Pro Pro Arg
            20                  25                  30

Glu Gln Asn Gly Gln Val Cys Gln Ile Cys Gly Asp Asp Val Gly Leu
        35                  40                  45

Ala Pro Gly Gly Asp Pro Phe Val Ala Cys Asn Glu Cys Ala Phe Pro
    50                  55                  60

Val Cys Arg Asp Cys Tyr Glu Tyr Glu Arg Arg Glu Gly Thr Gln Asn
65                  70                  75                  80

Cys Pro Gln Cys Lys Thr Arg Tyr Lys Arg Leu Lys Gly Cys Gln Arg
                85                  90                  95

Val Thr Gly Asp Glu Glu Asp Gly Val Asp Asp Leu Asp Asn Glu
            100                 105                 110

Phe Asn Trp Asp Gly His Asp Ser Gln Ser Val Ala Glu Ser Met Leu
        115                 120                 125

Tyr Gly His Met Ser Tyr Gly Arg Gly Asp Pro Asn Gly Ala Pro
    130                 135                 140

Gln Ala Phe Gln Leu Asn Pro Asn Val Pro Leu Leu Thr Asn Gly Gln
145                 150                 155                 160

Met Val Asp Asp Ile Pro Pro Glu Gln His Ala Leu Val Pro Ser Phe
                165                 170                 175

Met Gly Gly Gly Gly Lys Arg Ile His Pro Leu Pro Tyr Ala Asp Pro
            180                 185                 190

Ser Leu Pro Val Gln Pro Arg Ser Met Asp Pro Ser Lys Asp Leu Ala
        195                 200                 205
```

```
Ala Tyr Gly Tyr Gly Ser Val Ala Trp Lys Glu Arg Met Glu Asn Trp
    210                 215                 220
Lys Gln Arg Gln Glu Arg Met His Gln Thr Gly Asn Asp Gly Gly Gly
225                 230                 235                 240
Asp Asp Gly Asp Asp Ala Asp Leu Pro Leu Met Asp Glu Ala Arg Gln
            245                 250                 255
Gln Leu Ser Arg Lys Ile Pro Leu Pro Ser Ser Gln Ile Asn Pro Tyr
        260                 265                 270
Arg Met Ile Ile Ile Ile Arg Leu Val Val Leu Gly Phe Phe Phe His
    275                 280                 285
Tyr Arg Val Met His Pro Val Asn Asp Ala Phe Ala Leu Trp Leu Ile
    290                 295                 300
Ser Val Ile Cys Glu Ile Trp Phe Ala Met Ser Trp Ile Leu Asp Gln
305                 310                 315                 320
Phe Pro Lys Trp Phe Pro Ile Glu Arg Glu Thr Tyr Leu Asp Arg Leu
            325                 330                 335
Ser Leu Arg Phe Asp Lys Glu Gly Gln Pro Ser Gln Leu Ala Pro Ile
        340                 345                 350
Asp Phe Phe Val Ser Thr Val Asp Pro Leu Lys Glu Pro Pro Leu Val
        355                 360                 365
Thr Thr Asn Thr Val Leu Ser Ile Leu Ser Val Asp Tyr Pro Val Asp
370                 375                 380
Lys Val Ser Cys Tyr Val Ser Asp Asp Gly Ala Ala Met Leu Thr Phe
385                 390                 395                 400
Glu Ala Leu Ser Glu Thr Ser Glu Phe Ala Lys Lys Trp Val Pro Phe
            405                 410                 415
Cys Lys Arg Tyr Asn Ile Glu Pro Arg Ala Pro Glu Trp Tyr Phe Gln
        420                 425                 430
Gln Lys Ile Asp Tyr Leu Lys Asp Lys Val Ala Ala Asn Phe Val Arg
        435                 440                 445
Glu Arg Arg Ala Met Lys Arg Glu Tyr Glu Glu Phe Lys Val Arg Ile
    450                 455                 460
Asn Ala Leu Val Ala Lys Ala Gln Lys Val Pro Glu Glu Gly Trp Thr
465                 470                 475                 480
Met Gln Asp Gly Thr Pro Trp Pro Gly Asn Asn Val Arg Asp His Pro
            485                 490                 495
Gly Met Ile Gln Val Phe Leu Gly Gln Ser Gly Gly Leu Asp Cys Glu
        500                 505                 510
Gly Asn Glu Leu Pro Arg Leu Val Tyr Val Ser Arg Glu Lys Arg Pro
        515                 520                 525
Gly Tyr Asn His His Lys Lys Ala Gly Ala Met Asn Ala Leu Val Arg
    530                 535                 540
Val Ser Ala Val Leu Thr Asn Ala Pro Tyr Leu Leu Asn Leu Asp Cys
545                 550                 555                 560
Asp His Tyr Ile Asn Asn Ser Lys Ala Ile Lys Glu Ala Met Cys Phe
            565                 570                 575
Met Met Asp Pro Leu Leu Gly Lys Lys Val Cys Tyr Val Gln Phe Pro
        580                 585                 590
Gln Arg Phe Asp Gly Ile Asp Arg His Asp Arg Tyr Ala Asn Arg Asn
        595                 600                 605
Val Val Phe Phe Asp Ile Asn Met Lys Gly Leu Asp Gly Ile Gln Gly
    610                 615                 620
Pro Ile Tyr Val Gly Thr Gly Cys Val Phe Arg Arg Gln Ala Leu Tyr
```

```
                625                 630                 635                 640
       Gly Tyr Asp Ala Pro Lys Thr Lys Pro Pro Ser Arg Thr Cys Asn
                       645                 650                 655
       Cys Trp Pro Lys Trp Cys Phe Cys Cys Cys Phe Gly Asn Arg Lys
                       660                 665                 670
       Gln Lys Lys Thr Thr Lys Pro Lys Thr Glu Lys Lys Leu Leu Phe
                       675                 680                 685
       Phe Lys Lys Glu Glu Asn Gln Ser Pro Ala Tyr Ala Leu Gly Ile
                       690                 695                 700
       Asp Glu Ala Ala Pro Gly Ala Glu Asn Glu Lys Ala Gly Ile Val Asn
       705                 710                 715                 720
       Gln Gln Lys Leu Glu Lys Lys Phe Gly Gln Ser Ser Val Phe Val Thr
                       725                 730                 735
       Ser Thr Leu Leu Glu Asn Gly Gly Thr Leu Lys Ser Ala Ser Pro Ala
                       740                 745                 750
       Ser Leu Leu Lys Glu Ala Ile His Val Ile Ser Cys Gly Tyr Glu Asp
                       755                 760                 765
       Lys Thr Asp Trp Gly Lys Glu Ile Gly Trp Ile Tyr Gly Ser Val Thr
                       770                 775                 780
       Glu Asp Ile Leu Thr Gly Phe Lys Met His Cys His Gly Trp Arg Ser
       785                 790                 795                 800
       Ile Tyr Cys Ile Pro Lys Arg Val Ala Phe Lys Gly Ser Ala Pro Leu
                       805                 810                 815
       Asn Leu Ser Asp Arg Leu His Gln Val Leu Arg Trp Ala Leu Gly Ser
                       820                 825                 830
       Ile Glu Ile Phe Phe Ser Asn His Cys Pro Leu Trp Tyr Gly Tyr Gly
                       835                 840                 845
       Gly Gly Leu Lys Phe Leu Glu Arg Phe Ser Tyr Ile Asn Ser Ile Val
                       850                 855                 860
       Tyr Pro Trp Thr Ser Ile Pro Leu Leu Ala Tyr Cys Thr Leu Pro Ala
       865                 870                 875                 880
       Ile Cys Leu Leu Thr Gly Lys Phe Ile Thr Pro Glu Leu Asn Asn Val
                       885                 890                 895
       Ala Ser Leu Trp Phe Met Ser Leu Phe Ile Cys Ile Phe Ala Thr Ser
                       900                 905                 910
       Ile Leu Glu Met Arg Trp Ser Gly Val Gly Ile Asp Asp Trp Trp Arg
                       915                 920                 925
       Asn Glu Gln Phe Trp Val Ile Gly Gly Val Ser Ser His Leu Phe Ala
                       930                 935                 940
       Val Phe Gln Gly Leu Leu Lys Val Ile Ala Gly Val Asp Thr Ser Phe
       945                 950                 955                 960
       Thr Val Thr Ser Lys Gly Gly Asp Asp Glu Glu Phe Ser Glu Leu Tyr
                       965                 970                 975
       Thr Phe Lys Trp Thr Thr Leu Leu Ile Pro Pro Thr Thr Leu Leu Leu
                       980                 985                 990
       Leu Asn Phe Ile Gly Val Val Ala Gly Val Ser Asn Ala Ile Asn Asn
                       995                 1000                1005
       Gly Tyr Glu Ser Trp Gly Pro Leu Phe Gly Lys Leu Phe Phe Ala Phe
                       1010                1015                1020
       Trp Val Ile Val His Leu Tyr Pro Phe Leu Lys Gly Leu Val Gly Arg
       1025                1030                1035                1040
       Gln Asn Arg Thr Pro Thr Ile Val Ile Val Trp Ser Ile Leu Leu Ala
                       1045                1050                1055
```

```
Ser Ile Phe Ser Leu Leu Trp Val Arg Ile Asp Pro Phe Leu Ala Lys
        1060                1065                1070

Asp Asp Gly Pro Leu Leu Glu Glu Cys Gly Leu Asp Cys Asn
    1075                1080                1085

<210> SEQ ID NO 39
<211> LENGTH: 25
<212> TYPE: DNA
<213> ORGANISM: Zea mays

<400> SEQUENCE: 39
atggaggcga gcgccgggct ggtgg                                              25

<210> SEQ ID NO 40
<211> LENGTH: 25
<212> TYPE: DNA
<213> ORGANISM: Zea mays

<400> SEQUENCE: 40
ctagttgcaa tccaaaccac actcc                                              25

<210> SEQ ID NO 41
<211> LENGTH: 3725
<212> TYPE: DNA
<213> ORGANISM: Zea mays
<220> FEATURE:
<221> NAME/KEY: CDS
<222> LOCATION: (179)...(3400)

<400> SEQUENCE: 41
gcagcagcag caccaccact gcgcggcatt gcagcgagca agcgggaggg atctggggca        60
tggtggcggt cgctgccgct ccgctcgga  tctagagggc gcacgggct  gattgccctc       120 cgccggcctc gtcggtgtcg gtggagtgtg aatcggtgtg tgtaggagga gcgcggag        178 atg gcg gcc aac aag ggg atg gtg gca ggc tct cac aac cgc aac gag        226
Met Ala Ala Asn Lys Gly Met Val Ala Gly Ser His Asn Arg Asn Glu
 1               5                  10                  15 ttc gtc atg atc cgc cac gac ggc gac gcg cct gtc ccg gct aag ccc        274
Phe Val Met Ile Arg His Asp Gly Asp Ala Pro Val Pro Ala Lys Pro
             20                  25                  30 acg aag agt gcg aat ggg cag gtc tgc cag att tgt ggc gac act gtt        322
Thr Lys Ser Ala Asn Gly Gln Val Cys Gln Ile Cys Gly Asp Thr Val
         35                  40                  45 ggc gtt tca gcc act ggt gat gtc ttt gtt gcc tgc aat gag tgt gcc        370
Gly Val Ser Ala Thr Gly Asp Val Phe Val Ala Cys Asn Glu Cys Ala
     50                  55                  60 ttc cct gtc tgc cgc cct tgc tat gag tac gag cgc aag gaa ggg aac        418
Phe Pro Val Cys Arg Pro Cys Tyr Glu Tyr Glu Arg Lys Glu Gly Asn
 65                  70                  75                  80 caa tgc tgc cct cag tgc aag act aga tac aag aga cag aaa ggt agc        466
Gln Cys Cys Pro Gln Cys Lys Thr Arg Tyr Lys Arg Gln Lys Gly Ser
                 85                  90                  95 cct cga gtt cat ggt gat gat gag gag gaa gat gtt gat gac ctg gac        514
Pro Arg Val His Gly Asp Asp Glu Glu Glu Asp Val Asp Asp Leu Asp
            100                 105                 110 aat gaa ttc aac tat aag caa ggc aat ggg aag ggc cca gag tgg cag        562
Asn Glu Phe Asn Tyr Lys Gln Gly Asn Gly Lys Gly Pro Glu Trp Gln
        115                 120                 125 ctt caa gga gat gac gct gat ctg tct tca tct gct cgc cat gac cca        610
Leu Gln Gly Asp Asp Ala Asp Leu Ser Ser Ser Ala Arg His Asp Pro
    130                 135                 140
```

```
                                                        -continued cac cat cgg att cca cgc ctt aca agt gga caa cag ata tct gga gag       658
His His Arg Ile Pro Arg Leu Thr Ser Gly Gln Gln Ile Ser Gly Glu
145                 150                 155                 160 atc cct gat gca tcc cct gac cgt cat tct atc cgc agt cca aca tcg       706
Ile Pro Asp Ala Ser Pro Asp Arg His Ser Ile Arg Ser Pro Thr Ser
                165                 170                 175 agc tat gtt gat cca agc gtt cca gtt cct gtg agg att gtg gac ccc       754
Ser Tyr Val Asp Pro Ser Val Pro Val Pro Val Arg Ile Val Asp Pro
            180                 185                 190 tcg aag gac ttg aat tcc tat ggg ctt aat agt gtt gac tgg aag gaa       802
Ser Lys Asp Leu Asn Ser Tyr Gly Leu Asn Ser Val Asp Trp Lys Glu
        195                 200                 205 aga gtt gag agc tgg agg gtt aaa cag gac aaa aat atg ttg caa gtg       850
Arg Val Glu Ser Trp Arg Val Lys Gln Asp Lys Asn Met Leu Gln Val
    210                 215                 220 act aat aaa tat cca gag gct aga gga gac atg gag ggg act ggc tca       898
Thr Asn Lys Tyr Pro Glu Ala Arg Gly Asp Met Glu Gly Thr Gly Ser
225                 230                 235                 240 aat gga gaa gat atg caa atg gtt gat gat gca cgc cta cct ttg agc       946
Asn Gly Glu Asp Met Gln Met Val Asp Asp Ala Arg Leu Pro Leu Ser
                245                 250                 255 cgc att gtg cca att tcc tca aac cag ctc aac ctt tac cgg ata gta       994
Arg Ile Val Pro Ile Ser Ser Asn Gln Leu Asn Leu Tyr Arg Ile Val
            260                 265                 270 atc att ctc cgt ctt atc atc ctg tgc ttc ttc ttc caa tat cgt atc      1042
Ile Ile Leu Arg Leu Ile Ile Leu Cys Phe Phe Phe Gln Tyr Arg Ile
        275                 280                 285 agt cat cca gtg cgt aat gct tat gga ttg tgg cta gta tct gtt atc      1090
Ser His Pro Val Arg Asn Ala Tyr Gly Leu Trp Leu Val Ser Val Ile
    290                 295                 300 tgt gag gtc tgg ttt gcc ttg tcc tgg ctt cta gat cag ttc cca aaa      1138
Cys Glu Val Trp Phe Ala Leu Ser Trp Leu Leu Asp Gln Phe Pro Lys
305                 310                 315                 320 tgg tat cca atc aac cgt gag aca tat ctc gac agg ctt gca ttg agg      1186
Trp Tyr Pro Ile Asn Arg Glu Thr Tyr Leu Asp Arg Leu Ala Leu Arg
                325                 330                 335 tat gat aga gag gga gag cca tca cag ctg gct ccc att gat gtc ttt      1234
Tyr Asp Arg Glu Gly Glu Pro Ser Gln Leu Ala Pro Ile Asp Val Phe
            340                 345                 350 gtc agt aca gtg gat cca ttg aag gaa cct cca ctg atc aca gcc aac      1282
Val Ser Thr Val Asp Pro Leu Lys Glu Pro Pro Leu Ile Thr Ala Asn
        355                 360                 365 act gtt ttg tcc att ctt gct gtg gat tac cct gtt gac aaa gtg tca      1330
Thr Val Leu Ser Ile Leu Ala Val Asp Tyr Pro Val Asp Lys Val Ser
    370                 375                 380 tgc tat gtt tct gat gat ggc tca gct atg ctg act ttt gag tct ctc      1378
Cys Tyr Val Ser Asp Asp Gly Ser Ala Met Leu Thr Phe Glu Ser Leu
385                 390                 395                 400 tct gaa act gcc gaa ttt gct aga aag tgg gtt ccc ttt tgt aag aag      1426
Ser Glu Thr Ala Glu Phe Ala Arg Lys Trp Val Pro Phe Cys Lys Lys
                405                 410                 415 cac aat att gaa cca aga gct cca gaa ttt tac ttt gct caa aaa ata      1474
His Asn Ile Glu Pro Arg Ala Pro Glu Phe Tyr Phe Ala Gln Lys Ile
            420                 425                 430 gat tac ctg aag gac aaa att caa cct tca ttt gtt aag gaa aga cga      1522
Asp Tyr Leu Lys Asp Lys Ile Gln Pro Ser Phe Val Lys Glu Arg Arg
        435                 440                 445 gca atg aag aga gag tat gaa gaa ttc aaa ata aga atc aat gcc ctt      1570
Ala Met Lys Arg Glu Tyr Glu Glu Phe Lys Ile Arg Ile Asn Ala Leu
```

```
               450                 455                 460
gtt gcc aaa gca cag aaa gtg cct gaa gag ggg tgg acc atg gct gat      1618
Val Ala Lys Ala Gln Lys Val Pro Glu Glu Gly Trp Thr Met Ala Asp
465                 470                 475                 480 gga act gct tgg cct ggg aat aac cct agg gac cat cct ggc atg att      1666
Gly Thr Ala Trp Pro Gly Asn Asn Pro Arg Asp His Pro Gly Met Ile
                485                 490                 495 cag gtg ttc ttg ggg cac agt ggt ggg ctt gac act gat gga aat gaa      1714
Gln Val Phe Leu Gly His Ser Gly Gly Leu Asp Thr Asp Gly Asn Glu
    500                 505                 510 tta cca cgt ctt gtc tat gtc tct cgt gaa aag aga cca ggc ttt cag      1762
Leu Pro Arg Leu Val Tyr Val Ser Arg Glu Lys Arg Pro Gly Phe Gln
            515                 520                 525 cat cac aag aag gct ggt gca atg aat gca ctg att cgt gta tct gct      1810
His His Lys Lys Ala Gly Ala Met Asn Ala Leu Ile Arg Val Ser Ala
530                 535                 540 gtg ctg aca aat ggt gcc tat ctt ctc aat gtg gat tgt gac cat tac      1858
Val Leu Thr Asn Gly Ala Tyr Leu Leu Asn Val Asp Cys Asp His Tyr
545                 550                 555                 560 ttc aat agc agc aaa gct ctt aga gaa gca atg tgc ttc atg atg gat      1906
Phe Asn Ser Ser Lys Ala Leu Arg Glu Ala Met Cys Phe Met Met Asp
                565                 570                 575 cca gct cta gga agg aaa act tgt tat gta caa ttt cca caa aga ttt      1954
Pro Ala Leu Gly Arg Lys Thr Cys Tyr Val Gln Phe Pro Gln Arg Phe
            580                 585                 590 gat ggc att gac ttg cac gat cga tat gct aat agg aac ata gtc ttc      2002
Asp Gly Ile Asp Leu His Asp Arg Tyr Ala Asn Arg Asn Ile Val Phe
            595                 600                 605 ttt gat atc aac atg aaa ggt cta gat ggc att cag ggt cca gtc tat      2050
Phe Asp Ile Asn Met Lys Gly Leu Asp Gly Ile Gln Gly Pro Val Tyr
610                 615                 620 gtg gga aca gga tgc tgt ttc aat agg cag gct ttg tat gga tat gat      2098
Val Gly Thr Gly Cys Cys Phe Asn Arg Gln Ala Leu Tyr Gly Tyr Asp
625                 630                 635                 640 cct gtt ttg act gaa gct gat ctg gaa cct aac att gtt gtt aag agc      2146
Pro Val Leu Thr Glu Ala Asp Leu Glu Pro Asn Ile Val Val Lys Ser
                645                 650                 655 tgc tgt ggt aga agg aag aga aag aac aag agt tat atg gat agt caa      2194
Cys Cys Gly Arg Arg Lys Arg Lys Asn Lys Ser Tyr Met Asp Ser Gln
            660                 665                 670 agc cgt att atg aag aga aca gaa tct tca gct ccc atc ttt aac atg      2242
Ser Arg Ile Met Lys Arg Thr Glu Ser Ser Ala Pro Ile Phe Asn Met
            675                 680                 685 gaa gac atc gag gag ggt att gaa ggt tat gag gat gaa agg tca gtg      2290
Glu Asp Ile Glu Glu Gly Ile Glu Gly Tyr Glu Asp Glu Arg Ser Val
690                 695                 700 ctt atg tcc cag agg aaa ttg gag aaa cgc ttt ggt cag tct cca atc      2338
Leu Met Ser Gln Arg Lys Leu Glu Lys Arg Phe Gly Gln Ser Pro Ile
705                 710                 715                 720 ttc att gca tcc acc ttt atg act caa ggt ggc ata cca cct tca aca      2386
Phe Ile Ala Ser Thr Phe Met Thr Gln Gly Gly Ile Pro Pro Ser Thr
                725                 730                 735 aac cca gct tct cta ctg aag gaa gct atc cat gtt atc agc tgt ggg      2434
Asn Pro Ala Ser Leu Leu Lys Glu Ala Ile His Val Ile Ser Cys Gly
            740                 745                 750 tac gag gac aaa act gaa tgg gga aaa gag att ggc tgg atc tat ggt      2482
Tyr Glu Asp Lys Thr Glu Trp Gly Lys Glu Ile Gly Trp Ile Tyr Gly
            755                 760                 765 tca gtt aca gag gat att ctg act ggg ttt aaa atg cat gca aga ggc      2530
```

```
                                                        -continued

Ser Val Thr Glu Asp Ile Leu Thr Gly Phe Lys Met His Ala Arg Gly
    770                 775                 780 tgg caa tca atc tac tgc atg cca cca cga cct tgt ttc aag ggt tct    2578
Trp Gln Ser Ile Tyr Cys Met Pro Pro Arg Pro Cys Phe Lys Gly Ser
785                 790                 795                 800 gca cca atc aat ctt tct gat cgt ctt aat cag gtg ctc cgt tgg gct    2626
Ala Pro Ile Asn Leu Ser Asp Arg Leu Asn Gln Val Leu Arg Trp Ala
                805                 810                 815 ctt ggg tca gtg gaa att ctg ctt agc aga cat tgt cct ata tgg tat    2674
Leu Gly Ser Val Glu Ile Leu Leu Ser Arg His Cys Pro Ile Trp Tyr
            820                 825                 830 ggc tac aat ggg cga ttg aag ctt ttg gag agg ctg gct tac att aac    2722
Gly Tyr Asn Gly Arg Leu Lys Leu Leu Glu Arg Leu Ala Tyr Ile Asn
        835                 840                 845 acc att gtt tat cca atc aca tct gtt ccg ctt atc gcc tat tgt gtg    2770
Thr Ile Val Tyr Pro Ile Thr Ser Val Pro Leu Ile Ala Tyr Cys Val
    850                 855                 860 ctt cct gct atc tgt ctt ctt acc aat aaa ttt atc att cct gag att    2818
Leu Pro Ala Ile Cys Leu Leu Thr Asn Lys Phe Ile Ile Pro Glu Ile
865                 870                 875                 880 agt aat tat gct gga atg ttc ttc att ctt ctt ttt gcc tcc att ttc    2866
Ser Asn Tyr Ala Gly Met Phe Phe Ile Leu Leu Phe Ala Ser Ile Phe
                885                 890                 895 gca act ggt ata ttg gag ctc aga tgg agt ggt gtt ggc att gaa gat    2914
Ala Thr Gly Ile Leu Glu Leu Arg Trp Ser Gly Val Gly Ile Glu Asp
            900                 905                 910 tgg tgg aga aat gag cag ttt tgg gtt att ggt ggc acc tct gcc cat    2962
Trp Trp Arg Asn Glu Gln Phe Trp Val Ile Gly Gly Thr Ser Ala His
        915                 920                 925 ctc ttc gcg gtg ttc cag ggt ctg ctg aaa gtg ttg gct ggg att gat    3010
Leu Phe Ala Val Phe Gln Gly Leu Leu Lys Val Leu Ala Gly Ile Asp
    930                 935                 940 acc aac ttc aca gtt acc tca aag gca tct gat gag gat ggc gac ttt    3058
Thr Asn Phe Thr Val Thr Ser Lys Ala Ser Asp Glu Asp Gly Asp Phe
945                 950                 955                 960 gct gag cta tat gtg ttc aag tgg acc agt ttg ctc atc cct ccg acc    3106
Ala Glu Leu Tyr Val Phe Lys Trp Thr Ser Leu Leu Ile Pro Pro Thr
                965                 970                 975 act gtt ctt gtc att aac ctg gtc gga atg gtg gca gga att tcg tat    3154
Thr Val Leu Val Ile Asn Leu Val Gly Met Val Ala Gly Ile Ser Tyr
            980                 985                 990 gcc att aac agc ggc tac caa tcc tgg ggt ccg ctc ttt gga aag ctg    3202
Ala Ile Asn Ser Gly Tyr Gln Ser Trp Gly Pro Leu Phe Gly Lys Leu
        995                 1000                1005 ttc ttc tcg atc tgg gtg atc ctc cat ctc tac ccc ttc ctc aag ggt    3250
Phe Phe Ser Ile Trp Val Ile Leu His Leu Tyr Pro Phe Leu Lys Gly
    1010                1015                1020 ctc atg ggc agg cag aac cgc acg cca aca atc gtc atc gtt tgg tcc    3298
Leu Met Gly Arg Gln Asn Arg Thr Pro Thr Ile Val Ile Val Trp Ser
1025                1030                1035                1040 atc ctc ctt gcg tct atc ttc tcc ttg ctg tgg gtg aag atc gat cct    3346
Ile Leu Leu Ala Ser Ile Phe Ser Leu Leu Trp Val Lys Ile Asp Pro
                1045                1050                1055 ttc atc tcc ccg aca cag aaa gct gcc gcc ttg ggg caa tgt ggt gtg    3394
Phe Ile Ser Pro Thr Gln Lys Ala Ala Ala Leu Gly Gln Cys Gly Val
            1060                1065                1070 aac tgc tgatccagat tgtgactctt atctgaagag gctcagccaa agatctgccc    3450
Asn Cys cctcgtgtaa atacctgagg gggctagatg ggaattttt gttgtagatg aggatggatc     3510
```

```
tgcatccaag ttatgcctct gtttattagc ttcttcggtg ccggtgctgc tgcagacaat    3570
catggagcct ttctaccttg cttgtagtgc tggccagcag cgtaaattgt gaattctgca    3630 ttttttata cgtggtgttt attgttttag agtaaattat catttgtttg aggtaactat    3690
tcacacgaac tatatggcaa tgctgttatt taaaa                              3725
```

<210> SEQ ID NO 42
<211> LENGTH: 1074
<212> TYPE: PRT
<213> ORGANISM: Zea mays

<400> SEQUENCE: 42

```
Met Ala Ala Asn Lys Gly Met Val Ala Gly Ser His Asn Arg Asn Glu
 1               5                  10                  15

Phe Val Met Ile Arg His Asp Gly Asp Ala Pro Val Pro Ala Lys Pro
             20                  25                  30

Thr Lys Ser Ala Asn Gly Gln Val Cys Gln Ile Cys Gly Asp Thr Val
         35                  40                  45

Gly Val Ser Ala Thr Gly Asp Val Phe Val Ala Cys Asn Glu Cys Ala
     50                  55                  60

Phe Pro Val Cys Arg Pro Cys Tyr Glu Tyr Glu Arg Lys Glu Gly Asn
 65                  70                  75                  80

Gln Cys Cys Pro Gln Cys Lys Thr Arg Tyr Lys Arg Lys Gly Ser
                 85                  90                  95

Pro Arg Val His Gly Asp Asp Glu Glu Glu Asp Val Asp Asp Leu Asp
            100                 105                 110

Asn Glu Phe Asn Tyr Lys Gln Gly Asn Gly Lys Gly Pro Glu Trp Gln
        115                 120                 125

Leu Gln Gly Asp Asp Ala Asp Leu Ser Ser Ser Ala Arg His Asp Pro
    130                 135                 140

His His Arg Ile Pro Arg Leu Thr Ser Gly Gln Gln Ile Ser Gly Glu
145                 150                 155                 160

Ile Pro Asp Ala Ser Pro Asp Arg His Ser Ile Arg Ser Pro Thr Ser
                165                 170                 175

Ser Tyr Val Asp Pro Ser Val Pro Val Pro Val Arg Ile Val Asp Pro
            180                 185                 190

Ser Lys Asp Leu Asn Ser Tyr Gly Leu Asn Ser Val Asp Trp Lys Glu
        195                 200                 205

Arg Val Glu Ser Trp Arg Val Lys Gln Asp Lys Asn Met Leu Gln Val
    210                 215                 220

Thr Asn Lys Tyr Pro Glu Ala Arg Gly Asp Met Glu Gly Thr Gly Ser
225                 230                 235                 240

Asn Gly Glu Asp Met Gln Met Val Asp Asp Ala Arg Leu Pro Leu Ser
                245                 250                 255

Arg Ile Val Pro Ile Ser Ser Asn Gln Leu Asn Leu Tyr Arg Ile Val
            260                 265                 270

Ile Ile Leu Arg Leu Ile Ile Leu Cys Phe Phe Phe Gln Tyr Arg Ile
        275                 280                 285

Ser His Pro Val Arg Asn Ala Tyr Gly Leu Trp Leu Val Ser Val Ile
    290                 295                 300

Cys Glu Val Trp Phe Ala Leu Ser Trp Leu Leu Asp Gln Phe Pro Lys
305                 310                 315                 320

Trp Tyr Pro Ile Asn Arg Glu Thr Tyr Leu Asp Arg Leu Ala Leu Arg
                325                 330                 335
```

```
Tyr Asp Arg Glu Gly Glu Pro Ser Gln Leu Ala Pro Ile Asp Val Phe
            340                 345                 350

Val Ser Thr Val Asp Pro Leu Lys Glu Pro Pro Leu Ile Thr Ala Asn
            355                 360                 365

Thr Val Leu Ser Ile Leu Ala Val Asp Tyr Pro Val Asp Lys Val Ser
            370                 375                 380

Cys Tyr Val Ser Asp Asp Gly Ser Ala Met Leu Thr Phe Glu Ser Leu
385                 390                 395                 400

Ser Glu Thr Ala Glu Phe Ala Arg Lys Trp Val Pro Phe Cys Lys Lys
                405                 410                 415

His Asn Ile Glu Pro Arg Ala Pro Glu Phe Tyr Phe Ala Gln Lys Ile
            420                 425                 430

Asp Tyr Leu Lys Asp Lys Ile Gln Pro Ser Phe Val Lys Glu Arg Arg
            435                 440                 445

Ala Met Lys Arg Glu Tyr Glu Glu Phe Lys Ile Arg Ile Asn Ala Leu
            450                 455                 460

Val Ala Lys Ala Gln Lys Val Pro Glu Glu Gly Trp Thr Met Ala Asp
465                 470                 475                 480

Gly Thr Ala Trp Pro Gly Asn Asn Pro Arg Asp His Pro Gly Met Ile
                485                 490                 495

Gln Val Phe Leu Gly His Ser Gly Gly Leu Asp Thr Asp Gly Asn Glu
            500                 505                 510

Leu Pro Arg Leu Val Tyr Val Ser Arg Glu Lys Arg Pro Gly Phe Gln
            515                 520                 525

His His Lys Lys Ala Gly Ala Met Asn Ala Leu Ile Arg Val Ser Ala
            530                 535                 540

Val Leu Thr Asn Gly Ala Tyr Leu Leu Asn Val Asp Cys Asp His Tyr
545                 550                 555                 560

Phe Asn Ser Ser Lys Ala Leu Arg Glu Ala Met Cys Phe Met Met Asp
                565                 570                 575

Pro Ala Leu Gly Arg Lys Thr Cys Tyr Val Gln Phe Pro Gln Arg Phe
            580                 585                 590

Asp Gly Ile Asp Leu His Asp Arg Tyr Ala Asn Arg Asn Ile Val Phe
            595                 600                 605

Phe Asp Ile Asn Met Lys Gly Leu Asp Gly Ile Gln Gly Pro Val Tyr
            610                 615                 620

Val Gly Thr Gly Cys Cys Phe Asn Arg Gln Ala Leu Tyr Gly Tyr Asp
625                 630                 635                 640

Pro Val Leu Thr Glu Ala Asp Leu Glu Pro Asn Ile Val Val Lys Ser
                645                 650                 655

Cys Cys Gly Arg Arg Lys Arg Lys Asn Lys Ser Tyr Met Asp Ser Gln
            660                 665                 670

Ser Arg Ile Met Lys Arg Thr Glu Ser Ser Ala Pro Ile Phe Asn Met
            675                 680                 685

Glu Asp Ile Glu Glu Gly Ile Glu Gly Tyr Glu Asp Glu Arg Ser Val
            690                 695                 700

Leu Met Ser Gln Arg Lys Leu Glu Lys Arg Phe Gly Gln Ser Pro Ile
705                 710                 715                 720

Phe Ile Ala Ser Thr Phe Met Thr Gln Gly Ile Pro Pro Ser Thr
                725                 730                 735

Asn Pro Ala Ser Leu Leu Lys Glu Ala Ile His Val Ile Ser Cys Gly
            740                 745                 750
```

```
Tyr Glu Asp Lys Thr Glu Trp Gly Lys Glu Ile Gly Trp Ile Tyr Gly
        755                 760                 765

Ser Val Thr Glu Asp Ile Leu Thr Gly Phe Lys Met His Ala Arg Gly
        770                 775                 780

Trp Gln Ser Ile Tyr Cys Met Pro Pro Arg Pro Cys Phe Lys Gly Ser
785                 790                 795                 800

Ala Pro Ile Asn Leu Ser Asp Arg Leu Asn Gln Val Leu Arg Trp Ala
            805                 810                 815

Leu Gly Ser Val Glu Ile Leu Leu Ser Arg His Cys Pro Ile Trp Tyr
        820                 825                 830

Gly Tyr Asn Gly Arg Leu Lys Leu Leu Glu Arg Leu Ala Tyr Ile Asn
        835                 840                 845

Thr Ile Val Tyr Pro Ile Thr Ser Val Pro Leu Ile Ala Tyr Cys Val
        850                 855                 860

Leu Pro Ala Ile Cys Leu Leu Thr Asn Lys Phe Ile Ile Pro Glu Ile
865                 870                 875                 880

Ser Asn Tyr Ala Gly Met Phe Phe Ile Leu Leu Phe Ala Ser Ile Phe
            885                 890                 895

Ala Thr Gly Ile Leu Glu Leu Arg Trp Ser Gly Val Gly Ile Glu Asp
        900                 905                 910

Trp Trp Arg Asn Glu Gln Phe Trp Val Ile Gly Gly Thr Ser Ala His
        915                 920                 925

Leu Phe Ala Val Phe Gln Gly Leu Leu Lys Val Leu Ala Gly Ile Asp
        930                 935                 940

Thr Asn Phe Thr Val Thr Ser Lys Ala Ser Asp Glu Asp Gly Asp Phe
945                 950                 955                 960

Ala Glu Leu Tyr Val Phe Lys Trp Thr Ser Leu Leu Ile Pro Pro Thr
            965                 970                 975

Thr Val Leu Val Ile Asn Leu Val Gly Met Val Ala Gly Ile Ser Tyr
        980                 985                 990

Ala Ile Asn Ser Gly Tyr Gln Ser Trp Gly Pro Leu Phe Gly Lys Leu
        995                 1000                1005

Phe Phe Ser Ile Trp Val Ile Leu His Leu Tyr Pro Phe Leu Lys Gly
    1010                1015                1020

Leu Met Gly Arg Gln Asn Arg Thr Pro Thr Ile Val Ile Val Trp Ser
1025                1030                1035                1040

Ile Leu Leu Ala Ser Ile Phe Ser Leu Leu Trp Val Lys Ile Asp Pro
                1045                1050                1055

Phe Ile Ser Pro Thr Gln Lys Ala Ala Ala Leu Gly Gln Cys Gly Val
                1060                1065                1070

Asn Cys

<210> SEQ ID NO 43
<211> LENGTH: 25
<212> TYPE: DNA
<213> ORGANISM: Zea mays

<400> SEQUENCE: 43
atggcggcca acaaggggat ggtgg                                  25

<210> SEQ ID NO 44
<211> LENGTH: 25
<212> TYPE: DNA
<213> ORGANISM: Zea mays

<400> SEQUENCE: 44
```

```
tcagcagttc acaccacatt gcccc                                    25

<210> SEQ ID NO 45
<211> LENGTH: 3813
<212> TYPE: DNA
<213> ORGANISM: Zea mays
<220> FEATURE:
<221> NAME/KEY: CDS
<222> LOCATION: (215)...(3496)

<400> SEQUENCE: 45
ccacagctca tataccaaga gccggagcag cttagcgcag cccagagcgg cgccgcgcca    60
agcacaaccc ccacccgcca cagccgcgtg cgcatgtgag cggtcgccgc ggccgggaga   120
ccagaggagg ggaggactac gtgcatttcg ctgtgccgcc gccgcggggt tcgtgcgcga   180
gcgagatccg gcggggcggg gcgggggggcc tgag atg gag gct agc gcg ggg ctg   235
                                    Met Glu Ala Ser Ala Gly Leu
                                     1               5 gtg gcc ggc tcg cat aac cgg aac gag ctg gtg gtg atc cgc cgc gac    283
Val Ala Gly Ser His Asn Arg Asn Glu Leu Val Val Ile Arg Arg Asp
         10                  15                  20 cgc gag tcg gga gcc gcg ggc ggc gcg gcg cgc cgg gcg gag gcg          331
Arg Glu Ser Gly Ala Ala Gly Gly Ala Ala Arg Arg Ala Glu Ala
     25                  30                  35 ccg tgc cag ata tgc ggc gac gag gtc ggg gtg ggc ttc gac ggg gag    379
Pro Cys Gln Ile Cys Gly Asp Glu Val Gly Val Gly Phe Asp Gly Glu
 40                  45                  50                  55 ccc ttc gtg gcg tgc aac gag tgc gcc ttc ccc gtc tgc cgc gcc tgc    427
Pro Phe Val Ala Cys Asn Glu Cys Ala Phe Pro Val Cys Arg Ala Cys
                 60                  65                  70 tac gag tac gag cgc cgc gag ggc tcg caa gcg tgc ccg cag tgc agg    475
Tyr Glu Tyr Glu Arg Arg Glu Gly Ser Gln Ala Cys Pro Gln Cys Arg
             75                  80                  85 acc cgc tac aag cgc ctc aag ggc tgc ccg cgg gtg gcc ggc gac gag    523
Thr Arg Tyr Lys Arg Leu Lys Gly Cys Pro Arg Val Ala Gly Asp Glu
         90                  95                 100 gag gag gac ggc gtc gac gac ctg gag ggc gag ttc ggc ctg cag gac    571
Glu Glu Asp Gly Val Asp Asp Leu Glu Gly Glu Phe Gly Leu Gln Asp
    105                 110                 115 ggc gcc gcc cac gag gac gac ccg cag tac gtc gcc gag tcc atg ctc    619
Gly Ala Ala His Glu Asp Asp Pro Gln Tyr Val Ala Glu Ser Met Leu
120                 125                 130                 135 agg gcg cag atg agc tac ggc cgc ggc ggc gac gcg cac ccc ggc ttc    667
Arg Ala Gln Met Ser Tyr Gly Arg Gly Gly Asp Ala His Pro Gly Phe
                140                 145                 150 agc ccc gtc ccc aac gtg ccg ctc ctc acc aac ggc cag atg gtt gat    715
Ser Pro Val Pro Asn Val Pro Leu Leu Thr Asn Gly Gln Met Val Asp
            155                 160                 165 gac atc ccg ccg gag cag cac gcg ctc gtg ccg tcc tac atg agc ggc    763
Asp Ile Pro Pro Glu Gln His Ala Leu Val Pro Ser Tyr Met Ser Gly
        170                 175                 180 ggc ggc ggg ggc aag agg atc cac ccg ctc cct ttc gca gat ccc       811
Gly Gly Gly Gly Gly Lys Arg Ile His Pro Leu Pro Phe Ala Asp Pro
    185                 190                 195 aac ctt cca gtg caa ccg aga tcc atg gac ccg tcc aag gat ctg gcc   859
Asn Leu Pro Val Gln Pro Arg Ser Met Asp Pro Ser Lys Asp Leu Ala
200                 205                 210                 215 gcc tac gga tat ggc agc gtg gcc tgg aag gag aga atg gag ggc tgg   907
Ala Tyr Gly Tyr Gly Ser Val Ala Trp Lys Glu Arg Met Glu Gly Trp
                220                 225                 230
```

```
aag cag aag cag gag cgc ctg cag cat gtc agg agc gag ggt ggc ggt      955
Lys Gln Lys Gln Glu Arg Leu Gln His Val Arg Ser Glu Gly Gly Gly
        235                 240                 245 gat tgg gat ggc gac gat gca gat ctg cca cta atg gat gaa gct agg     1003
Asp Trp Asp Gly Asp Asp Ala Asp Leu Pro Leu Met Asp Glu Ala Arg
250                 255                 260 cag cca ttg tcc aga aaa gtc cct ata tca tca agc cga att aat ccc     1051
Gln Pro Leu Ser Arg Lys Val Pro Ile Ser Ser Ser Arg Ile Asn Pro
    265                 270                 275 tac agg atg att atc gtt atc cgg ttg gtg gtt ttg ggt ttc ttc ttc     1099
Tyr Arg Met Ile Ile Val Ile Arg Leu Val Val Leu Gly Phe Phe Phe
280                 285                 290                 295 cac tac cga gtg atg cat ccg gcg aaa gat gca ttt gca ttg tgg ctc     1147
His Tyr Arg Val Met His Pro Ala Lys Asp Ala Phe Ala Leu Trp Leu
                300                 305                 310 ata tct gta atc tgt gaa atc tgg ttt gcg atg tcc tgg att ctt gat     1195
Ile Ser Val Ile Cys Glu Ile Trp Phe Ala Met Ser Trp Ile Leu Asp
                    315                 320                 325 cag ttc cca aag tgg ctt cca atc gag aga gag act tac ctg gac cgt     1243
Gln Phe Pro Lys Trp Leu Pro Ile Glu Arg Glu Thr Tyr Leu Asp Arg
        330                 335                 340 ttg tca cta agg ttt gac aag gaa ggt caa ccc tct cag ctt gct cca     1291
Leu Ser Leu Arg Phe Asp Lys Glu Gly Gln Pro Ser Gln Leu Ala Pro
345                 350                 355 atc gac ttc ttt gtc agt acg gtt gat ccc aca aag gaa cct ccc ttg     1339
Ile Asp Phe Phe Val Ser Thr Val Asp Pro Thr Lys Glu Pro Pro Leu
    360                 365                 370                 375 gtc aca gcg aac act gtc ctt tcc atc ctt tct gtg gat tat ccg gtt     1387
Val Thr Ala Asn Thr Val Leu Ser Ile Leu Ser Val Asp Tyr Pro Val
                380                 385                 390 gag aag gtc tcc tgc tat gtt tct gat gat ggt gct gca atg ctt acg     1435
Glu Lys Val Ser Cys Tyr Val Ser Asp Asp Gly Ala Ala Met Leu Thr
                    395                 400                 405 ttt gaa gca ttg tct gaa aca tct gaa ttt gca aag aaa tgg gtt cct     1483
Phe Glu Ala Leu Ser Glu Thr Ser Glu Phe Ala Lys Lys Trp Val Pro
        410                 415                 420 ttc agc aaa aag ttt aat atc gag cct cgt gct cct gag tgg tac ttc     1531
Phe Ser Lys Lys Phe Asn Ile Glu Pro Arg Ala Pro Glu Trp Tyr Phe
425                 430                 435 caa cag aag ata gac tac ctg aaa gac aag gtt gct gct tca ttt gtt     1579
Gln Gln Lys Ile Asp Tyr Leu Lys Asp Lys Val Ala Ala Ser Phe Val
440                 445                 450                 455 agg gag agg agg gcg atg aag aga gaa tac gag gaa ttc aag gta agg     1627
Arg Glu Arg Arg Ala Met Lys Arg Glu Tyr Glu Glu Phe Lys Val Arg
                460                 465                 470 atc aat gcc ttg gtt gca aaa gcc caa aag gtt cct gag gaa gga tgg     1675
Ile Asn Ala Leu Val Ala Lys Ala Gln Lys Val Pro Glu Glu Gly Trp
                    475                 480                 485 aca atg caa gat gga agc ccc tgg cct gga aac aac gta cgc gat cat     1723
Thr Met Gln Asp Gly Ser Pro Trp Pro Gly Asn Asn Val Arg Asp His
        490                 495                 500 cct gga atg att cag gta ttc ctt ggc caa agt ggc ggt cgt gat gtg     1771
Pro Gly Met Ile Gln Val Phe Leu Gly Gln Ser Gly Gly Arg Asp Val
505                 510                 515 gaa gga aat gag ttg cct cgc ctg gtt tat gtc tcg aga gaa aag agg     1819
Glu Gly Asn Glu Leu Pro Arg Leu Val Tyr Val Ser Arg Glu Lys Arg
520                 525                 530                 535 cca ggt tat aac cat cac aag aag gct ggt gcc atg aat gca ctg gtc     1867
Pro Gly Tyr Asn His His Lys Lys Ala Gly Ala Met Asn Ala Leu Val
```

-continued

```
                540                 545                 550
cgt gtc tct gct gtc tta tca aat gct gca tac cta ttg aac ttg gac    1915
Arg Val Ser Ala Val Leu Ser Asn Ala Ala Tyr Leu Leu Asn Leu Asp
            555                 560                 565 tgt gat cac tac atc aac aat agc aag gcc ata aaa gag gct atg tgt    1963
Cys Asp His Tyr Ile Asn Asn Ser Lys Ala Ile Lys Glu Ala Met Cys
            570                 575                 580 ttc atg atg gat cct ttg gtg ggg aag aaa gtg tgc tat gta cag ttc    2011
Phe Met Met Asp Pro Leu Val Gly Lys Lys Val Cys Tyr Val Gln Phe
            585                 590                 595 cct cag agg ttt gat ggt att gac aaa aat gat cga tac gct aac agg    2059
Pro Gln Arg Phe Asp Gly Ile Asp Lys Asn Asp Arg Tyr Ala Asn Arg
600                 605                 610                 615 aac gtt gtc ttt ttt gac atc aac atg aaa ggt ttg gac ggt att caa    2107
Asn Val Val Phe Phe Asp Ile Asn Met Lys Gly Leu Asp Gly Ile Gln
            620                 625                 630 gga ccc att tat gtg ggt act gga tgt gtt ttc aga cgg cag gca ctg    2155
Gly Pro Ile Tyr Val Gly Thr Gly Cys Val Phe Arg Arg Gln Ala Leu
            635                 640                 645 tat ggt tat gat gct cct aaa acg aag aag cca cca tca aga act tgc    2203
Tyr Gly Tyr Asp Ala Pro Lys Thr Lys Lys Pro Pro Ser Arg Thr Cys
            650                 655                 660 aac tgc tgg ccc aag tgg tgc ctc tct tgc tgc tgc agc agg aac aag    2251
Asn Cys Trp Pro Lys Trp Cys Leu Ser Cys Cys Cys Ser Arg Asn Lys
665                 670                 675 aat aaa aag aag act aca aaa cca aag acg gag aag aag aaa aga tta    2299
Asn Lys Lys Lys Thr Thr Lys Pro Lys Thr Glu Lys Lys Lys Arg Leu
680                 685                 690                 695 ttt ttc aag aaa gca gaa aac cca tct cct gca tat gct ttg ggt gaa    2347
Phe Phe Lys Lys Ala Glu Asn Pro Ser Pro Ala Tyr Ala Leu Gly Glu
            700                 705                 710 att gat gaa ggt gct cca ggt gct gat atc gag aag gcc gga atc gta    2395
Ile Asp Glu Gly Ala Pro Gly Ala Asp Ile Glu Lys Ala Gly Ile Val
            715                 720                 725 aat caa cag aaa cta gag aag aaa ttt ggg cag tct tct gtt ttt gtc    2443
Asn Gln Gln Lys Leu Glu Lys Lys Phe Gly Gln Ser Ser Val Phe Val
            730                 735                 740 gca tca aca ctt ctt gag aac gga ggg acc ctg aag agc gca agt cca    2491
Ala Ser Thr Leu Leu Glu Asn Gly Gly Thr Leu Lys Ser Ala Ser Pro
745                 750                 755 gct tct ctt ctg aag gaa gct ata cat gtt atc agc tgc ggc tac gaa    2539
Ala Ser Leu Leu Lys Glu Ala Ile His Val Ile Ser Cys Gly Tyr Glu
760                 765                 770                 775 gac aag acc gac tgg gga aaa gag att ggc tgg att tac gga tcg atc    2587
Asp Lys Thr Asp Trp Gly Lys Glu Ile Gly Trp Ile Tyr Gly Ser Ile
            780                 785                 790 aca gag gat atc ttg act gga ttt aag atg cac tgc cat ggc tgg cgg    2635
Thr Glu Asp Ile Leu Thr Gly Phe Lys Met His Cys His Gly Trp Arg
            795                 800                 805 tct att tac tgc atc ccg aag cgg cct gca ttc aaa ggt tct gcg cct    2683
Ser Ile Tyr Cys Ile Pro Lys Arg Pro Ala Phe Lys Gly Ser Ala Pro
            810                 815                 820 ctg aac ctt tcc gac cgt ctt cac cag gtc ctt cgc tgg gcc ctt ggg    2731
Leu Asn Leu Ser Asp Arg Leu His Gln Val Leu Arg Trp Ala Leu Gly
825                 830                 835 tcc gtc gaa att ttc ttc agc aag cac tgc cca ctt tgg tac gga tac    2779
Ser Val Glu Ile Phe Phe Ser Lys His Cys Pro Leu Trp Tyr Gly Tyr
840                 845                 850                 855 ggc ggc ggg cta aaa ttc ctg gaa agg ttt tct tat atc aac tcc atc    2827
```

```
                    Gly Gly Gly Leu Lys Phe Leu Glu Arg Phe Ser Tyr Ile Asn Ser Ile
                                    860                 865                 870 gtt tat ccc tgg acg tcc att cct ctc ctg gct tac tgt acc ttg cct          2875
Val Tyr Pro Trp Thr Ser Ile Pro Leu Leu Ala Tyr Cys Thr Leu Pro
                875                 880                 885 gcc atc tgc ctg ctc acg ggg aag ttt atc aca cca gag ctt acc aat          2923
Ala Ile Cys Leu Leu Thr Gly Lys Phe Ile Thr Pro Glu Leu Thr Asn
                890                 895                 900 gtc gcc agt atc tgg ttc atg gca ctt ttc atc tgc atc tcc gtg acc          2971
Val Ala Ser Ile Trp Phe Met Ala Leu Phe Ile Cys Ile Ser Val Thr
                905                 910                 915 ggc atc ctg gaa atg agg tgg agt ggc gtg gcc atc gac gac tgg tgg          3019
Gly Ile Leu Glu Met Arg Trp Ser Gly Val Ala Ile Asp Asp Trp Trp
920                 925                 930                 935 agg aac gag cag ttc tgg gtc atc gga ggc gtt tcg gcg cat ctg ttc          3067
Arg Asn Glu Gln Phe Trp Val Ile Gly Gly Val Ser Ala His Leu Phe
                940                 945                 950 gcg gtg ttc cag ggc ctg ctg aag gtg ttc gcc ggc atc gac acg agc          3115
Ala Val Phe Gln Gly Leu Leu Lys Val Phe Ala Gly Ile Asp Thr Ser
                955                 960                 965 ttc acc gtg acg tcg aag gcc ggg gac gac gag gag ttc tcg gag ctg          3163
Phe Thr Val Thr Ser Lys Ala Gly Asp Asp Glu Glu Phe Ser Glu Leu
                970                 975                 980 tac acg ttc aag tgg acc acc ctg ctg ata ccc ccg acc acg ctc ctc          3211
Tyr Thr Phe Lys Trp Thr Thr Leu Leu Ile Pro Pro Thr Thr Leu Leu
                985                 990                 995 ctg ctg aac ttc atc ggg gtg gtg gcc ggg atc tcg aac gcg atc aac          3259
Leu Leu Asn Phe Ile Gly Val Val Ala Gly Ile Ser Asn Ala Ile Asn
1000                1005                1010                1015 aac ggg tac gag tcg tgg ggc ccc ctg ttc ggg aag ctc ttc ttc gcc          3307
Asn Gly Tyr Glu Ser Trp Gly Pro Leu Phe Gly Lys Leu Phe Phe Ala
                1020                1025                1030 ttc tgg gtg atc gtc cac ctg tac ccg ttc ctc aag ggt ctg gtg ggg          3355
Phe Trp Val Ile Val His Leu Tyr Pro Phe Leu Lys Gly Leu Val Gly
                1035                1040                1045 agg cag aac agg acg ccg acg atc gtc atc gtc tgg tcc atc ctg ctg          3403
Arg Gln Asn Arg Thr Pro Thr Ile Val Ile Val Trp Ser Ile Leu Leu
                1050                1055                1060 gcc tcg atc ttc tcg ctc ctg tgg gtc cgc gtc gac ccg ttc ctc gcc          3451
Ala Ser Ile Phe Ser Leu Leu Trp Val Arg Val Asp Pro Phe Leu Ala
                1065                1070                1075 aag agc aac ggc ccg ctc ctg gag gag tgt ggc ctg gac tgc aac              3496
Lys Ser Asn Gly Pro Leu Leu Glu Glu Cys Gly Leu Asp Cys Asn
1080                1085                1090 tgaagtgggg gccccctgtc actcgaagtt ctgtcacggg cgaattacgc ctgatttttt         3556
gttgttgttg ttgttggaat tctttgctgt agatagaaac cacatgtcca cggcatctct         3616
gctgtgtcca ttggagcagg agagaggtgc ctgctgctgt tgttgagta aattaaaagt          3676 tttaaagtta tacagtgatg cacattccag tgcccagtgt attccctttt tacagtctgt         3736
atattagcga caaaggacat attggttagg agtttgattc ttttgtaaaa aaaaaaaaa          3796 aaaaaaaaaa aaaaaaa                                                        3813

<210> SEQ ID NO 46
<211> LENGTH: 1094
<212> TYPE: PRT
<213> ORGANISM: Zea mays

<400> SEQUENCE: 46
```

-continued

```
Met Glu Ala Ser Ala Gly Leu Val Ala Gly Ser His Asn Arg Asn Glu
 1               5                  10                  15

Leu Val Val Ile Arg Arg Asp Arg Glu Ser Gly Ala Ala Gly Gly Gly
             20                  25                  30

Ala Ala Arg Arg Ala Glu Ala Pro Cys Gln Ile Cys Gly Asp Glu Val
         35                  40                  45

Gly Val Gly Phe Asp Gly Glu Pro Phe Val Ala Cys Asn Glu Cys Ala
 50                  55                  60

Phe Pro Val Cys Arg Ala Cys Tyr Glu Tyr Glu Arg Arg Glu Gly Ser
 65                  70                  75                  80

Gln Ala Cys Pro Gln Cys Arg Thr Arg Tyr Lys Arg Leu Lys Gly Cys
                 85                  90                  95

Pro Arg Val Ala Gly Asp Glu Glu Asp Gly Val Asp Asp Leu Glu
                100                 105                 110

Gly Glu Phe Gly Leu Gln Asp Gly Ala Ala His Glu Asp Asp Pro Gln
            115                 120                 125

Tyr Val Ala Glu Ser Met Leu Arg Ala Gln Met Ser Tyr Gly Arg Gly
        130                 135                 140

Gly Asp Ala His Pro Gly Phe Ser Pro Val Pro Asn Val Pro Leu Leu
145                 150                 155                 160

Thr Asn Gly Gln Met Val Asp Asp Ile Pro Pro Glu Gln His Ala Leu
                165                 170                 175

Val Pro Ser Tyr Met Ser Gly Gly Gly Gly Gly Lys Arg Ile His
            180                 185                 190

Pro Leu Pro Phe Ala Asp Pro Asn Leu Pro Val Gln Pro Arg Ser Met
        195                 200                 205

Asp Pro Ser Lys Asp Leu Ala Ala Tyr Gly Tyr Gly Ser Val Ala Trp
210                 215                 220

Lys Glu Arg Met Glu Gly Trp Lys Gln Lys Gln Glu Arg Leu Gln His
225                 230                 235                 240

Val Arg Ser Glu Gly Gly Gly Asp Trp Asp Gly Asp Asp Ala Asp Leu
                245                 250                 255

Pro Leu Met Asp Glu Ala Arg Gln Pro Leu Ser Arg Lys Val Pro Ile
            260                 265                 270

Ser Ser Ser Arg Ile Asn Pro Tyr Arg Met Ile Ile Val Ile Arg Leu
        275                 280                 285

Val Val Leu Gly Phe Phe His Tyr Arg Val Met His Pro Ala Lys
    290                 295                 300

Asp Ala Phe Ala Leu Trp Leu Ile Ser Val Ile Cys Glu Ile Trp Phe
305                 310                 315                 320

Ala Met Ser Trp Ile Leu Asp Gln Phe Pro Lys Trp Leu Pro Ile Glu
                325                 330                 335

Arg Glu Thr Tyr Leu Asp Arg Leu Ser Leu Arg Phe Asp Lys Glu Gly
            340                 345                 350

Gln Pro Ser Gln Leu Ala Pro Ile Asp Phe Phe Val Ser Thr Val Asp
        355                 360                 365

Pro Thr Lys Glu Pro Pro Leu Val Thr Ala Asn Thr Val Leu Ser Ile
    370                 375                 380

Leu Ser Val Asp Tyr Pro Val Glu Lys Val Ser Cys Tyr Val Ser Asp
385                 390                 395                 400

Asp Gly Ala Ala Met Leu Thr Phe Glu Ala Leu Ser Glu Thr Ser Glu
                405                 410                 415

Phe Ala Lys Lys Trp Val Pro Phe Ser Lys Lys Phe Asn Ile Glu Pro
```

-continued

```
                420             425             430
Arg Ala Pro Glu Trp Tyr Phe Gln Gln Lys Ile Asp Tyr Leu Lys Asp
            435                 440                 445
Lys Val Ala Ala Ser Phe Val Arg Glu Arg Arg Ala Met Lys Arg Glu
450                 455                 460
Tyr Glu Glu Phe Lys Val Arg Ile Asn Ala Leu Val Ala Lys Ala Gln
465                 470                 475                 480
Lys Val Pro Glu Glu Gly Trp Thr Met Gln Asp Gly Ser Pro Trp Pro
                485                 490                 495
Gly Asn Asn Val Arg Asp His Pro Gly Met Ile Gln Val Phe Leu Gly
            500                 505                 510
Gln Ser Gly Gly Arg Asp Val Glu Gly Asn Glu Leu Pro Arg Leu Val
            515                 520                 525
Tyr Val Ser Arg Glu Lys Arg Pro Gly Tyr Asn His His Lys Lys Ala
            530                 535                 540
Gly Ala Met Asn Ala Leu Val Arg Val Ser Ala Val Leu Ser Asn Ala
545                 550                 555                 560
Ala Tyr Leu Leu Asn Leu Asp Cys Asp His Tyr Ile Asn Asn Ser Lys
                565                 570                 575
Ala Ile Lys Glu Ala Met Cys Phe Met Met Asp Pro Leu Val Gly Lys
            580                 585                 590
Lys Val Cys Tyr Val Gln Phe Pro Gln Arg Phe Asp Gly Ile Asp Lys
            595                 600                 605
Asn Asp Arg Tyr Ala Asn Arg Asn Val Val Phe Phe Asp Ile Asn Met
            610                 615                 620
Lys Gly Leu Asp Gly Ile Gln Gly Pro Ile Tyr Val Gly Thr Gly Cys
625                 630                 635                 640
Val Phe Arg Arg Gln Ala Leu Tyr Gly Tyr Asp Ala Pro Lys Thr Lys
                645                 650                 655
Lys Pro Pro Ser Arg Thr Cys Asn Cys Trp Pro Lys Trp Cys Leu Ser
            660                 665                 670
Cys Cys Cys Ser Arg Asn Lys Asn Lys Lys Thr Thr Lys Pro Lys
            675                 680                 685
Thr Glu Lys Lys Lys Arg Leu Phe Phe Lys Lys Ala Glu Asn Pro Ser
            690                 695                 700
Pro Ala Tyr Ala Leu Gly Glu Ile Asp Glu Gly Ala Pro Gly Ala Asp
705                 710                 715                 720
Ile Glu Lys Ala Gly Ile Val Asn Gln Gln Lys Leu Glu Lys Lys Phe
                725                 730                 735
Gly Gln Ser Ser Val Phe Val Ala Ser Thr Leu Leu Glu Asn Gly Gly
            740                 745                 750
Thr Leu Lys Ser Ala Ser Pro Ala Ser Leu Leu Lys Glu Ala Ile His
            755                 760                 765
Val Ile Ser Cys Gly Tyr Glu Asp Lys Thr Asp Trp Gly Lys Glu Ile
            770                 775                 780
Gly Trp Ile Tyr Gly Ser Ile Thr Glu Asp Ile Leu Thr Gly Phe Lys
785                 790                 795                 800
Met His Cys His Gly Trp Arg Ser Ile Tyr Cys Ile Pro Lys Arg Pro
                805                 810                 815
Ala Phe Lys Gly Ser Ala Pro Leu Asn Leu Ser Asp Arg Leu His Gln
            820                 825                 830
Val Leu Arg Trp Ala Leu Gly Ser Val Glu Ile Phe Phe Ser Lys His
            835                 840                 845
```

Cys Pro Leu Trp Tyr Gly Tyr Gly Gly Leu Lys Phe Leu Glu Arg
     850                 855                 860

Phe Ser Tyr Ile Asn Ser Ile Val Tyr Pro Trp Thr Ser Ile Pro Leu
865                 870                 875                 880

Leu Ala Tyr Cys Thr Leu Pro Ala Ile Cys Leu Leu Thr Gly Lys Phe
                885                 890                 895

Ile Thr Pro Glu Leu Thr Asn Val Ala Ser Ile Trp Phe Met Ala Leu
            900                 905                 910

Phe Ile Cys Ile Ser Val Thr Gly Ile Leu Glu Met Arg Trp Ser Gly
        915                 920                 925

Val Ala Ile Asp Asp Trp Trp Arg Asn Glu Gln Phe Trp Val Ile Gly
    930                 935                 940

Gly Val Ser Ala His Leu Phe Ala Val Phe Gln Gly Leu Leu Lys Val
945                 950                 955                 960

Phe Ala Gly Ile Asp Thr Ser Phe Thr Val Thr Ser Lys Ala Gly Asp
                965                 970                 975

Asp Glu Glu Phe Ser Glu Leu Tyr Thr Phe Lys Trp Thr Thr Leu Leu
            980                 985                 990

Ile Pro Pro Thr Thr Leu Leu Leu Asn Phe Ile Gly Val Val Ala
        995                 1000                1005

Gly Ile Ser Asn Ala Ile Asn Asn Gly Tyr Glu Ser Trp Gly Pro Leu
    1010                1015                1020

Phe Gly Lys Leu Phe Phe Ala Phe Trp Val Ile Val His Leu Tyr Pro
1025                1030                1035                1040

Phe Leu Lys Gly Leu Val Gly Arg Gln Asn Arg Thr Pro Thr Ile Val
                1045                1050                1055

Ile Val Trp Ser Ile Leu Leu Ala Ser Ile Phe Ser Leu Leu Trp Val
            1060                1065                1070

Arg Val Asp Pro Phe Leu Ala Lys Ser Asn Gly Pro Leu Leu Glu Glu
        1075                1080                1085

Cys Gly Leu Asp Cys Asn
    1090

<210> SEQ ID NO 47
<211> LENGTH: 25
<212> TYPE: DNA
<213> ORGANISM: Zea mays

<400> SEQUENCE: 47
atggaggcta gcgcggggct ggtgg                                              25

<210> SEQ ID NO 48
<211> LENGTH: 25
<212> TYPE: DNA
<213> ORGANISM: Zea mays

<400> SEQUENCE: 48
tcagttgcag tccaggccac actcc                                              25

<210> SEQ ID NO 49
<211> LENGTH: 3746
<212> TYPE: DNA
<213> ORGANISM: Zea mays
<220> FEATURE:
<221> NAME/KEY: CDS
<222> LOCATION: (321)...(3449)

<400> SEQUENCE: 49

-continued

```
ctaggatcaa aaccgtctcg ccgctgcaat aatcttttgt caattcttaa tccctcgcgt    60
cgacagcgac agcggaacca actcacgttg ccgcggcttc ctccatcggt gcggtgccct   120
gtccttttct ctcgtccctc ctcccccgt atagttaagc cccgcccgc tactactact    180 actagcagca gcagcgctct cgcagcggga gatgcggtgt tgatccgtgc cccgctcgga   240
tctcgggact ggtgccggct ctgcccaggc cccaggctcc aggccagctc cctcgacgtt   300
tctcggcgag ctcgcttgcc atg gag ggc gac gcg gac ggc gtg aag tcg ggg   353
                       Met Glu Gly Asp Ala Asp Gly Val Lys Ser Gly
                        1               5                  10
```

| | | | | | | | | | | | | | | | | |
|---|---|---|---|---|---|---|---|---|---|---|---|---|---|---|---|---|
| agg | cgc | ggt | ggc | gga | cag | gtg | tgc | cag | atc | tgc | ggc | gac | ggc | gtg | ggc | 401 |
| Arg | Arg | Gly | Gly | Gly | Gln | Val | Cys | Gln | Ile | Cys | Gly | Asp | Gly | Val | Gly | |
| | | | 15 | | | | 20 | | | | 25 | | | | | |

| acc | acg | gcg | gag | ggg | gac | gtc | ttc | gcc | gcc | tgc | gac | gtc | tgc | ggg | ttt | 449 |
|---|---|---|---|---|---|---|---|---|---|---|---|---|---|---|---|---|
| Thr | Thr | Ala | Glu | Gly | Asp | Val | Phe | Ala | Ala | Cys | Asp | Val | Cys | Gly | Phe | |
| | | 30 | | | | 35 | | | | 40 | | | | | | |

| ccg | gtg | tgc | cgc | ccc | tgc | tac | gag | tac | gag | cgc | aag | gac | ggc | acg | cag | 497 |
|---|---|---|---|---|---|---|---|---|---|---|---|---|---|---|---|---|
| Pro | Val | Cys | Arg | Pro | Cys | Tyr | Glu | Tyr | Glu | Arg | Lys | Asp | Gly | Thr | Gln | |
| | 45 | | | | 50 | | | | 55 | | | | | | | |

| gcg | tgc | ccc | cag | tgc | aag | acc | aag | tac | aag | cgc | cac | aag | ggg | agc | ccg | 545 |
|---|---|---|---|---|---|---|---|---|---|---|---|---|---|---|---|---|
| Ala | Cys | Pro | Gln | Cys | Lys | Thr | Lys | Tyr | Lys | Arg | His | Lys | Gly | Ser | Pro | |
| 60 | | | | 65 | | | | 70 | | | | | | | 75 | |

| gcg | atc | cgt | ggg | gag | gaa | gga | gac | gac | act | gat | gcc | gat | agc | gac | ttc | 593 |
|---|---|---|---|---|---|---|---|---|---|---|---|---|---|---|---|---|
| Ala | Ile | Arg | Gly | Glu | Glu | Gly | Asp | Asp | Thr | Asp | Ala | Asp | Ser | Asp | Phe | |
| | | | 80 | | | | 85 | | | | 90 | | | | | |

| aat | tac | ctt | gca | tct | ggc | aat | gag | gac | cag | aag | cag | aag | att | gcc | gac | 641 |
|---|---|---|---|---|---|---|---|---|---|---|---|---|---|---|---|---|
| Asn | Tyr | Leu | Ala | Ser | Gly | Asn | Glu | Asp | Gln | Lys | Gln | Lys | Ile | Ala | Asp | |
| | | 95 | | | | 100 | | | | 105 | | | | | | |

| aga | atg | cgc | agc | tgg | cgc | atg | aac | gtt | ggg | ggc | agc | ggg | gat | gtt | ggt | 689 |
|---|---|---|---|---|---|---|---|---|---|---|---|---|---|---|---|---|
| Arg | Met | Arg | Ser | Trp | Arg | Met | Asn | Val | Gly | Gly | Ser | Gly | Asp | Val | Gly | |
| | 110 | | | | 115 | | | | 120 | | | | | | | |

| cgc | ccc | aag | tat | gac | agt | ggc | gag | atc | ggg | ctt | acc | aag | tat | gac | agt | 737 |
|---|---|---|---|---|---|---|---|---|---|---|---|---|---|---|---|---|
| Arg | Pro | Lys | Tyr | Asp | Ser | Gly | Glu | Ile | Gly | Leu | Thr | Lys | Tyr | Asp | Ser | |
| 125 | | | | 130 | | | | 135 | | | | | | | | |

| ggc | gag | att | cct | cgg | gga | tac | atc | cca | tca | gtc | act | aac | agc | cag | atc | 785 |
|---|---|---|---|---|---|---|---|---|---|---|---|---|---|---|---|---|
| Gly | Glu | Ile | Pro | Arg | Gly | Tyr | Ile | Pro | Ser | Val | Thr | Asn | Ser | Gln | Ile | |
| 140 | | | | 145 | | | | 150 | | | | 155 | | | | |

| tca | gga | gaa | atc | cct | ggt | gct | tcc | cct | gac | cat | cat | atg | atg | tcc | cca | 833 |
|---|---|---|---|---|---|---|---|---|---|---|---|---|---|---|---|---|
| Ser | Gly | Glu | Ile | Pro | Gly | Ala | Ser | Pro | Asp | His | His | Met | Met | Ser | Pro | |
| | | | 160 | | | | 165 | | | | 170 | | | | | |

| act | ggg | aac | att | ggc | aag | cgt | gct | cca | ttt | ccc | tat | gtg | aac | cat | tcg | 881 |
|---|---|---|---|---|---|---|---|---|---|---|---|---|---|---|---|---|
| Thr | Gly | Asn | Ile | Gly | Lys | Arg | Ala | Pro | Phe | Pro | Tyr | Val | Asn | His | Ser | |
| | | 175 | | | | 180 | | | | 185 | | | | | | |

| cca | aat | ccg | tca | agg | gag | ttc | tct | ggt | agc | att | ggg | aat | gtt | gcc | tgg | 929 |
|---|---|---|---|---|---|---|---|---|---|---|---|---|---|---|---|---|
| Pro | Asn | Pro | Ser | Arg | Glu | Phe | Ser | Gly | Ser | Ile | Gly | Asn | Val | Ala | Trp | |
| | 190 | | | | 195 | | | | 200 | | | | | | | |

| aaa | gag | agg | gtt | gat | ggc | tgg | aaa | atg | aag | cag | gac | aag | ggg | acg | att | 977 |
|---|---|---|---|---|---|---|---|---|---|---|---|---|---|---|---|---|
| Lys | Glu | Arg | Val | Asp | Gly | Trp | Lys | Met | Lys | Gln | Asp | Lys | Gly | Thr | Ile | |
| 205 | | | | 210 | | | | 215 | | | | | | | | |

| ccc | atg | acg | aat | ggc | aca | agc | att | gct | ccc | tct | gag | ggt | cgg | ggt | gtt | 1025 |
|---|---|---|---|---|---|---|---|---|---|---|---|---|---|---|---|---|
| Pro | Met | Thr | Asn | Gly | Thr | Ser | Ile | Ala | Pro | Ser | Glu | Gly | Arg | Gly | Val | |
| 220 | | | 225 | | | | 230 | | | | 235 | | | | | |

| ggt | gat | att | gat | gca | tca | act | gat | tac | aac | atg | gaa | gat | gcc | tta | ttg | 1073 |
|---|---|---|---|---|---|---|---|---|---|---|---|---|---|---|---|---|
| Gly | Asp | Ile | Asp | Ala | Ser | Thr | Asp | Tyr | Asn | Met | Glu | Asp | Ala | Leu | Leu | |
| | | | 240 | | | | 245 | | | | 250 | | | | | |

| aac | gac | gaa | act | cga | cag | cct | cta | tct | agg | aaa | gtt | cca | ctt | cct | tcc | 1121 |
|---|---|---|---|---|---|---|---|---|---|---|---|---|---|---|---|---|
| Asn | Asp | Glu | Thr | Arg | Gln | Pro | Leu | Ser | Arg | Lys | Val | Pro | Leu | Pro | Ser | |
| | | 255 | | | | 260 | | | | 265 | | | | | | |

-continued

| | |
|---|---|
| tcc agg ata aat cca tac agg atg gtc att gtg ctg cga ttg att gtt<br>Ser Arg Ile Asn Pro Tyr Arg Met Val Ile Val Leu Arg Leu Ile Val<br>            270                   275                   280 | 1169 |
| cta agc atc ttc ttg cac tac cgt atc aca aat cct gtg cgc aat gca<br>Leu Ser Ile Phe Leu His Tyr Arg Ile Thr Asn Pro Val Arg Asn Ala<br>285                 290                   295 | 1217 |
| tac cca tta tgg ctt cta tct gtt ata tgt gag atc tgg ttt gct ctt<br>Tyr Pro Leu Trp Leu Leu Ser Val Ile Cys Glu Ile Trp Phe Ala Leu<br>300                 305                   310                 315 | 1265 |
| tcg tgg ata ttg gat cag ttc cct aag tgg ttt cca atc aac cgg gag<br>Ser Trp Ile Leu Asp Gln Phe Pro Lys Trp Phe Pro Ile Asn Arg Glu<br>            320                   325                   330 | 1313 |
| acg tac ctt gat agg ctg gca tta agg tat gac cgg gaa ggt gag cca<br>Thr Tyr Leu Asp Arg Leu Ala Leu Arg Tyr Asp Arg Glu Gly Glu Pro<br>               335                   340                 345 | 1361 |
| tct cag ttg gct gct gtt gac att ttc gtc agt aca gtc gac cca atg<br>Ser Gln Leu Ala Ala Val Asp Ile Phe Val Ser Thr Val Asp Pro Met<br>350                 355                   360 | 1409 |
| aag gag cct cct ctt gtc act gcc aat acc gtg cta tcc att ctt gct<br>Lys Glu Pro Pro Leu Val Thr Ala Asn Thr Val Leu Ser Ile Leu Ala<br>            365                   370                 375 | 1457 |
| gtg gat tac cct gtg gat aag gtc tct tgc tat gta tct gat gat gga<br>Val Asp Tyr Pro Val Asp Lys Val Ser Cys Tyr Val Ser Asp Asp Gly<br>380                 385                   390                 395 | 1505 |
| gct gcg atg ctg aca ttt gat gca cta gct gag act tca gag ttt gct<br>Ala Ala Met Leu Thr Phe Asp Ala Leu Ala Glu Thr Ser Glu Phe Ala<br>               400                   405                 410 | 1553 |
| aga aaa tgg gta cca ttt gtt aag aag tac aac att gaa cct aga gct<br>Arg Lys Trp Val Pro Phe Val Lys Lys Tyr Asn Ile Glu Pro Arg Ala<br>               415                   420                 425 | 1601 |
| cct gaa tgg tac ttc tcc cag aaa att gat tac ttg aag gac aaa gtg<br>Pro Glu Trp Tyr Phe Ser Gln Lys Ile Asp Tyr Leu Lys Asp Lys Val<br>            430                   435                 440 | 1649 |
| cac cct tca ttt gtt aaa gac cgc cgg gcc atg aag aga gaa tat gaa<br>His Pro Ser Phe Val Lys Asp Arg Arg Ala Met Lys Arg Glu Tyr Glu<br>               445                   450                 455 | 1697 |
| gaa ttc aaa gtt agg gta aat ggc ctt gtt gct aag gca cag aaa gtt<br>Glu Phe Lys Val Arg Val Asn Gly Leu Val Ala Lys Ala Gln Lys Val<br>460                 465                   470                 475 | 1745 |
| cct gag gaa gga tgg atc atg caa gat ggc aca cca tgg cca gga aac<br>Pro Glu Glu Gly Trp Ile Met Gln Asp Gly Thr Pro Trp Pro Gly Asn<br>                 480                   485                 490 | 1793 |
| aat acc agg gac cat cct gga atg att cag gtt ttc ctt ggt cac agt<br>Asn Thr Arg Asp His Pro Gly Met Ile Gln Val Phe Leu Gly His Ser<br>            495                   500                 505 | 1841 |
| ggt ggc ctt gat act gag ggc aat gag cta ccc cgt ttg gtc tat gtt<br>Gly Gly Leu Asp Thr Glu Gly Asn Glu Leu Pro Arg Leu Val Tyr Val<br>510                 515                   520 | 1889 |
| tct cgt gaa aag cgt cct gga ttc cag cat cac aag aaa gct ggt gcc<br>Ser Arg Glu Lys Arg Pro Gly Phe Gln His His Lys Lys Ala Gly Ala<br>            525                   530                 535 | 1937 |
| atg aat gct ctt gtt cgt gtc tca gct gtg ctt acc aat gga caa tac<br>Met Asn Ala Leu Val Arg Val Ser Ala Val Leu Thr Asn Gly Gln Tyr<br>540                 545                   550                 555 | 1985 |
| atg ttg aat ctt gat tgt gat cac tac att aac aac agt aag gct ctc<br>Met Leu Asn Leu Asp Cys Asp His Tyr Ile Asn Asn Ser Lys Ala Leu<br>               560                   565                 570 | 2033 |
| agg gaa gct atg tgc ttc ctt atg gac cct aac cta gga agg agt gtc<br>Arg Glu Ala Met Cys Phe Leu Met Asp Pro Asn Leu Gly Arg Ser Val<br>            575                   580                 585 | 2081 |

```
tgc tac gtc cag ttt ccc cag aga ttc gat ggc att gac agg aat gat        2129
Cys Tyr Val Gln Phe Pro Gln Arg Phe Asp Gly Ile Asp Arg Asn Asp
            590                 595                 600 cga tat gcc aac agg aac acc gtg ttt ttc gat att aac ttg aga ggt        2177
Arg Tyr Ala Asn Arg Asn Thr Val Phe Phe Asp Ile Asn Leu Arg Gly
605                 610                 615 ctt gat ggc atc caa gga cca gtt tat gtc gga act ggc tgt gtt ttc        2225
Leu Asp Gly Ile Gln Gly Pro Val Tyr Val Gly Thr Gly Cys Val Phe
620                 625                 630                 635 aac cga aca gct cta tat ggt tat gag ccc cca att aag cag aag aag        2273
Asn Arg Thr Ala Leu Tyr Gly Tyr Glu Pro Pro Ile Lys Gln Lys Lys
            640                 645                 650 ggt ggt ttc ttg tca tca cta tgt ggc ggt agg aag aag gca agc aaa        2321
Gly Gly Phe Leu Ser Ser Leu Cys Gly Gly Arg Lys Lys Ala Ser Lys
            655                 660                 665 tca aag aag ggc tcg gac aag aag aag tcg cag aag cat gtg gac agt        2369
Ser Lys Lys Gly Ser Asp Lys Lys Lys Ser Gln Lys His Val Asp Ser
            670                 675                 680 tct gtg cca gta ttc aac ctt gaa gat ata gag gag gga gtt gaa ggc        2417
Ser Val Pro Val Phe Asn Leu Glu Asp Ile Glu Glu Gly Val Glu Gly
685                 690                 695 gct gga ttt gac gac gag aaa tca ctt ctt atg tct caa atg agc ctg        2465
Ala Gly Phe Asp Asp Glu Lys Ser Leu Leu Met Ser Gln Met Ser Leu
700                 705                 710                 715 gag aag aga ttt ggc cag tcc gca gcg ttt gtt gcc tcc act ctg atg        2513
Glu Lys Arg Phe Gly Gln Ser Ala Ala Phe Val Ala Ser Thr Leu Met
                720                 725                 730 gag tat ggt ggt gtt cct cag tcc gca act ccg gag tct ctt ctg aaa        2561
Glu Tyr Gly Gly Val Pro Gln Ser Ala Thr Pro Glu Ser Leu Leu Lys
            735                 740                 745 gaa gct atc cat gtt ata agc tgt ggc tat gag gac aag act gaa tgg        2609
Glu Ala Ile His Val Ile Ser Cys Gly Tyr Glu Asp Lys Thr Glu Trp
            750                 755                 760 gga act gag atc ggg tgg atc tac ggt tct gtg aca gaa gac att ctc        2657
Gly Thr Glu Ile Gly Trp Ile Tyr Gly Ser Val Thr Glu Asp Ile Leu
765                 770                 775 acc gga ttc aag atg cac gcg cga ggc tgg cgg tcg atc tac tgc atg        2705
Thr Gly Phe Lys Met His Ala Arg Gly Trp Arg Ser Ile Tyr Cys Met
780                 785                 790                 795 ccc aag cgg cca gct ttc aag ggg tct gcc ccc atc aat ctt tcg gac        2753
Pro Lys Arg Pro Ala Phe Lys Gly Ser Ala Pro Ile Asn Leu Ser Asp
                800                 805                 810 cgt ctg aac cag gtg ctc cgg tgg gct ctt ggg tcc gtg gag atc ctc        2801
Arg Leu Asn Gln Val Leu Arg Trp Ala Leu Gly Ser Val Glu Ile Leu
            815                 820                 825 ttc agc cgg cac tgc ccc ctg tgg tac ggc tac gga ggg cgg ctc aag        2849
Phe Ser Arg His Cys Pro Leu Trp Tyr Gly Tyr Gly Gly Arg Leu Lys
            830                 835                 840 ttc ctg gag aga ttc gcg tac atc aac acc acc atc tac ccg ctc acg        2897
Phe Leu Glu Arg Phe Ala Tyr Ile Asn Thr Thr Ile Tyr Pro Leu Thr
845                 850                 855 tcc atc ccg ctt ctc atc tac tgc atc ctg ccc gcc atc tgt ctg ctc        2945
Ser Ile Pro Leu Leu Ile Tyr Cys Ile Leu Pro Ala Ile Cys Leu Leu
860                 865                 870                 875 acc gga aag ttc atc att cca gag atc agc aac ttc gcc agc atc tgg        2993
Thr Gly Lys Phe Ile Ile Pro Glu Ile Ser Asn Phe Ala Ser Ile Trp
                880                 885                 890 ttc atc tcc ctc ttc atc tcg atc ttc gcc acg ggc atc ctg gag atg        3041
Phe Ile Ser Leu Phe Ile Ser Ile Phe Ala Thr Gly Ile Leu Glu Met
```

-continued

```
                895                 900                 905
agg tgg agc ggg gtg ggc atc gac gag tgg tgg agg aac gag cag ttc     3089
Arg Trp Ser Gly Val Gly Ile Asp Glu Trp Trp Arg Asn Glu Gln Phe
        910                 915                 920 tgg gtg atc ggg ggc atc tcc gcg cac ctc ttc gcc gtg ttc cag ggc     3137
Trp Val Ile Gly Gly Ile Ser Ala His Leu Phe Ala Val Phe Gln Gly
925                 930                 935 ctg ctc aag gtg ctg gcc ggc atc gac acc aac ttc acc gtc acc tcc     3185
Leu Leu Lys Val Leu Ala Gly Ile Asp Thr Asn Phe Thr Val Thr Ser
940                 945                 950                 955 aag gcc tcg gac gag gac ggc gac ttc gcg gag ctg tac atg ttc aag     3233
Lys Ala Ser Asp Glu Asp Gly Asp Phe Ala Glu Leu Tyr Met Phe Lys
                960                 965                 970 tgg acg acg ctc ctg atc ccg ccc acc acc atc ctg atc atc aac ctg     3281
Trp Thr Thr Leu Leu Ile Pro Pro Thr Thr Ile Leu Ile Ile Asn Leu
            975                 980                 985 gtc ggc gtc gtc gcc ggc atc tcc tac gcc atc aac agc gga tac cag     3329
Val Gly Val Val Ala Gly Ile Ser Tyr Ala Ile Asn Ser Gly Tyr Gln
        990                 995                 1000 tcg tgg ggc ccg ctc ttc ggc aag ctc ttc ttc gcc ttc tgg gtc atc     3377
Ser Trp Gly Pro Leu Phe Gly Lys Leu Phe Phe Ala Phe Trp Val Ile
    1005                1010                1015 gtc cac ctg tac ccg ttc ctc aag ggc ctc atg ggc agg cag aac cgc     3425
Val His Leu Tyr Pro Phe Leu Lys Gly Leu Met Gly Arg Gln Asn Arg
1020                1025                1030                1035 acc ccg acc atc gtc gtc gtc tgg gccatcctgc tggcgtccat cttctccttg   3479
Thr Pro Thr Ile Val Val Val Trp
                1040 ctgtgggttc gcatcgaccc cttcaccacc cgcgtcactg gcccggatac ccagacgtgt   3539 ggcatcaact gctagggaag tggaaggttt gtactttgta gaaacggagg aataccacgt   3599 gccatctgtt gtctgttaag ttatatatat ataagcagca agtggcgtta tttacagcta   3659 cgtacagacc agtggatatt gtttaccaca aagtttact tgtgttaata tgcattcttt    3719 tgttgatata aaaaaaaaaa aaaaaaa                                       3746

<210> SEQ ID NO 50
<211> LENGTH: 1043
<212> TYPE: PRT
<213> ORGANISM: Zea mays

<400> SEQUENCE: 50

Met Glu Gly Asp Ala Asp Gly Val Lys Ser Gly Arg Arg Gly Gly
  1               5                  10                  15

Gln Val Cys Gln Ile Cys Gly Asp Gly Val Gly Thr Thr Ala Glu Gly
            20                  25                  30

Asp Val Phe Ala Ala Cys Asp Val Cys Gly Phe Pro Val Cys Arg Pro
        35                  40                  45

Cys Tyr Glu Tyr Glu Arg Lys Asp Gly Thr Gln Ala Cys Pro Gln Cys
    50                  55                  60

Lys Thr Lys Tyr Lys Arg His Lys Gly Ser Pro Ala Ile Arg Gly Glu
65                  70                  75                  80

Glu Gly Asp Asp Thr Asp Ala Asp Ser Asp Phe Asn Tyr Leu Ala Ser
                85                  90                  95

Gly Asn Glu Asp Gln Lys Gln Lys Ile Ala Asp Arg Met Arg Ser Trp
            100                 105                 110

Arg Met Asn Val Gly Gly Ser Gly Asp Val Gly Arg Pro Lys Tyr Asp
        115                 120                 125
```

-continued

```
Ser Gly Glu Ile Gly Leu Thr Lys Tyr Asp Ser Gly Glu Ile Pro Arg
    130                 135                 140
Gly Tyr Ile Pro Ser Val Thr Asn Ser Gln Ile Ser Gly Glu Ile Pro
145                 150                 155                 160
Gly Ala Ser Pro Asp His His Met Met Ser Pro Thr Gly Asn Ile Gly
                165                 170                 175
Lys Arg Ala Pro Phe Pro Tyr Val Asn His Ser Pro Asn Pro Ser Arg
            180                 185                 190
Glu Phe Ser Gly Ser Ile Gly Asn Val Ala Trp Lys Glu Arg Val Asp
        195                 200                 205
Gly Trp Lys Met Lys Gln Asp Lys Gly Thr Ile Pro Met Thr Asn Gly
    210                 215                 220
Thr Ser Ile Ala Pro Ser Glu Gly Arg Gly Val Gly Asp Ile Asp Ala
225                 230                 235                 240
Ser Thr Asp Tyr Asn Met Glu Asp Ala Leu Leu Asn Asp Glu Thr Arg
                245                 250                 255
Gln Pro Leu Ser Arg Lys Val Pro Leu Pro Ser Ser Arg Ile Asn Pro
            260                 265                 270
Tyr Arg Met Val Ile Val Leu Arg Leu Ile Val Leu Ser Ile Phe Leu
        275                 280                 285
His Tyr Arg Ile Thr Asn Pro Val Arg Asn Ala Tyr Pro Leu Trp Leu
    290                 295                 300
Leu Ser Val Ile Cys Glu Ile Trp Phe Ala Leu Ser Trp Ile Leu Asp
305                 310                 315                 320
Gln Phe Pro Lys Trp Phe Pro Ile Asn Arg Glu Thr Tyr Leu Asp Arg
                325                 330                 335
Leu Ala Leu Arg Tyr Asp Arg Glu Gly Glu Pro Ser Gln Leu Ala Ala
            340                 345                 350
Val Asp Ile Phe Val Ser Thr Val Asp Pro Met Lys Glu Pro Pro Leu
        355                 360                 365
Val Thr Ala Asn Thr Val Leu Ser Ile Leu Ala Val Asp Tyr Pro Val
    370                 375                 380
Asp Lys Val Ser Cys Tyr Val Ser Asp Asp Gly Ala Ala Met Leu Thr
385                 390                 395                 400
Phe Asp Ala Leu Ala Glu Thr Ser Glu Phe Ala Arg Lys Trp Val Pro
                405                 410                 415
Phe Val Lys Lys Tyr Asn Ile Glu Pro Arg Ala Pro Glu Trp Tyr Phe
            420                 425                 430
Ser Gln Lys Ile Asp Tyr Leu Lys Asp Lys Val His Pro Ser Phe Val
        435                 440                 445
Lys Asp Arg Arg Ala Met Lys Arg Glu Tyr Glu Glu Phe Lys Val Arg
    450                 455                 460
Val Asn Gly Leu Val Ala Lys Ala Gln Lys Val Pro Glu Glu Gly Trp
465                 470                 475                 480
Ile Met Gln Asp Gly Thr Pro Trp Pro Gly Asn Asn Thr Arg Asp His
                485                 490                 495
Pro Gly Met Ile Gln Val Phe Leu Gly His Ser Gly Gly Leu Asp Thr
            500                 505                 510
Glu Gly Asn Glu Leu Pro Arg Leu Val Tyr Val Ser Arg Glu Lys Arg
        515                 520                 525
Pro Gly Phe Gln His His Lys Lys Ala Gly Ala Met Asn Ala Leu Val
    530                 535                 540
```

```
Arg Val Ser Ala Val Leu Thr Asn Gly Gln Tyr Met Leu Asn Leu Asp
545                 550                 555                 560

Cys Asp His Tyr Ile Asn Asn Ser Lys Ala Leu Arg Glu Ala Met Cys
                565                 570                 575

Phe Leu Met Asp Pro Asn Leu Gly Arg Ser Val Cys Tyr Val Gln Phe
            580                 585                 590

Pro Gln Arg Phe Asp Gly Ile Asp Arg Asn Asp Arg Tyr Ala Asn Arg
        595                 600                 605

Asn Thr Val Phe Phe Asp Ile Asn Leu Arg Gly Leu Asp Gly Ile Gln
    610                 615                 620

Gly Pro Val Tyr Val Gly Thr Gly Cys Val Phe Asn Arg Thr Ala Leu
625                 630                 635                 640

Tyr Gly Tyr Glu Pro Pro Ile Lys Gln Lys Gly Gly Phe Leu Ser
                645                 650                 655

Ser Leu Cys Gly Gly Arg Lys Lys Ala Ser Lys Ser Lys Lys Gly Ser
            660                 665                 670

Asp Lys Lys Lys Ser Gln Lys His Val Asp Ser Ser Val Pro Val Phe
        675                 680                 685

Asn Leu Glu Asp Ile Glu Glu Gly Val Glu Gly Ala Gly Phe Asp Asp
    690                 695                 700

Glu Lys Ser Leu Leu Met Ser Gln Met Ser Leu Glu Lys Arg Phe Gly
705                 710                 715                 720

Gln Ser Ala Ala Phe Val Ala Ser Thr Leu Met Glu Tyr Gly Gly Val
                725                 730                 735

Pro Gln Ser Ala Thr Pro Glu Ser Leu Leu Lys Glu Ala Ile His Val
            740                 745                 750

Ile Ser Cys Gly Tyr Glu Asp Lys Thr Glu Trp Gly Thr Glu Ile Gly
        755                 760                 765

Trp Ile Tyr Gly Ser Val Thr Glu Asp Ile Leu Thr Gly Phe Lys Met
    770                 775                 780

His Ala Arg Gly Trp Arg Ser Ile Tyr Cys Met Pro Lys Arg Pro Ala
785                 790                 795                 800

Phe Lys Gly Ser Ala Pro Ile Asn Leu Ser Asp Arg Leu Asn Gln Val
                805                 810                 815

Leu Arg Trp Ala Leu Gly Ser Val Glu Ile Leu Phe Ser Arg His Cys
            820                 825                 830

Pro Leu Trp Tyr Gly Tyr Gly Gly Arg Leu Lys Phe Leu Glu Arg Phe
        835                 840                 845

Ala Tyr Ile Asn Thr Thr Ile Tyr Pro Leu Thr Ser Ile Pro Leu Leu
    850                 855                 860

Ile Tyr Cys Ile Leu Pro Ala Ile Cys Leu Leu Thr Gly Lys Phe Ile
865                 870                 875                 880

Ile Pro Glu Ile Ser Asn Phe Ala Ser Ile Trp Phe Ile Ser Leu Phe
                885                 890                 895

Ile Ser Ile Phe Ala Thr Gly Ile Leu Glu Met Arg Trp Ser Gly Val
            900                 905                 910

Gly Ile Asp Glu Trp Trp Arg Asn Glu Gln Phe Trp Val Ile Gly Gly
        915                 920                 925

Ile Ser Ala His Leu Phe Ala Val Phe Gln Gly Leu Leu Lys Val Leu
    930                 935                 940

Ala Gly Ile Asp Thr Asn Phe Thr Val Thr Ser Lys Ala Ser Asp Glu
945                 950                 955                 960

Asp Gly Asp Phe Ala Glu Leu Tyr Met Phe Lys Trp Thr Thr Leu Leu
```

```
                        965                 970                 975
Ile Pro Pro Thr Thr Ile Leu Ile Ile Asn Leu Val Gly Val Val Ala
                980                 985                 990
Gly Ile Ser Tyr Ala Ile Asn Ser Gly Tyr Gln Ser Trp Gly Pro Leu
                995                1000                1005
Phe Gly Lys Leu Phe Phe Ala Phe Trp Val Ile Val His Leu Tyr Pro
               1010                1015                1020
Phe Leu Lys Gly Leu Met Gly Arg Gln Asn Arg Thr Pro Thr Ile Val
1025                1030                1035                1040

Val Val Trp

<210> SEQ ID NO 51
<211> LENGTH: 25
<212> TYPE: DNA
<213> ORGANISM: Zea mays

<400> SEQUENCE: 51
atggagggcg acgcggacgg cgtga                                              25

<210> SEQ ID NO 52
<211> LENGTH: 25
<212> TYPE: DNA
<213> ORGANISM: Zea mays

<400> SEQUENCE: 52
ctagcagttg atgccacacg tctgg                                              25

<210> SEQ ID NO 53
<211> LENGTH: 3753
<212> TYPE: DNA
<213> ORGANISM: Zea mays
<220> FEATURE:
<221> NAME/KEY: CDS
<222> LOCATION: (184)...(3408)

<400> SEQUENCE: 53
cagcagcaga agcactgcgc ggcattgcag cgatcgagcg ggaggaattt ggggcatggt        60
ggtcgccaac gccgctcgga tctagaggcc cgcacgggcc gattggtctc cgcccgcctc       120
gtcggtgttg gtgtcgttgg cgtgtggagc cgtctcggtg ggagcagcgg ggagggagcg       180 gag atg gcg gcc aac aag ggg atg gtg gcg ggc tcg cac aac cgc aac         228
    Met Ala Ala Asn Lys Gly Met Val Ala Gly Ser His Asn Arg Asn
    1               5                   10                  15 gag ttc gtc atg atc cgc cac gac ggc gat gtg ccg ggc tcg gct aag         276
Glu Phe Val Met Ile Arg His Asp Gly Asp Val Pro Gly Ser Ala Lys
                20                  25                  30 ccc aca aag agt gcg aat gga cag gtc tgc cag att tgc ggt gac tct         324
Pro Thr Lys Ser Ala Asn Gly Gln Val Cys Gln Ile Cys Gly Asp Ser
            35                  40                  45 gtg ggt gtt tca gcc act ggt gat gtc ttt gtt gcc tgc aat gag tgt         372
Val Gly Val Ser Ala Thr Gly Asp Val Phe Val Ala Cys Asn Glu Cys
        50                  55                  60 gcc ttc cct gtc tgc cgc cca tgc tat gag tat gag cgc aag gag ggg         420
Ala Phe Pro Val Cys Arg Pro Cys Tyr Glu Tyr Glu Arg Lys Glu Gly
    65                  70                  75 aac caa tgc tgc ccc cag tgc aag act aga tac aag aga cag aaa ggt         468
Asn Gln Cys Cys Pro Gln Cys Lys Thr Arg Tyr Lys Arg Gln Lys Gly
80                  85                  90                  95 agc cct cga gtt cat ggt gat gag gat gag gaa gat gtt gat gac cta         516
Ser Pro Arg Val His Gly Asp Glu Asp Glu Glu Asp Val Asp Asp Leu
```

```
                 100                 105                 110
gac aat gaa ttc aac tac aag caa ggc agt ggg aaa ggc cca gag tgg    564
Asp Asn Glu Phe Asn Tyr Lys Gln Gly Ser Gly Lys Gly Pro Glu Trp
            115                 120                 125 caa ctg caa gga gat gat gct gat ctg tct tca tct gct cgc cat gag    612
Gln Leu Gln Gly Asp Asp Ala Asp Leu Ser Ser Ser Ala Arg His Glu
        130                 135                 140 cca cat cat cgg att cca cgc ctg aca agc ggt caa cag ata tct gga    660
Pro His His Arg Ile Pro Arg Leu Thr Ser Gly Gln Gln Ile Ser Gly
    145                 150                 155 gag att cct gat gct tcc cct gac cgt cat tct atc cgc agt cca aca    708
Glu Ile Pro Asp Ala Ser Pro Asp Arg His Ser Ile Arg Ser Pro Thr
160                 165                 170                 175 tcg agc tat gtt gat cca agc gtc cca gtt cct gtg agg att gtg gac    756
Ser Ser Tyr Val Asp Pro Ser Val Pro Val Pro Val Arg Ile Val Asp
                180                 185                 190 ccc tcg aag gac ttg aat tcc tat ggg ctt aat agt gtt gac tgg aag    804
Pro Ser Lys Asp Leu Asn Ser Tyr Gly Leu Asn Ser Val Asp Trp Lys
            195                 200                 205 gaa aga gtt gag agc tgg agg gtt aaa cag gac aaa aat atg atg caa    852
Glu Arg Val Glu Ser Trp Arg Val Lys Gln Asp Lys Asn Met Met Gln
        210                 215                 220 gtg act aat aaa tat cca gag gct aga gga gga gac atg gag ggg act    900
Val Thr Asn Lys Tyr Pro Glu Ala Arg Gly Gly Asp Met Glu Gly Thr
    225                 230                 235 ggc tca aat gga gaa gat atg caa atg gtt gat gat gca cgg cta cct    948
Gly Ser Asn Gly Glu Asp Met Gln Met Val Asp Asp Ala Arg Leu Pro
240                 245                 250                 255 ttg agc cgt atc gtg cca att tcc tca aac cag ctc aac ctt tac cgg    996
Leu Ser Arg Ile Val Pro Ile Ser Ser Asn Gln Leu Asn Leu Tyr Arg
                260                 265                 270 gta gtg atc att ctc cgt ctt atc atc ctg tgc ttc ttc ttc cag tat    1044
Val Val Ile Ile Leu Arg Leu Ile Ile Leu Cys Phe Phe Phe Gln Tyr
            275                 280                 285 cgt gtc agt cat cca gtg cgt gat gct tat gga tta tgg cta gta tct    1092
Arg Val Ser His Pro Val Arg Asp Ala Tyr Gly Leu Trp Leu Val Ser
        290                 295                 300 gtt atc tgc gag gtc tgg ttt gcc ttg tct tgg ctt cta gat cag ttc    1140
Val Ile Cys Glu Val Trp Phe Ala Leu Ser Trp Leu Leu Asp Gln Phe
    305                 310                 315 cca aaa tgg tat cca atc aac cgt gag aca tat ctt gac agg ctt gca    1188
Pro Lys Trp Tyr Pro Ile Asn Arg Glu Thr Tyr Leu Asp Arg Leu Ala
320                 325                 330                 335 ttg agg tat gat aga gag gga gag cca tca cag ctg gct ccc att gat    1236
Leu Arg Tyr Asp Arg Glu Gly Glu Pro Ser Gln Leu Ala Pro Ile Asp
                340                 345                 350 gtc ttc gtc agt aca gtg gat cca ttg aag gaa cct cca ctg atc aca    1284
Val Phe Val Ser Thr Val Asp Pro Leu Lys Glu Pro Pro Leu Ile Thr
            355                 360                 365 gcc aac act gtt ttg tcc att ctt tct gtg gat tac cct gtt gac aaa    1332
Ala Asn Thr Val Leu Ser Ile Leu Ser Val Asp Tyr Pro Val Asp Lys
        370                 375                 380 gtg tca tgc tat gtt tct gat gat ggt tca gct atg ctg act ttt gag    1380
Val Ser Cys Tyr Val Ser Asp Asp Gly Ser Ala Met Leu Thr Phe Glu
    385                 390                 395 tct ctc tca gaa acc gca gaa ttt gct aga aag tgg gtt ccc ttt tgt    1428
Ser Leu Ser Glu Thr Ala Glu Phe Ala Arg Lys Trp Val Pro Phe Cys
400                 405                 410                 415 aag aag cac aat att gaa cca aga gct cca gaa ttt tac ttt gct caa    1476
```

```
                Lys Lys His Asn Ile Glu Pro Arg Ala Pro Glu Phe Tyr Phe Ala Gln
                            420                 425                 430 aaa ata gat tac ctg aag gac aaa att caa cct tca ttt gtt aag gaa       1524
Lys Ile Asp Tyr Leu Lys Asp Lys Ile Gln Pro Ser Phe Val Lys Glu
            435                 440                 445 aga cgc gca atg aag agg gag tat gaa gaa ttc aaa gta aga atc aat       1572
Arg Arg Ala Met Lys Arg Glu Tyr Glu Glu Phe Lys Val Arg Ile Asn
        450                 455                 460 gcc ctt gtt gcc aaa gca cag aaa gtg cct gaa gag ggg tgg acc atg       1620
Ala Leu Val Ala Lys Ala Gln Lys Val Pro Glu Glu Gly Trp Thr Met
465                 470                 475 gct gat gga act gca tgg cct ggg aat aat cct agg gac cat cct ggc       1668
Ala Asp Gly Thr Ala Trp Pro Gly Asn Asn Pro Arg Asp His Pro Gly
480                 485                 490                 495 atg att cag gtt ttc ttg ggg cac agt ggt ggg ctc gac act gat gga       1716
Met Ile Gln Val Phe Leu Gly His Ser Gly Gly Leu Asp Thr Asp Gly
                500                 505                 510 aat gag tta cca cgt ctt gtc tat gtc tct cgt gaa aag aga cca ggc       1764
Asn Glu Leu Pro Arg Leu Val Tyr Val Ser Arg Glu Lys Arg Pro Gly
            515                 520                 525 ttt cag cat cac aag aag gct ggt gca atg aat gcg ctg att cgt gta       1812
Phe Gln His His Lys Lys Ala Gly Ala Met Asn Ala Leu Ile Arg Val
        530                 535                 540 tct gct gtg ctg aca aat ggt gcc tat ctt ctc aat gtg gat tgc gac       1860
Ser Ala Val Leu Thr Asn Gly Ala Tyr Leu Leu Asn Val Asp Cys Asp
545                 550                 555 cat tac ttc aat agc agc aaa gct ctt aga gaa gca atg tgc ttc atg       1908
His Tyr Phe Asn Ser Ser Lys Ala Leu Arg Glu Ala Met Cys Phe Met
560                 565                 570                 575 atg gat ccg gct cta gga agg aaa act tgt tat gta caa ttt cca cag       1956
Met Asp Pro Ala Leu Gly Arg Lys Thr Cys Tyr Val Gln Phe Pro Gln
                580                 585                 590 aga ttt gat ggc att gac ttg cac gat cga tat gct aat cgg aac ata       2004
Arg Phe Asp Gly Ile Asp Leu His Asp Arg Tyr Ala Asn Arg Asn Ile
            595                 600                 605 gtt ttc ttt gat atc aac atg aaa ggt ctg gat ggc att cag ggt cca       2052
Val Phe Phe Asp Ile Asn Met Lys Gly Leu Asp Gly Ile Gln Gly Pro
        610                 615                 620 gtt tac gtg gga aca gga tgc tgt ttc aat aga cag gct ttg tat gga       2100
Val Tyr Val Gly Thr Gly Cys Cys Phe Asn Arg Gln Ala Leu Tyr Gly
625                 630                 635 tac gat cct gtt ttg act gaa gct gat ctg gag cca aac att gtt att       2148
Tyr Asp Pro Val Leu Thr Glu Ala Asp Leu Glu Pro Asn Ile Val Ile
640                 645                 650                 655 aag agc tgc tgt ggt aga agg aag aaa aag aac aag agt tat atg gat       2196
Lys Ser Cys Cys Gly Arg Arg Lys Lys Lys Asn Lys Ser Tyr Met Asp
                660                 665                 670 agt caa agc cgt att atg aag aga aca gaa tct tca gct ccc atc ttc       2244
Ser Gln Ser Arg Ile Met Lys Arg Thr Glu Ser Ser Ala Pro Ile Phe
            675                 680                 685 aat atg gaa gac atc gaa gag ggt att gaa ggt tac gag gat gaa agg       2292
Asn Met Glu Asp Ile Glu Glu Gly Ile Glu Gly Tyr Glu Asp Glu Arg
        690                 695                 700 tca gtg ctt atg tcc cag agg aaa ttg gag aaa cgc ttt ggt cag tct       2340
Ser Val Leu Met Ser Gln Arg Lys Leu Glu Lys Arg Phe Gly Gln Ser
705                 710                 715 cct att ttc att gca tcc acc ttt atg aca caa ggt ggc ata cca cct       2388
Pro Ile Phe Ile Ala Ser Thr Phe Met Thr Gln Gly Gly Ile Pro Pro
720                 725                 730                 735
```

```
tca aca aac cca gct tct cta cta aag gaa gct atc cat gtc atc agt       2436
Ser Thr Asn Pro Ala Ser Leu Leu Lys Glu Ala Ile His Val Ile Ser
            740                 745                 750 tgt gga tat gag gac aaa act gaa tgg gga aaa gag att ggc tgg atc       2484
Cys Gly Tyr Glu Asp Lys Thr Glu Trp Gly Lys Glu Ile Gly Trp Ile
        755                 760                 765 tat ggt tca gta acg gag gat att ctg act ggg ttt aaa atg cat gca       2532
Tyr Gly Ser Val Thr Glu Asp Ile Leu Thr Gly Phe Lys Met His Ala
        770                 775                 780 agg ggc tgg caa tca atc tac tgc atg cca cca cga cct tgt ttc aag       2580
Arg Gly Trp Gln Ser Ile Tyr Cys Met Pro Pro Arg Pro Cys Phe Lys
    785                 790                 795 ggt tct gca cca atc aat ctt tcc gat cgt ctt aat cag gtg ctc cgt       2628
Gly Ser Ala Pro Ile Asn Leu Ser Asp Arg Leu Asn Gln Val Leu Arg
800                 805                 810                 815 tgg gct ctt ggg tca gtg gaa att ctg ctt agt aga cat tgt cct atc       2676
Trp Ala Leu Gly Ser Val Glu Ile Leu Leu Ser Arg His Cys Pro Ile
                820                 825                 830 tgg tat ggt tac aat gga cga ttg aag ctt ttg gag agg ctg gct tac       2724
Trp Tyr Gly Tyr Asn Gly Arg Leu Lys Leu Leu Glu Arg Leu Ala Tyr
            835                 840                 845 atc aac act att gta tat cca atc aca tcc att ccg ctt att gcc tat       2772
Ile Asn Thr Ile Val Tyr Pro Ile Thr Ser Ile Pro Leu Ile Ala Tyr
        850                 855                 860 tgt gtg ctt ccc gct atc tgc ctc ctt acc aat aaa ttt atc att cct       2820
Cys Val Leu Pro Ala Ile Cys Leu Leu Thr Asn Lys Phe Ile Ile Pro
        865                 870                 875 gag att agc aat tat gct ggg atg ttc ttc att ctt ctt ttc gcc tcc       2868
Glu Ile Ser Asn Tyr Ala Gly Met Phe Phe Ile Leu Leu Phe Ala Ser
880                 885                 890                 895 att ttt gcc act ggt ata ttg gag ctt aga tgg agt ggt gtt ggc att       2916
Ile Phe Ala Thr Gly Ile Leu Glu Leu Arg Trp Ser Gly Val Gly Ile
                900                 905                 910 gaa gat tgg tgg aga aat gag cag ttt tgg gtt att ggt ggc acc tct       2964
Glu Asp Trp Trp Arg Asn Glu Gln Phe Trp Val Ile Gly Gly Thr Ser
            915                 920                 925 gcc cat ctc ttc gca gtg ttc cag ggt ctg ctg aaa gtg ttg gct ggg       3012
Ala His Leu Phe Ala Val Phe Gln Gly Leu Leu Lys Val Leu Ala Gly
        930                 935                 940 att gat acc aac ttc aca gtt acc tca aag gca tct gat gag gat ggc       3060
Ile Asp Thr Asn Phe Thr Val Thr Ser Lys Ala Ser Asp Glu Asp Gly
        945                 950                 955 gac ttt gct gag cta tat gtg ttc aag tgg acc agt ttg ctc att cct       3108
Asp Phe Ala Glu Leu Tyr Val Phe Lys Trp Thr Ser Leu Leu Ile Pro
960                 965                 970                 975 ccg acc act gtt ctt gtc att aac ctg gtc gga atg gtg gca gga att       3156
Pro Thr Thr Val Leu Val Ile Asn Leu Val Gly Met Val Ala Gly Ile
                980                 985                 990 tct tat gcc att aac agt ggc tac caa tcc tgg ggt ccg ctc ttt gga       3204
Ser Tyr Ala Ile Asn Ser Gly Tyr Gln Ser Trp Gly Pro Leu Phe Gly
            995                 1000                1005 aag ctg ttc ttc tcg atc tgg gtg atc ctc cat ctc tac ccc ttc ctc       3252
Lys Leu Phe Phe Ser Ile Trp Val Ile Leu His Leu Tyr Pro Phe Leu
        1010                1015                1020 aag ggt ctc atg gga agg cag aac cgc aca cca aca atc gtc att gtc       3300
Lys Gly Leu Met Gly Arg Gln Asn Arg Thr Pro Thr Ile Val Ile Val
        1025                1030                1035 tgg tcc atc ctt ctt gca tct atc ttc tcc ttg ctg tgg gtg aag atc       3348
Trp Ser Ile Leu Leu Ala Ser Ile Phe Ser Leu Leu Trp Val Lys Ile
1040                1045                1050                1055
```

```
gat cct ttc atc tcc ccg aca cag aaa gct gct gcc ttg ggg caa tgt    3396
Asp Pro Phe Ile Ser Pro Thr Gln Lys Ala Ala Ala Leu Gly Gln Cys
            1060                1065                1070 ggc gtc aac tgc tgatcgagac agtgactctt atttgaagag gctcaatcaa        3448
Gly Val Asn Cys
        1075 gatctgcccc ctcgtgtaaa tacctgagga ggctagatgg gaattccttt tgttgtaggt  3508 gaggatggat ttgcatctaa gttatgcctc tgttcattag cttcttccgt gccggtgctg  3568 ctgcggacta agaatcacgg agcctttcta ccttccatgt agcgccagcc agcagcgtaa  3628 gatgtgaatt ttgaagtttt gttatgcgtg cagtttattg ttttagagta aattatcatt  3688 tgtttgtggg aactgttcac acgagcttat aatggcaatg ctgttattta aaaaaaaaaa  3748 aaaaa                                                              3753
```

<210> SEQ ID NO 54
<211> LENGTH: 1075
<212> TYPE: PRT
<213> ORGANISM: Zea mays

<400> SEQUENCE: 54

```
Met Ala Ala Asn Lys Gly Met Val Ala Gly Ser His Asn Arg Asn Glu
  1               5                  10                  15

Phe Val Met Ile Arg His Asp Gly Asp Val Pro Gly Ser Ala Lys Pro
             20                  25                  30

Thr Lys Ser Ala Asn Gly Gln Val Cys Gln Ile Cys Gly Asp Ser Val
         35                  40                  45

Gly Val Ser Ala Thr Gly Asp Val Phe Val Ala Cys Asn Glu Cys Ala
     50                  55                  60

Phe Pro Val Cys Arg Pro Cys Tyr Glu Tyr Glu Arg Lys Glu Gly Asn
 65                  70                  75                  80

Gln Cys Cys Pro Gln Cys Lys Thr Arg Tyr Lys Arg Gln Lys Gly Ser
                 85                  90                  95

Pro Arg Val His Gly Asp Glu Asp Glu Glu Asp Val Asp Asp Leu Asp
            100                 105                 110

Asn Glu Phe Asn Tyr Lys Gln Gly Ser Gly Lys Gly Pro Glu Trp Gln
        115                 120                 125

Leu Gln Gly Asp Asp Ala Asp Leu Ser Ser Ser Ala Arg His Glu Pro
    130                 135                 140

His His Arg Ile Pro Arg Leu Thr Ser Gly Gln Gln Ile Ser Gly Glu
145                 150                 155                 160

Ile Pro Asp Ala Ser Pro Asp Arg His Ser Ile Arg Ser Pro Thr Ser
                165                 170                 175

Ser Tyr Val Asp Pro Ser Val Pro Val Pro Val Arg Ile Val Asp Pro
            180                 185                 190

Ser Lys Asp Leu Asn Ser Tyr Gly Leu Asn Ser Val Asp Trp Lys Glu
        195                 200                 205

Arg Val Glu Ser Trp Arg Val Lys Gln Asp Lys Asn Met Met Gln Val
    210                 215                 220

Thr Asn Lys Tyr Pro Glu Ala Arg Gly Gly Asp Met Glu Gly Thr Gly
225                 230                 235                 240

Ser Asn Gly Glu Asp Met Gln Met Val Asp Asp Ala Arg Leu Pro Leu
                245                 250                 255

Ser Arg Ile Val Pro Ile Ser Ser Asn Gln Leu Asn Leu Tyr Arg Val
            260                 265                 270
```

-continued

```
Val Ile Ile Leu Arg Leu Ile Ile Leu Cys Phe Phe Phe Gln Tyr Arg
        275                 280                 285
Val Ser His Pro Val Arg Asp Ala Tyr Gly Leu Trp Leu Val Ser Val
        290                 295                 300
Ile Cys Glu Val Trp Phe Ala Leu Ser Trp Leu Leu Asp Gln Phe Pro
305                 310                 315                 320
Lys Trp Tyr Pro Ile Asn Arg Glu Thr Tyr Leu Asp Arg Leu Ala Leu
                    325                 330                 335
Arg Tyr Asp Arg Glu Gly Glu Pro Ser Gln Leu Ala Pro Ile Asp Val
            340                 345                 350
Phe Val Ser Thr Val Asp Pro Leu Lys Glu Pro Pro Leu Ile Thr Ala
            355                 360                 365
Asn Thr Val Leu Ser Ile Leu Ser Val Asp Tyr Pro Val Asp Lys Val
        370                 375                 380
Ser Cys Tyr Val Ser Asp Asp Gly Ser Ala Met Leu Thr Phe Glu Ser
385                 390                 395                 400
Leu Ser Glu Thr Ala Glu Phe Ala Arg Lys Trp Val Pro Phe Cys Lys
                    405                 410                 415
Lys His Asn Ile Glu Pro Arg Ala Pro Glu Phe Tyr Phe Ala Gln Lys
            420                 425                 430
Ile Asp Tyr Leu Lys Asp Lys Ile Gln Pro Ser Phe Val Lys Glu Arg
            435                 440                 445
Arg Ala Met Lys Arg Glu Tyr Glu Glu Phe Lys Val Arg Ile Asn Ala
        450                 455                 460
Leu Val Ala Lys Ala Gln Lys Val Pro Glu Glu Gly Trp Thr Met Ala
465                 470                 475                 480
Asp Gly Thr Ala Trp Pro Gly Asn Asn Pro Arg Asp His Pro Gly Met
                    485                 490                 495
Ile Gln Val Phe Leu Gly His Ser Gly Gly Leu Asp Thr Asp Gly Asn
            500                 505                 510
Glu Leu Pro Arg Leu Val Tyr Val Ser Arg Glu Lys Arg Pro Gly Phe
        515                 520                 525
Gln His His Lys Lys Ala Gly Ala Met Asn Ala Leu Ile Arg Val Ser
        530                 535                 540
Ala Val Leu Thr Asn Gly Ala Tyr Leu Leu Asn Val Asp Cys Asp His
545                 550                 555                 560
Tyr Phe Asn Ser Ser Lys Ala Leu Arg Glu Ala Met Cys Phe Met Met
                    565                 570                 575
Asp Pro Ala Leu Gly Arg Lys Thr Cys Tyr Val Gln Phe Pro Gln Arg
            580                 585                 590
Phe Asp Gly Ile Asp Leu His Asp Arg Tyr Ala Asn Arg Asn Ile Val
            595                 600                 605
Phe Phe Asp Ile Asn Met Lys Gly Leu Asp Gly Ile Gln Gly Pro Val
        610                 615                 620
Tyr Val Gly Thr Gly Cys Cys Phe Asn Arg Gln Ala Leu Tyr Gly Tyr
625                 630                 635                 640
Asp Pro Val Leu Thr Glu Ala Asp Leu Glu Pro Asn Ile Val Ile Lys
                    645                 650                 655
Ser Cys Cys Gly Arg Arg Lys Lys Asn Lys Ser Tyr Met Asp Ser
            660                 665                 670
Gln Ser Arg Ile Met Lys Arg Thr Glu Ser Ser Ala Pro Ile Phe Asn
            675                 680                 685
```

-continued

```
Met Glu Asp Ile Glu Glu Gly Ile Glu Gly Tyr Asp Glu Arg Ser
690                 695                 700
Val Leu Met Ser Gln Arg Lys Leu Glu Lys Arg Phe Gly Gln Ser Pro
705                 710                 715                 720
Ile Phe Ile Ala Ser Thr Phe Met Thr Gln Gly Gly Ile Pro Pro Ser
            725                 730                 735
Thr Asn Pro Ala Ser Leu Leu Lys Glu Ala Ile His Val Ile Ser Cys
            740                 745                 750
Gly Tyr Glu Asp Lys Thr Glu Trp Gly Lys Glu Ile Gly Trp Ile Tyr
        755                 760                 765
Gly Ser Val Thr Glu Asp Ile Leu Thr Gly Phe Lys Met His Ala Arg
770                 775                 780
Gly Trp Gln Ser Ile Tyr Cys Met Pro Pro Arg Pro Cys Phe Lys Gly
785                 790                 795                 800
Ser Ala Pro Ile Asn Leu Ser Asp Arg Leu Asn Gln Val Leu Arg Trp
            805                 810                 815
Ala Leu Gly Ser Val Glu Ile Leu Leu Ser Arg His Cys Pro Ile Trp
            820                 825                 830
Tyr Gly Tyr Asn Gly Arg Leu Lys Leu Leu Glu Arg Leu Ala Tyr Ile
        835                 840                 845
Asn Thr Ile Val Tyr Pro Ile Thr Ser Ile Pro Leu Ile Ala Tyr Cys
850                 855                 860
Val Leu Pro Ala Ile Cys Leu Leu Thr Asn Lys Phe Ile Ile Pro Glu
865                 870                 875                 880
Ile Ser Asn Tyr Ala Gly Met Phe Phe Ile Leu Leu Phe Ala Ser Ile
            885                 890                 895
Phe Ala Thr Gly Ile Leu Glu Leu Arg Trp Ser Gly Val Gly Ile Glu
            900                 905                 910
Asp Trp Trp Arg Asn Glu Gln Phe Trp Val Ile Gly Gly Thr Ser Ala
            915                 920                 925
His Leu Phe Ala Val Phe Gln Gly Leu Leu Lys Val Leu Ala Gly Ile
        930                 935                 940
Asp Thr Asn Phe Thr Val Thr Ser Lys Ala Ser Asp Glu Asp Gly Asp
945                 950                 955                 960
Phe Ala Glu Leu Tyr Val Phe Lys Trp Thr Ser Leu Leu Ile Pro Pro
            965                 970                 975
Thr Thr Val Leu Val Ile Asn Leu Val Gly Met Val Ala Gly Ile Ser
            980                 985                 990
Tyr Ala Ile Asn Ser Gly Tyr Gln Ser Trp Gly Pro Leu Phe Gly Lys
        995                 1000                1005
Leu Phe Phe Ser Ile Trp Val Ile Leu His Leu Tyr Pro Phe Leu Lys
    1010                1015                1020
Gly Leu Met Gly Arg Gln Asn Arg Thr Pro Thr Ile Val Ile Val Trp
1025                1030                1035                1040
Ser Ile Leu Leu Ala Ser Ile Phe Ser Leu Leu Trp Val Lys Ile Asp
            1045                1050                1055
Pro Phe Ile Ser Pro Thr Gln Lys Ala Ala Ala Leu Gly Gln Cys Gly
            1060                1065                1070
Val Asn Cys
    1075

<210> SEQ ID NO 55
<211> LENGTH: 25
<212> TYPE: DNA
```

<213> ORGANISM: Zea mays

<400> SEQUENCE: 55

```
atggcggcca acaagggat ggtgg                                    25
```

<210> SEQ ID NO 56
<211> LENGTH: 25
<212> TYPE: DNA
<213> ORGANISM: Zea mays

<400> SEQUENCE: 56

```
tcagcagttg acgccacatt gcccc                                   25
```

<210> SEQ ID NO 57
<211> LENGTH: 3704
<212> TYPE: DNA
<213> ORGANISM: Zea mays
<220> FEATURE:
<221> NAME/KEY: CDS
<222> LOCATION: (272)...(3499)

<400> SEQUENCE: 57

```
gtcgacccac gcttccggtc ggttccgcgt cccttttccc ctcccccctc cgtcgccgcc    60
tcgagcgagc tccaccactt gctcctgcgc gaggtgaaca ctgggttagg gccactgcca   120
ccgctgggct gcctctgctt ctgcctctcc cgccagcgcg cgagcccggg ggcgattcgg   180
cgccggcacg cggagggga agccgaggaa tgcggtgagt cggcggggt ccggcgtttg   240 tgaactcgtg gagggctcgg attggtgcgc c atg gac ggc ggc gac gcc acg    292
                                   Met Asp Gly Gly Asp Ala Thr
                                    1               5
```

```
aat tcg ggg aag cat gtg gcc ggg cag gtg tgc cag atc tgc ggc gac    340
Asn Ser Gly Lys His Val Ala Gly Gln Val Cys Gln Ile Cys Gly Asp
         10                  15                  20 ggc gtg ggc acc gcg gcg gac ggc gac ctc ttc acc gcc tgc gac gtc    388
Gly Val Gly Thr Ala Ala Asp Gly Asp Leu Phe Thr Ala Cys Asp Val
     25                  30                  35 tgc ggc ttc ccc gtg tgc cgc cca tgc tac gag tac gag cgc aag gac    436
Cys Gly Phe Pro Val Cys Arg Pro Cys Tyr Glu Tyr Glu Arg Lys Asp
 40                  45                  50                  55 ggc acc cag gcg tgc ccg cag tgc aag act aag tac aag cgc cac aaa    484
Gly Thr Gln Ala Cys Pro Gln Cys Lys Thr Lys Tyr Lys Arg His Lys
                 60                  65                  70 ggg agc cca cca gta cac ggt gag gaa aat gag gat gtg gat gct gac    532
Gly Ser Pro Pro Val His Gly Glu Glu Asn Glu Asp Val Asp Ala Asp
             75                  80                  85 gat gtg agt gac tac aac tac caa gca tct ggc aac cag gat cag aag    580
Asp Val Ser Asp Tyr Asn Tyr Gln Ala Ser Gly Asn Gln Asp Gln Lys
         90                  95                 100 caa aag att gct gag aga atg ctc act tgg cgg aca aac tca cgt ggc    628
Gln Lys Ile Ala Glu Arg Met Leu Thr Trp Arg Thr Asn Ser Arg Gly
     105                 110                 115 agt gat att ggc ctg gct aag tat gac agc ggt gaa att ggg cat ggg    676
Ser Asp Ile Gly Leu Ala Lys Tyr Asp Ser Gly Glu Ile Gly His Gly
120                 125                 130                 135 aag tat gac agt ggt gag atc cct cgt gga tat atc ccg tca cta act    724
Lys Tyr Asp Ser Gly Glu Ile Pro Arg Gly Tyr Ile Pro Ser Leu Thr
                 140                 145                 150 cat agc cag atc tca gga gag att cct gga gct tcc cct gat cat atg    772
His Ser Gln Ile Ser Gly Glu Ile Pro Gly Ala Ser Pro Asp His Met
             155                 160                 165
```

-continued

| | |
|---|---|
| atg tct cct gtt ggg aac att ggc agg cgt gga cat caa ttt cct tat<br>Met Ser Pro Val Gly Asn Ile Gly Arg Arg Gly His Gln Phe Pro Tyr<br>170                 175                         180 | 820 |
| gta aat cat tct cca aac cca tcg agg gag ttc tcc ggt agc ctt ggc<br>Val Asn His Ser Pro Asn Pro Ser Arg Glu Phe Ser Gly Ser Leu Gly<br>     185                 190                     195 | 868 |
| aat gtt gca tgg aaa gag agg gtg gat gga tgg aaa atg aag gat aaa<br>Asn Val Ala Trp Lys Glu Arg Val Asp Gly Trp Lys Met Lys Asp Lys<br>200                 205                    210                215 | 916 |
| ggt gca att cct atg acc aat gga aca agc att gct cca tca gaa ggg<br>Gly Ala Ile Pro Met Thr Asn Gly Thr Ser Ile Ala Pro Ser Glu Gly<br>               220                     225                     230 | 964 |
| cgt gga gtt gct gat att gat gct tct act gat tat aac atg gaa gat<br>Arg Gly Val Ala Asp Ile Asp Ala Ser Thr Asp Tyr Asn Met Glu Asp<br>               235                     240                     245 | 1012 |
| gcc tta ctg aat gat gaa act cgg caa cct cta tct aga aaa gtg cca<br>Ala Leu Leu Asn Asp Glu Thr Arg Gln Pro Leu Ser Arg Lys Val Pro<br>250                 255                         260 | 1060 |
| att cct tca tcc aga ata aat ccg tac aga atg gtc att gtg cta cgt<br>Ile Pro Ser Ser Arg Ile Asn Pro Tyr Arg Met Val Ile Val Leu Arg<br>     265                 270                     275 | 1108 |
| ttg gct gtt cta tgc ata ttc ttg cgc tac cgt atc aca cat cct gtg<br>Leu Ala Val Leu Cys Ile Phe Leu Arg Tyr Arg Ile Thr His Pro Val<br>280                 285                    290                295 | 1156 |
| aac aat gca tat cca ctg tgg ctt tta tcc gtc ata tgt gag atc tgg<br>Asn Asn Ala Tyr Pro Leu Trp Leu Leu Ser Val Ile Cys Glu Ile Trp<br>               300                     305                  310 | 1204 |
| ttt gct ttg tcc tgg att ttg gat cag ttc cca aag tgg tcc cca atc<br>Phe Ala Leu Ser Trp Ile Leu Asp Gln Phe Pro Lys Trp Ser Pro Ile<br>               315                     320                     325 | 1252 |
| aac cgt gaa aca tac ctt gat aga ctg gct tta agg tat gac cga gaa<br>Asn Arg Glu Thr Tyr Leu Asp Arg Leu Ala Leu Arg Tyr Asp Arg Glu<br>               330                     335                     340 | 1300 |
| ggt gaa cca tct caa tta gct cct gtt gat att ttt gtc agt act gtg<br>Gly Glu Pro Ser Gln Leu Ala Pro Val Asp Ile Phe Val Ser Thr Val<br>345                 350                         355 | 1348 |
| gat cca atg aag gag cct cct ctt gtc act gca aat act gtg ctt tcc<br>Asp Pro Met Lys Glu Pro Pro Leu Val Thr Ala Asn Thr Val Leu Ser<br>360                 365                370                375 | 1396 |
| atc ctt gct gtc gat tat ccg gtt gac aag gta tct tgc tat gtt tcg<br>Ile Leu Ala Val Asp Tyr Pro Val Asp Lys Val Ser Cys Tyr Val Ser<br>               380                     385                  390 | 1444 |
| gat gat gga gct gct atg ctg act ttt gat gct ctc tct gaa act tca<br>Asp Asp Gly Ala Ala Met Leu Thr Phe Asp Ala Leu Ser Glu Thr Ser<br>               395                     400                     405 | 1492 |
| gag ttt gct aga aaa tgg gtt ccg ttc tgt aag aag tac aac ata gag<br>Glu Phe Ala Arg Lys Trp Val Pro Phe Cys Lys Lys Tyr Asn Ile Glu<br>               410                     415                     420 | 1540 |
| cct agg gcc ccg gaa tgg tac ttt gct cag aaa att gat tac ttg aaa<br>Pro Arg Ala Pro Glu Trp Tyr Phe Ala Gln Lys Ile Asp Tyr Leu Lys<br>425                 430                         435 | 1588 |
| gac aaa gtt caa acc tca ttt gtg aaa gaa cgc cgg gcc atg aag aga<br>Asp Lys Val Gln Thr Ser Phe Val Lys Glu Arg Arg Ala Met Lys Arg<br>440                 445                    450                455 | 1636 |
| gaa tat gaa gaa ttc aaa gtt cgt atc aat ggt ctt gta gcc aag gca<br>Glu Tyr Glu Glu Phe Lys Val Arg Ile Asn Gly Leu Val Ala Lys Ala<br>               460                     465                     470 | 1684 |
| caa aaa gtt ccc gag gag gga tgg atc atg caa gat ggt aca cct tgg<br>Gln Lys Val Pro Glu Glu Gly Trp Ile Met Gln Asp Gly Thr Pro Trp<br>                   475                     480                485 | 1732 |

```
cct ggg aac aat act agg gac cat cct gga atg att cag gtt ttc ctg    1780
Pro Gly Asn Asn Thr Arg Asp His Pro Gly Met Ile Gln Val Phe Leu
            490                 495                 500 ggt cac agt gga ggg ctt gac gtt gaa ggc aat gaa ctt cct cgt ttg    1828
Gly His Ser Gly Gly Leu Asp Val Glu Gly Asn Glu Leu Pro Arg Leu
505                 510                 515 gtt tat gtg tct cgt gaa aaa cgt cct gga ttc caa cat cac aag aag    1876
Val Tyr Val Ser Arg Glu Lys Arg Pro Gly Phe Gln His His Lys Lys
520                 525                 530                 535 gct ggt gcc atg aat gca ctt gtt cgt gta tca gct gtc ctt act aat    1924
Ala Gly Ala Met Asn Ala Leu Val Arg Val Ser Ala Val Leu Thr Asn
                540                 545                 550 ggg caa tac atg ttg aat ctt gat tgt gac cac tac atc aat aat agc    1972
Gly Gln Tyr Met Leu Asn Leu Asp Cys Asp His Tyr Ile Asn Asn Ser
            555                 560                 565 aag gct ctt cga gaa gct atg tgc ttc ctt atg gac cca aac cta gga    2020
Lys Ala Leu Arg Glu Ala Met Cys Phe Leu Met Asp Pro Asn Leu Gly
        570                 575                 580 agg aat gtc tgt tat gtc caa ttt cct cag agg ttt gat ggt att gat    2068
Arg Asn Val Cys Tyr Val Gln Phe Pro Gln Arg Phe Asp Gly Ile Asp
585                 590                 595 agg aat gac cga tat gca aac agg aac act gtg ttt ttc gat att aac    2116
Arg Asn Asp Arg Tyr Ala Asn Arg Asn Thr Val Phe Phe Asp Ile Asn
600                 605                 610                 615 ttg aga ggt ctt gac ggc att caa ggg cca gtt tat gtg gga act ggt    2164
Leu Arg Gly Leu Asp Gly Ile Gln Gly Pro Val Tyr Val Gly Thr Gly
                620                 625                 630 tgt gtg ttt aac aga acg gcc tta tat ggt tat gag cct cca gtc aag    2212
Cys Val Phe Asn Arg Thr Ala Leu Tyr Gly Tyr Glu Pro Pro Val Lys
            635                 640                 645 aaa aaa aag cca ggc ttc ttc tct tcg ctt tgt ggg gga agg aaa aag    2260
Lys Lys Lys Pro Gly Phe Phe Ser Ser Leu Cys Gly Gly Arg Lys Lys
        650                 655                 660 acg tca aaa tct aag aag agc tcg gaa aag aag aag tca cat aga cac    2308
Thr Ser Lys Ser Lys Lys Ser Ser Glu Lys Lys Lys Ser His Arg His
665                 670                 675 gca gac agt tct gta cca gta ttt aat ctc gaa gat ata gag gaa ggg    2356
Ala Asp Ser Ser Val Pro Val Phe Asn Leu Glu Asp Ile Glu Glu Gly
680                 685                 690                 695 att gaa ggt tct cag ttt gat gat gag aaa tcg ctg att atg tct caa    2404
Ile Glu Gly Ser Gln Phe Asp Asp Glu Lys Ser Leu Ile Met Ser Gln
                700                 705                 710 atg agc ttg gag aag aga ttt ggc cag tcc agt gtt ttt gta gcc tct    2452
Met Ser Leu Glu Lys Arg Phe Gly Gln Ser Ser Val Phe Val Ala Ser
            715                 720                 725 act ctg atg gaa tat ggt ggt gtt cca caa tct gca act cca gag tct    2500
Thr Leu Met Glu Tyr Gly Gly Val Pro Gln Ser Ala Thr Pro Glu Ser
        730                 735                 740 ctt ctg aaa gaa gct att cat gtc atc agc tgt ggc tat gag gac aaa    2548
Leu Leu Lys Glu Ala Ile His Val Ile Ser Cys Gly Tyr Glu Asp Lys
745                 750                 755 act gac tgg gga act gag att ggg tgg atc tat ggt tct gtt aca gaa    2596
Thr Asp Trp Gly Thr Glu Ile Gly Trp Ile Tyr Gly Ser Val Thr Glu
760                 765                 770                 775 gac att ctc acc gga ttc aag atg cat gct cga ggc tgg cga tca atc    2644
Asp Ile Leu Thr Gly Phe Lys Met His Ala Arg Gly Trp Arg Ser Ile
                780                 785                 790 tac tgc atg cct aag cga cca gct ttc aag gga tct gct cct atc aac    2692
Tyr Cys Met Pro Lys Arg Pro Ala Phe Lys Gly Ser Ala Pro Ile Asn
```

```
                       795                  800                  805
ctt tcg gat cgt ttg aat caa gtg ctt cgg tgg gct ctt ggt tcc att        2740
Leu Ser Asp Arg Leu Asn Gln Val Leu Arg Trp Ala Leu Gly Ser Ile
            810                  815                  820 gaa att ctt ttc agc agg cat tgt ccc ata tgg tat ggc tat gga ggc        2788
Glu Ile Leu Phe Ser Arg His Cys Pro Ile Trp Tyr Gly Tyr Gly Gly
825                  830                  835 cgg ctt aaa ttc ctg gag aga ttt gct tat atc aac aca aca att tat        2836
Arg Leu Lys Phe Leu Glu Arg Phe Ala Tyr Ile Asn Thr Thr Ile Tyr
840                  845                  850                  855 cca ctc aca tca atc ccg ctc ctc ctg tac tgc ata ttg cca gca gtt        2884
Pro Leu Thr Ser Ile Pro Leu Leu Leu Tyr Cys Ile Leu Pro Ala Val
                860                  865                  870 tgt ctt ctc act ggg aag ttc atc atc cca aag att agt aac cta gag        2932
Cys Leu Leu Thr Gly Lys Phe Ile Ile Pro Lys Ile Ser Asn Leu Glu
            875                  880                  885 agt gtt tgg ttt ata tcg ctc ttt atc tca atc ttt gcc act ggt atc        2980
Ser Val Trp Phe Ile Ser Leu Phe Ile Ser Ile Phe Ala Thr Gly Ile
            890                  895                  900 ctt gag atg agg tgg agt ggt gtt ggc att gat gaa tgg tgg agg aac        3028
Leu Glu Met Arg Trp Ser Gly Val Gly Ile Asp Glu Trp Trp Arg Asn
            905                  910                  915 gag cag ttc tgg gtc att ggt ggt att tct gcg cat tta ttt gcc gtc        3076
Glu Gln Phe Trp Val Ile Gly Gly Ile Ser Ala His Leu Phe Ala Val
920                  925                  930                  935 ttc cag ggt ctc ctg aag gtg ctt gct ggt atc gac acg agc ttc act        3124
Phe Gln Gly Leu Leu Lys Val Leu Ala Gly Ile Asp Thr Ser Phe Thr
            940                  945                  950 gtc acc tct aag gcc act gac gaa gaa ggt gat ttt gcc gag ctc tac        3172
Val Thr Ser Lys Ala Thr Asp Glu Glu Gly Asp Phe Ala Glu Leu Tyr
            955                  960                  965 atg ttc aag tgg aca acg ctt ctg atc cca cca acc act att ttg atc        3220
Met Phe Lys Trp Thr Thr Leu Leu Ile Pro Pro Thr Thr Ile Leu Ile
            970                  975                  980 atc aac ctg gtc ggc gtg gtc gct ggc att tcc tac gca atc aat agc        3268
Ile Asn Leu Val Gly Val Val Ala Gly Ile Ser Tyr Ala Ile Asn Ser
        985                  990                  995 ggt tac cag tca tgg gga cct ctt ttc ggg aag ctc ttc ttt gcg ttc        3316
Gly Tyr Gln Ser Trp Gly Pro Leu Phe Gly Lys Leu Phe Phe Ala Phe
1000                 1005                 1010                 1015 tgg gtg att gtc cac ctg tac ccc ttc ctc aag ggc ctc atg ggg aag        3364
Trp Val Ile Val His Leu Tyr Pro Phe Leu Lys Gly Leu Met Gly Lys
                1020                 1025                 1030 cag aac cgc acg ccg acc att gtc gtt gtc tgg gct atc ctc ctt gcg        3412
Gln Asn Arg Thr Pro Thr Ile Val Val Val Trp Ala Ile Leu Leu Ala
            1035                 1040                 1045 tcg atc ttt tcc ctg atg tgg gtt cgt atc gat cca ttc acc acc cgg        3460
Ser Ile Phe Ser Leu Met Trp Val Arg Ile Asp Pro Phe Thr Thr Arg
            1050                 1055                 1060 gtc act ggc cct gat atc gcg aaa tgt ggc atc aac tgc taggatgagc        3509
Val Thr Gly Pro Asp Ile Ala Lys Cys Gly Ile Asn Cys
            1065                 1070                 1075 tgaagatagt taaagagtgg aactagacgc attgtgcatc gtaagttatc agtgggtggc     3569 tcttttata gtatggtagg aacttggtcg ggagacgtta attacatatg ctatatgtac      3629
ctccgctggt ctttatccgt aagttaatat atatactgct ttgagaatta aaaaaaaaa      3689 aaaaagggcg gccgc                                                      3704
```

<210> SEQ ID NO 58
<211> LENGTH: 1076
<212> TYPE: PRT
<213> ORGANISM: Zea mays

<400> SEQUENCE: 58

```
Met Asp Gly Gly Asp Ala Thr Asn Ser Gly Lys His Val Ala Gly Gln
 1               5                  10                  15

Val Cys Gln Ile Cys Gly Asp Gly Val Gly Thr Ala Ala Asp Gly Asp
            20                  25                  30

Leu Phe Thr Ala Cys Asp Val Cys Gly Phe Pro Val Cys Arg Pro Cys
        35                  40                  45

Tyr Glu Tyr Glu Arg Lys Asp Gly Thr Gln Ala Cys Pro Gln Cys Lys
 50                  55                  60

Thr Lys Tyr Lys Arg His Lys Gly Ser Pro Pro Val His Gly Glu Glu
 65                  70                  75                  80

Asn Glu Asp Val Asp Ala Asp Val Ser Asp Tyr Asn Tyr Gln Ala
                 85                  90                  95

Ser Gly Asn Gln Asp Gln Lys Gln Lys Ile Ala Glu Arg Met Leu Thr
            100                 105                 110

Trp Arg Thr Asn Ser Arg Gly Ser Asp Ile Gly Leu Ala Lys Tyr Asp
        115                 120                 125

Ser Gly Glu Ile Gly His Gly Lys Tyr Asp Ser Gly Glu Ile Pro Arg
    130                 135                 140

Gly Tyr Ile Pro Ser Leu Thr His Ser Gln Ile Ser Gly Glu Ile Pro
145                 150                 155                 160

Gly Ala Ser Pro Asp His Met Met Ser Pro Val Gly Asn Ile Gly Arg
                165                 170                 175

Arg Gly His Gln Phe Pro Tyr Val Asn His Ser Pro Asn Pro Ser Arg
            180                 185                 190

Glu Phe Ser Gly Ser Leu Gly Asn Val Ala Trp Lys Glu Arg Val Asp
        195                 200                 205

Gly Trp Lys Met Lys Asp Lys Gly Ala Ile Pro Met Thr Asn Gly Thr
    210                 215                 220

Ser Ile Ala Pro Ser Glu Gly Arg Gly Val Ala Asp Ile Asp Ala Ser
225                 230                 235                 240

Thr Asp Tyr Asn Met Glu Asp Ala Leu Leu Asn Asp Glu Thr Arg Gln
                245                 250                 255

Pro Leu Ser Arg Lys Val Pro Ile Pro Ser Ser Arg Ile Asn Pro Tyr
            260                 265                 270

Arg Met Val Ile Val Leu Arg Leu Ala Val Leu Cys Ile Phe Leu Arg
        275                 280                 285

Tyr Arg Ile Thr His Pro Val Asn Asn Ala Tyr Pro Leu Trp Leu Leu
    290                 295                 300

Ser Val Ile Cys Glu Ile Trp Phe Ala Leu Ser Trp Ile Leu Asp Gln
305                 310                 315                 320

Phe Pro Lys Trp Ser Pro Ile Asn Arg Glu Thr Tyr Leu Asp Arg Leu
                325                 330                 335

Ala Leu Arg Tyr Asp Arg Glu Gly Glu Pro Ser Gln Leu Ala Pro Val
            340                 345                 350

Asp Ile Phe Val Ser Thr Val Asp Pro Met Lys Glu Pro Pro Leu Val
        355                 360                 365

Thr Ala Asn Thr Val Leu Ser Ile Leu Ala Val Asp Tyr Pro Val Asp
    370                 375                 380
```

-continued

```
Lys Val Ser Cys Tyr Val Ser Asp Asp Gly Ala Ala Met Leu Thr Phe
385                 390                 395                 400

Asp Ala Leu Ser Glu Thr Ser Glu Phe Ala Arg Lys Trp Val Pro Phe
            405                 410                 415

Cys Lys Lys Tyr Asn Ile Glu Pro Arg Ala Pro Glu Trp Tyr Phe Ala
            420                 425                 430

Gln Lys Ile Asp Tyr Leu Lys Asp Lys Val Gln Thr Ser Phe Val Lys
            435                 440                 445

Glu Arg Arg Ala Met Lys Arg Glu Tyr Glu Glu Phe Lys Val Arg Ile
        450                 455                 460

Asn Gly Leu Val Ala Lys Ala Gln Lys Val Pro Glu Glu Gly Trp Ile
465                 470                 475                 480

Met Gln Asp Gly Thr Pro Trp Pro Gly Asn Asn Thr Arg Asp His Pro
                485                 490                 495

Gly Met Ile Gln Val Phe Leu Gly His Ser Gly Gly Leu Asp Val Glu
                500                 505                 510

Gly Asn Glu Leu Pro Arg Leu Val Tyr Val Ser Arg Glu Lys Arg Pro
            515                 520                 525

Gly Phe Gln His His Lys Lys Ala Gly Ala Met Asn Ala Leu Val Arg
        530                 535                 540

Val Ser Ala Val Leu Thr Asn Gly Gln Tyr Met Leu Asn Leu Asp Cys
545                 550                 555                 560

Asp His Tyr Ile Asn Asn Ser Lys Ala Leu Arg Glu Ala Met Cys Phe
                565                 570                 575

Leu Met Asp Pro Asn Leu Gly Arg Asn Val Cys Tyr Val Gln Phe Pro
                580                 585                 590

Gln Arg Phe Asp Gly Ile Asp Arg Asn Asp Arg Tyr Ala Asn Arg Asn
            595                 600                 605

Thr Val Phe Phe Asp Ile Asn Leu Arg Gly Leu Asp Gly Ile Gln Gly
        610                 615                 620

Pro Val Tyr Val Gly Thr Gly Cys Val Phe Asn Arg Thr Ala Leu Tyr
625                 630                 635                 640

Gly Tyr Glu Pro Pro Val Lys Lys Lys Pro Gly Phe Phe Ser Ser
                645                 650                 655

Leu Cys Gly Gly Arg Lys Lys Thr Ser Lys Ser Lys Lys Ser Ser Glu
            660                 665                 670

Lys Lys Lys Ser His Arg His Ala Asp Ser Ser Val Pro Val Phe Asn
            675                 680                 685

Leu Glu Asp Ile Glu Glu Gly Ile Glu Gly Ser Gln Phe Asp Asp Glu
            690                 695                 700

Lys Ser Leu Ile Met Ser Gln Met Ser Leu Glu Lys Arg Phe Gly Gln
705                 710                 715                 720

Ser Ser Val Phe Val Ala Ser Thr Leu Met Glu Tyr Gly Gly Val Pro
                725                 730                 735

Gln Ser Ala Thr Pro Glu Ser Leu Leu Lys Glu Ala Ile His Val Ile
            740                 745                 750

Ser Cys Gly Tyr Glu Asp Lys Thr Asp Trp Gly Thr Glu Ile Gly Trp
            755                 760                 765

Ile Tyr Gly Ser Val Thr Glu Asp Ile Leu Thr Gly Phe Lys Met His
        770                 775                 780

Ala Arg Gly Trp Arg Ser Ile Tyr Cys Met Pro Lys Arg Pro Ala Phe
785                 790                 795                 800

Lys Gly Ser Ala Pro Ile Asn Leu Ser Asp Arg Leu Asn Gln Val Leu
```

```
                    805                 810                 815
Arg Trp Ala Leu Gly Ser Ile Glu Ile Leu Phe Ser Arg His Cys Pro
                820                 825                 830

Ile Trp Tyr Gly Tyr Gly Gly Arg Leu Lys Phe Leu Glu Arg Phe Ala
            835                 840                 845

Tyr Ile Asn Thr Thr Ile Tyr Pro Leu Thr Ser Ile Pro Leu Leu Leu
        850                 855                 860

Tyr Cys Ile Leu Pro Ala Val Cys Leu Leu Thr Gly Lys Phe Ile Ile
    865                 870                 875                 880

Pro Lys Ile Ser Asn Leu Glu Ser Val Trp Phe Ile Ser Leu Phe Ile
                885                 890                 895

Ser Ile Phe Ala Thr Gly Ile Leu Glu Met Arg Trp Ser Gly Val Gly
            900                 905                 910

Ile Asp Glu Trp Trp Arg Asn Glu Gln Phe Trp Val Ile Gly Gly Ile
        915                 920                 925

Ser Ala His Leu Phe Ala Val Phe Gln Gly Leu Leu Lys Val Leu Ala
    930                 935                 940

Gly Ile Asp Thr Ser Phe Thr Val Thr Ser Lys Ala Thr Asp Glu Glu
945                 950                 955                 960

Gly Asp Phe Ala Glu Leu Tyr Met Phe Lys Trp Thr Thr Leu Leu Ile
                965                 970                 975

Pro Pro Thr Thr Ile Leu Ile Ile Asn Leu Val Gly Val Val Ala Gly
            980                 985                 990

Ile Ser Tyr Ala Ile Asn Ser Gly Tyr Gln Ser Trp Gly Pro Leu Phe
        995                 1000                1005

Gly Lys Leu Phe Phe Ala Phe Trp Val Ile Val His Leu Tyr Pro Phe
    1010                1015                1020

Leu Lys Gly Leu Met Gly Lys Gln Asn Arg Thr Pro Thr Ile Val Val
1025                1030                1035                1040

Val Trp Ala Ile Leu Leu Ala Ser Ile Phe Ser Leu Met Trp Val Arg
                1045                1050                1055

Ile Asp Pro Phe Thr Thr Arg Val Thr Gly Pro Asp Ile Ala Lys Cys
            1060                1065                1070

Gly Ile Asn Cys
    1075

<210> SEQ ID NO 59
<211> LENGTH: 25
<212> TYPE: DNA
<213> ORGANISM: Zea mays

<400> SEQUENCE: 59
atggacggcg gcgacgccac gaatt                                          25

<210> SEQ ID NO 60
<211> LENGTH: 25
<212> TYPE: DNA
<213> ORGANISM: Zea mays

<400> SEQUENCE: 60
ctagcagttg atgccacatt tcgcg                                          25

<210> SEQ ID NO 61
<211> LENGTH: 36
<212> TYPE: DNA
<213> ORGANISM: Artificial Sequence
<220> FEATURE:
```

```
<223> OTHER INFORMATION: oligonucleotide probe

<400> SEQUENCE: 61
tcgacccacg cgtccgaaaa aaaaaaaaaa aaaaaa                                    36
```

CELLULOSE SYNTHASE ENCODING NUCLEIC ACIDS AND USES THEREOF

CROSS REFERENCE TO RELATED APPLICATION

This divisional application claims priority to and hereby incorporates by reference, application Ser. No. 11/493,187 filed Jul. 26, 2006, now granted as U.S. Pat. No. 7,312,377, which was a divisional of application Ser. No. 10/961,254 filed Oct. 8, 2004, now granted as U.S. Pat. No. 7,214,852, which was a divisional of application Ser. No. 10/160,719 filed Jun. 3, 2002, now granted as U.S. Pat. No. 6,803,498, which was a continuation of non-provisional application 09/371,383 filed Aug. 6, 1999, now abandoned, and provisional application 60/096,822 filed Aug. 17, 1998.

TECHNICAL FIELD

The present invention relates generally to plant molecular biology. More specifically, it relates to nucleic acids and methods for modulating their expression in plants.

BACKGROUND OF THE INVENTION

Polysaccharides constitute the bulk of the plant cell walls and have been traditionally classified into three categories: cellulose, hemicellulose, and pectin. Fry, (1988), The growing plant cell wall: Chemical and metabolic analysis. New York: Longman Scientific & Technical. Whereas cellulose is made at the plasma membrane and directly laid down into the cell wall, hemicellulosic and pectic polymers are first made in the Golgi apparatus and then exported to the cell wall by exocytosis. Ray, et al., (1976) *Ber. Deutsch. Bot. Ges. Bd.* 89:121-146. The variety of chemical linkages in the pectic and hemicellulosic polysaccharides indicates that there must be tens of polysaccharide synthases in the Golgi apparatus. Darvill, et al., (1980). The primary cell walls of flowering plants. In The Plant Cell (N. E. Tolbert, ed.), Vol. 1 in Series: The biochemistry of plants: A comprehensive treatise, eds. P. K. Stumpf and E. E. Conn (New York: Academic Press), pp. 91-162.

Cellulose, by virtue of its ability to form semicrystalline microfibrils, has a very high tensile strength which approaches that of some metals. Niklas, (1992) Plant Biomechanics: An engineering approach to plant form and function, The University of Chicago Press, pp. 607. Bending strength of the culm of normal and brittle-culm mutants of barley has been found to be directly correlated with the concentration of cellulose in the cell wall. Kokubo, et al., (1989) *Plant Physiology* 91:876-882; Kokubo, et al., (1991) *Plant Physiology* 97:509-514.

Even though sugar and polysaccharide compositions of the plant cell walls have been well characterized, very limited progress has been made toward identification of the enzymes involved in polysaccharides formation, the reason being their labile nature and recalcitrance to solubilization by available detergents. Sporadic claims for the identification of cellulose synthase from plant sources have been made over the years. Callaghan and Benziman, (1984), *Nature* 311:165-167; Okuda, et al., (1993) *Plant Physiol.* 101:1131-1142. However, these claims have been met with skepticism. Callaghan and Benziman, (1985) *Nature* 314:383-384; Delmer, et al., (1993) *Plant Physiol.* 103:307-308. It was only recently that a putative gene for plant cellulose synthase (CelA) was cloned from the developing cotton fibers based on homology to the bacterial gene. Pear, et al., *Proc. Natl. Acad. Sci.* (USA) 93:12637-12642; Saxena, et al., (1990), *Plant Molecular Biology* 15:673-684; see also, WO 9818949.

As brittle snap is a major problem in corn breeding, what is needed in the art are compositions and methods for manipulating cellulose concentration in the cell wall and thereby altering plant stalk quality for improved standability or silage. The present invention provides these and other advantages.

SUMMARY OF THE INVENTION

Generally, it is the object of the present invention to provide nucleic acids and proteins relating to cellulose synthases. It is an object of the present invention to provide: 1) nucleic acids and proteins relating to maize cellulose synthases; 2) transgenic plants comprising the nucleic acids of the present invention; 3) methods for modulating, in a transgenic plant, the expression of the nucleic acids of the present invention.

Therefore, in one aspect, the present invention relates to an isolated nucleic acid comprising a member selected from the group consisting of (a) a polynucleotide having a specified sequence identity to a polynucleotide encoding a polypeptide of the present invention; (b) a polynucleotide which is complementary to the polynucleotide of (a); and (c) a polynucleotide comprising a specified number of contiguous nucleotides from a polynucleotide of (a) or (b). The isolated nucleic acid can be DNA or RNA.

In another aspect, the present invention relates to recombinant expression cassettes, comprising a nucleic acid of the present invention operably linked to a promoter.

In some embodiments, the nucleic acid is operably linked in antisense orientation to the promoter.

In another aspect, the present invention is directed to a host cell transfected with the recombinant expression cassette.

In a further aspect, the present invention relates to an isolated protein comprising a polypeptide having a specified number of contiguous amino acids encoded by an isolated nucleic acid of the present invention.

In another aspect, the present invention relates to an isolated nucleic acid comprising a polynucleotide of specified length which selectively hybridizes under stringent conditions to a polynucleotide of the present invention, or a complement thereof. In some embodiments, the isolated nucleic acid is operably linked to a promoter.

In yet another aspect, the present invention relates to an isolated nucleic acid comprising a polynucleotide, the polynucleotide having a specified sequence identity to an identical length of a nucleic acid of the present invention or a complement thereof.

In another aspect, the present invention relates to an isolated nucleic acid comprising a polynucleotide having a sequence of a nucleic acid amplified from a *Zea mays* nucleic acid library using at least two primers or their complements, one of which selectively hybridizes under stringent conditions to a locus of the nucleic acid comprising the 5' terminal coding region and the other primer selectively hybridizing, under stringent conditions, to a locus of the nucleic acid comprising the 3' terminal coding region, and wherein both primers selectively hybridize within the coding region. In some embodiments, the nucleic acid library is a cDNA library.

In another aspect, the present invention relates to a recombinant expression cassette comprising a nucleic acid, wherein the nucleic acid is operably linked to a promoter. In some embodiments, the present invention relates to a host cell transfected with this recombinant expression cassette. In some embodiments, the present invention relates to a protein of the present invention which is produced from this host cell.

In a further aspect, the present invention relates to a heterologous promoter operably linked to a non-isolated polynucleotide of the present invention, wherein the polypeptide is encoded by a nucleic acid amplified from a nucleic acid library.

In yet another aspect, the present invention relates to a transgenic plant comprising a recombinant expression cassette comprising a plant promoter operably linked to any of the isolated nucleic acids of the present invention. In some embodiments, the transgenic plant is Zea mays. The present invention also provides transgenic seed from the transgenic plant.

In a further aspect, the present invention relates to a method of modulating expression of the genes encoding the proteins of the present invention in a plant cell capable of plant regeneration, comprising the steps of (a) transforming a plant cell with a recombinant expression cassette comprising a polynucleotide of the present invention operably linked to a promoter; (b) growing the plant cell under plant growing conditions; and (c) inducing expression of the polynucleotide for a time sufficient to modulate expression of the genes in the plant. In some embodiments, the plant is maize. Expression of the genes encoding the proteins of the present invention can be increased or decreased relative to a non-transformed control plant.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and electronics Terms (5$^{th}$ edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing, et al., Ed., American Society for Microbiology, Washington, D.C. (1993). The product of amplification is termed an amplicon.

The term "antibody" includes reference to antigen binding forms of antibodies (e.g., Fab, F(ab)$_2$). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "antigen" includes reference to a substance to which an antibody can be generated and/or to which the antibody is specifically immunoreactive. The specific immunoreactive sites within the antigen are known as epitopes or antigenic determinants. These epitopes can be a linear array of monomers in a polymeric composition—such as amino acids in a protein—or consist of or comprise a more complex secondary or tertiary structure. Those of skill will recognize that all immunogens (i.e., substances capable of eliciting an immune response) are antigens; however some antigens, such as haptens, are not immunogens but may be made immunogenic by coupling to a carrier molecule. An antibody immunologically reactive with a particular antigen can be generated in vivo or by recombinant methods such as selection of libraries of recombinant antibodies in phage or similar vectors. See, e.g., Huse, et al., (1989) *Science* 246:1275-1281; and Ward, et al., (1989) *Nature* 341:544-546; and Vaughan, et al., (1996) *Nature Biotech.* 14:309-314.

As used herein, "antisense orientation" includes reference to a duplex polynucleotide sequence which is operably linked to a promoter in an orientation where the antisense strand is transcribed. The antisense strand is sufficiently complementary to an endogenous transcription product such that translation of the endogenous transcription product is often inhibited.

As used herein, "chromosomal region" includes reference to a length of a chromosome which may be measured by reference to the linear segment of DNA which it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein which encodes a polypeptide also describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80% or 90% of the native protein for it's native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolumn* (*Proc. Natl. Acad. Sci.* (*USA*) 82:2306-2309 (1985)), or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray, et al., (1989) *Nucl. Acids Res.* 17:477-498). Thus, the maize preferred codon for a particular amino acid may be derived from known gene sequences from maize. Maize codon usage for 28 genes from maize plants are listed in Table 4 of Murray, et al., above.

As used herein "full-length sequence" in reference to a specified polynucleotide or its encoded protein means having the entire amino acid sequence of, a native (non-synthetic), endogenous, catalytically active form of the specified protein. Methods to determine whether a sequence is full-length are well known in the art including such exemplary techniques as northern or western blots, primer extension, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN<u>AUG</u>G, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

The term "gene activity" refers to one or more steps involved in gene expression, including transcription, translation, and the functioning of the protein encoded by the gene.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the expression vector. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

By "immunologically reactive conditions" or "immunoreactive conditions" is meant conditions which allow an antibody, generated to a particular epitope, to bind to that epitope to a detectably greater degree (e.g., at least 2-fold over background) than the antibody binds to substantially all other epitopes in a reaction mixture comprising the particular epitope. Immunologically reactive conditions are dependent upon the format of the antibody binding reaction and typically are those utilized in immunoassay protocols. See Harlow and Lane, *Antibodies, A Laboratory Manual*, Cold Spring Harbor Publications, New York (1988), for a description of immunoassay formats and conditions.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is: (1) substantially or essentially free from components which normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a locus in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by non-natural, synthetic (i.e., "man-made") methods performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling, et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

Unless otherwise stated, the term "cellulose synthase nucleic acid" is a nucleic acid of the present invention and means a nucleic acid comprising a polynucleotide of the present invention (a "cellulose synthase polynucleotide") encoding a cellulose synthase polypeptide. A "cellulose synthase gene" is a gene of the present invention and refers to a non-heterologous genomic form of a full-length cellulose synthase polynucleotide.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes in that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook, et al., *Molecular Cloning—A Laboratory Manual,* 2nd ed., Vol. 1-3 (1989); and *Current Protocols in Molecular Biology*, F. M. Ausubel, et al., Eds., Current Protocols, a joint venture between Greene Publishing Associates, Inc. and John Wiley & Sons, Inc. (1994 Supplement).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant parts or organs (e.g., leaves, stems, roots, etc.), plant cells, seeds and progeny of same. Plant cell, as used herein includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants. Particularly preferred plants include maize, soybean, sunflower, sorghum, canola, wheat, alfalfa, cotton, rice, barley and millet.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Exemplary modifications are described in most basic texts, such as, *Proteins—Structure and Molecular Properties,* 2nd ed., T. E. Creighton, W. H. Freeman and Company, New York (1993). Many detailed reviews are available on this subject, such as, for example, those provided by Wold, F., Post-translational Protein Modifications: Perspectives and Prospects, pp. 1-12 in *Posttranslational Covalent Modification of Proteins*, B. C. Johnson, Ed., Academic Press, New York (1983); Seifter, et al., (1990) *Meth. Enzymol.* 182:626-646 and Rattan, et al., *Protein Synthesis: Posttranslational Modifications and Aging, Ann. N.Y. Acad. Sci.* 663: 48-62 (1992). It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini.

In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionine-less amino terminal variants of the protein of the invention. In general, as used herein, the term polypeptide encompasses all such modifications, particularly those that are present in polypeptides synthesized by expressing a polynucleotide in a host cell.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

The term "cellulose synthase polypeptide" is a polypeptide of the present invention and refers to one or more amino acid sequences, in glycosylated or non-glycosylated form. The term is also inclusive of fragments, variants, homologs, alleles or precursors (e.g., preproproteins or proproteins) thereof. A "cellulose synthase protein" is a protein of the present invention and comprises a cellulose synthase polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "specifically reactive", includes reference to a binding reaction between an antibody and a protein having an epitope recognized by the antigen binding site of the antibody. This binding reaction is determinative of the presence of a protein having the recognized epitope amongst the presence of a heterogeneous population of proteins and other biologics. Thus, under designated immunoassay conditions, the specified antibodies bind to an analyte having the recognized epitope to a substantially greater degree (e.g., at least 2-fold over background) than to substantially all other analytes lacking the epitope which are present in the sample.

The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2× SSC (20× SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1× SSC at 55 to 60° C. Exemplary high stringency conditions include hybridization in 50% formamide, 1 M NaCl, 1% SDS at 37° C., and a wash in 0.1× SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Optimal alignment of sequences for comparison may be conducted by the local homology algorithm of Smith and Waterman, (1981) *Adv. Appl. Math.* 2:482; by the homology alignment algorithm of Needleman and Wunsch, (1970) *J. Mol. Biol.* 48:443; by the search for similarity method of Pearson and Lipman, (1988) *Proc. Natl. Acad. Sci.* 85:2444; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, (1988) *Gene* 73:237-244; Higgins and Sharp, (1989) *CABIOS* 5:151-153; Corpet, et al., (1988) *Nucleic Acids Research* 16:10881-90; Huang, et al., (1992) *Computer Applications in the Biosciences* 8:155-65, and Pearson, et al., (1994) *Methods in Molecular Biology* 24:307-331. The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul, et al., (1997) *Nucleic Acids Res.* 25:3389-3402. Software for performing BLAST analyses is publicly available, e.g., through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff and Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin and Altschul, (1993) *Proc. Nat'l. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) *Comput. Chem.*, 17:149-163) and XNU (Claverie and States, (1993) *Comput. Chem.*, 17:191-201) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) *Computer Applic. Biol. Sci.*, 4:11-17 e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 90% and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) (ii) The terms "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch, (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

DETAILED DESCRIPTION OF THE INVENTION

Overview

The present invention provides, among other things, compositions and methods for modulating (i.e., increasing or decreasing) the level of polypeptides of the present invention in plants. In particular, the polypeptides of the present invention can be expressed at developmental stages, in tissues, and/or in quantities which are uncharacteristic of non-recombinantly engineered plants. Thus, the present invention provides utility in such exemplary applications as improvement of stalk quality for improved stand or silage. Further, the present invention provides for an increased concentration of cellulose in the pericarp; hardening the kernel and thus improving its handling ability.

The present invention also provides isolated nucleic acid comprising polynucleotides of sufficient length and complementarity to a gene of the present invention to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms) of the gene, or for use as molecular markers in plant breeding programs. The isolated nucleic acids of the present invention can also be used for recombinant expression of their encoded polypeptides, or for use as immunogens in the preparation and/or screening of antibodies. The isolated nucleic acids of the present invention can also be employed for use in sense or antisense suppression of one or more genes of the present invention in a host cell, tissue, or plant. Attachment of chemical agents which bind, intercalate, cleave and/or crosslink to the isolated nucleic acids of the present invention can also be used to modulate transcription or translation.

The present invention also provides isolated proteins comprising a polypeptide of the present invention (e.g., preproenzyme, proenzyme, or enzymes). The present invention also provides proteins comprising at least one epitope from a polypeptide of the present invention. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, or for purification of polypeptides of the present invention.

The isolated nucleic acids and proteins of the present invention can be used over a broad range of plant types, particularly monocots such as the species of the Family Graminiae including *Sorghum bicolor* and *Zea mays*. The isolated nucleic acid and proteins of the present invention can also be used in species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Triticum, Bambusa, Dendrocalamus,* and *Melocanna.*

Nucleic Acids

The present invention provides, among other things, isolated nucleic acids of RNA, DNA, and analogs and/or chimeras thereof, comprising a polynucleotide of the present invention.

A polynucleotide of the present invention is inclusive of:

(a) a polynucleotide encoding a polypeptide of SEQ ID NOS: 2, 6, 10, 14, 18, 22, 26, 30, 34, 38, 42, 46, 50, 54 and 58, and conservatively modified and polymorphic variants thereof, including exemplary polynucleotides of SEQ ID NOS: 1, 5, 9, 13, 17, 21, 25, 29, 33, 37, 41, 45, 49, 53 and 57;

(b) a polynucleotide which is the product of amplification from a *Zea mays* nucleic acid library using primer pairs which selectively hybridize under stringent conditions to loci within a polynucleotide selected from the group consisting of SEQ ID NOS: 1, 5, 9, 13, 17, 21, 25, 29, 33, 37, 41, 45, 49, 53 and 57, wherein the polynucleotide has substantial sequence identity to a polynucleotide selected from the group consisting of SEQ ID NOS: 1, 5, 9, 13, 17, 21, 25, 29, 33, 37, 41, 45, 49, 53 and 57;

(c) a polynucleotide which selectively hybridizes to a polynucleotide of (a) or (b);

(d) a polynucleotide having a specified sequence identity with polynucleotides of (a), (b) or (c);

(e) a polynucleotide encoding a protein having a specified number of contiguous amino acids from a prototype polypeptide, wherein the protein is specifically recognized by antisera elicited by presentation of the protein and wherein the protein does not detectably immunoreact to antisera which has been fully immunosorbed with the protein;

(f) complementary sequences of polynucleotides of (a), (b), (c), (d) or (e); and (g) a polynucleotide comprising at least a specific number of contiguous nucleotides from a polynucleotide of (a), (b), (c), (d), (e) or (f).

A. Polynucleotides Encoding a Polypeptide of the Present Invention or Conservatively Modified or Polymorphic Variants Thereof As indicated in (a), above, the present invention provides isolated nucleic acids comprising a polynucleotide of the present invention, wherein the polynucleotide encodes a polypeptide of the present invention, or conservatively modified or polymorphic variants thereof. Those of skill in the art will recognize that the degeneracy of the genetic code allows for a plurality of polynucleotides to encode for the identical amino acid sequence. Such "silent variations" can be used, for example, to selectively hybridize and detect allelic variants of polynucleotides of the present invention. Accordingly, the present invention includes polynucleotides of SEQ ID NOS: 1, 5, 9, 13, 17, 21, 25, 29, 33, 37, 41, 45, 49, 53 and 57, and silent variations of polynucleotides encoding a polypeptide of SEQ ID NOS: 2, 6, 10, 14, 18, 22, 26, 30, 34, 38, 42, 46, 50, 54 and 58. The present invention further provides isolated nucleic acids comprising polynucleotides encoding conservatively modified variants of a polypeptide of SEQ ID NOS: 2, 6, 10, 14, 18, 22, 26, 30, 34, 38, 42, 46, 50, 54 and 58. Additionally, the present invention further provides isolated nucleic acids comprising polynucleotides encoding one or more polymorphic (allelic) variants of polypeptides/polynucleotides. Polymorphic variants are frequently used to follow segregation of chromosomal regions in, for example, marker assisted selection methods for crop improvement.

B. Polynucleotides Amplified from a *Zea mays* Nucleic Acid Library

As indicated in (b) above, the present invention provides an isolated nucleic acid comprising a polynucleotide of the present invention, wherein the polynucleotides are amplified from a *Zea mays* nucleic acid library. *Zea mays* lines B73, PHRE1, A632, BMS-P2#10, W23, and Mo17 are known and publicly available. Other publicly known and available maize lines can be obtained from the Maize Genetics Cooperation (Urbana, Ill.). The nucleic acid library may be a cDNA library, a genomic library, or a library generally constructed from nuclear transcripts at any stage of intron processing. cDNA libraries can be normalized to increase the representation of relatively rare cDNAs. In optional embodiments, the cDNA library is constructed using a full-length cDNA synthesis method. Examples of such methods include Oligo-Capping (Maruyama and Sugano, (1994) *Gene* 138:171-174), Biotinylated CAP Trapper (Carninci, et al., (1996) *Genomics* 37:327-336), and CAP Retention Procedure (Edery, et al., (1995) *Molecular and Cellular Biology* 15:3363-3371). cDNA synthesis is often catalyzed at 50-55° C. to prevent formation of RNA secondary structure. Examples of reverse transcriptases that are relatively stable at these temperatures are SuperScript II Reverse Transcriptase (Life Technologies, Inc.), AMV Reverse Transcriptase (Boehringer Mannheim) and RetroAmp Reverse Transcriptase (Epicentre). Rapidly growing tissues, or rapidly dividing cells are preferably used as mRNA sources such as from the elongating internode of corn plants.

The polynucleotides of the present invention include those amplified using the following primer pairs:

SEQ ID NOS: 3 and 4 which yield an amplicon comprising a sequence having substantial identity to SEQ ID NO: 1;

SEQ ID NOS: 7 and 8 which yield an amplicon comprising a sequence having substantial identity to SEQ ID NO: 5; and SEQ ID NOS: 11 and 12 which yield an amplicon comprising a sequence having substantial identity to SEQ ID NO: 9.

SEQ ID NOS: 15 and 16 which yield an amplicon comprising a sequence having substantial identity to SEQ ID NO: 13.

SEQ ID NOS: 19 and 20 which yield an amplicon comprising a sequence having substantial identity to SEQ ID NO: 17;

SEQ ID NOS: 23 and 24 which yield an amplicon comprising a sequence having substantial identity to SEQ ID NO: 21; and SEQ ID NOS: 27 and 28 which yield an amplicon comprising a sequence having substantial identity to SEQ ID NO: 25.

SEQ ID NOS: 31 and 32 which yield an amplicon comprising a sequence having substantial identity to SEQ ID NO: 29.

SEQ ID NOS: 35 and 36 which yield an amplicon comprising a sequence having substantial identity to SEQ ID NO: 33;

SEQ ID NOS: 39 and 40 which yield an amplicon comprising a sequence having substantial identity to SEQ ID NO: 37; and SEQ ID NOS: 43 and 44 which yield an amplicon comprising a sequence having substantial identity to SEQ ID NO: 41.

SEQ ID NOS: 47 and 48 which yield an amplicon comprising a sequence having substantial identity to SEQ ID NO: 45.

SEQ ID NOS: 51 and 52 which yield an amplicon comprising a sequence having substantial identity to SEQ ID NO: 49;

SEQ ID NOS: 55 and 56 which yield an amplicon comprising a sequence having substantial identity to SEQ ID NO: 53; and SEQ ID NOS: 59 and 60 which yield an amplicon comprising a sequence having substantial identity to SEQ ID NO: 57.

The present invention also provides subsequences of the polynucleotides of the present invention. A variety of subsequences can be obtained using primers which selectively hybridize under stringent conditions to at least two sites within a polynucleotide of the present invention, or to two sites within the nucleic acid which flank and comprise a polynucleotide of the present invention, or to a site within a polynucleotide of the present invention and a site within the nucleic acid which comprises it. Primers are chosen to selectively hybridize, under stringent hybridization conditions, to a polynucleotide of the present invention. Generally, the primers are complementary to a subsequence of the target nucleic acid which they amplify. As those skilled in the art will appreciate, the sites to which the primer pairs will selectively hybridize are chosen such that a single contiguous nucleic acid can be formed under the desired amplification conditions.

In optional embodiments, the primers will be constructed so that they selectively hybridize under stringent conditions to a sequence (or its complement) within the target nucleic acid which comprises the codon encoding the carboxy or amino terminal amino acid residue (i.e., the 3' terminal coding region and 5' terminal coding region, respectively) of the polynucleotides of the present invention. Optionally within these embodiments, the primers will be constructed to selectively hybridize entirely within the coding region of the target polynucleotide of the present invention such that the product of amplification of a cDNA target will consist of the coding region of that cDNA. The primer length in nucleotides is selected from the group of integers consisting of from at least 15 to 50. Thus, the primers can be at least 15, 18, 20, 25, 30, 40 or 50 nucleotides in length. Those of skill will recognize that a lengthened primer sequence can be employed to increase specificity of binding (i.e., annealing) to a target sequence. A non-annealing sequence at the 5' end of a primer (a "tail") can be added, for example, to introduce a cloning site at the terminal ends of the amplicon.

The amplification products can be translated using expression systems well known to those of skill in the art and as discussed, infra. The resulting translation products can be confirmed as polypeptides of the present invention by, for example, assaying for the appropriate catalytic activity (e.g., specific activity and/or substrate specificity), or verifying the presence of one or more linear epitopes which are specific to a polypeptide of the present invention. Methods for protein synthesis from PCR derived templates are known in the art and available commercially. See, e.g., Amersham Life Sciences, Inc, Catalog '97, p. 354.

Methods for obtaining 5' and/or 3' ends of a vector insert are well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego, 1990), pp. 28-38); see also, U.S. Pat. No. 5,470,722, and *Current Protocols in Molecular Biology*, Unit 15.6, Ausubel, et al., Eds., Greene Publishing and Wiley-Interscience, New York (1995); Frohman and Martin, (1989) *Techniques* 1:165.

C. Polynucleotides which Selectively Hybridize to a Polynucleotide of (A) or (B)

As indicated in (c), above, the present invention provides isolated nucleic acids comprising polynucleotides of the present invention, wherein the polynucleotides selectively hybridize, under selective hybridization conditions, to a polynucleotide of paragraphs (A) or (B) as discussed, above. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: corn, canola, soybean, cotton, wheat, sorghum, sunflower, oats, sugar cane, millet, barley, and rice. Optionally, the cDNA library comprises at least 80% full-length sequences, preferably at least 85% or 90% full-length sequences, and more preferably at least 95% full-length sequences. The cDNA libraries can be normalized to increase the representation of rare sequences. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

D. Polynucleotides Having a Specific Sequence Identity with the Polynucleotides of (A), (B) or (C)

As indicated in (d), above, the present invention provides isolated nucleic acids comprising polynucleotides of the present invention, wherein the polynucleotides have a specified identity at the nucleotide level to a polynucleotide as disclosed above in paragraphs (A), (B) or (C). The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 80%, 85%, 90% or 95%.

Optionally, the polynucleotides of this embodiment will share an epitope with a polypeptide encoded by the polynucleotides of (A), (B) or (C). Thus, these polynucleotides encode a first polypeptide which elicits production of antisera comprising antibodies which are specifically reactive to a second polypeptide encoded by a polynucleotide of (A), (B) or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B) or (C), or for purification of, or in immunoassays for, polypeptides encoded by the polynucleotides of (A), (B) or (C). The polynucleotides of this embodiment embrace nucleic acid sequences which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Application Publication Nos. 91/17271, 91/18980, 91/19818 and 93/08278. Other systems for generating libraries of peptides have aspects of both in vitro chemical synthesis and recombinant methods. See, PCT Patent Application Publication Nos. 92/05258, 92/14843 and 96/19256. See also, U.S. Pat. Nos. 5,658,754 and 5,643,768. Peptide display libraries, vectors, and screening kits are commercially available from such suppliers as Invitrogen (Carlsbad, Calif.).

E. Polynucleotides Encoding a Protein Having a Subsequence from a Prototype Polypeptide and is Cross-Reactive to the Prototype Polypeptide As indicated in (e), above, the present invention provides isolated nucleic acids comprising polynucleotides of the present invention, wherein the polynucleotides encode a protein having a subsequence of contiguous amino acids from a prototype polypeptide of the present invention such as are provided in (a), above. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45 or 50, contiguous amino acids from the prototype polypeptide. Further, the number of such subsequences encoded by a polynucleotide of the instant embodiment can be any integer selected from the group consisting of from 1 to 20, such as 2, 3, 4 or 5. The subsequences can be separated by any integer of nucleotides from 1 to the number of nucleotides in the sequence such as at least 5, 10, 15, 25, 50, 100 or 200 nucleotides.

The proteins encoded by polynucleotides of this embodiment, when presented as an immunogen, elicit the production of polyclonal antibodies which specifically bind to a prototype polypeptide such as but not limited to, a polypeptide encoded by the polynucleotide of (a) or (b), above. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In a preferred assay method, fully immunosorbed and pooled antisera which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants, and minor recombinant modifications to a prototype polypeptide.

A polynucleotide of the present invention optionally encodes a protein having a molecular weight as the non-glycosylated protein within 20% of the molecular weight of the full-length non-glycosylated polypeptides of the present invention. Molecular weight can be readily determined by SDS-PAGE under reducing conditions. Preferably, the molecular weight is within 15% of a full length polypeptide of the present invention, more preferably within 10% or 5%, and most preferably within 3%, 2% or 1% of a full length polypeptide of the present invention. Molecular weight determination of a protein can be conveniently performed by SDS-PAGE under denaturing conditions.

Optionally, the polynucleotides of this embodiment will encode a protein having a specific activity at least 50%, 60%, 80% or 90% of the native, endogenous (i.e., non-isolated), full-length polypeptide of the present invention. Further, the proteins encoded by polynucleotides of this embodiment will optionally have a substantially similar affinity constant ($K_m$) and/or catalytic activity (i.e., the microscopic rate constant, $k_{cat}$) as the native endogenous, full-length protein. Those of skill in the art will recognize that $k_{cat}/K_m$ value determines the specificity for competing substrates and is often referred to as the specificity constant. Proteins of this embodiment can have a $k_{cat}/K_m$ value at least 10% of a non-isolated full-length polypeptide of the present invention as determined using the endogenous substrate of that polypeptide. Optionally, the $k_{cat}/K_m$ value will be at least 20%, 30%, 40%, 50% and most preferably at least 60%, 70%, 80%, 90% or 95% the $k_{cat}/K_m$ value of the non-isolated, full-length polypeptide of the present invention. Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow, or rapid quenching techniques), flash photolysis, or relaxation methods (e.g., temperature jumps) in conjunction with such exemplary methods of measuring as spectrophotometry, spectrofluorimetry, nuclear magnetic resonance, or radioactive procedures. Kinetic values are conveniently obtained using a Lineweaver-Burk or Eadie-Hofstee plot.

F. Polynucleotides Complementary to the Polynucleotides of (A)-(E)

As indicated in (f), above, the present invention provides isolated nucleic acids comprising polynucleotides complementary to the polynucleotides of paragraphs A-E, above. As those of skill in the art will recognize, complementary sequences base-pair throughout the entirety of their length with the polynucleotides of (A)-(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides which are Subsequences of the Polynucleotides of (A)-(F)

As indicated in (g), above, the present invention provides isolated nucleic acids comprising polynucleotides which comprise at least 15 contiguous bases from the polynucleotides of (A) through (F) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 30, 40, 50, 60, 75 or 100 contiguous nucleotides in length from the polynucleotides of (A)-(F). Optionally, the number of such subsequences encoded by a polynucleotide of the instant embodiment can be any integer selected from the group consisting of from 1 to 20, such as 2, 3, 4 or 5. The subsequences can be separated by any integer of nucleotides from 1 to the number of nucleotides in the sequence such as at least 5, 10, 15, 25, 50, 100 or 200 nucleotides.

The subsequences of the present invention can comprise structural characteristics of the sequence from which it is derived. Alternatively, the subsequences can lack certain structural characteristics of the larger sequence from which it is derived. For example, a subsequence from a polynucleotide encoding a polypeptide having at least one linear epitope in common with a prototype polypeptide sequence as provided in (a), above, may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot. In preferred embodiments the monocot is Zea mays.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. A polynucleotide of the present invention can be attached to a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known and extensively described in the art. For a description of various nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. While isolation of RNA, and construction of cDNA and genomic libraries is well known to those of ordinary skill in the art, the following highlights some of the methods employed.

A1 mRNA Isolation and Purification

Total RNA from plant cells comprises such nucleic acids as mitochondrial RNA, chloroplastic RNA, rRNA, tRNA, hnRNA and mRNA. Total RNA preparation typically involves lysis of cells and removal of proteins, followed by precipitation of nucleic acids. Extraction of total RNA from plant cells can be accomplished by a variety of means. Frequently, extraction buffers include a strong detergent such as SDS and an organic denaturant such as guanidinium isothiocyanate, guanidine hydrochloride or phenol. Following total RNA isolation, poly(A)$^+$ mRNA is typically purified from the remainder RNA using oligo(dT) cellulose. Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli, Pa.). See also, U.S. Pat. Nos. 5,614,391 and 5,459,253. The mRNA can be fractionated into populations with size ranges of about 0.5, 1.0, 1.5, 2.0, 2.5 or 3.0 kb. The cDNA synthesized for each of these fractions can be size selected to the same size range as its mRNA prior to vector insertion. This method helps eliminate truncated cDNA formed by incompletely reverse transcribed mRNA.

A2. Construction of a cDNA Library

Construction of a cDNA library generally entails five steps. First, first strand cDNA synthesis is initiated from a poly(A)$^+$ mRNA template using a poly(dT) primer or random hexanucleotides. Second, the resultant RNA-DNA hybrid is converted into double stranded cDNA, typically by a combination of RNAse H and DNA polymerase I (or Klenow fragment). Third, the termini of the double stranded cDNA are ligated to adaptors. Ligation of the adaptors will produce cohesive ends for cloning. Fourth, size selection of the double stranded cDNA eliminates excess adaptors and primer fragments, and eliminates partial cDNA molecules due to degradation of mRNAs or the failure of reverse transcriptase to synthesize complete first strands. Fifth, the cDNAs are ligated into cloning vectors and packaged. cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). cDNA synthesis kits are available from a variety of commercial vendors such as Stratagene or Pharmacia.

A number of cDNA synthesis protocols have been described which provide substantially pure full-length cDNA libraries. Substantially pure full-length cDNA libraries are constructed to comprise at least 90%, and more preferably at least 93% or 95% full-length inserts amongst clones containing inserts. The length of insert in such libraries can be from 0 to 8, 9, 10, 11, 12, 13 or more kilobase pairs. Vectors to accommodate inserts of these sizes are known in the art and available commercially. See, e.g., Stratagene's lambda ZAP Express (cDNA cloning vector with 0 to 12 kb cloning capacity).

An exemplary method of constructing a greater than 95% pure full-length cDNA library is described by Carninci, et al., (1996) *Genomics*, 37:327-336. In that protocol, the cap-structure of eukaryotic mRNA is chemically labeled with biotin. By using streptavidin-coated magnetic beads, only the full-length first-strand cDNA/mRNA hybrids are selectively recovered after RNase I treatment. The method provides a high yield library with an unbiased representation of the starting mRNA population. Other methods for producing full-length libraries are known in the art. See, e.g., Edery, et al., (1995) *Mol. Cell. Biol.*, 15(6):3363-3371; and PCT Application WO 96/34981.

A3. Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented.

A number of approaches to normalize cDNA libraries are known in the art. One approach is based on hybridization to genomic DNA. The frequency of each hybridized cDNA in the resulting normalized library would be proportional to that of each corresponding gene in the genomic DNA. Another approach is based on kinetics. If cDNA reannealing follows second-order kinetics, rarer species anneal less rapidly and the remaining single-stranded fraction of cDNA becomes progressively more normalized during the course of the hybridization. Specific loss of any species of cDNA, regardless of its abundance, does not occur at any Cot value. Construction of normalized libraries is described in Ko, (1990) *Nucl. Acids. Res.*, 18(19):5705-5711; Patanjali, et al., (1991) *Proc. Natl. Acad. U.S.A.* 88:1943-1947; U.S. Pat. Nos. 5,482,685 and 5,637,685. In an exemplary method described by Soares, et al., normalization resulted in reduction of the abundance of clones from a range of four orders of magnitude to a narrow range of only 1 order of magnitude. *Proc. Natl. Acad. Sci. USA*, 91:9228-9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote, et al. in, *Plant Molecular Biology: A Laboratory Manual*, Clark, Ed., Springer-Verlag, Berlin (1997); Kho and Zarbl, (1991) *Technique* 3(2):58-63; Sive and St. John, (1988) *Nucl. Acids Res.*, 16(22):10937; *Current Protocols in Molecular Biology*, Ausubel, et al., Eds., Greene Publishing and Wiley-Interscience, New York (1995); and, Swaroop, (1991) et al., *Nucl. Acids Res.*, 19(8):1954. cDNA subtraction kits are commercially available. See, e.g., PCR-Select (Clontech).

A4. Construction of a Genomic Library

To construct genomic libraries, large segments of genomic DNA are generated by random fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al., *Molecular Cloning: A Laboratory Manual*, 2nd Ed., Cold Spring Harbor Laboratory Vols. 1-3 (1989), Methods in Enzymology, Vol.

152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

A5. Nucleic Acid Screening and Isolation Methods

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100 percent; however, it should be understood that minor sequence variations in the probes and primers may be compensated for by reducing the stringency of the hybridization and/or wash medium.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, Sambrook, and Ausubel, as well as Mullis, et al., U.S. Pat. No. 4,683,202 (1987); and, *PCR Protocols A Guide to Methods and Applications*, Innis, et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger, et al., describe a PCR-based method in which the longest cDNA is identified in the first step so that incomplete clones can be eliminated from study. *BioTechniques*, 22(3): 481-486 (1997). In that method, a primer pair is synthesized with one primer annealing to the 5' end of the sense strand of the desired cDNA and the other primer to the vector. Clones are pooled to allow large-scale screening. By this procedure, the longest possible clone is identified amongst candidate clones. Further, the PCR product is used solely as a diagnostic for the presence of the desired cDNA and does not utilize the PCR product itself. Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang, et al., (1979) *Meth. Enzymol.* 68:90-99; the phosphodiester method of Brown, et al., (1979) *Meth. Enzymol.* 68:109-151; the diethylphosphoramidite method of Beaucage, et al., (1981) *Tetra. Lett.* 22:1859-1862; the solid phase phosphoramidite triester method described by Beaucage and Caruthers, (1981) *Tetra. Letts.* 22(20):1859-1862, e.g., using an automated synthesizer, e.g., as described in Needham-VanDevanter, et al., (1984) *Nucleic Acids Res.*, 12:6159-6168; and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

Recombinant Expression Cassettes

The present invention further provides recombinant expression cassettes comprising a nucleic acid of the present invention. A nucleic acid sequence coding for the desired polynucleotide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter, the actin promoter, the F3.7 promoter, and other transcription initiation regions from various plant genes known to those of skill.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds, or flowers. The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter functional in a plant cell, such as in Zea mays, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling, et al., PCT/US93/03868), or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

Methods for identifying promoters with a particular expression pattern, in terms of, e.g., tissue type, cell type, stage of development, and/or environmental conditions, are well known in the art. See, e.g., *The Maize Handbook*, Chapters 114-115, Freeling and Walbot, Eds., Springer, New York (1994); *Corn and Corn Improvement,* $3^{rd}$ edition, Chapter 6, Sprague and Dudley, Eds., American Society of Agronomy, Madison, Wis. (1988). A typical step in promoter isolation methods is identification of gene products that are expressed with some degree of specificity in the target tissue. Amongst the range of methodologies are: differential hybridization to cDNA libraries; subtractive hybridization; differential display; differential 2-D protein gel electrophoresis; DNA probe arrays; and isolation of proteins known to be expressed with some specificity in the target tissue. Such methods are well known to those of skill in the art. Commercially available products for identifying promoters are known in the art such as Clontech's (Palo Alto, Calif.) Universal GenomeWalker Kit.

For the protein-based methods, it is helpful to obtain the amino acid sequence for at least a portion of the identified protein, and then to use the protein sequence as the basis for preparing a nucleic acid that can be used as a probe to identify either genomic DNA directly, or preferably, to identify a cDNA clone from a library prepared from the target tissue. Once such a cDNA clone has been identified, that sequence can be used to identify the sequence at the 5' end of the transcript of the indicated gene. For differential hybridization, subtractive hybridization and differential display, the nucleic acid sequence identified as enriched in the target tissue is used to identify the sequence at the 5' end of the transcript of the indicated gene. Once such sequences are identified, starting either from protein sequences or nucleic acid sequences, any of these sequences identified as being from the gene transcript can be used to screen a genomic library prepared from the target organism. Methods for identifying and confirming the transcriptional start site are well known in the art.

In the process of isolating promoters expressed under particular environmental conditions or stresses, or in specific tissues, or at particular developmental stages, a number of genes are identified that are expressed under the desired circumstances, in the desired tissue, or at the desired stage. Further analysis will reveal expression of each particular gene in one or more other tissues of the plant. One can identify a promoter with activity in the desired tissue or condition but that do not have activity in any other common tissue.

To identify the promoter sequence, the 5' portions of the clones described here are analyzed for sequences characteristic of promoter sequences. For instance, promoter sequence elements include the TATA box consensus sequence (TATAAT), which is usually an AT-rich stretch of 5-10 bp located approximately 20 to 40 base pairs upstream of the transcription start site. Identification of the TATA box is well known in the art. For example, one way to predict the location of this element is to identify the transcription start site using standard RNA-mapping techniques such as primer extension, S1 analysis, and/or RNase protection. To confirm the presence of the AT-rich sequence, a structure-function analysis can be performed involving mutagenesis of the putative region and quantification of the mutation's effect on expression of a linked downstream reporter gene. See, e.g., *The Maize Handbook*, Chapter 114, Freeling and Walbot, Eds., Springer, New York, (1994).

In plants, further upstream from the TATA box, at positions −80 to −100, there is typically a promoter element (i.e., the CAAT box) with a series of adenines surrounding the trinucleotide G (or T) N G. Messing, et al., in *Genetic Engineering in Plants*, Kosage, Meredith and Hollaender, Eds., pp. 221-227 (1983). In maize, there is no well conserved CAAT box but there are several short, conserved protein-binding motifs upstream of the TATA box. These include motifs for the trans-acting transcription factors involved in light regulation, anaerobic induction, hormonal regulation, or anthocyanin biosynthesis, as appropriate for each gene.

Once promoter and/or gene sequences are known, a region of suitable size is selected from the genomic DNA that is 5' to the transcriptional start, or the translational start site, and such sequences are then linked to a coding sequence. If the transcriptional start site is used as the point of fusion, any of a number of possible 5' untranslated regions can be used in between the transcriptional start site and the partial coding sequence. If the translational start site at the 3' end of the specific promoter is used, then it is linked directly to the methionine start codon of a coding sequence.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, (1988) *Mol. Cell. Biol.* 8:4395-4405; Callis, et al., (1987) *Genes Dev.* 1:1183-1200. Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, New York (1994).

The vector comprising the sequences from a polynucleotide of the present invention will typically comprise a marker gene which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers, et al., (1987) *Meth. In Enzymol.* 153:253-277. These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl, et al., (1987) *Gene* 61:1-11 and Berger, et al., (1989) *Proc. Natl. Acad. Sci. U.S.A.* 86:8402-8406. Another useful vector herein is plasmid pBI101.2 that is available from Clontech Laboratories, Inc. (Palo Alto, Calif.).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy, et al., (1988) *Proc. Nat'l. Acad. Sci.* (USA) 85:8805-8809; and Hiatt, et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli, et al., (1990) *The Plant Cell* 2:279-289 and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff, et al., (1988) *Nature* 334:585-591.

A variety of cross-linking agents, alkylating agents and radical generating species as pendant groups on polynucleotides of the present invention can be used to bind, label, detect, and/or cleave nucleic acids. For example, Vlassov, et al., (1986) *Nucleic Acids Res* 14:4065-4076, describe covalent bonding of a single-stranded DNA fragment with alkylating derivatives of nucleotides complementary to target sequences. A report of similar work by the same group is that by Knorre, et al., (1985) *Biochimie* 67:785-789. Iverson and Dervan also showed sequence-specific cleavage of single-stranded DNA mediated by incorporation of a modified nucleotide which was capable of activating cleavage (*J Am Chem Soc* 109:1241-1243 (1987)). Meyer, et al., (1989) *J Am Chem Soc* 111:8517-8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, et al., (1988) *Biochemistry* 27:3197-3203. Use of crosslinking in triple-helix forming probes was also disclosed by Home, et al., (1990) *J Am Chem Soc* 112:2435-2437. Use of N4, N4-ethanocytosine as an alkylating agent to crosslink to single-stranded oligonucleotides has also been described by Webb and Matteucci, (1986) *J Am Chem Soc* 108:2764-2765; *Nucleic Acids Res* 14:7661-7674 (1986); Feteritz, et al., (1991) *J. Am. Chem. Soc.* 113:4000. Various compounds to bind, detect, label, and/or cleave nucleic acids are known in the art. See, for example, U.S. Pat. Nos. 5,543,507; 5,672,593; 5,484,908; 5,256,648 and 5,681941.

Proteins

The isolated proteins of the present invention comprise a polypeptide having at least 10 amino acids encoded by any one of the polynucleotides of the present invention as discussed more fully, above, or polypeptides which are conservatively modified variants thereof. The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 20, 25, 30, 35 or 40 amino acids in length, often at least 50, 60, 70, 80 or 90 amino acids in length. Further, the number of such subsequences can be any integer selected from the group consisting of from 1 to 20, such as 2, 3, 4 or 5.

As those of skill will appreciate, the present invention includes catalytically active polypeptides of the present invention (i.e., enzymes). Catalytically active polypeptides have a specific activity of at least 20%, 30%, or 40%, and preferably at least 50%, 60% or 70%, and most preferably at least 80%, 90% or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40% or 50%, that of the native (non-synthetic), endogenous polypeptide; and more preferably at least 60%, 70%, 80% or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

A. Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang, et al., (1977) *Nature* 198:1056), the tryptophan (trp) promoter system (Goeddel, et al., (1980) *Nucleic Acids Res.* 8:4057) and the lambda derived P L promoter and N-gene ribosome binding site (Shimatake, et al., (1981) *Nature* 292:128). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus* sp. and *Salmonella* (Palva, et al., (1983) *Gene* 22:229-235; Mosbach, et al., (1983) *Nature* 302:543-545).

B. Expression in Eukaryotes

A variety of eukaryotic expression systems such as yeast, insect cell lines, plant and mammalian cells, are known to those of skill in the art. As explained briefly below, a of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, et al., *Methods in Yeast Genetics*, Cold Spring Harbor Laboratory (1982) is a well recognized work describing the various methods available to produce the protein in yeast. Two widely utilized yeast for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen, et al., (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th edition, 1992).

Appropriate vectors for expressing proteins of the present invention in insect cells are usually derived from the SF9 baculovirus. Suitable insect cell lines include mosquito larvae, silkworm, armyworm, moth and *Drosophila* cell lines such as a Schneider cell line (See, Schneider, (1987) *Embryol. Exp. Morphol.* 27:353-365.

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., (1983) *J. Virol.* 45:773-781). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in *DNA Cloning Vol. II a Practical Approach*, D. M. Glover, Ed., IRL Press, Arlington, Va. pp. 213-238 (1985).

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for efficient transformation/transfection may be employed.

A. Plant Transformation

A DNA sequence coding for the desired polynucleotide of the present invention, for example a cDNA or a genomic sequence encoding a full length protein, will be used to construct a recombinant expression cassette which can be introduced into the desired plant.

Isolated nucleic acid acids of the present invention can be introduced into plants according techniques known in the art. Generally, recombinant expression cassettes as described above and suitable for transformation of plant cells are prepared. Techniques for transforming a wide variety of higher plant species are well known and described in the technical, scientific, and patent literature. See, for example, Weising, et al., (1988) *Ann. Rev. Genet.* 22:421-477. For example, the DNA construct may be introduced directly into the genomic DNA of the plant cell using techniques such as electroporation, PEG poration, particle bombardment, silicon fiber delivery, or microinjection of plant cell protoplasts or embryogenic callus. See, e.g., Tomes, et al., Direct DNA Transfer into Intact Plant Cells via Microprojectile Bombardment, pp. 197-213 in Plant Cell, Tissue and Organ Culture, Fundamental Methods, (eds. O. L. Gamborg and G. C. Phillips, Springer-Verlag Berlin Heidelberg New York, 1995). Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using polyethylene glycol precipitation is described in Paszkowski, et al., (1984) *Embo J.* 3:2717-2722. Electroporation techniques are described in Fromm, et al., (1985) *Proc. Natl. Acad. Sci.* 82:5824. Ballistic transformation techniques are described in Klein, et al., (1987) *Nature* 327:70-73.

*Agrobacterium tumefaciens*-meditated transformation techniques are well described in the scientific literature. See, for example, Horsch, et al., (1984) *Science* 233:496-498, and Fraley, et al., (1983) *Proc. Natl. Acad. Sci.* 80:4803. Although *Agrobacterium* is useful primarily in dicots, certain monocots can be transformed by *Agrobacterium*. For instance, *Agrobacterium* transformation of maize is described in U.S. Pat. No. 5,550,318.

Other methods of transfection or transformation include (1) *Agrobacterium rhizogenes*-mediated transformation (see, e.g., Lichtenstein and Fuller In: Genetic Engineering, vol. 6, PWJ Rigby, Ed., London, Academic Press, 1987; and Lichtenstein, C. P., and Draper, J, In: DNA Cloning, Vol. II, D. M. Glover, Ed., Oxford, IRI Press, 1985), PCT Patent Application Number PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman, et al., (1984) *Plant Cell Physiol.* 25:1353), (3) the vortexing method (see, e.g., Kindle, (1990) *Proc. Natl. Acad. Sci., USA* 87:1228).

DNA can also be introduced into plants by direct DNA transfer into pollen as described by Zhou, et al., (1983) *Methods in Enzymology* 101:433; Hess, (1987) *Intern Rev. Cytol.* 107:367; Luo, et al., (1988) *Plant Mol. Biol. Reporter* 6:165. Expression of polypeptide coding genes can be obtained by injection of the DNA into reproductive organs of a plant as described by Pena, et al., (1987) *Nature* 325:274. DNA can also be injected directly into the cells of immature embryos and the rehydration of desiccated embryos as described by Neuhaus, et al., (1987) *Theor. Appl. Genet.* 75:30; and Benbrook, et al., in Proceedings Bio Expo 1986, Butterworth, Stoneham, Mass., pp. 27-54 (1986). A variety of plant viruses that can be employed as vectors are known in the art and include cauliflower mosaic virus (CaMV), geminivirus, brome mosaic virus, and tobacco mosaic virus.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, *Biochemical Methods in Cell Culture and Virology*, Dowden, Hutchinson and Ross, Inc. (1977).

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3-284 in *The Peptides: Analysis, Synthesis, Biology. Vol. 2: Special Methods in Peptide Synthesis, Part A*; Merrifield, et al., (1963) *J. Am. Chem. Soc.* 85:2149-2156, and Stewart, et al., *Solid Phase Peptide Synthesis, 2nd* ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide)) is known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium, typically relying on a biocide and/or herbicide marker which has been introduced together with a polynucleotide of the present invention. For transformation and regeneration of maize see, Gordon-Kamm, et al., (1990) *The Plant Cell* 2:603-618.

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans, et al., *Protoplasts Isolation and Culture, Handbook of Plant Cell Culture*, Macmillan Publishing Company, New York, pp. 124-176 (1983); and Binding, *Regeneration of Plants, Plant Protoplasts*, CRC Press, Boca Raton, pp. 21-73 (1985).

The regeneration of plants containing the foreign gene introduced by *Agrobacterium* from leaf explants can be achieved as described by Horsch, et al., (1985) *Science* 227:1229-1231. In this procedure, transformants are grown in the presence of a selection agent and in a medium that induces the regeneration of shoots in the plant species being transformed as described by Fraley, et al., (1983) *Proc. Natl. Acad. Sci. U.S.A.* 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee, et al., (1987) *Ann. Rev. of Plant Phys.* 38:467-486. The regeneration of plants from either single plant protoplasts or various explants is well known in the art. See, for example, Methods for Plant Molecular Biology, Weissbach and Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, New York (1994); *Corn and Corn Improvement*, $3^{rd}$ edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

Modulating Polypeptide Levels and/or Composition

The present invention further provides a method for modulating (i.e., increasing or decreasing) the concentration or composition of the polypeptides of the present invention in a plant or part thereof. Modulation can be effected by increasing or decreasing the concentration and/or the composition (i.e., the ratio of the polypeptides of the present invention) in a plant. The method comprises transforming a plant cell with a recombinant expression cassette comprising a polynucleotide of the present invention as described above to obtain a transformed plant cell, growing the transformed plant cell under plant forming conditions, and inducing expression of a polynucleotide of the present invention in the plant for a time sufficient to modulate concentration and/or composition in the plant or plant part.

In some embodiments, the content and/or composition of polypeptides of the present invention in a plant may be modulated by altering, in vivo or in vitro, the promoter of a non-isolated gene of the present invention to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling, et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or composition of polypeptides of the present invention in the plant. Plant forming conditions are well known in the art and discussed briefly, above.

In general, concentration or composition is increased or decreased by at least 5%, 10%, 20%, 30%, 40%, 50%, 60%, 70%, 80% or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, above. Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots, particularly maize.

Molecular Markers

The present invention provides a method of genotyping a plant comprising a polynucleotide of the present invention. Preferably, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp. 7-21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2 or 1 cM of a gene of the present invention.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or Pst I genomic clones. The length of the probes is discussed in greater detail, above, but are typically at least 15 bases in length, more preferably at least 20, 25, 30, 35, 40 or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCP); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Exemplary polymorphic variants are provided in Table I, above. Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTR's and Codon Preference

In general, translational efficiency has been found to be regulated by specific sequence elements in the 5' non-coding or untranslated region (5' UTR) of the RNA. Positive sequence motifs include translational initiation consensus sequences (Kozak, (1987) *Nucleic Acids Res.* 15:8125) and the 7-methylguanosine cap structure (Drummond, et al., (1985) *Nucleic Acids Res.* 13:7375). Negative elements include stable intramolecular 5' UTR stem-loop structures (Muesing, et al., (1987) *Cell* 48:691) and AUG sequences or short open reading frames preceded by an appropriate AUG in the 5' UTR (Kozak, above, Rao, et al., (1988) *Mol. and Cell. Biol.* 8:284). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see, Devereaux, et al., (1984) *Nucleic Acids Res.* 12:387-395) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50 or 100.

Sequence Shuffling

The present invention provides methods for sequence shuffling using polynucleotides of the present invention, and compositions resulting therefrom. Sequence shuffling is described in PCT Patent Application Publication Number 96/19256. See also, Zhang, et al., (1997) *Proc. Natl. Acad. Sci. USA* 94:4504-4509. Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased $K_m$ and/or increased $K_{cat}$ over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention; and, (b) a consensus sequence of at least three homologous polynucleotides or polypeptides, respectively, of the present invention. The generic sequence of the present invention comprises each species of polypeptide or polynucleotide embraced by the generic polypeptide or polynucleotide, sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phyla, or kingdoms. For example, a polynucleotide having a consensus sequences from a gene family of *Zea mays* can be used to generate antibody or nucleic acid probes or primers to other Gramineae species such as wheat, rice, or sorghum. Alternatively, a polynucleotide having a consensus sequence generated from orthologous genes can be used to identify or isolate orthologs of other taxa. Typically, a polynucleotide having a consensus sequence will be at least 9, 10, 15, 20, 25, 30 or 40 amino acids in length, or 20, 30, 40, 50, 100 or 150 nucleotides in length. As those of skill in the art are aware, a conservative amino acid substitution can be used for amino acids which differ amongst aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous, or paralogous sequences as provided herein. Optionally, similar sequences used in generating a consensus or generic sequence are identified using the BLAST algorithm's smallest sum probability (P(N)). Various suppliers of sequence-analysis software are listed in chapter 7 of *Current Protocols in Molecular Biology*, F. M. Ausubel, et al., Eds., Current Protocols, a joint venture between Greene Publishing Associates, Inc. and John Wiley & Sons, Inc. (Supplement 30). A polynucleotide sequence is considered similar to a reference sequence if the smallest sum probability in a comparison of the test nucleic acid to the reference nucleic acid is less than about 0.1, more preferably less than about 0.01, or 0.001, and most preferably less than about 0.0001, or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCHER. Conveniently, default parameters of such software can be used to generate consensus or generic sequences.

Detection of Nucleic Acids

The present invention further provides methods for detecting a polynucleotide of the present invention in a nucleic acid sample suspected of comprising a polynucleotide of the present invention, such as a plant cell lysate, particularly a lysate of corn. In some embodiments, a gene of the present invention or portion thereof can be amplified prior to the step of contacting the nucleic acid sample with a polynucleotide of the present invention. The nucleic acid sample is contacted with the polynucleotide to form a hybridization complex. The polynucleotide hybridizes under stringent conditions to a gene encoding a polypeptide of the present invention. Formation of the hybridization complex is used to detect a gene encoding a polypeptide of the present invention in the nucleic acid sample. Those of skill will appreciate that an isolated nucleic acid comprising a polynucleotide of the present invention should lack cross-hybridizing sequences in common with non-target genes that would yield a false positive result.

Detection of the hybridization complex can be achieved using any number of well known methods. For example, the nucleic acid sample, or a portion thereof, may be assayed by hybridization formats including but not limited to, solution phase, solid phase, mixed phase, or in situ hybridization assays. Briefly, in solution (or liquid) phase hybridizations, both the target nucleic acid and the probe or primer are free to interact in the reaction mixture. In solid phase hybridization assays, probes or primers are typically linked to a solid support where they are available for hybridization with target nucleic in solution. In mixed phase, nucleic acid intermediates in solution hybridize to target nucleic acids in solution as well as to a nucleic acid linked to a solid support. In in situ hybridization, the target nucleic acid is liberated from its cellular surroundings in such as to be available for hybridization within the cell while preserving the cellular morphology for subsequent interpretation and analysis. The following articles provide an overview of the various hybridization assay formats: Singer, et al., (1986) *Biotechniques* 4(3):230-250; Haze, et al., (1984) *Methods in Virology*, Vol. VII, pp. 189-226; Wilkinson, The theory and practice of in situ hybridization in: *In situ Hybridization*, D. G. Wilkinson, Ed., IRL Press, Oxford University Press, Oxford; and *Nucleic Acid Hybridization: A Practical Approach*, Hames, B. D. and Higgins, S. J., Eds., IRL Press (1987).

Nucleic Acid Labels and Detection Methods

The means by which nucleic acids of the present invention are labeled is not a critical aspect of the present invention and can be accomplished by any number of methods currently known or later developed. Detectable labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate, magnetic beads, fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads.

Nucleic acids of the present invention can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radio-active isotope depends on research preferences due to ease of synthesis, stability, and half lives of the selected isotopes. Other labels include ligands which bind to antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation. Labeling the nucleic acids of the present invention is readily achieved such as by the use of labeled PCR primers.

In some embodiments, the label is simultaneously incorporated during the amplification step in the preparation of the nucleic acids. Thus, for example, polymerase chain reaction (PCR) with labeled primers or labeled nucleotides will provide a labeled amplification product. In another embodiment, transcription amplification using a labeled nucleotide (e.g., fluorescein-labeled UTP and/or CTP) incorporates a label into the transcribed nucleic acids.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore, or a chemiluminescent compound. Enzymes of interest as labels will primarily be hydrolases, such as phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g., luminol. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody.

Probes can also be labeled by direct conjugation with a label. For example, cloned DNA probes have been coupled directly to horseradish peroxidase or alkaline phosphatase, (Renz and Kurz, (1984) *A Colorimetric Method for DNA Hybridization, Nucl. Acids Res.* 12:3435-3444) and synthetic oligonucleotides have been coupled directly with alkaline phosphatase (Jablonski, et al., (1986) *Preparation of Oligodeoxynucleotide-Alkaline Phosphatase Conjugates and Their Use as Hybridization Probes, Nuc. Acids. Res.* 14:6115-6128; and Li, et al., (1987) *Enzyme-linked Synthetic Oligonucleotide probes: Non-Radioactive Detection of Enterotoxigenic Escherichia Coli in Faeca Specimens, Nucl. Acids Res.* 15:5275-5287).

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

Antibodies to Proteins

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill. The following discussion is presented as a general overview of the techniques available; however, one of skill will recognize that many variations upon the following methods are known.

A number of immunogens are used to produce antibodies specifically reactive with a protein of the present invention. An isolated recombinant, synthetic, or native polynucleotide of the present invention are the preferred immunogens (antigen) for the production of monoclonal or polyclonal antibodies. Those of skill will readily understand that the proteins of the present invention are typically denatured, and optionally reduced, prior to formation of antibodies for screening expression libraries or other assays in which a putative protein of the present invention is expressed or denatured in a non-native secondary, tertiary, or quartenary structure. Non-isolated polypeptides of the present invention can be used either in pure or impure form.

The protein of the present invention is then injected into an animal capable of producing antibodies. Either monoclonal or polyclonal antibodies can be generated for subsequent use in immunoassays to measure the presence and quantity of the protein of the present invention. Methods of producing polyclonal antibodies are known to those of skill in the art. In brief, an immunogen (antigen), preferably a purified protein, a protein coupled to an appropriate carrier (e.g., GST, keyhole limpet hemanocyanin, etc.), or a protein incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the protein of interest. When appropriately high titers of antibody to the immunogen are obtained, blood is collected from the animal and antisera are prepared. Further fractionation of the antisera to enrich for antibodies reactive to the protein is performed where desired (See, e.g., Coligan, *Current Protocols in Immunology*, Wiley/Greene, NY (1991); and Harlow and Lane, *Antibodies: A Laboratory Manual*, Cold Spring Harbor Press, NY (1989)).

Antibodies, including binding fragments and single chain recombinant versions thereof, against predetermined fragments of a protein of the present invention are raised by immunizing animals, e.g., with conjugates of the fragments with carrier proteins as described above. Typically, the immunogen of interest is a protein of at least about 5 amino acids, more typically the protein is 10 amino acids in length, preferably, 15 amino acids in length and more preferably the protein is 20 amino acids in length or greater. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from cells secreting the desired antibody. Monoclonals antibodies are screened for binding to a protein from which the immunogen was derived. Specific monoclonal and polyclonal antibodies will usually have an antibody binding site with an affinity constant for its cognate monovalent antigen at least between $10^6$-$10^7$, usually at least $10^8$, preferably at least $10^9$, more preferably at least $10^{10}$, and most preferably at least $10^{11}$ liters/mole.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology*, 4th ed., Stites, et al., Eds., Lange Medical Publications, Los Altos, Calif., and references cited therein; Harlow and Lane, Supra; Goding, *Monoclonal Antibodies: Principles and Practice*, 2nd ed., Academic Press, New York, N.Y. (1986); and Kohler and Milstein, (1975) *Nature* 256:495-497. Summarized briefly, this method proceeds by injecting an animal with an immunogen comprising a protein of the present invention. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of recombinant antibodies in phage or similar vectors (see, e.g., Huse, et al., (1989) *Science* 246:1275-1281; and Ward, et al., (1989) *Nature* 341:544-546; and Vaughan, et al., (1996) *Nature Biotechnology*, 14:309-314). Alternatively, high avidity human monoclonal antibodies can be obtained from transgenic mice comprising fragments of the unrearranged human heavy and light chain Ig loci (i.e., minilocus transgenic mice). Fishwild, et al., (1996) *Nature Biotech.* 14:845-851. Also, recombinant immunoglobulins may be produced. See, Cabilly, U.S. Pat. No. 4,816,567; and Queen, et al., (1989) *Proc. Natl. Acad. Sci.* 86:10029-10033.

The antibodies of this invention are also used for affinity chromatography in isolating proteins of the present invention. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified protein are released.

The antibodies can be used to screen expression libraries for particular expression products such as normal or abnormal protein. Usually the antibodies in such a procedure are labeled with a moiety allowing easy detection of presence of antigen by antibody binding.

Antibodies raised against a protein of the present invention can also be used to raise anti-idiotypic antibodies. These are useful for detecting or diagnosing various pathological conditions related to the presence of the respective antigens.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Protein Immunoassays

Means of detecting the proteins of the present invention are not critical aspects of the present invention. In a preferred embodiment, the proteins are detected and/or quantified using any of a number of well recognized immunological binding assays (see, e.g., U.S. Pat. Nos. 4,366,241; 4,376,110; 4,517,288 and 4,837,168). For a review of the general immunoassays, see also, Methods in Cell Biology, Vol. 37: *Antibodies in Cell Biology*, Asai, Ed., Academic Press, Inc. New York (1993); *Basic and Clinical Immunology* 7th Edition, Stites and Terr, Eds. (1991). Moreover, the immunoassays of the present invention can be performed in any of several configurations, e.g., those reviewed in *Enzyme Immunoassay*, Maggio, Ed., CRC Press, Boca Raton, Fla. (1980); Tijan, Practice and Theory of Enzyme Immunoassays, *Laboratory Techniques in Biochemistry and Molecular Biology*, Elsevier Science Publishers B.V., Amsterdam (1985); Harlow and Lane, above; *Immunoassay: A Practical Guide*, Chan, Ed., Academic Press, Orlando, Fla. (1987); *Principles and Practice of Immunoassaysm*, Price and Newman Eds., Stockton Press, NY (1991); and *Non-isotopic Immunoassays*, Ngo, Ed., Plenum Press, NY (1988). Immunological binding assays (or immunoassays) typically utilize a "capture agent" to specifically bind to and often immobilize the analyte (in this case, a protein of the present invention). The capture agent is a moiety that specifically binds to the analyte. In a preferred embodiment, the capture agent is an antibody that specifically binds a protein(s) of the present invention. The antibody may be produced by any of a number of means known to those of skill in the art as described herein.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled protein of the present invention or a labeled antibody specifically reactive to a protein of the present invention. Alternatively, the labeling agent may be a third moiety, such as another antibody, that specifically binds to the antibody/protein complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally, Kronval, et al., (1973) *J. Immunol.* 111:1401-1406 and Akerstrom, et al., (1985) *J. Immunol.* 135:2589-2542).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

While the details of the immunoassays of the present invention may vary with the particular format employed, the method of detecting a protein of the present invention in a biological sample generally comprises the steps of contacting the biological sample with an antibody which specifically reacts, under immunologically reactive conditions, to a protein of the present invention. The antibody is allowed to bind to the protein under immunologically reactive conditions, and the presence of the bound antibody is detected directly or indirectly.

A Non-Competitive Assay Formats

Immunoassays for detecting proteins of the present invention include competitive and noncompetitive formats. Non-competitive immunoassays are assays in which the amount of captured analyte (i.e., a protein of the present invention) is directly measured. In one preferred "sandwich" assay, for example, the capture agent (e.g., an antibody specifically reactive, under immunoreactive conditions, to a protein of the present invention) can be bound directly to a solid substrate where they are immobilized. These immobilized antibodies then capture the protein present in the test sample. The protein thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

B. Competitive Assay Formats

In competitive assays, the amount of analyte present in the sample is measured indirectly by measuring the amount of an added (exogenous) analyte (e.g., a protein of the present invention) displaced (or competed away) from a capture agent (e.g., an antibody specifically reactive, under immunoreactive conditions, to the protein) by the analyte present in the sample. In one competitive assay, a known amount of analyte is added to the sample and the sample is then contacted with a capture agent that specifically binds a protein of the present invention. The amount of protein bound to the capture agent is inversely proportional to the concentration of analyte present in the sample.

In a particularly preferred embodiment, the antibody is immobilized on a solid substrate. The amount of protein bound to the antibody may be determined either by measuring the amount of protein present in a protein/antibody complex, or alternatively by measuring the amount of remaining uncomplexed protein. The amount of protein may be detected by providing a labeled protein.

A hapten inhibition assay is another preferred competitive assay. In this assay a known analyte, (such as a protein of the present invention) is immobilized on a solid substrate. A known amount of antibody specifically reactive, under immunoreactive conditions, to the protein is added to the sample, and the sample is then contacted with the immobilized protein. In this case, the amount of antibody bound to the immobilized protein is inversely proportional to the amount of protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

C. Generation of Pooled Antisera for Use in Immunoassays

A protein that specifically binds to or that is specifically immunoreactive with an antibody generated against a defined immunogen is determined in an immunoassay. The immunoassay uses a polyclonal antiserum which is raised to a polypeptide of the present invention (i.e., the immunogenic polypeptide). This antiserum is selected to have low crossreactivity against other proteins and any such crossreactivity is removed by immunoabsorption prior to use in the immunoassay (e.g., by immunosorbtion of the antisera with a protein of different substrate specificity (e.g., a different enzyme) and/or a protein with the same substrate specificity but of a different form).

In order to produce antisera for use in an immunoassay, a polypeptide of the present invention is isolated as described herein. For example, recombinant protein can be produced in a mammalian or other eukaryotic cell line. An inbred strain of mice is immunized with the protein using a standard adjuvant, such as Freund's adjuvant, and a standard mouse immunization protocol (see, Harlow and Lane, above). Alternatively, a synthetic polypeptide derived from the sequences disclosed herein and conjugated to a carrier protein is used as an immunogen. Polyclonal sera are collected and titered against the immunogenic polypeptide in an immunoassay, for example, a solid phase immunoassay with the immunogen immobilized on a solid support. Polyclonal antisera with a titer of $10^4$ or greater are selected and tested for their cross reactivity against polypeptides of different forms or substrate specificity, using a competitive binding immunoassay such as the one described in Harlow and Lane, above, at pages 570-573. Preferably, two or more distinct forms of polypeptides are used in this determination. These distinct types of polypeptides are used as competitors to identify antibodies which are specifically bound by the polypeptide being assayed for. The competitive polypeptides can be produced as recombinant proteins and isolated using standard molecular biology and protein chemistry techniques as described herein.

Immunoassays in the competitive binding format are used for crossreactivity determinations. For example, the immunogenic polypeptide is immobilized to a solid support. Proteins added to the assay compete with the binding of the antisera to the immobilized antigen. The ability of the above proteins to compete with the binding of the antisera to the immobilized protein is compared to the immunogenic polypeptide. The percent crossreactivity for the above proteins is calculated, using standard calculations. Those antisera with less than 10% crossreactivity with a distinct form of a polypeptide are selected and pooled. The cross-reacting antibodies are then removed from the pooled antisera by immunoabsorption with a distinct form of a polypeptide.

The immunoabsorbed and pooled antisera are then used in a competitive binding immunoassay as described herein to compare a second "target" polypeptide to the immunogenic polypeptide. In order to make this comparison, the two polypeptides are each assayed at a wide range of concentrations and the amount of each polypeptide required to inhibit 50% of the binding of the antisera to the immobilized protein is determined using standard techniques. If the amount of the target polypeptide required is less than twice the amount of the immunogenic polypeptide that is required, then the target polypeptide is said to specifically bind to an antibody generated to the immunogenic protein. As a final determination of specificity, the pooled antisera is fully immunosorbed with the immunogenic polypeptide until no binding to the polypeptide used in the immunosorbtion is detectable. The fully immunosorbed antisera is then tested for reactivity with the test polypeptide. If no reactivity is observed, then the test polypeptide is specifically bound by the antisera elicited by the immunogenic protein.

D. Other Assay Formats

In a particularly preferred embodiment, Western blot (immunoblot) analysis is used to detect and quantify the presence of protein of the present invention in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind a protein of the present invention. The antibodies specifically bind to the protein on the solid support. These antibodies may be directly labeled or alternatively may be subsequently detected using labeled antibodies (e.g., labeled sheep anti-mouse antibodies) that specifically bind to the antibodies.

E. Quantification of Proteins.

The proteins of the present invention may be detected and quantified by any of a number of means well known to those of skill in the art. These include analytic biochemical methods such as electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-1 inked immunosorbent assays (ELISAs), immunofluorescent assays, and the like.

F. Reduction of Non-Specific Binding

One of skill will appreciate that it is often desirable to reduce non-specific binding in immunoassays and during analyte purification. Where the assay involves an antigen, antibody, or other capture agent immobilized on a solid substrate, it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin are widely used.

G. Immunoassay Labels

The labeling agent can be, e.g., a monoclonal antibody, a polyclonal antibody, a binding protein or complex, or a polymer such as an affinity matrix, carbohydrate or lipid. Detectable labels suitable for use in the present invention include any composition detectable by spectroscopic, radioisotopic, photochemical, biochemical, immunochemical, electrical, optical or chemical means. Detection may proceed by any known method, such as immunoblotting, western analysis, gel-mobility shift assays, fluorescent in situ hybridization analysis (FISH), tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The particular label or detectable group used in the assay is not a critical aspect of the invention. The detectable group can be any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads, fluorescent dyes, radiolabels, enzymes, and colorimetric labels or colored glass or plastic beads, as discussed for nucleic acid labels, above.

The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Assays for Compounds that Modulate Enzymatic Activity or Expression

The present invention also provides means for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60% and most preferably at least 70% or 80% of the specific activity of the native, full-length polypeptide of the present invention (e.g., enzyme). Generally, the polypeptide will be present in a range sufficient to determine the effect of the compound, typically about 1 nM to 10 µM. Likewise, the compound will be present in a concentration of from about 1 nM to 10 µM. Those of skill will understand that such factors as enzyme concentration, ligand concentrations (i.e., substrates, products, inhibitors, activators), pH, ionic strength, and temperature will be controlled so as to obtain useful kinetic data and determine the presence of absence of a compound that binds or modulates polypeptide activity. Methods of measuring enzyme kinetics is well known in the art. See, e.g., Segel, *Biochemical Calculations*, $2^{nd}$ ed., John Wiley and Sons, New York (1976).

Although the present invention has been described in some detail by way of illustration and example for purposes of clarity of understanding, it will be obvious that certain changes and modifications may be practiced within the scope of the appended claims.

EXAMPLE 1

This example describes the construction cDNA libraries.

Total RNA Isolation

Total RNA was isolated from corn tissues with TRizol Reagent (Life Technology Inc. Gaithersburg, Md.) using a modification of the guanidine isothiocyanate/acid-phenol procedure described by Chomczynski and Sacchi (Chomczynski and Sacchi, (1987) *Anal. Biochem.* 162:156). In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

Poly(A)+ RNA Isolation

The selection of poly(A)+ RNA from total RNA was performed using PolyATact system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringent condition and eluted by RNase-free deionized water.

cDNA Library Construction cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between of Not I and Sal I sites.

EXAMPLE 2

This example describes cDNA sequencing and library subtraction.

Sequencing Template Preparation

Individual colonies were picked and DNA was prepared either by PCR with M13 forward primers and M13 reverse primers, or by plasmid isolation. All the cDNA clones were sequenced using M13 reverse primers.

Q-bot Subtraction Procedure cDNA libraries subjected to the subtraction procedure were plated out on 22×22 cm² agar plate at density of about 3,000 colonies per plate. The plates were incubated in a 37° C. incubator for 12-24 hours. Colonies were picked into 384-well plates by a robot colony picker, Q-bot (GENETIX Limited). These plates were incubated overnight at 37° C.

Once sufficient colonies were picked, they were pinned onto 22×22 cm² nylon membranes using Q-bot. Each membrane contained 9,216 colonies or 36,864 colonies. These membranes were placed onto agar plate with appropriate antibiotic. The plates were incubated at 37° C. for overnight.

After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of the filters were place into Proteinase K solution, incubated at 37° C. for 40-50 minutes. The filters were placed on dry filter papers to dry overnight. DNA was then cross-linked to nylon membrane by UV light treatment.

Colony hybridization was conducted as described by Sambrook, J., Fritsch, E. F. and Maniatis, T., (in Molecular Cloning: A laboratory Manual, 2$^{nd}$ Edition). The following probes were used in colony hybridization:

1. First strand cDNA from the same tissue as the library was made from to remove the most redundant clones.
2. 48-192 most redundant cDNA clones from the same library based on previous sequencing data.
3. 192 most redundant cDNA clones in the entire corn partial sequence database.
4. A Sal-A20 oligo nucleotide: TCG ACC CAC GCG TCC GAA AAA AAA AAA AAA AAA AAA, removes clones containing a poly A tail but no cDNA.
5. cDNA clones derived from rRNA.

The image of the autoradiography was scanned into computer and the signal intensity and cold colony addresses of each colony was analyzed. Re-arraying of cold-colonies from 384 well plates to 96 well plates was conducted using Q-bot.

EXAMPLE 3

This example describes identification of the gene from a computer homology search.

Gene identities were determined by conducting BLAST (Basic Local Alignment Search Tool; Altschul, et al., (1993) *J. Mol. Biol.* 215:403-410; see also, www.ncbi.nlm.nih.gov/BLAST/) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences were analyzed for similarity to all publicly available DNA sequences contained in the "nr" database using the BLASTN algorithm. The DNA sequences were translated in all reading frames and compared for similarity to all publicly available protein sequences contained in the "nr" database using the BLASTX algorithm (Gish and States, (1993) *Nature Genetics* 3:266-272) provided by the NCBI. In some cases, the sequencing data from two or more clones containing overlapping segments of DNA were used to construct contiguous DNA sequences.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. An isolated nucleic acid encoding a functional cellulose synthase, said polynucleotide selected from the group consisting of:
   (a) a polynucleotide having at least 95% sequence identity, as determined by the BLAST 2.0 algorithm under default parameters, to the full length polypeptide sequence of SEQ ID NO: 2;
   (b) a polynucleotide encoding a polypeptide of SEQ ID NO: 2; and
   (c) a polynucleotide of SEQ ID NO: 1.

2. A recombinant expression cassette, comprising the polynucleotide of claim 1 operably linked, in sense or anti-sense orientation, to a promoter.

3. A host cell comprising the recombinant expression cassette of claim 2.

4. A transgenic plant comprising a recombinant expression cassette of claim 2.

5. The transgenic plant of claim 4, wherein the plant is a monocot.

6. The transgenic plant of claim 4, wherein the plant is selected from the group consisting of: maize, soybean, sunflower, sorghum, canola, wheat, alfalfa, cotton, rice, barley and millet.

7. A transgenic seed from the transgenic plant of claim 4.

8. A method of modulating the level of cellulose synthase in a plant cell, comprising:
   (a) transforming the plant cell with a recombinant expression cassette comprising the polynucleotide of claim 1 operably linked to a promoter; and
   (b) culturing the transformed plant cell under plant cell growing conditions; wherein the level of cellulose synthase in said transformed plant cell is modulated.

9. The method of claim 8, further comprising regenerating a plant from the transformed plant cell.

10. The method of claim 9, wherein the plant is selected from the group consisting of: maize, soybean, sunflower, sorghum, canola, wheat, alfalfa, cotton, rice, barley and millet.

11. The method of claim 8, wherein the promoter is a tissue-preferred promoter.

12. The method of claim 8, wherein the level of cellulose synthase is increased.

13. The method of claim 8 wherein the polynucleotide encoding a functional cellulose synthase is SEQ ID NO: 1.

* * * * *